United States Patent
Klasen-Memmer et al.

(10) Patent No.: US 11,274,254 B2
(45) Date of Patent: *Mar. 15, 2022

(54) COMPOUNDS FOR THE HOMEOTROPIC ALIGNMENT OF LIQUID-CRYSTALLINE MEDIA

(71) Applicant: Merck Patent GmbH, Darmstadt (DE)

(72) Inventors: Melanie Klasen-Memmer, Heuchelheim (DE); Edward Plummer, Frankfurt am Main (DE); Rocco Fortte, Frankfurt am Main (DE); Helmut Haensel, Muehltal (DE); Timo Uebel, Darmstadt (DE); Tamara Lehmann, Otzberg (DE)

(73) Assignee: Merck Patent GmbH, Darmstadt (DE)

( * ) Notice: Subject to any disclaimer, the term of this patent is extended or adjusted under 35 U.S.C. 154(b) by 70 days.

This patent is subject to a terminal disclaimer.

(21) Appl. No.: 16/267,530

(22) Filed: Feb. 5, 2019

(65) Prior Publication Data

US 2019/0241809 A1   Aug. 8, 2019

(30) Foreign Application Priority Data

Feb. 5, 2018 (DE) .......................... 102018000894.1

(51) Int. Cl.
| | |
|---|---|
| *C09K 19/56* | (2006.01) |
| *C09K 19/12* | (2006.01) |
| *C09K 19/04* | (2006.01) |
| *C09K 19/02* | (2006.01) |
| *C09K 19/30* | (2006.01) |
| *C07C 69/54* | (2006.01) |
| *C07C 69/602* | (2006.01) |
| *C09K 19/54* | (2006.01) |

(52) U.S. Cl.
CPC .............. *C09K 19/56* (2013.01); *C07C 69/54* (2013.01); *C07C 69/602* (2013.01); *C09K 19/02* (2013.01); *C09K 19/04* (2013.01); *C09K 19/12* (2013.01); *C09K 19/3003* (2013.01); *C09K 19/542* (2013.01); *C09K 2019/0425* (2013.01); *C09K 2019/0448* (2013.01); *C09K 2019/125* (2013.01); *C09K 2019/548* (2013.01)

(58) Field of Classification Search
CPC ...................................................... C09K 19/30
See application file for complete search history.

(56) References Cited

U.S. PATENT DOCUMENTS

| | | |
|---|---|---|
| 4,764,263 A | 8/1988 | Gregory et al. |
| 9,809,748 B2 | 11/2017 | Archetti et al. |
| 10,273,409 B2 | 4/2019 | Graziano et al. |
| 10,294,426 B2 | 5/2019 | Archetti et al. |
| 2015/0252265 A1* | 9/2015 | Archetti ................ G02F 1/1341 349/130 |
| 2018/0002604 A1 | 1/2018 | Yoon et al. |
| 2018/0023001 A1* | 1/2018 | Tanaka ................ C09K 19/3001 252/299.4 |
| 2018/0171231 A1 | 6/2018 | Archetti et al. |
| 2018/0208849 A1 | 7/2018 | Saito |
| 2018/0258346 A1 | 9/2018 | Yun et al. |
| 2020/0308488 A1* | 10/2020 | Shimizu ................ C08F 20/30 |

FOREIGN PATENT DOCUMENTS

| | | |
|---|---|---|
| DE | 102011108708 A1 | 3/2012 |
| DE | 102015008172 A1 | 1/2016 |
| EP | 0291865 B1 | 8/1992 |
| EP | 2918658 A2 | 9/2015 |
| EP | 3246305 A1 | 11/2017 |
| EP | 3263673 A1 | 1/2018 |
| WO | 17013981 A | 1/2017 |
| WO | 17041893 A1 | 3/2017 |
| WO | 17045740 A1 | 3/2017 |
| WO | WO-2019124153 A1 * | 6/2019 ............. C09K 19/20 |

OTHER PUBLICATIONS

Supplementary search report in corresponding EP19155191.0 dated Jun. 12, 2019 (pp. 1-12).

* cited by examiner

*Primary Examiner* — Chanceity N Robinson
(74) *Attorney, Agent, or Firm* — Millen White Zelano and Branigan, PC; Richard Traverso

(57) ABSTRACT

Liquid-crystalline media (LC media) comprising self-aligning mesogens (self-alignment additives) which effect homeotropic (vertical) alignment of the LC media at a surface or the cell walls of a liquid-crystal display (LC display). The self-alignment additives contain five-ring systems. LC displays having homeotropic alignment of the liquid-crystalline medium (LC medium) without conventional alignment layers are provided.

18 Claims, No Drawings

COMPOUNDS FOR THE HOMEOTROPIC ALIGNMENT OF LIQUID-CRYSTALLINE MEDIA

The present invention relates to liquid-crystalline media (LC media) comprising novel self-aligning mesogens (self-alignment additives) which effect homeotropic (vertical) alignment of the LC media at a surface or the cell walls of a liquid-crystal display (LC display). The novel self-alignment additives contain five-ring systems. The invention also encompasses LC displays having homeotropic alignment of the liquid-crystalline medium (LC medium) without conventional alignment layers.

The principle of electrically controlled birefringence, the ECB effect or also DAP (deformation of aligned phases) effect, was described for the first time in 1971 (M. F. Schieckel and K. Fahrenschon, "Deformation of nematic liquid crystals with vertical orientation in electrical fields", Appl. Phys. Lett. 19 (1971), 3912). This was followed by papers by J. F. Kahn (Appl. Phys. Lett. 20 (1972), 1193) and G. Labrunie and J. Robert (J. Appl. Phys. 44 (1973), 4869).

The papers by J. Robert and F. Clerc (SID 80 Digest Techn. Papers (1980), 30), J. Duchene (Displays 7 (1986), 3) and H. Schad (SID 82 Digest Techn. Papers (1982), 244) showed that liquid-crystalline phases must have high values for the ratio of the elastic constants $K_3/K_1$, high values for the optical anisotropy $\Delta n$ and values for the dielectric anisotropy of $\Delta\varepsilon \leq -0.5$ in order to be suitable for use in high-information display elements based on the ECB effect. Electro-optical display elements based on the ECB effect have homeotropic edge alignment (VA technology= vertically aligned).

Displays which use the ECB effect, as so-called VAN (vertically aligned nematic) displays, for example in the MVA (multi-domain vertical alignment, for example: Yoshide, H. et al., paper 3.1: "MVA LCD for Notebook or Mobile PCs . . . ", SID 2004 International Symposium, Digest of Technical Papers, XXXV, Book I, pp. 6 to 9, and Liu, C. T. et al., paper 15.1: "A 46-inch TFT-LCD HDTV Technology . . . ", SID 2004 International Symposium, Digest of Technical Papers, XXXV, Book II, pp. 750 to 753), PVA (patterned vertical alignment, for example: Kim, Sang Soo, paper 15.4: "Super PVA Sets New State-of-the-Art for LCD-TV", SID 2004 International Symposium, Digest of Technical Papers, XXXV, Book II, pp. 760 to 763), ASV (advanced super view, for example: Shigeta, Mitzuhiro and Fukuoka, Hirofumi, paper 15.2: "Development of High Quality LCDTV", SID 2004 International Symposium, Digest of Technical Papers, XXXV, Book II, pp. 754 to 757) modes, have established themselves as one of the three more recent types of liquid-crystal display that are currently the most important, in particular for television applications, besides IPS (in-plane switching) displays (for example: Yeo, S. D., paper 15.3: "An LC Display for the TV Application", SID 2004 International Symposium, Digest of Technical Papers, XXXV, Book II, pp. 758 & 759) and the long-known TN (twisted nematic) displays. The technologies are compared in general form, for example, in Souk, Jun, SID Seminar 2004, seminar M-6: "Recent Advances in LCD Technology", Seminar Lecture Notes, M-6/1 to M-6/26, and Miller, Ian, SID Seminar 2004, seminar M-7: "LCD-Television", Seminar Lecture Notes, M-7/1 to M-7/32. Although the response times of modern ECB displays have already been significantly improved by addressing methods with overdrive, for example: Kim, Hyeon Kyeong et al., paper 9.1: "A 57-in. Wide UXGA TFT-LCD for HDTV Application", SID 2004 International Symposium, Digest of Technical Papers, XXXV, Book I, pp. 106 to 109, the achievement of video-compatible response times, in particular on switching of grey shades, is still a problem which has not yet been satisfactorily solved.

Considerable effort is associated with the production of VA displays having two or more domains of different preferential direction. It is an aim of this invention to simplify the production processes and the display devices themselves without giving up the advantages of VA technology, such as relatively short response times and good viewing-angle dependence.

VA displays which comprise LC media having positive dielectric anisotropy are described in S. H. Lee et al. *Appl. Phys. Lett.* (1997), 71, 2851-2853.

These displays use interdigital electrodes arranged on a substrate surface (in-plane addressing electrode configuration having a comb-shaped structure), as employed, inter alia, in the commercially available IPS (in-plane switching) displays (as disclosed, for example, in DE 40 00 451 and EP 0 588 568), and have a homeotropic arrangement of the liquid-crystal medium, which changes to a planar arrangement on application of an electric field.

Further developments of the above-mentioned display can be found, for example, in K. S. Hun et al. *J. Appl. Phys.* (2008), 104, 084515 (DSIPS: 'double-side in-plane switching' for improvements of driver voltage and transmission), M. Jiao et al. *App. Phys. Lett* (2008), 92, 111101 (DFFS: 'dual fringe field switching' for improved response times) and Y. T. Kim et al. *Jap. J. App. Phys.* (2009), 48, 110205 (VAS: 'viewing angle switchable' LCD). In addition, VA-IPS displays are also known under the name HT-VA (high transmittance VA).

In all such displays (referred to below in general as VA-IPS displays), an alignment layer is applied to both substrate surfaces for homeotropic alignment of the LC medium; the production of this layer has hitherto been associated with considerable effort.

It is an aim of this invention to simplify the production processes themselves without giving up the advantages of VA or VA-IPS technology, such as relatively short response times, good viewing-angle dependence and high contrast.

Industrial application of these effects in electro-optical display elements requires LC phases, which have to satisfy a multiplicity of requirements. Particularly important here are chemical resistance to moisture, air, the materials in the substrate surfaces and physical influences, such as heat, infrared, visible and ultraviolet radiation and direct and alternating electric fields.

Furthermore, industrially usable LC phases are required to have a liquid-crystalline mesophase in a suitable temperature range and low viscosity.

VA and VA-IPS displays are generally intended to have very high specific resistance at the same time as a large working-temperature range, short response times and a low threshold voltage, with the aid of which various grey shades can be produced.

In conventional VA and VA-IPS displays, a polyimide layer on the substrate surfaces ensures homeotropic alignment of the liquid crystal. The production of a suitable alignment layer in the display requires considerable effort. In addition, interactions of the alignment layer with the LC medium may impair the electrical resistance of the display. Owing to possible interactions of this type, the number of suitable liquid-crystal components is considerably reduced. It would therefore be desirable to achieve homeotropic alignment of the LC medium without polyimide.

The disadvantage of the active-matrix TN displays frequently used is due to their comparatively low contrast, the relatively high viewing-angle dependence and the difficulty of producing grey shades in these displays.

VA displays have significantly better viewing-angle dependences and are therefore used principally for televisions and monitors.

A further development are the so-called PS or PSA ("polymer stabilised" or "polymer sustained alignment") displays. The PSA displays are distinguished by the shortening of the response times without significant adverse effects on other parameters, such as, in particular, the favourable viewing-angle dependence of the contrast.

In these displays, a small amount (for example 0.3% by weight, typically <1% by weight) of one or more polymerisable compound(s) is added to the LC medium and, after introduction into the LC cell, is polymerised or crosslinked in situ, usually by UV photopolymerisation, between the electrodes with or without an applied electrical voltage. The addition of polymerisable mesogenic or liquid-crystalline compounds, also known as reactive mesogens or "RMs", to the LC mixture has proven particularly suitable. PSA technology has hitherto been employed principally for LC media having negative dielectric anisotropy.

In the meantime, the principle of polymer stabilisation has been used in diverse classical LC displays. Thus, for example, PS-VA, PS-OCB, PS-IPS, PS-FFS and PS-TN displays are known. The polymerisation of the polymerisable compound(s) preferably takes place with an applied electrical voltage in the case of PS-VA and PS-OCB displays, and with or without an applied electrical voltage in the case of PS-IPS displays. As can be demonstrated in test cells, the PS(A) method results in a 'pretilt' in the cell. In the case of PS-OCB displays, for example, it is possible for the bend structure to be stabilised so that an offset voltage is unnecessary or can be reduced. In the case of PS-VA displays, the pretilt has a positive effect on the response times. A standard pixel and electrode layout can be used for PS-VA displays. In addition, however, it is also possible, for example, to manage with only one structured electrode side and no protrusions, which significantly simplifies production and at the same time results in very good contrast at the same time as very good light transmission.

PS-VA displays are described, for example, in JP 10-036847 A, EP 1 170 626 A2, U.S. Pat. Nos. 6,861,107, 7,169,449, US 2004/0191428 A1, US 2006/0066793 A1 and US 2006/0103804 A1. PS-OCB displays are described, for example, in T.-J- Chen et al., Jpn. J. Appl. Phys. (2006), 45, 2702-2704 and S. H. Kim, L.-C- Chien, Jpn. J. Appl. Phys. (2004), 43, 7643-7647. PS-IPS displays are described, for example, in U.S. Pat. No. 6,177,972 and Appl. Phys. Lett. (1999), 75(21), 3264. PS-TN displays are described, for example, in Optics Express (2004), 12(7), 1221. PS-VA-IPS displays are disclosed, for example, in WO 2010/089092 A1.

Like the conventional LC displays described above, PS displays can be operated as active-matrix or passive-matrix (PM) displays. In the case of active-matrix displays, individual pixels are usually addressed by integrated, non-linear active elements, such as, for example, transistors (for example thin-film transistors or "TFTs"), while in the case of passive-matrix displays, individual pixels are usually addressed by the multiplex method, both methods being known from the prior art.

In particular for monitor and especially TV applications, optimisation of the response times, but also of the contrast and luminance (i.e. also transmission), of the LC display is still sought after. The PSA method can provide crucial advantages here. In particular in the case of PS-VA displays, a shortening of the response times, which correlate with a pretilt which can be measured in test cells, can be achieved without significant adverse effects on other parameters.

In the prior art, polymerisable compounds of the following formula, for example, are used for PS-VA:

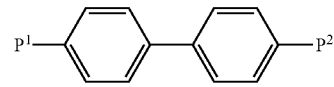

in which $P^{1/2}$ denotes a polymerisable group, usually an acrylate or methacrylate group, as described, for example, in U.S. Pat. No. 7,169,449.

The effort for the production of a polyimide layer, treatment of the layer and improvement with bumps or polymer layers is relatively great. A simplifying technology which on the one hand reduces production costs and on the other hand helps to optimise the image quality (viewing-angle dependence, contrast, response times) is therefore desirable.

The specifications EP 2918658 A2 and US 2015/0252265 A1 describe self-aligning, in some cases polymerisable mesogens containing an anchor group (e.g. OH) and liquid-crystalline media comprising such additives. The additives disclosed there have a different structure to the compounds according to the invention. The present compounds contain five ring systems in a linear sequence.

However, the existing approaches for obtaining VA display applications without a polyimide layer are not yet entirely satisfactory. For commercial displays, high demends are made of the processibility. This requires properties such as, for example, good solubility, rapid tilt-angle adjustment, good tilt stability and a low tendency towards mura defects.

The present invention relates to compounds of the following formula I, and to an LC medium comprising a low-molecular-weight, unpolymerisable, liquid-crystalline component and a polymerisable or polymerised component comprising one or more compounds of the formula I, where the polymerised component is obtainable by polymerisation of the polymerisable component, $$R^1\text{-}[A^2\text{-}Z^2]_m\text{-}A^1\text{-}R^a \qquad \text{I}$$

in which
m denotes 4,
$A^1$ denotes an aromatic, heteroaromatic, alicyclic or heterocyclic group, which may also contain anellated rings and which may also be mono- or polysubstituted by a group L or -Sp-P,
$A^2$ in each case, independently of one another, denotes an aromatic, heteroaromatic, alicyclic or heterocyclic group, which may also contain anellated rings and which may also be mono- or polysubstituted by a group L or -Sp-P,
L in each case, independently of one another, denotes unbranched or branched alkyl, alkenyl, alkoxy, alkylcarbonyl, alkoxycarbonyl, alkylcarbonyloxy or alkoxycarbonyloxy having 1 to 25 C atoms, in which, in addition, one or more H atoms may be replaced by F or Cl, or denotes F, Cl, Br, I, —CN, —NO$_2$, —NCO, —NCS, —OCN, —SCN, —C(=O)N(R$^0$)R$^{00}$ or cycloalkyl having 3 to 6 C atoms,
P denotes a polymerisable group,
Sp denotes a spacer group (also called spacer) or a single bond, $Z^2$ in each case, independently of one another, denotes a single bond, —O—, —S—, —CO—, —CO—O—, —OCO—, —O—CO—O—, —OCH$_2$—, —CH$_2$O—, —SCH$_2$—, —CH$_2$S—, —CF$_2$O—, —OCF$_2$—, —CF$_2$S—, —SCF$_2$—, —(CH$_2$)$_{n1}$—, —CF$_2$CH$_2$—, —CH$_2$CF$_2$—, —(CF$_2$)$_{n1}$—, —CH=CH—, —CF=CF—, —C≡C—, —CH=CH—COO—, —OCO—CH=CH— or —(CR$^0$R$^{00}$)$_{n1}$—, n1 denotes 1, 2, 3 or 4, $R^0$ in each case, independently of one another, denotes alkyl having 1 to 12 C atoms, $R^{00}$ in each case, independently of one another, denotes H or alkyl having 1 to 12 C atoms, $R^1$ denotes an alkyl radical having 1 to 25 C atoms, where, in addition, one or more CH$_2$ groups in this radical may in each case be replaced, independently of one another, by —CH=CH—, —C≡C—, —CF$_2$O—, —OCF$_2$—,

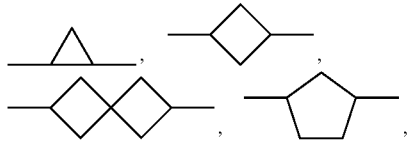

—O—, —S—, —CO—, —CO—O— or —O—CO— in such a way that O/S atoms are not linked directly to one another, and in which, in addition, one or more H atoms may be replaced by F or Cl, or denotes H, or a group -Sp-P, $R^a$ denotes an anchor group of the formula

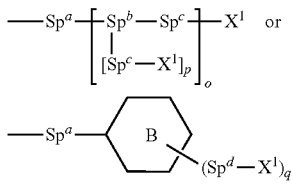

p denotes 1 or 2, q denotes 2 or 3,

B denotes a substituted or unsubstituted ring system or condensed ring system, o denotes 0 or 1, $X^1$, independently of one another, denotes OH, SH, NH$_2$, NHR$^{11}$, NR$^{11}_2$, C(O)OH or —CHO, $R^{11}$ denotes alkyl having 1 to 12 C atoms, which may be linear or branched, and in which H may be substituted by fluorine or alkoxy having 1 to 8 C atoms, $Sp^a$, $Sp^c$, $Sp^d$ in each case, independently of one another, denote a spacer group or a single bond, and $Sp^b$ denotes a tri- or tetravalent group.

The polymerisable or polymerised component of the LC medium optionally comprises further polymerisable compounds. Those which are suitable for the PS principle are preferably used here.

In accordance with a preferred embodiment, the compounds of the formula I according to the invention are polymerisable in that they contain one, two or more polymerisable groups (P). A preferred embodiment of the invention is therefore also a polymer which contains monomers of the formula I, i.e. a polymer which is built up at least partly from corresponding polymerisation product. A polymer of this type is generally distributed homogeneously or in-homogeneously in a liquid-crystalline medium or deposited in full or part on an adjacent substrate, where mixed forms of these states are included.

The invention furthermore relates to an LC display comprising an LC cell having two substrates and at least two electrodes, where at least one substrate is transparent to light and at least one substrate has one or two electrodes, and a layer of an LC medium according to the invention located between the substrates. The LC display is preferably one of the PS type.

The invention furthermore relates to the use of compounds of the formula I as additive for LC media for effecting homeotropic alignment with respect to a surface delimiting the LC medium.

A further aspect of the present invention is a process for the preparation of an LC medium according to the invention, which is characterised in that one or more optionally polymerisable self-alignment additives (compounds of the formula I) are mixed with a low-molecular-weight, liquid-crystalline component, and optionally one or more further polymerisable compounds are added.

The invention furthermore relates to a process for the production of an LC display comprising an LC cell having two substrates and at least two electrodes, where at least one substrate is transparent to light and at least one substrate has one or two electrodes, comprising the process steps:

filling of the cell with an LC medium according to the invention, where homeotropic (vertical) alignment of the LC medium with respect to the substrate surfaces becomes established, and polymerisation of the polymerisable component(s), optionally with application of a voltage to the cell or under the action of an electric field, in one or more process steps.

The use according to the invention of the self-alignment additives as additives of LC media is not tied to particular LC media. The LC medium or the unpolymerisable component present therein can have positive or negative dielectric anisotropy. The LC medium is preferably nematic, since most displays based on the VA principle comprise nematic LC media.

The self-alignment additive is introduced into the LC medium as additive. It effects homeotropic alignment of the liquid crystal with respect to the substrate surfaces (such as, for example, a surface made from glass or coated with ITO or with polyimide). In view of the investigations in connection with this invention, it appears that the polar anchor group interacts with the substrate surface. This causes the self-alignment additives on the substrate surface to align and induce a homeotropic alignment of the adjacent LC medium."

In particular, preference is given to anchor groups $R^a$ which do not consist only of a simple OH group. For the anchor group $R^a$ of the formula

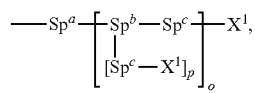

the group $Sp^a$ for o=0 is therefore preferably a spacer group, and not only a single bond. $Sp^a$ is particularly preferably an unbranched or branched alkylene chain having 1 to 8 C atoms, in which one or more CH$_2$ groups may be replaced by —O—, —NH—, —NR$^3$—, —S— and —(CO)—, so that O/S atoms are not linked directly to one another, and in which, in addition, one or more H atoms may be replaced by F, Cl or —OH.

The self-alignment additives according to the invention are predominantly crystalline solids at room temperature, as a consequence of which the handling and storability are improved compared with, for example, oily substances. The melting point can furthermore be varied towards advantageous values by variation of the side chains.

In addition, the compounds provide the LC media with comparatively good VHR values under applicational conditions, i.e. after the UV irradiation process of display manufacture. This now also enables mixture concepts which have hitherto resulted in instabilities in the exposure test to be achieved with the additives according to the invention. The other parameters of VA displays, such as, for example, the response times or the stability of the tilt angle in the production of PS-VA displays, are not adversely affected by the additives according to the invention. The LC media have very good processability in the production of VA displays and comparatively low mura defects.

The LC cell of the LC display according to the invention preferably has no alignment layer, in particular no polyimide layer for homeotropic alignment of the LC medium. Alignment layer here means a layer which is already present before the cell is filled. The polymerised component of the LC medium is in this connection not regarded as an alignment layer. An LC cell may nevertheless have an alignment layer or a comparable layer, but this layer is preferably not the sole cause of the homeotropic alignment, but instead supports or modifies the effect of the self-alignment additive. Rubbing of, for example, polyimide layers is, in accordance with the invention, not necessary in order to achieve homeotropic alignment of the LC medium with respect to the substrate surface. The LC display according to the invention is preferably a VA display comprising an LC medium having negative dielectric anisotropy and electrodes arranged on opposite substrates. Alternatively, it is a VA-IPS display comprising an LC medium having positive dielectric anisotropy and interdigital electrodes arranged at least on one substrate.

The self-alignment additive of the formula I is preferably employed in a concentration of less than 10% by weight, particularly preferably ≤5% by weight and very particularly ≤3% by weight. It is preferably employed in a concentration of at least 0.05% by weight, preferably at least 0.2% by weight. The use of 0.1 to 2.5% by weight of the self-alignment additive generally already results in completely homeotropic alignment of the LC layer in the case of the usual cell thicknesses (3 to 4 μm) with the conventional substrate materials and under the conventional conditions of the production processes of an LC display. Due to the polymerisable nature, higher concentrations of self-alignment additives are also possible without influencing the LC medium in the long term, since the polymerisable substance is bound again by the polymerisation.

Further preferred and illustrative embodiments of the self-alignment additives of the formula I according to the invention and sub-formulae thereof are disclosed below.

By definition, the anchor group $R^a$ contains one, two or three groups $X^1$, which are intended to serve as binding member to a surface. In accordance with formula I, compounds where n=1 and the sub-formulae IC and IC-1 to IC-3 (cf. formula I, n=1) are defined in such a way that the anchor group $R^a$ for these (preferably) only contains a single OH group.

The spacer groups $Sp^a$ to $Sp^c$ are intended to form a flexible bond between the mesogenic group with rings and the group(s) $X^1$. The structure of the spacer groups is therefore very variable and in the most general case of the formula I not definitively defined. The person skilled in the art will recognise that a multiplicity of possible variations of chains come into question here.

An anchor group of the formula

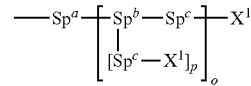

as defined above and below,
preferably stands for an anchor group selected from the following formulae:

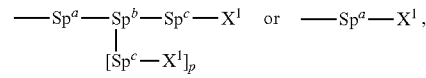

in which in each case independently the groups are as defined above and below,
particularly preferably for a group of the formulae

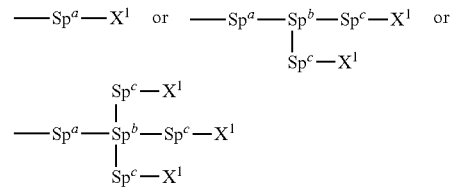

in which in each case independently the groups are as defined above and below.

The group $Sp^b$ preferably denotes a trivalent group of the formulae selected from $C(R^3)$ or N (for p=1), or the tetravalent group C (carbon atom, for p=2).

The trivalent group $Sp^b$ particularly preferably denotes $CR^3$ (for p=1) or C (for p=2), in particular $CR^3$, in which $R^3$ denotes H or an alkyl radical having 1 to 10 C atoms, which is linear or branched, and in which H may be substituted by fluorine or alkoxy having 1 to 8 C atoms.

The group $R^3$ in $Sp^b$ (as trivalent group) preferably denotes H or an alkyl radical having 1 to 10 C atoms, which is linear or branched. The melting point of the additives of the formula (I) according to the invention can be adjusted through the choice of the radical $R^3$. The radical $R^3$ may also have an influence on the homogeneous distribution of the additives on the substrate surface. In a preferred embodiment, $Sp^b$ is a group —$C(R^3)$, in which $R^3$ denotes H or a radical having 1 to 8 C atoms, for example preferably $C(CH_2CH_2CH_3)$, $C(CH_2CH_2CH_2CH_3)$, $C(CH_2CH(CH_3)CH_3)$ or $C(CH_2CH_2C(CH_3)_3)$. Preferred radicals $R^3$ are also disclosed below in the explicit anchor groups.

The group $Sp^a$ for o=0 preferably does not denote a single bond. Preference is given to an unbranched or branched alkylene chain having 1 to 8 C atoms, in which one or more $CH_2$ groups may be replaced by —O—, —NH—, —$NR^3$—, —S— or —(CO)—, so that O/S atoms are not linked directly to one another, and in which, in addition, one or more H atoms may be replaced by F, Cl or —OH, or for o=1 additionally also denotes a single bond, particularly preferably a group selected from the formulae: —CH$_2$—, —CH$_2$CH$_2$—, —OCH$_2$CH$_2$—, —CH$_2$CH$_2$CH$_2$—, —OCH$_2$CH$_2$CH$_2$—, —CH$_2$CH$_2$CH$_2$CH$_2$—, —OCH$_2$CH$_2$CH$_2$CH$_2$—, —CH$_2$CH$_2$OCH$_2$CH$_2$— and —OCH$_2$CH$_2$OCH$_2$CH$_2$—, particularly preferably —CH$_2$—, —OCH$_2$—, —CH$_2$CH$_2$—, —OCH$_2$CH$_2$—, —OCH$_2$CH$_2$CH$_2$—, —OCH$_2$CH$_2$CH$_2$CH$_2$— and —CH$_2$CH$_2$CH$_2$—.

The group Sp$^c$ preferably does not denote a single bond, preferably denotes an unbranched or branched alkylene chain having 1 to 8 C atoms, in which one or more CH$_2$ groups may be replaced by —O—, and in which, in addition, one or more H atoms may be replaced by F, Cl or —OH, preferably a group selected from the formulae —CH$_2$—, —CH$_2$CH$_2$—, —CH$_2$CH$_2$CH$_2$—, —CH$_2$CH$_2$CH$_2$CH$_2$— and —CH$_2$CH$_2$OCH$_2$CH$_2$—, particularly preferably —CH$_2$—.

The group Sp$^d$ preferably denotes an unbranched or branched alkylene chain having 1 to 8 C atoms, in which one or more CH$_2$ groups may be replaced by —O—, —NH—, —NR$^3$—, —S— and —(CO)—, so that O/S atoms are not linked directly to one another, and in which, in addition, one or more H atoms may be replaced by F, Cl or —OH.

In a preferred embodiment, the anchor group R$^a$ denotes a radical of the formula

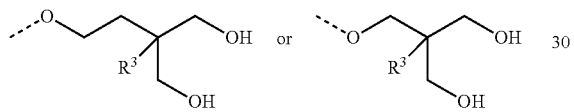

in which R$^3$ denotes H or an alkyl radical having 1 to 10 C atoms, which is linear or branched, and in which H may be substituted by fluorine or alkoxy having 1 to 8 C atoms. R$^3$ particularly preferably denotes a straight-chain alkyl group having 1, 2, 3, 4, 5 or 6 C atoms or H.

The group R$^1$ preferably denotes an unsubstituted alkyl radical or alkoxy radical having 1 to 15 carbon atoms or an alkenyl, alkenyloxy or alkynyl radical having 2 to 15 C atoms, which are in each case optionally mono- or polyhalogenated. R$^1$ particularly preferably denotes an alkyl radical having 2 to 8 carbon atoms The group A$^2$ in the formula I preferably denotes, in each case independently, 1,4- or 1,3-phenylene, naphthalene-1,4-diyl or naphthalene-2,6-diyl, where, in addition, one or more CH groups in these groups may be replaced by N, cyclohexane-1,4-diyl, in which, in addition, one or more non-adjacent CH$_2$ groups may be replaced by O and/or S, 3,3'-bicyclobutylidene, 1,4-cyclohexenylene, bicyclo[1.1.1]pentane-1,3-diyl, bicyclo[2.2.2]octane-1,4-diyl, spiro-[3.3]heptane-2,6-diyl, piperidine-1,4-diyl, decahydronaphthalene-2,6-diyl, 1,2,3,4-tetrahydronaphthalene-2,6-diyl, indane-2,5-diyl or octahydro-4,7-methanoindane-2,5-diyl, perhydrocyclopenta[a]phenanthrene-3,17-diyl (in particular gonane-3,17-diyl), where all these groups may be unsubstituted or mono- or polysubstituted by a group L.

The groups A$^1$, A$^2$ particularly preferably each independently denote a group selected from
a) the group consisting of 1,4-phenylene, 2,6-naphthylene and 1,3-phenylene, in which, in addition, one or more H atoms may be replaced by L and/or -Sp-P,
b) the group consisting of trans-1,4-cyclohexylene and 1,4-cyclohexenylene, in which, in addition, one or more non-adjacent CH$_2$ groups may be replaced by —O— and/or —S— and in which, in addition, one or more H atoms may be replaced by F, L and/or -Sp-P.

The groups A$^1$ and A$^2$ particularly preferably each independently denote a group selected from
a) the group consisting of 1,4-phenylene, in which, in addition, one or more H atoms may be replaced by L and/or -Sp-P,
b) of trans-1,4-cyclohexylene, in which, in addition, one or two non-adjacent CH$_2$ groups may be replaced by —O— and in which, in addition, one or more H atoms may be replaced by F, L and/or -Sp-P.

In particular, the groups A$^1$ and A$^2$ denote a group in accordance with the preceding sub-groups a). A$^2$ very particularly preferably independently denotes 1,4-phenylene or cyclohexane-1,4-diyl, each of which may be mono- or poly-substituted by a group L.

The group A$^1$ of the formula I particularly preferably denotes a ring group of the formula

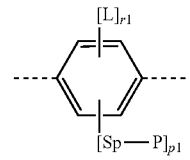

where
L, Sp, P are defined as above,
r1 denotes 0 or 1, and
p1 denotes 1 or 2.

The anchor group R$^a$ in the above formulae particularly preferably contains one, two or three OH groups particularly preferably one or two OH groups.

Particularly preferred anchor groups of the formula R$^a$ are selected from the following sub-formulae, where the group R$^a$ is bonded to the respective formula via the dashed bond:

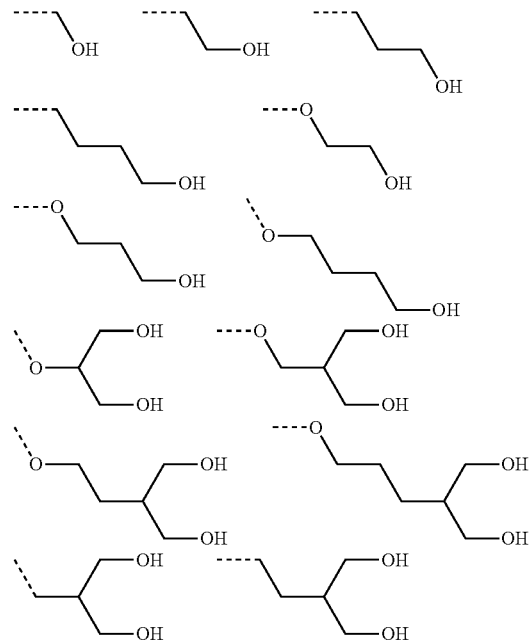

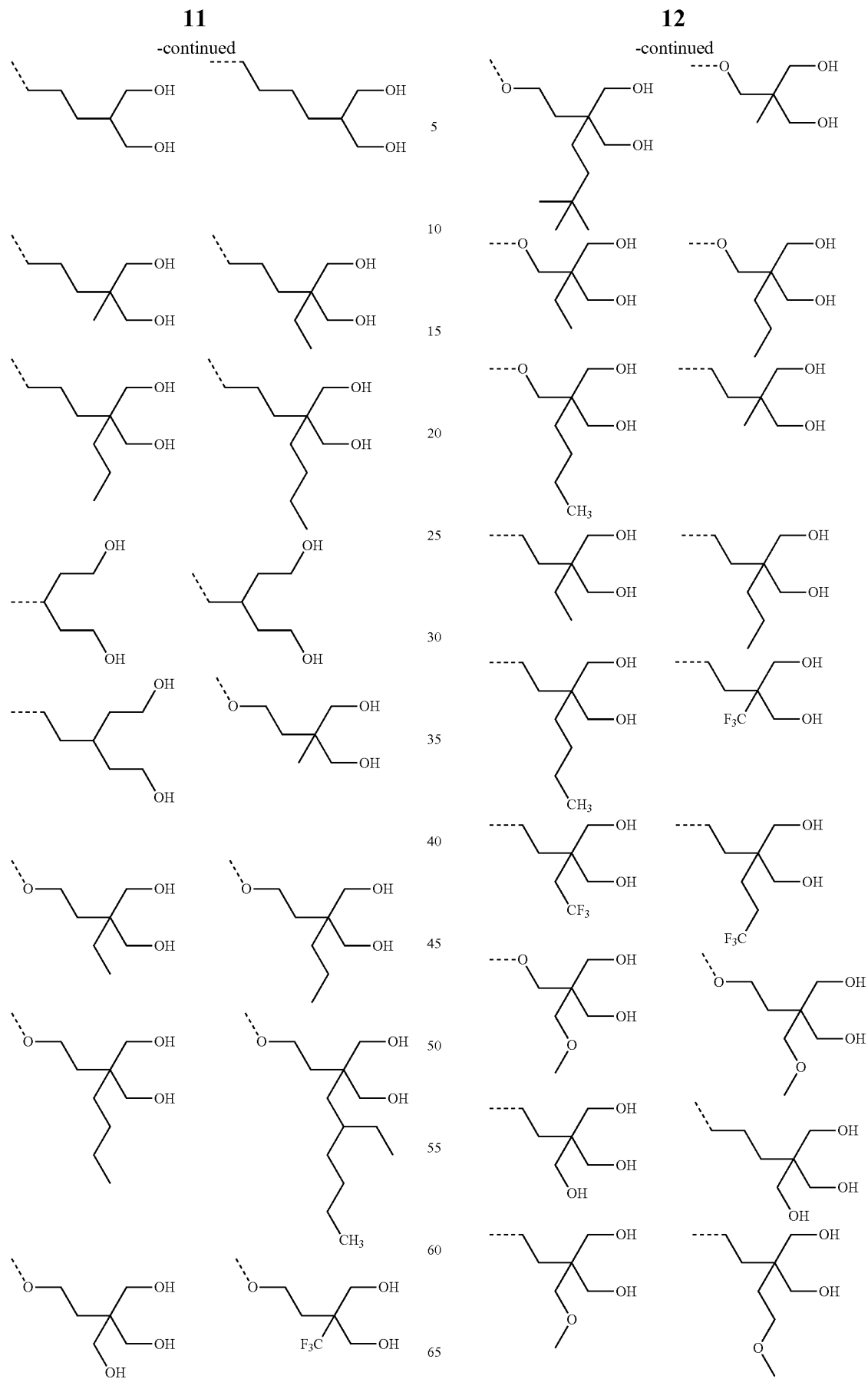

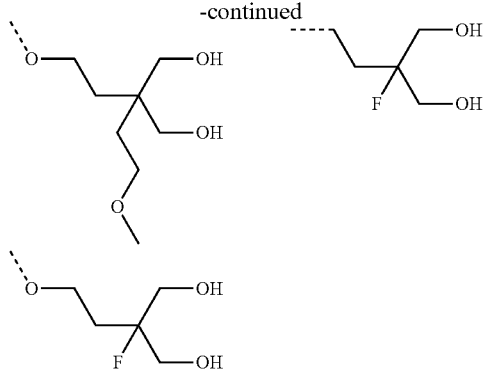

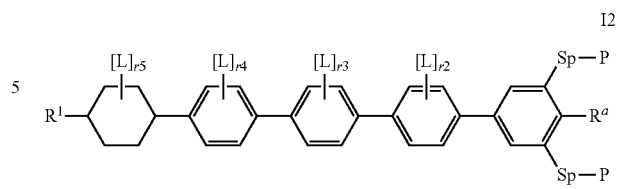

In the formula I and sub-formulae thereof, the variables r3 and r4 shown in formulae I-A and I-B below, preferably both denote 0. The variable r1 shown in formulae I-A and I-B below, preferably denotes 0 or 1. The variable r2 shown in formulae I-A and I-B below, preferably denotes 0 or 1.

The compound of the formula I preferably contains at least one polymerisable group P within the groups $A^1$, $A^2$ and $Z^2$, as are present. The number of polymerisable groups P in the additives of the formula I according to the invention is preferably 1 or 2, in particular 2. The groups are preferably localised on one of the rings $A^1$ or $A^2$, in particular on ring $A^1$.

The polymerisable group is particularly preferably a methacrylate group. The spacer group Sp is preferably a group of the formula —$(CH_2)_n$—, where n=1, 2, 3, 4 or 5, in particular —$(CH_2)_3$—.

The group L preferably denotes H, F, Cl, $CH_3$, ethyl, propyl, cyclopropyl or isopropyl.

The bridge group $Z^2$ of the formula I and associated sub-formulae preferably denotes a single bond.

A preferred self-alignment additive of the formula I is an additive of the formula I-A or I-B:

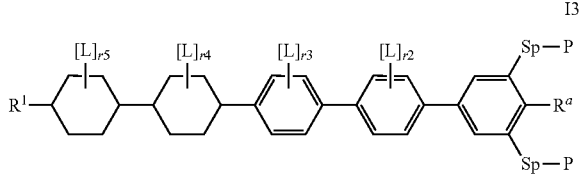

preferably I-A,
and in particular an additive selected from the formulae I-1, I-2 and I-3:

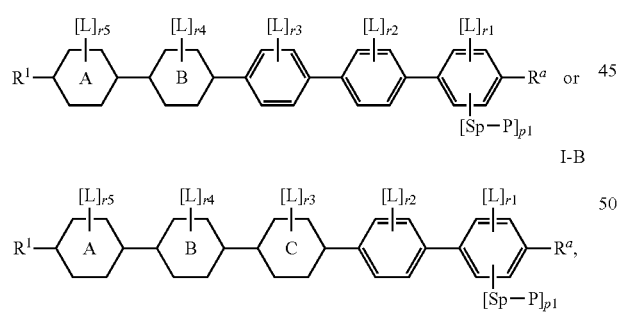

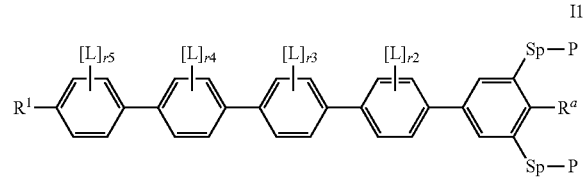

in which, in each case independently, $R^1$, Sp, P, L and $R^a$ are defined as for formula I, and rings A, B and C in each case independently denote a ring of the formula

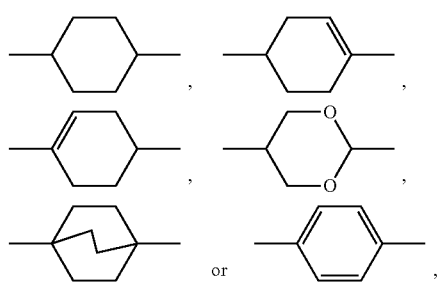

preferably of the formula

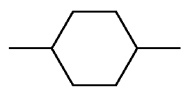

p1 denotes 1 or 2, preferably 2, and r1, r2, r3, r4, r5 each independently denote 0, 1 or 2, preferably 0 or 1, and specifically, in each case independently:

r1 preferably denotes 0, r2 preferably denotes 1, r3 preferably denotes 1, r4 preferably denotes 0 or 1, and r5 preferably denotes 0 or 1, particularly preferably 0.

Particularly preferred self-alignment additives according to the invention are selected from the following formulae:

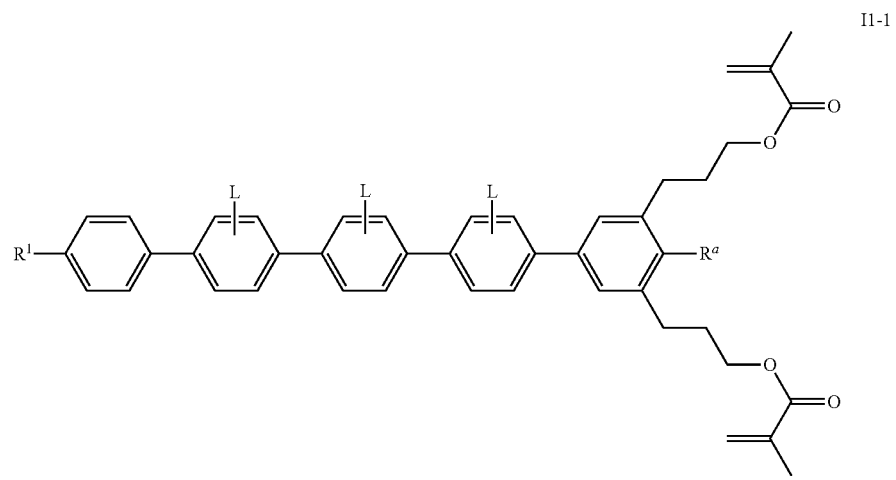
I1-1
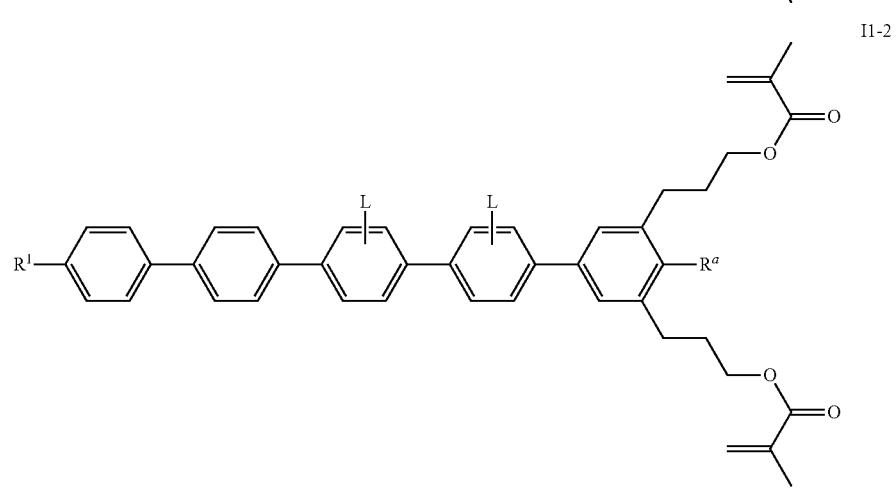
I1-2
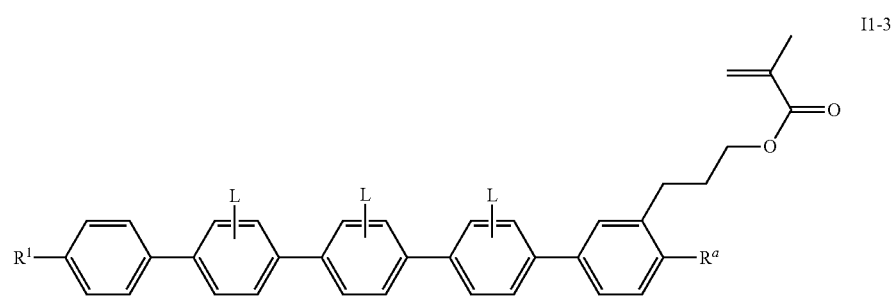
I1-3
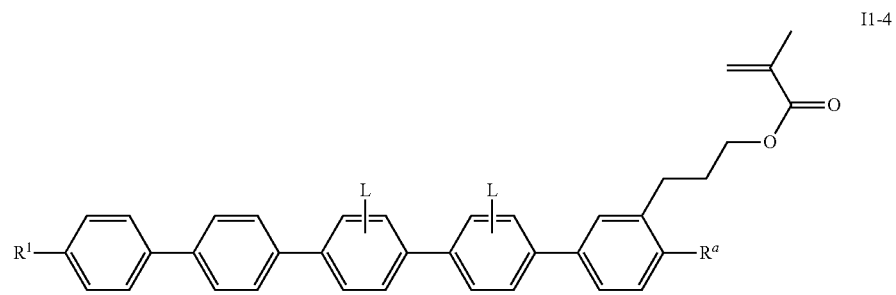
I1-4

I1-5
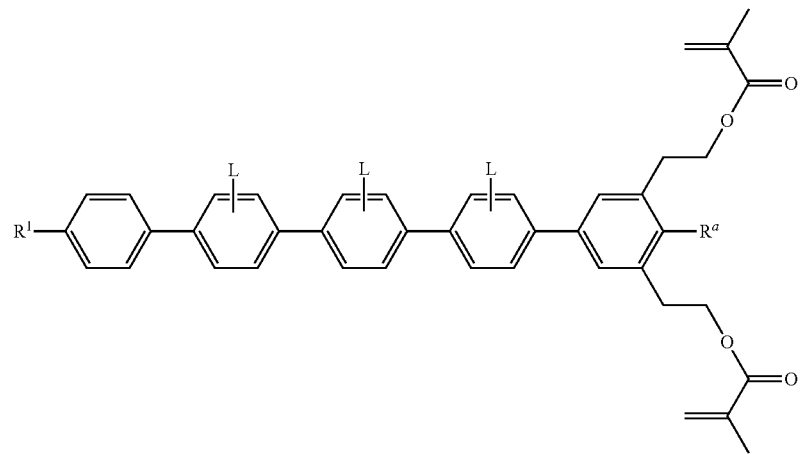
I1-6
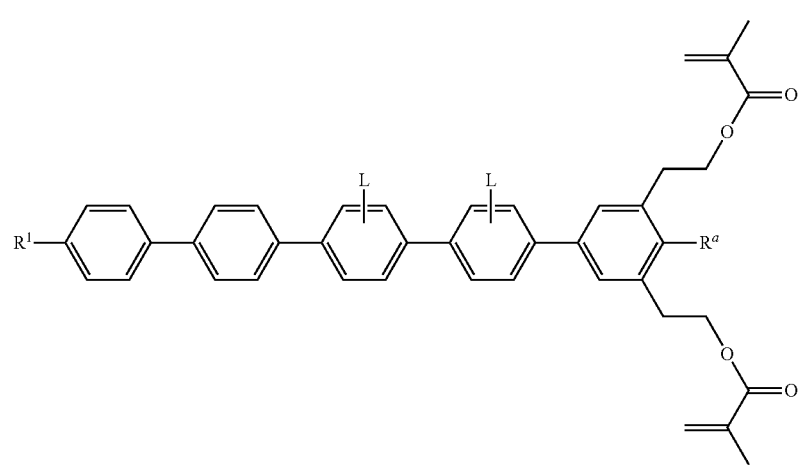
I1-7
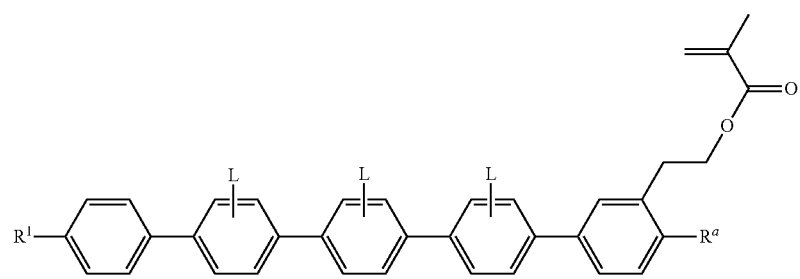
I1-8
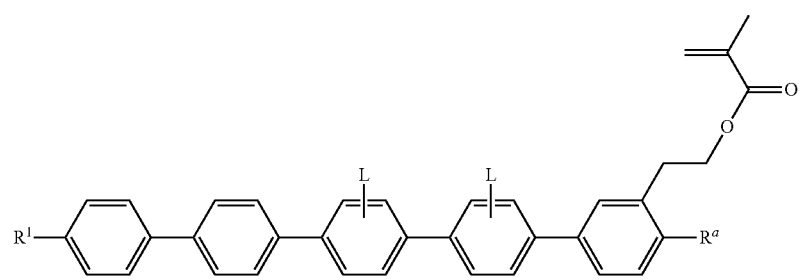

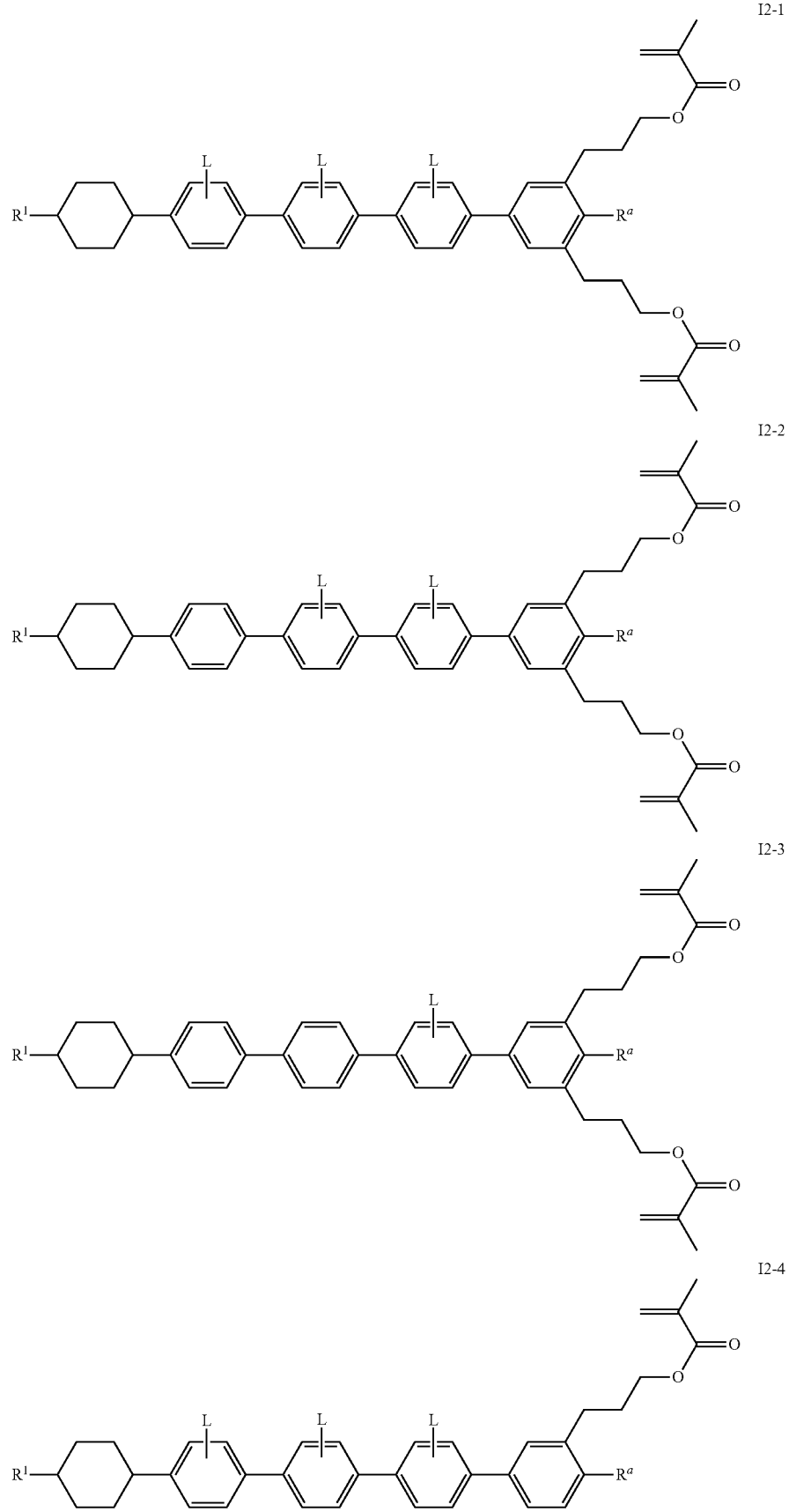

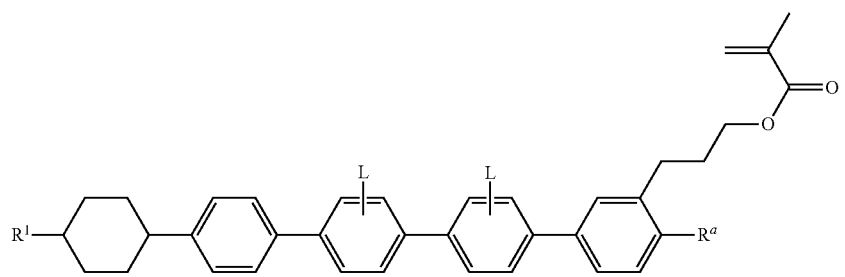
I2-5
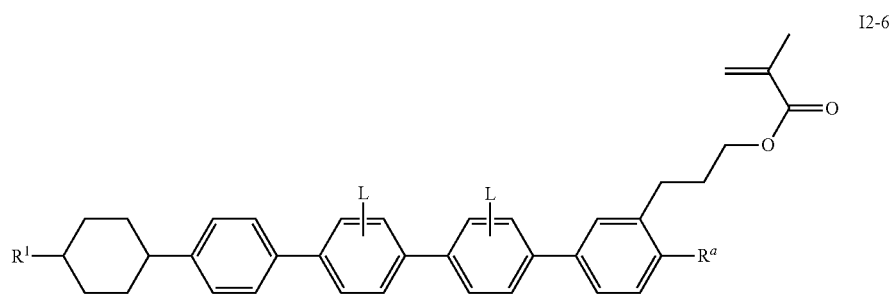
I2-6
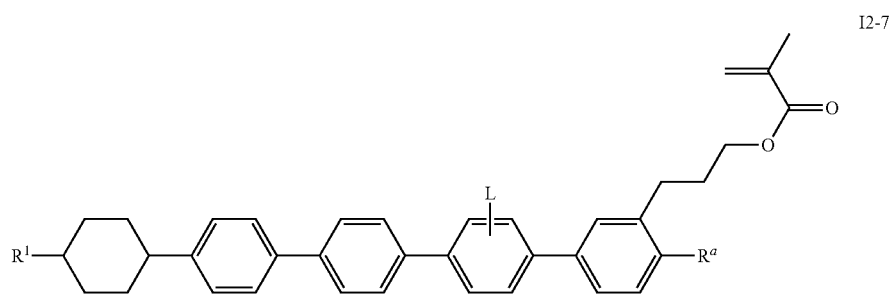
I2-7
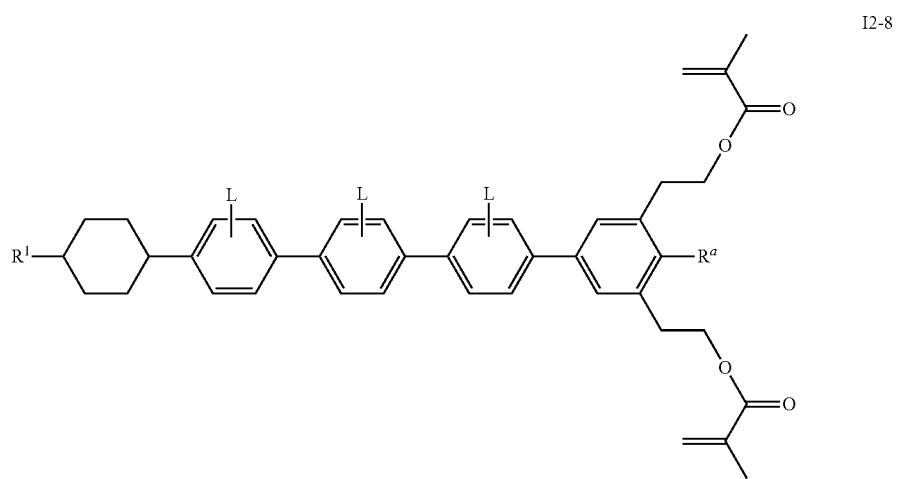
I2-8

-continued
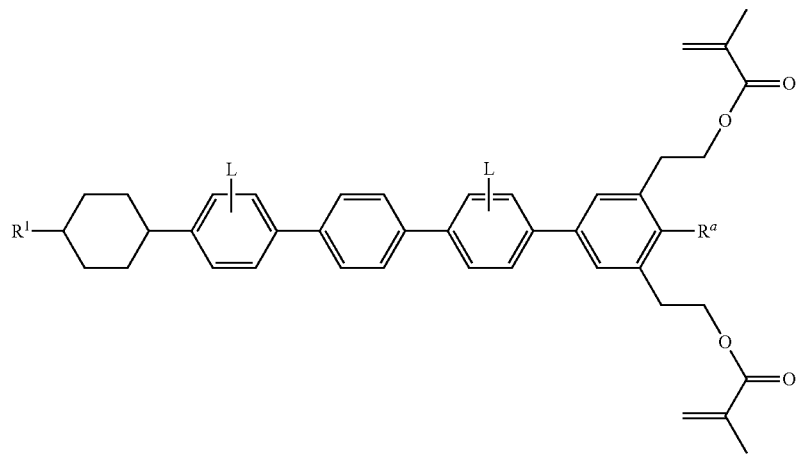
I2-9
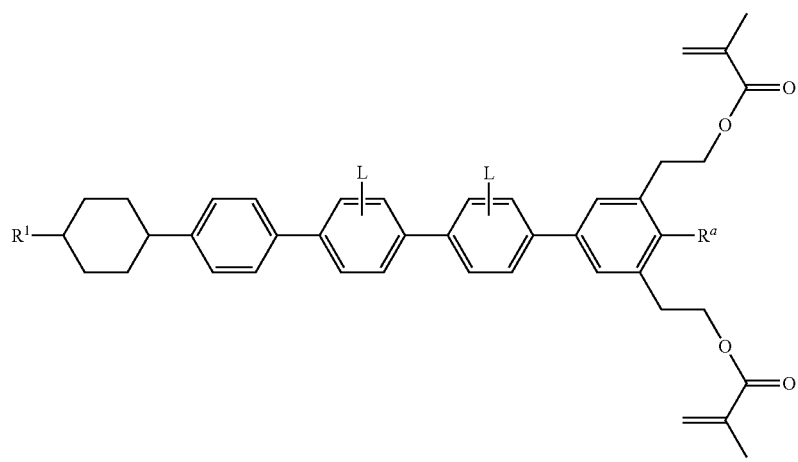
I2-10
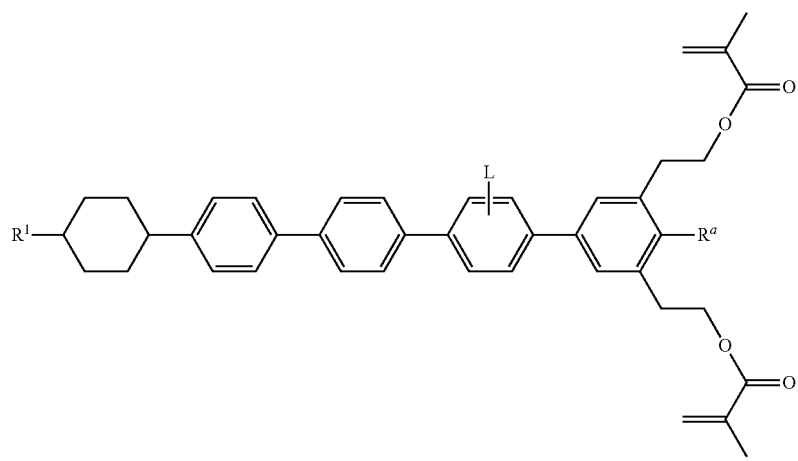
I2-11
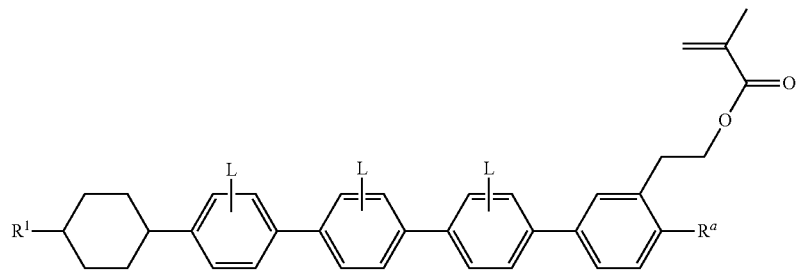
I2-12

-continued
I2-13
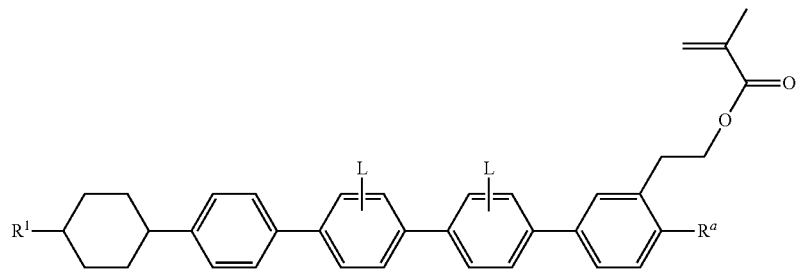
I2-14
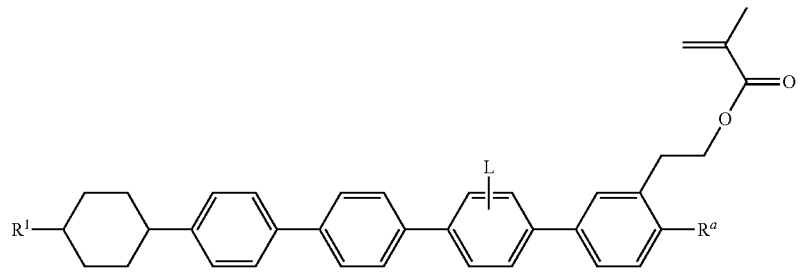
I3-1
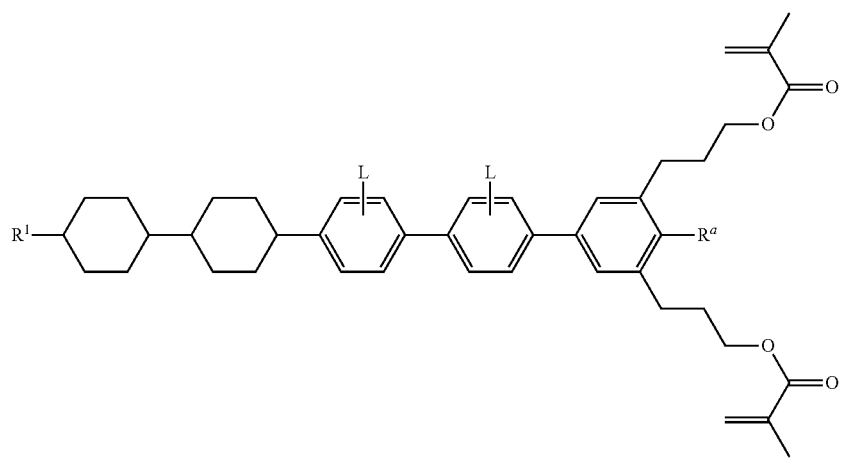
I3-2
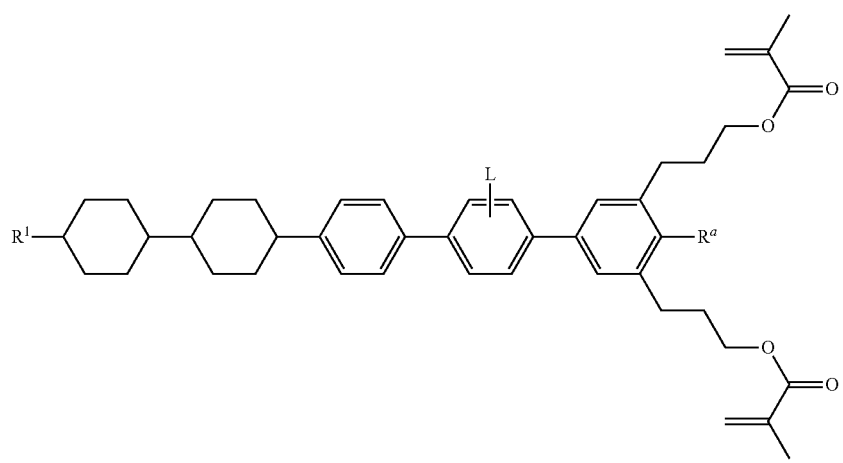

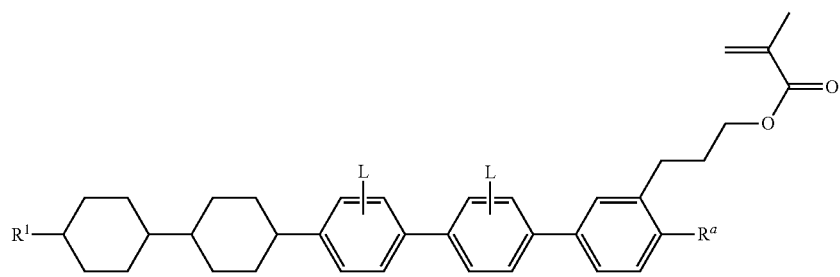
I3-3
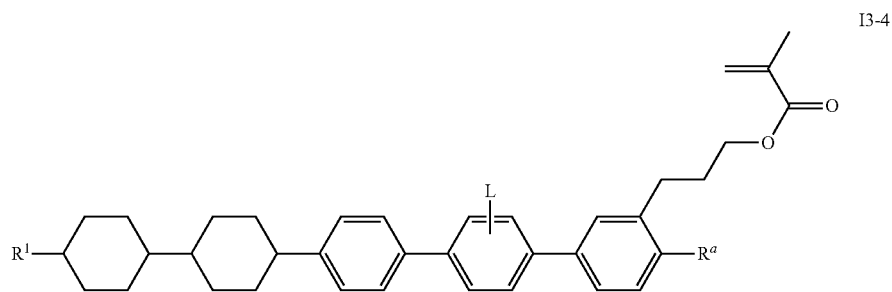
I3-4
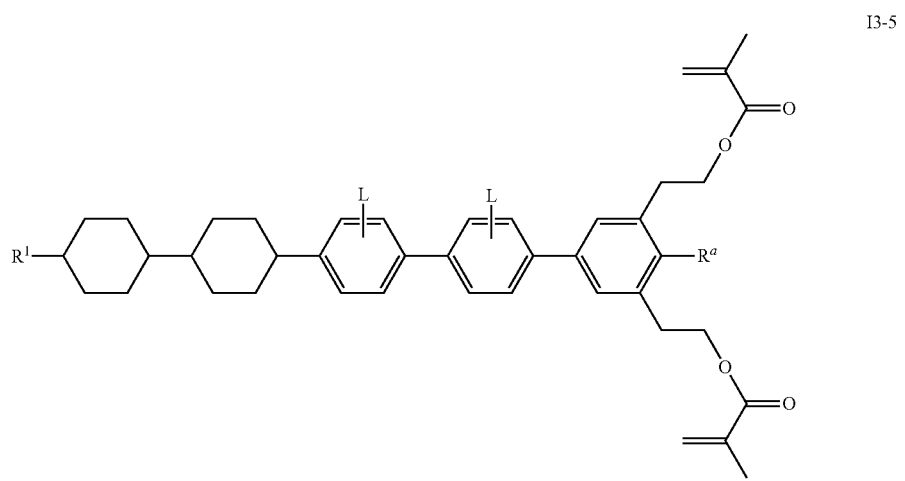
I3-5
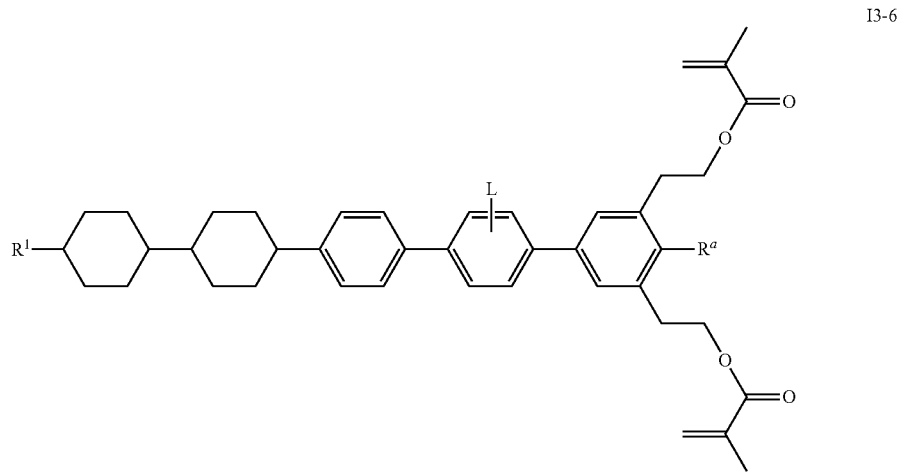
I3-6

I3-7
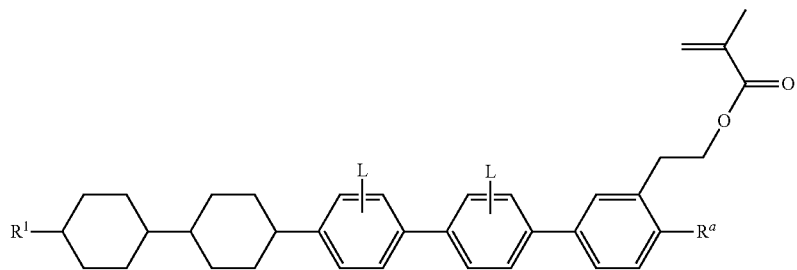
in which $R^1$, L and $R^a$ in each case independently are defined as for formula I and sub-formulae thereof. The substituents L can therefore adopt different meanings if they occur multiple times.
The following formulae are illustrative of very particularly preferred self-alignment additives:
I-1
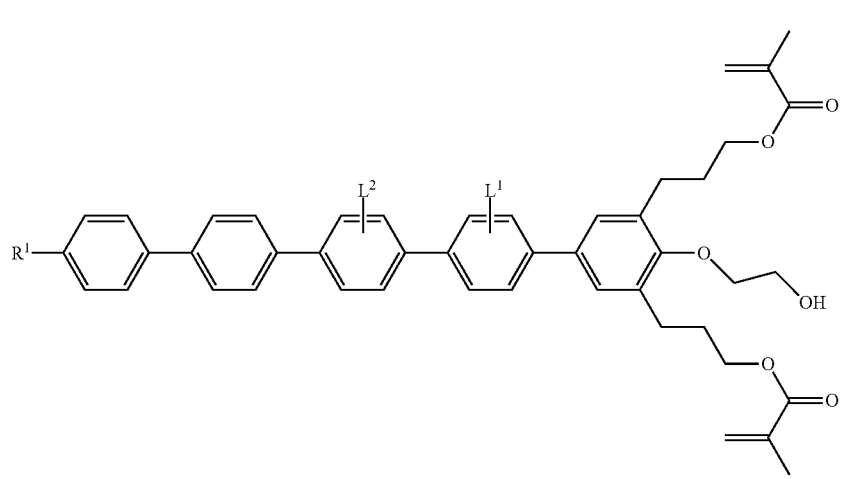
I-2
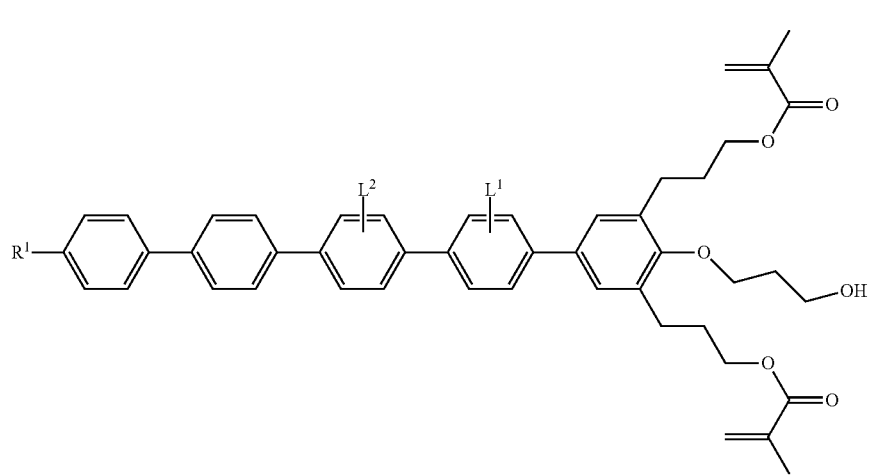

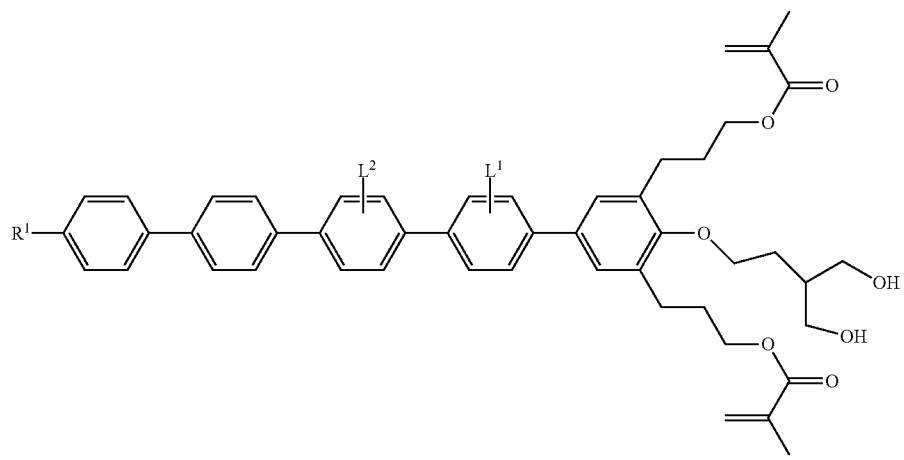
I-3
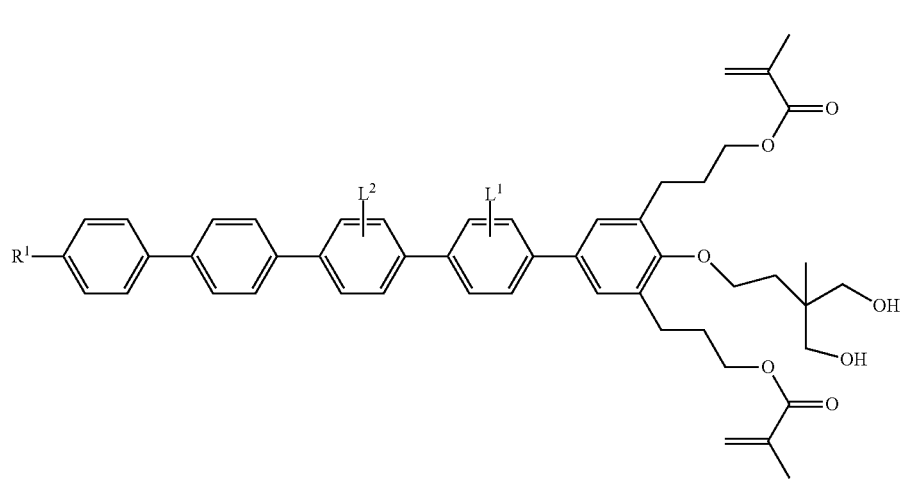
I-4
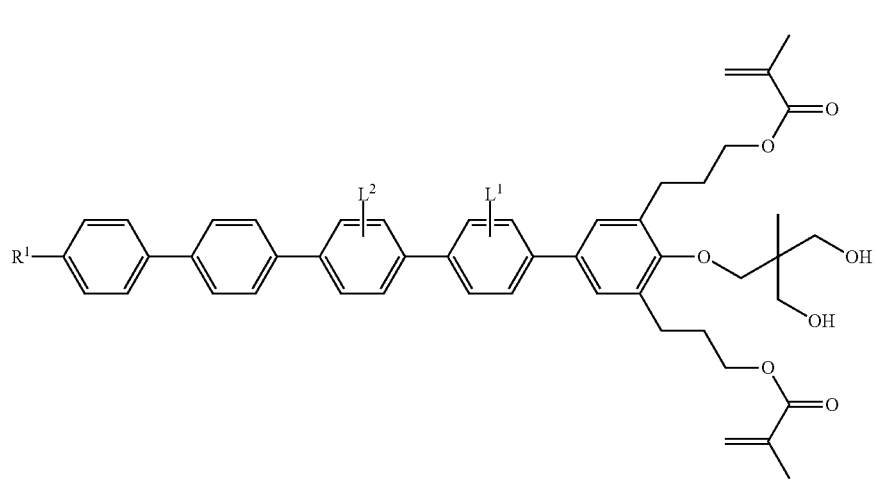
I-5

I-6
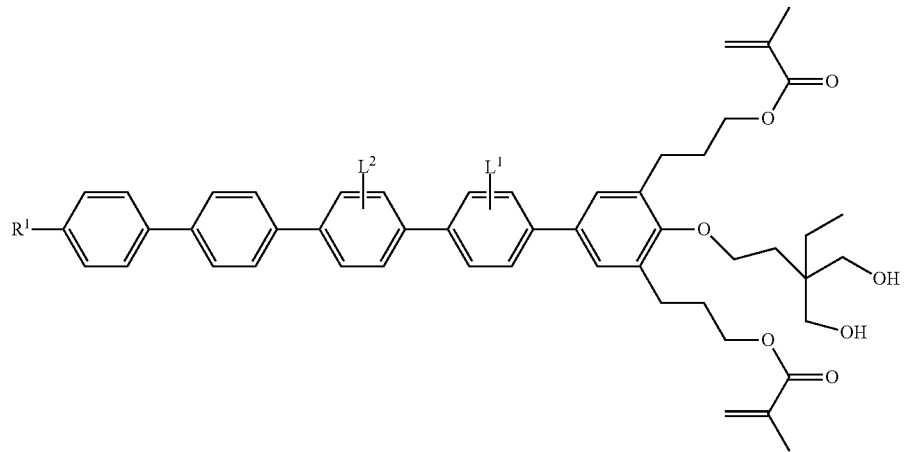
I-7
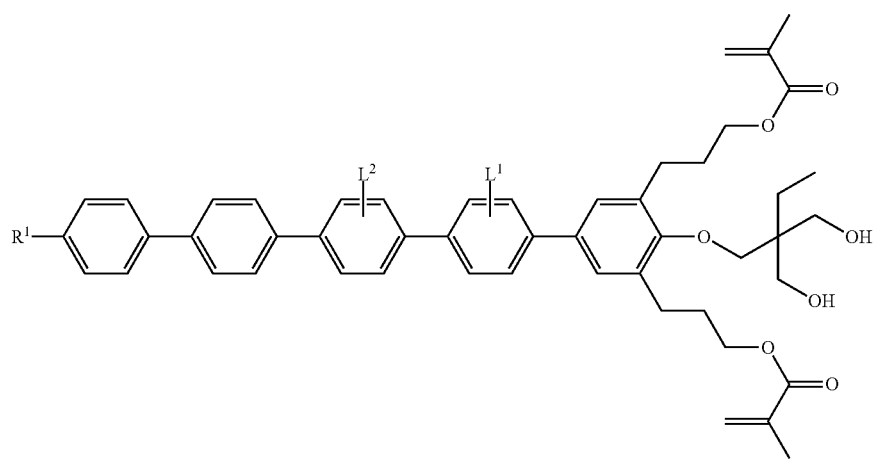
I-8
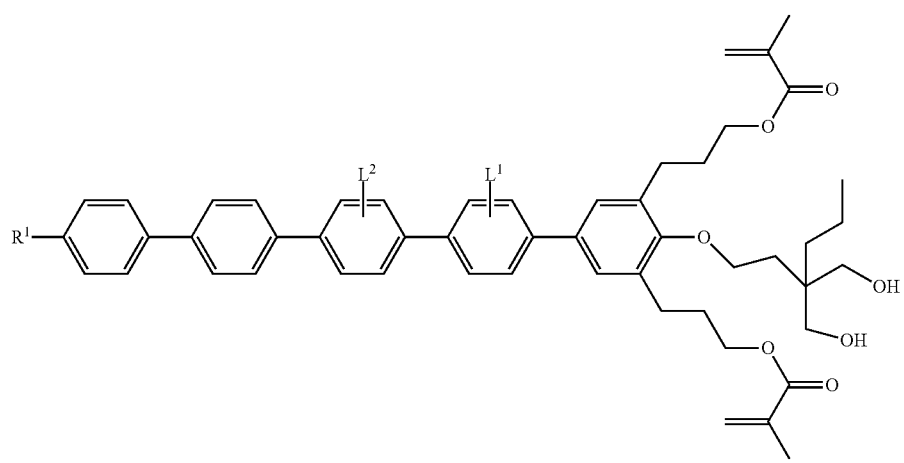

I-9
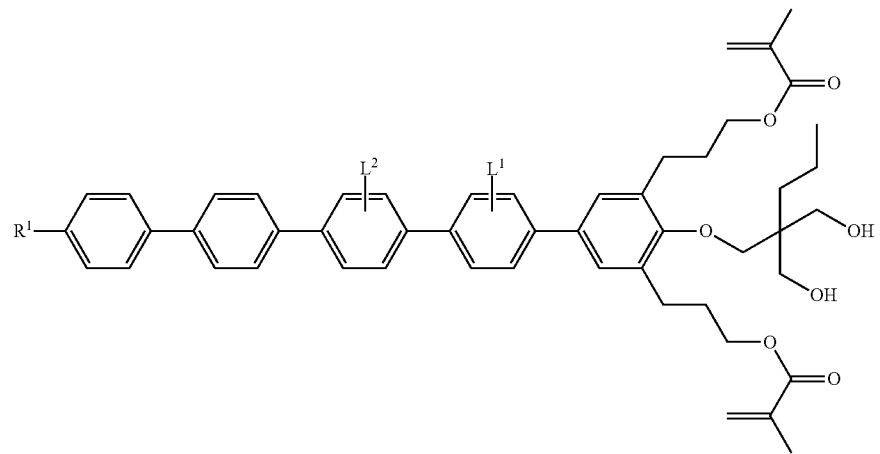
I-10
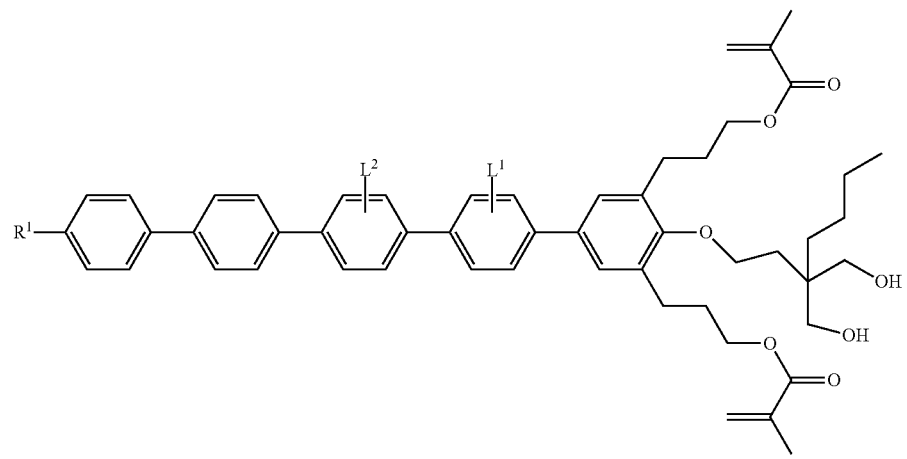
I-11
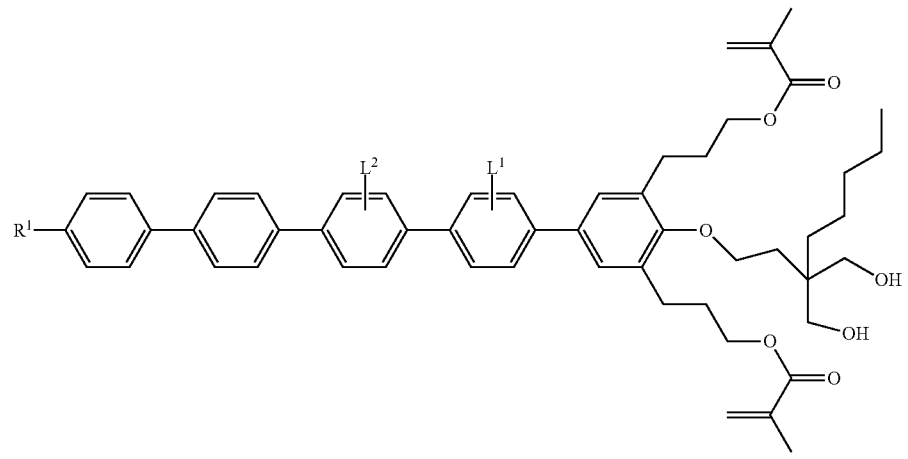

I-12
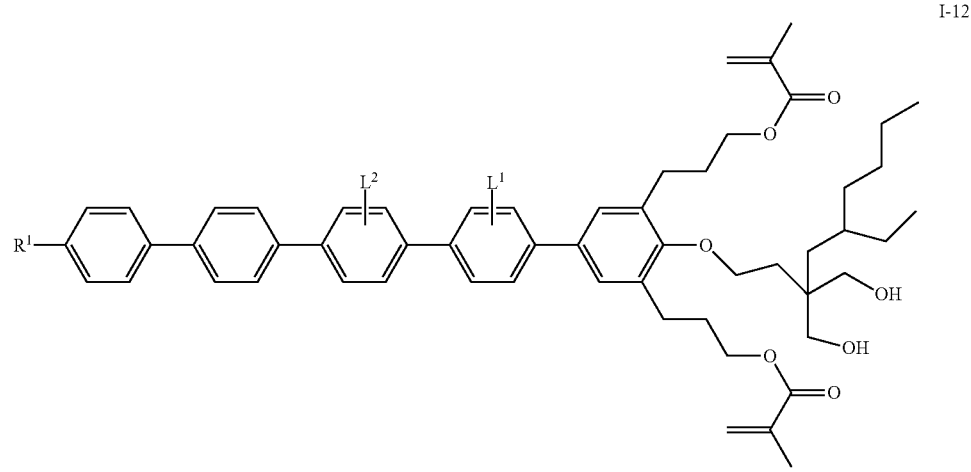
I-13
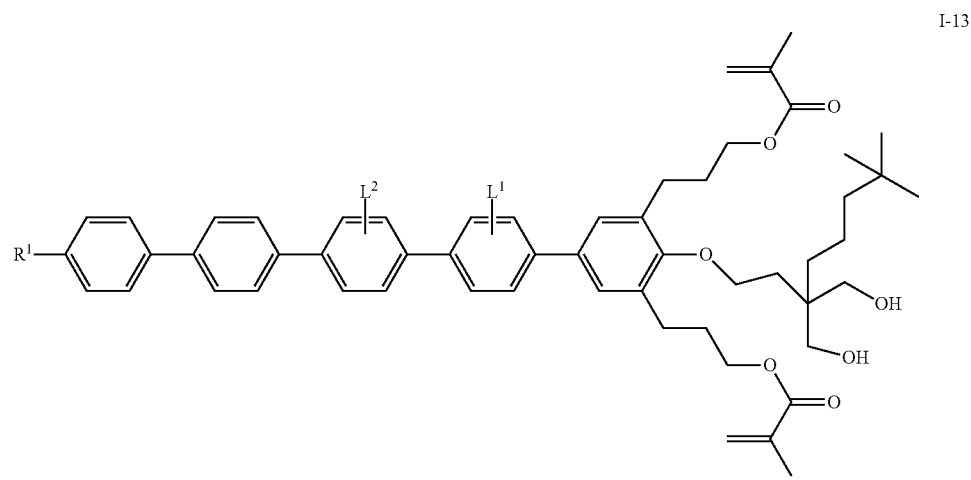
I-14
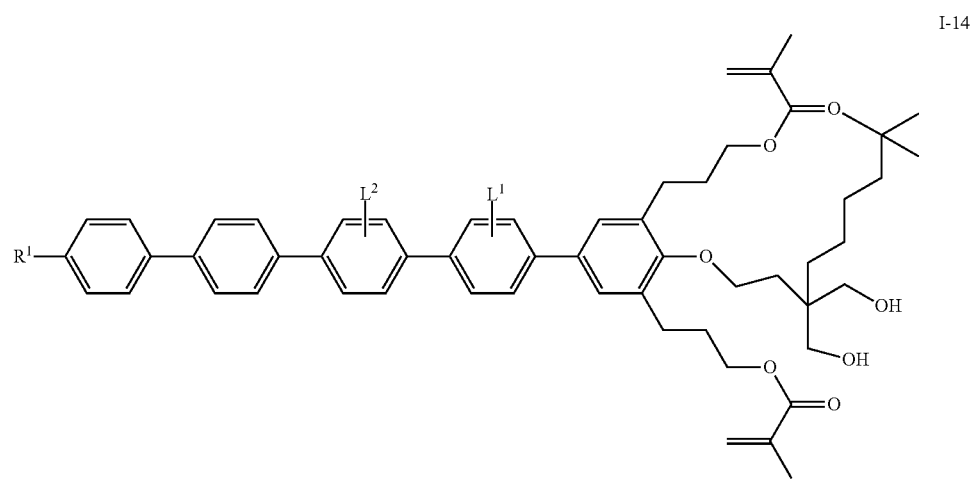

I-15
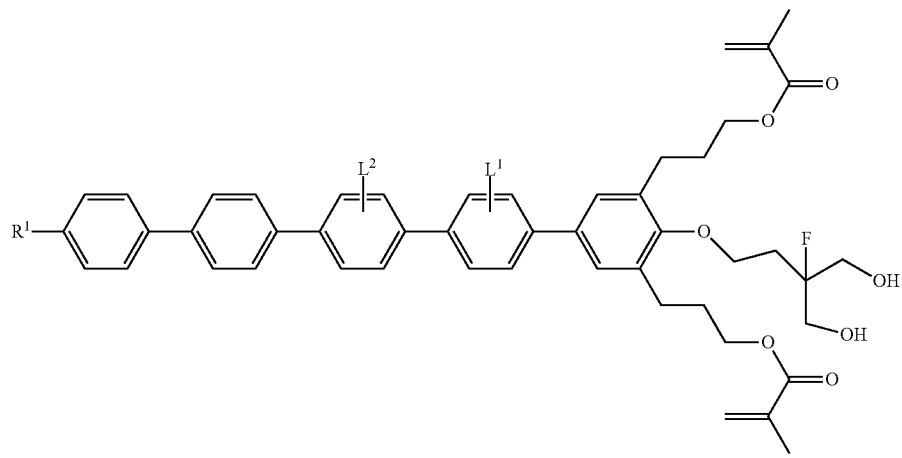
I-16
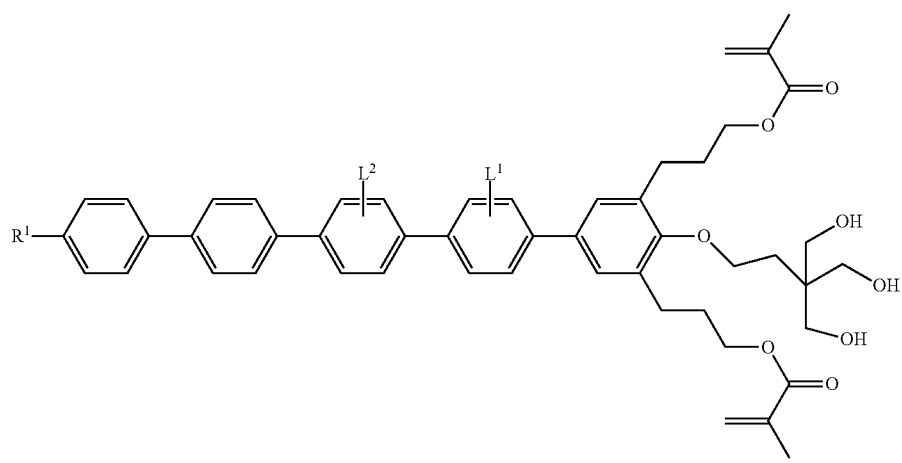
I-17
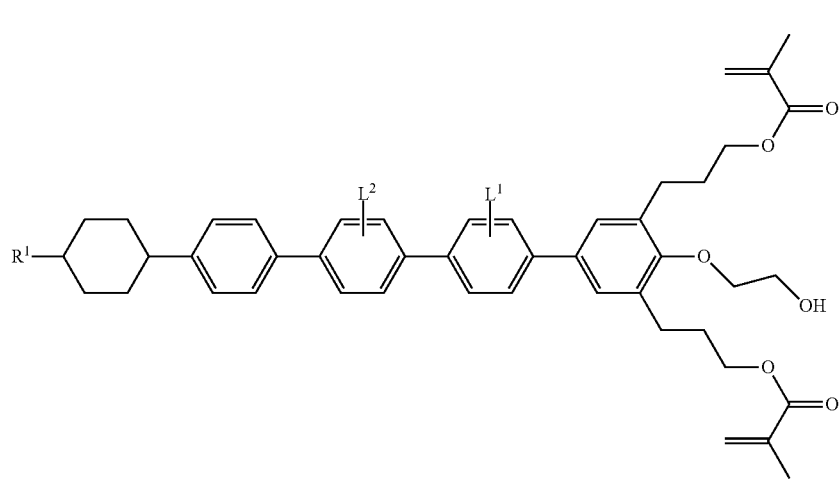

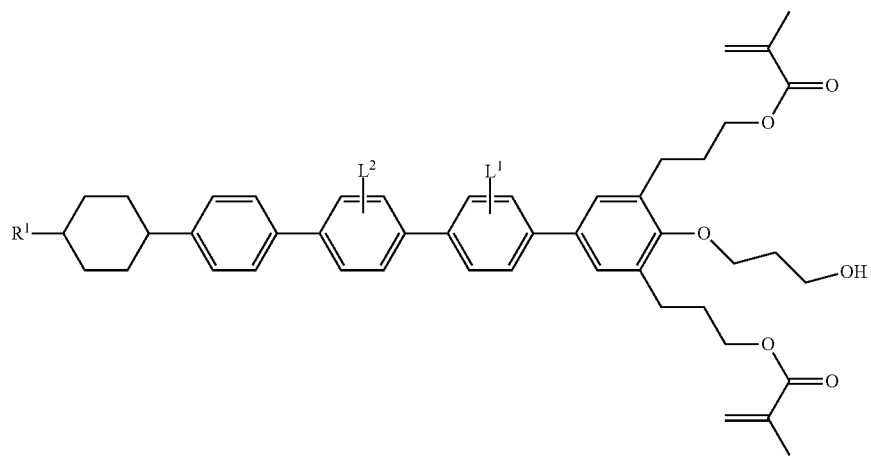
I-18
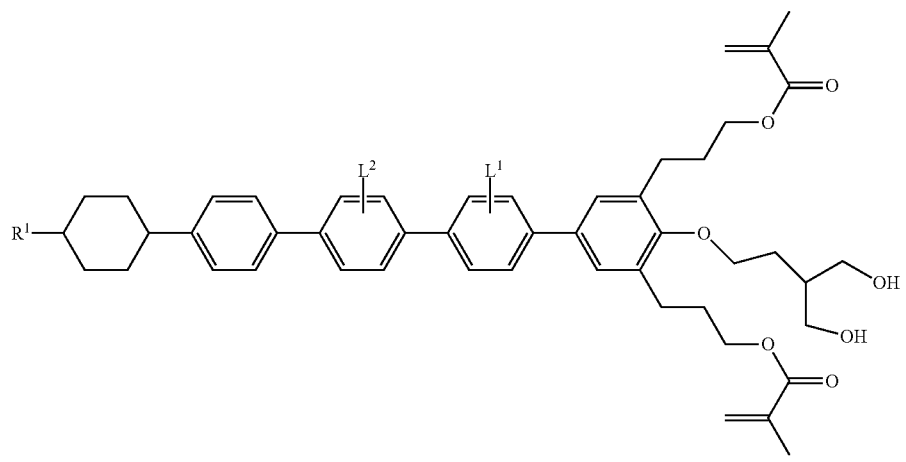
I-19
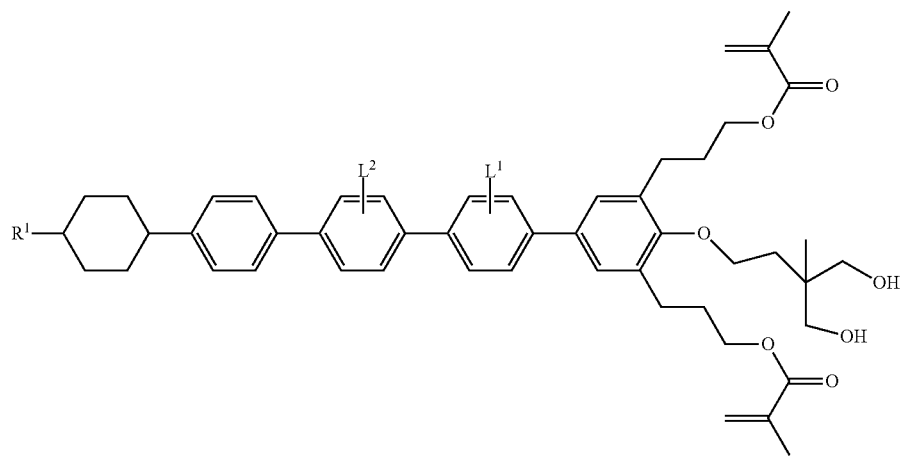
I-20

I-21
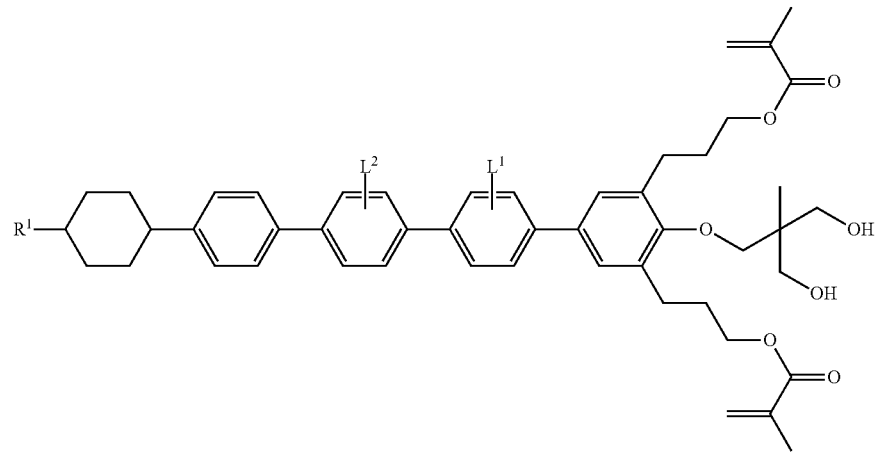
I-22
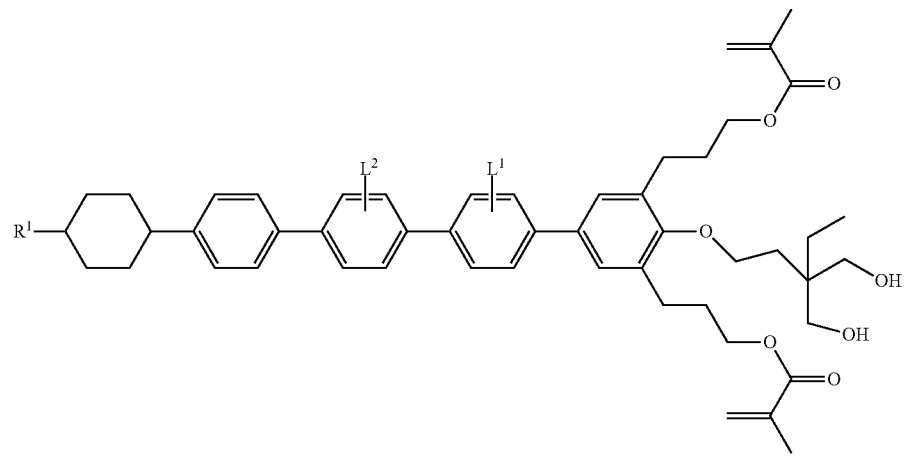
I-23
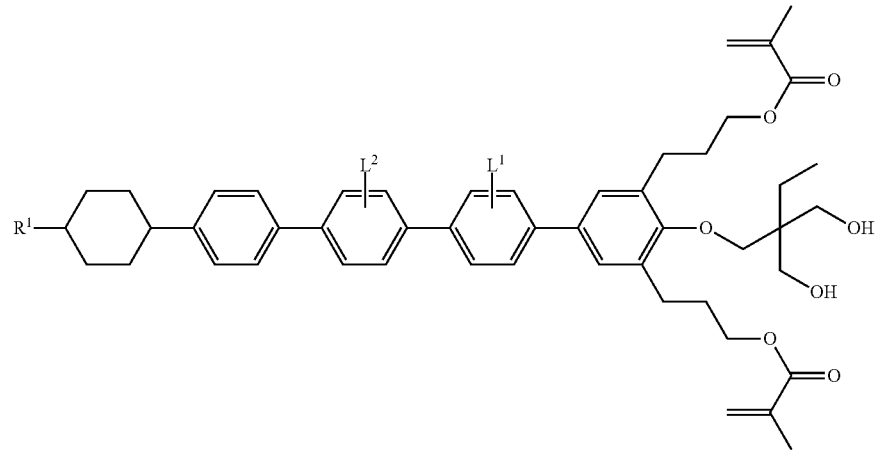

-continued
I-24
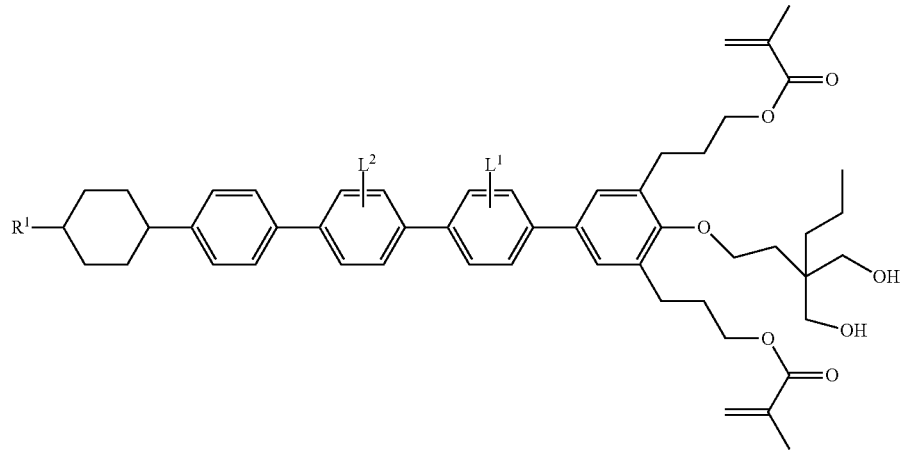
I-25
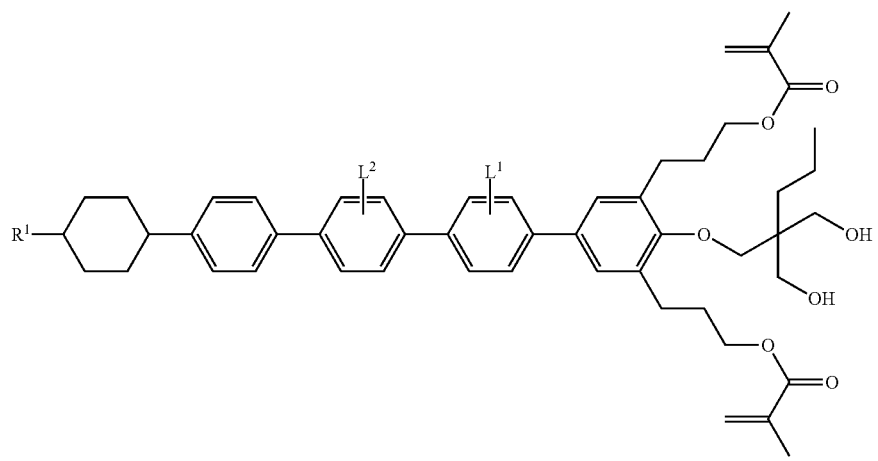
I-26
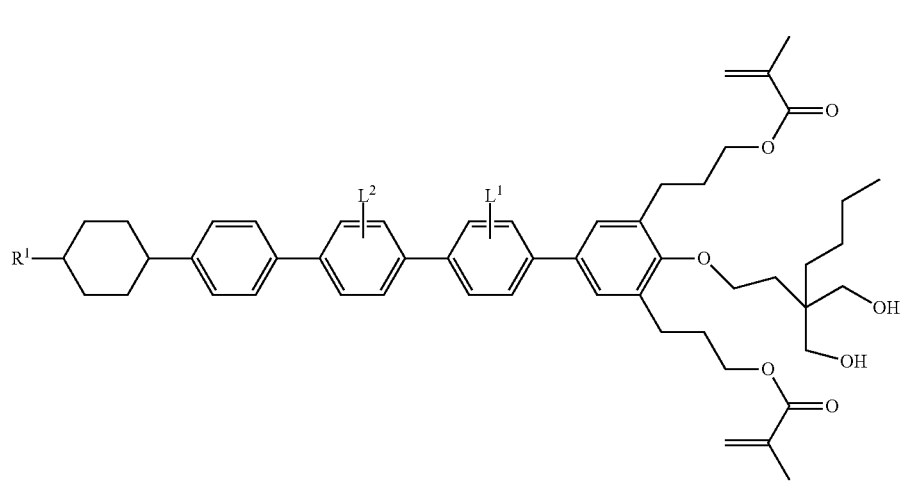

-continued
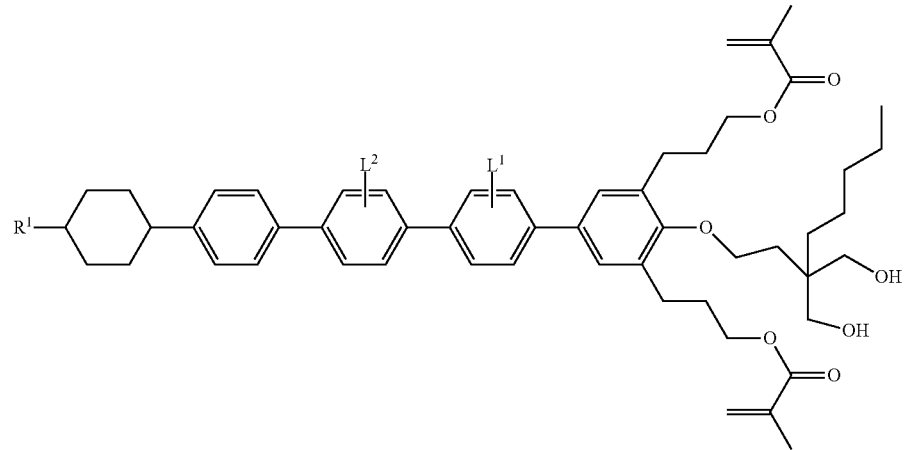
I-27
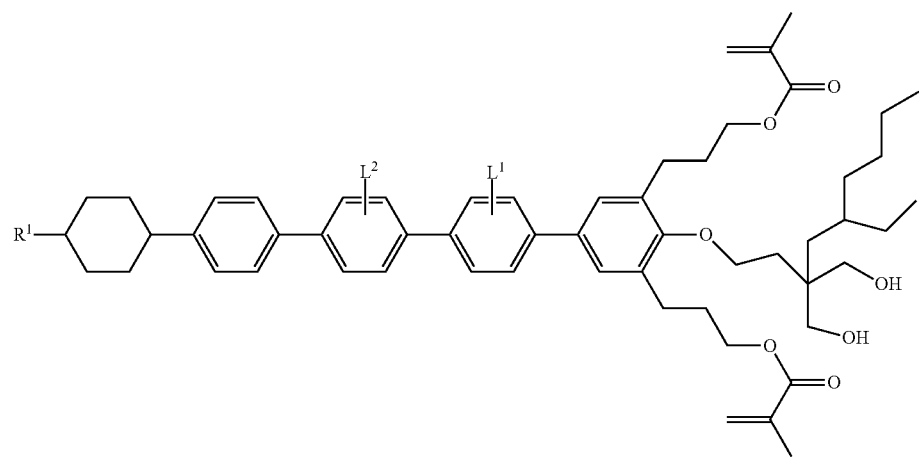
I-28
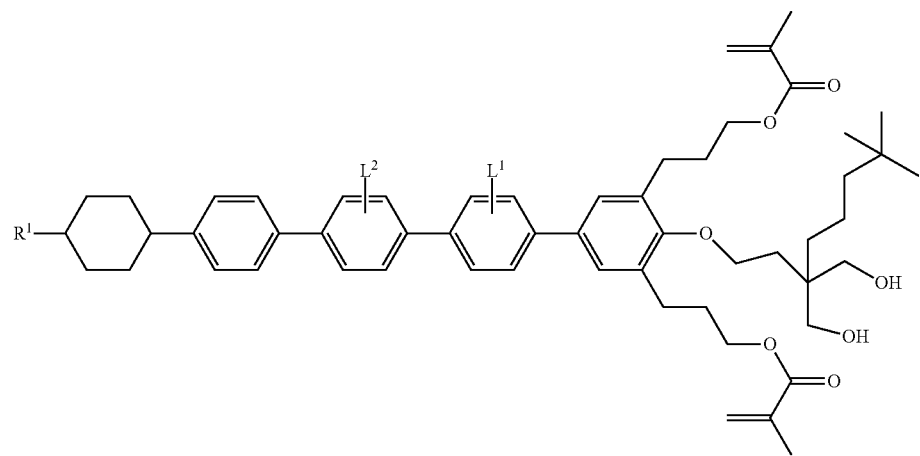
I-29

-continued
I-30
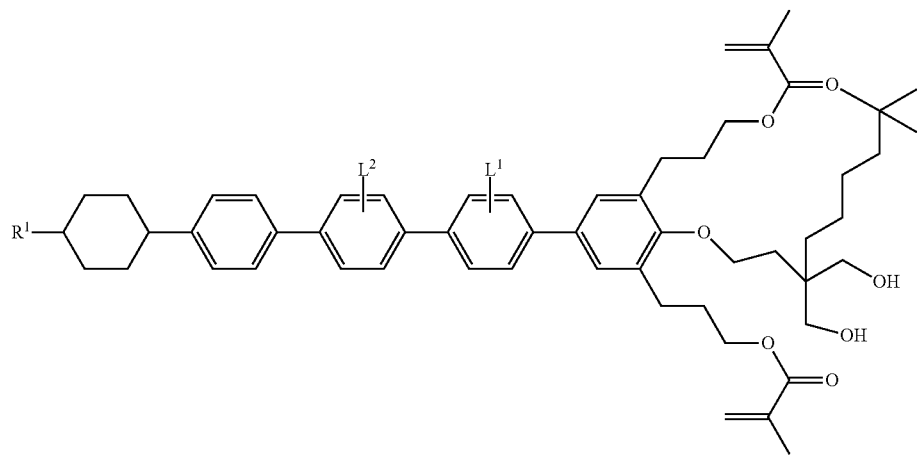
I-31
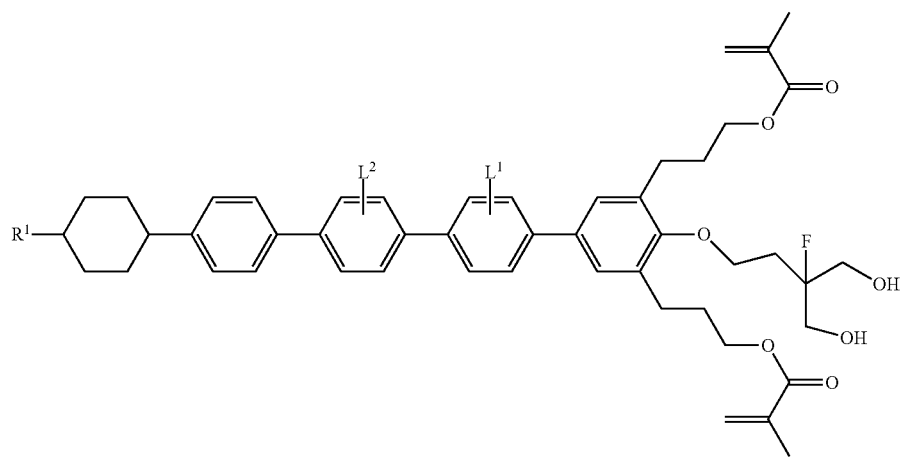
I-32
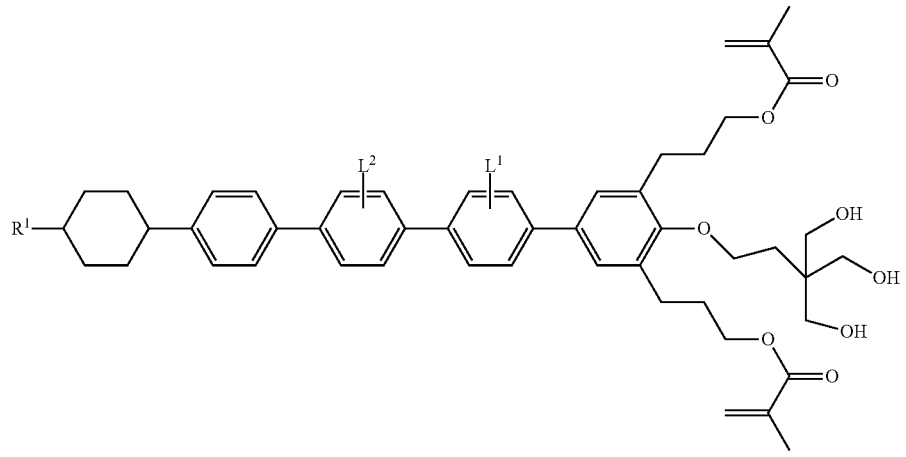

-continued
I-33
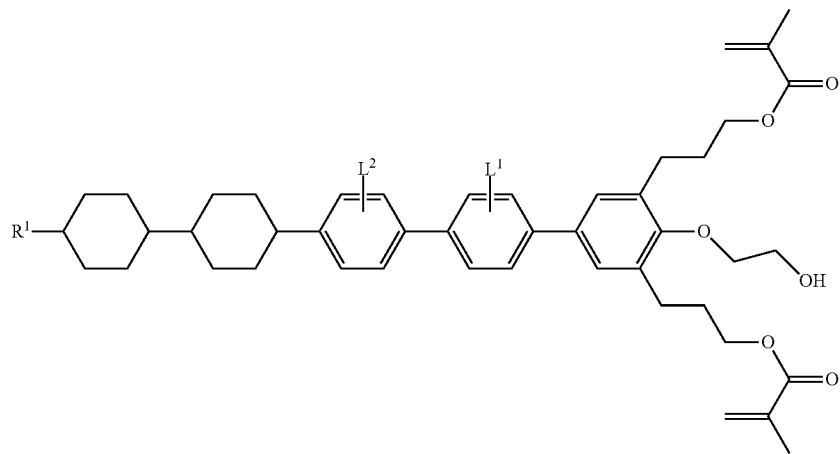
I-34
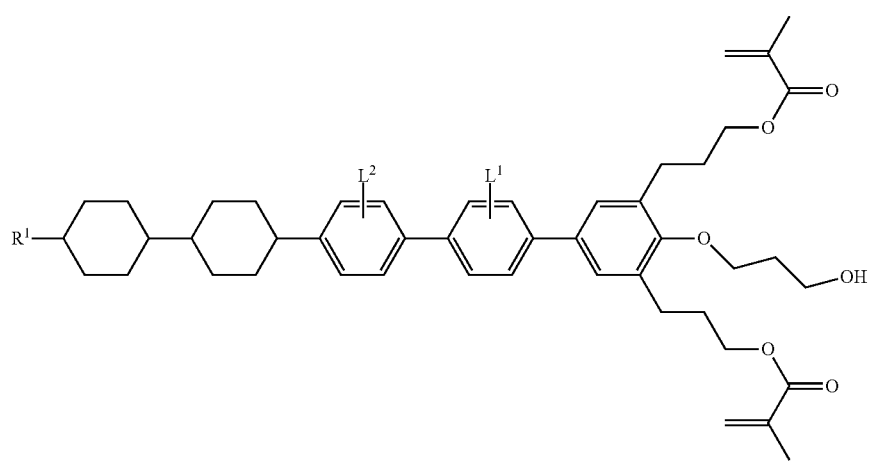
I-35
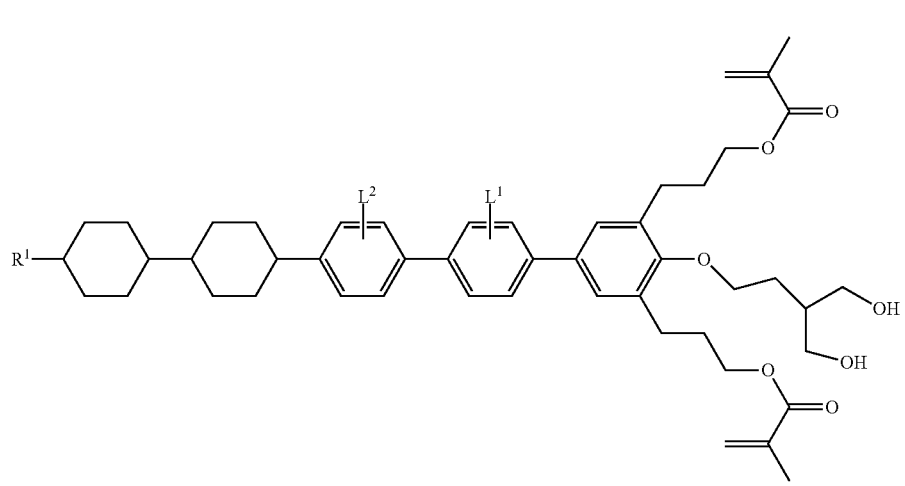

I-36
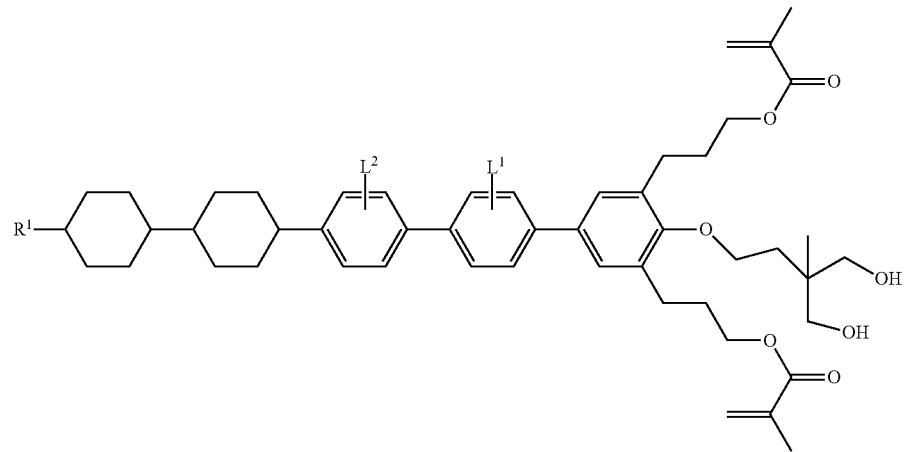
I-37
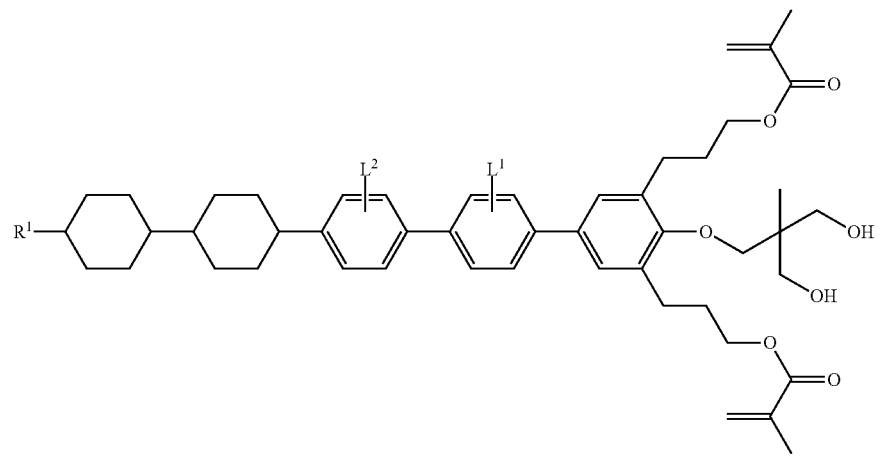
I-38
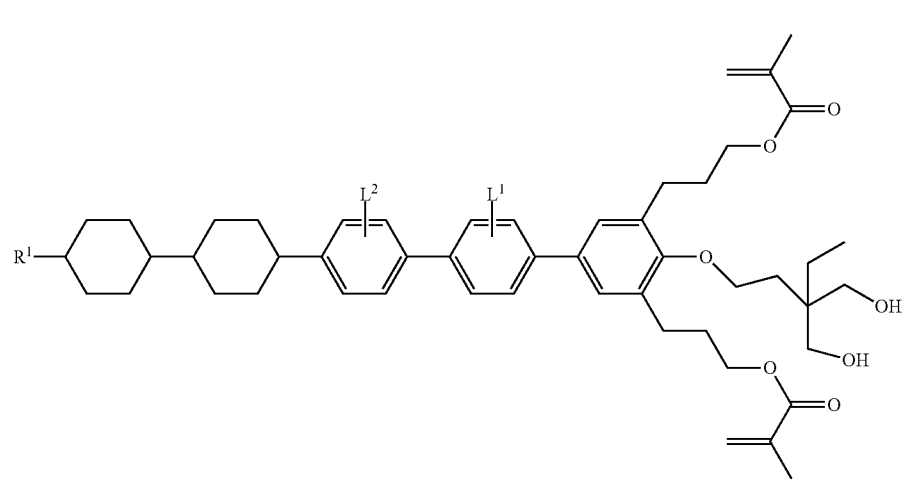

-continued
I-39
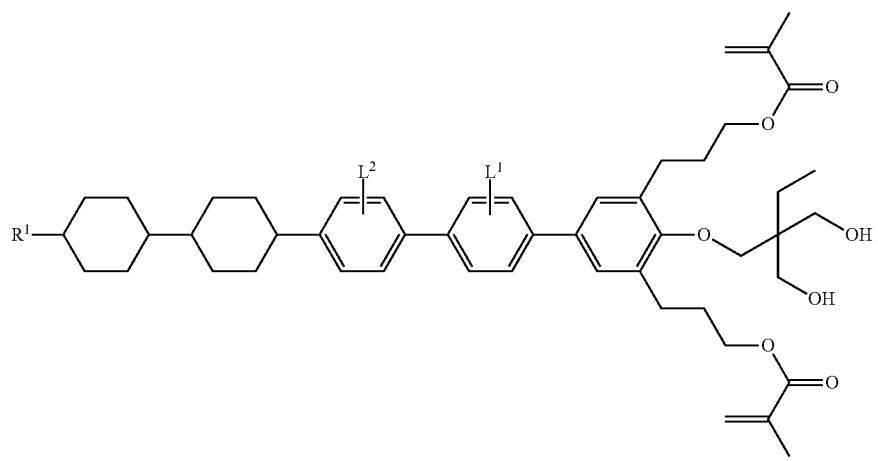
I-40
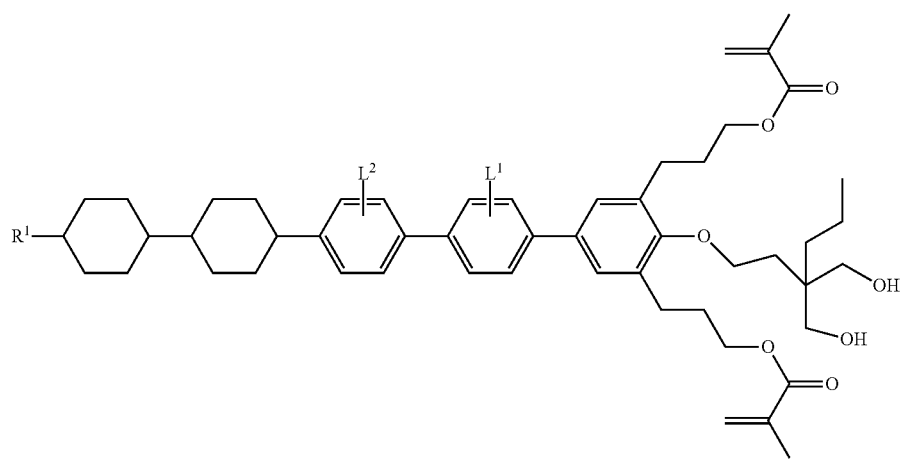
I-41
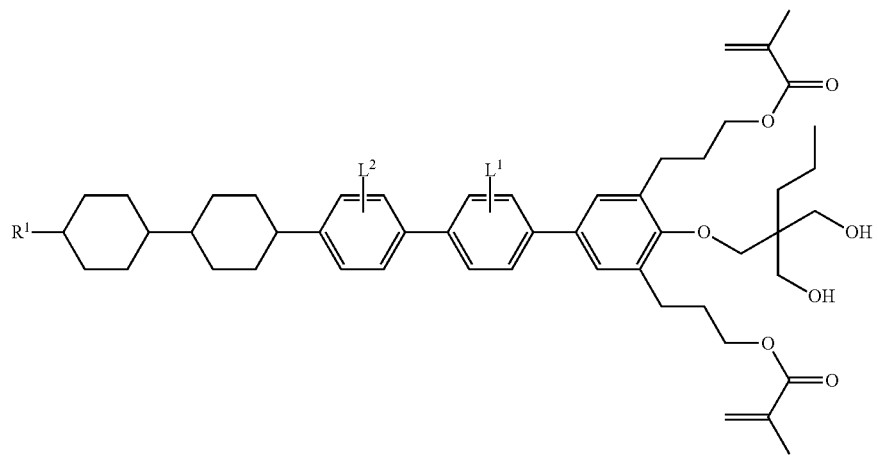

I-42
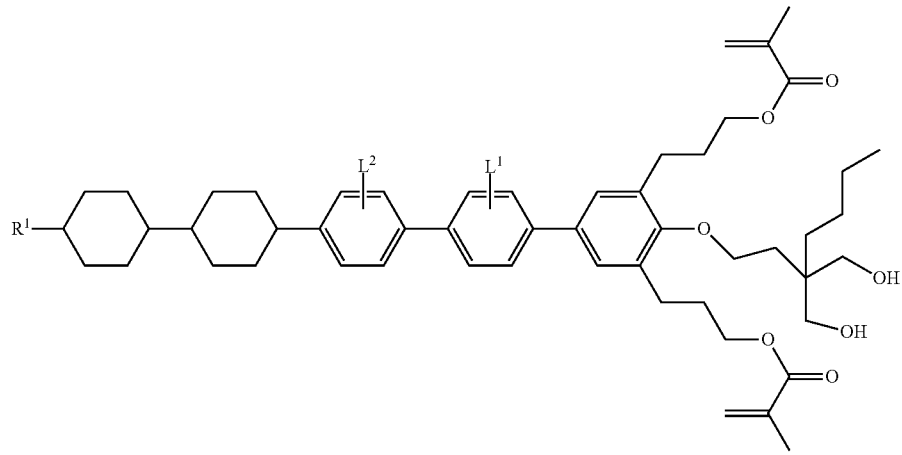
I-43
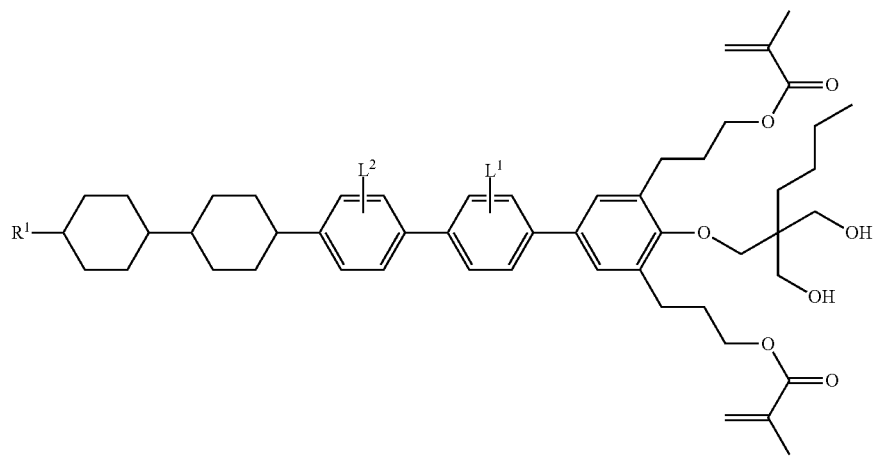
I-44
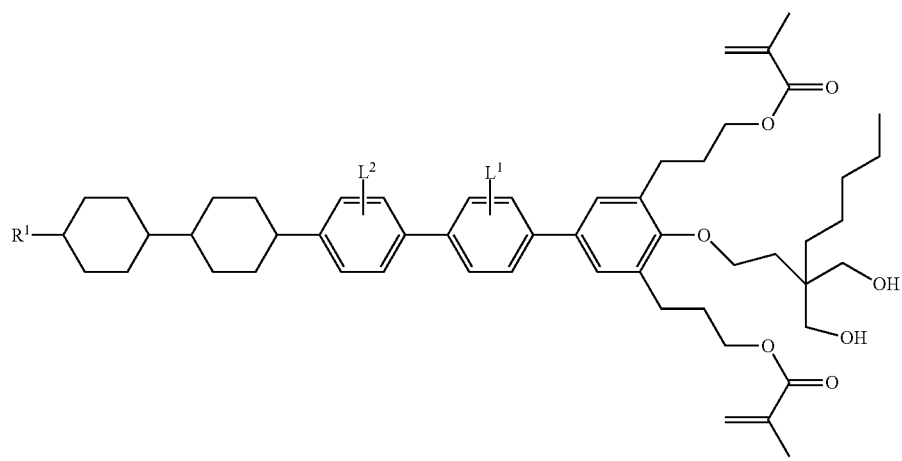

-continued
I-45
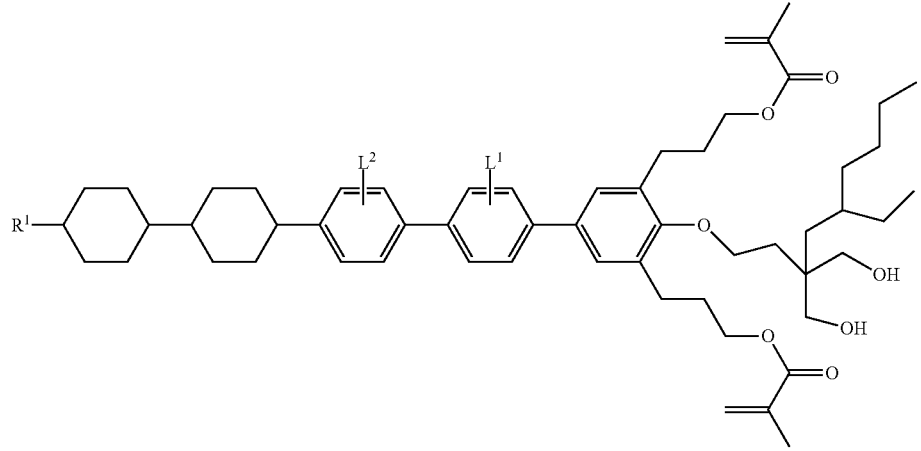
I-46
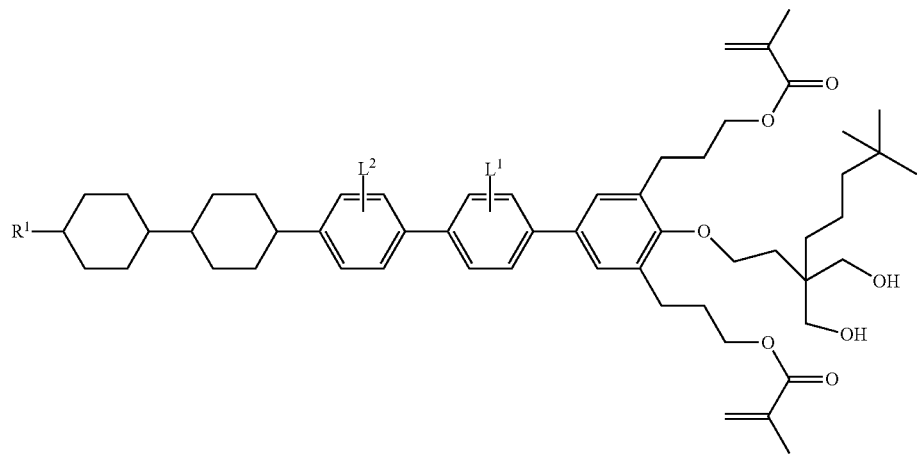
I-47
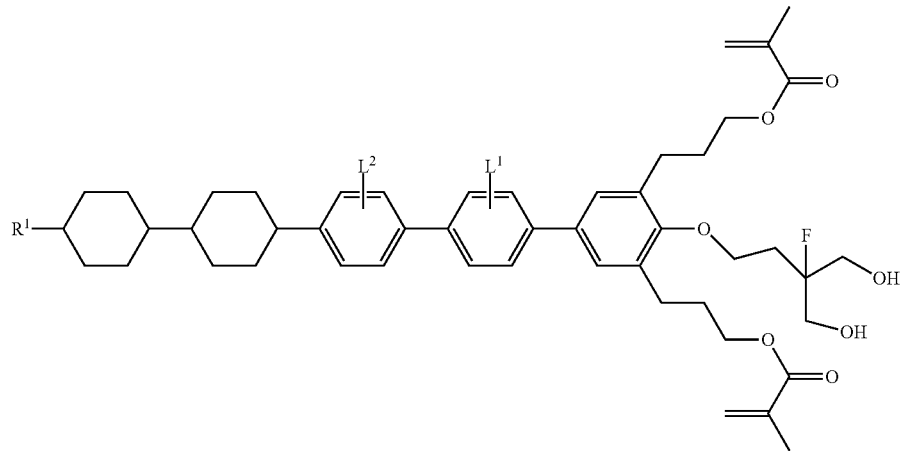

-continued
I-48
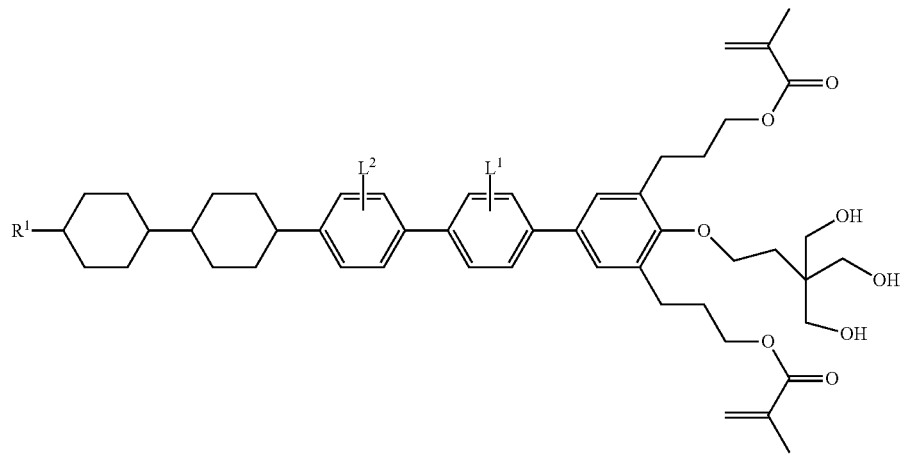
I-49
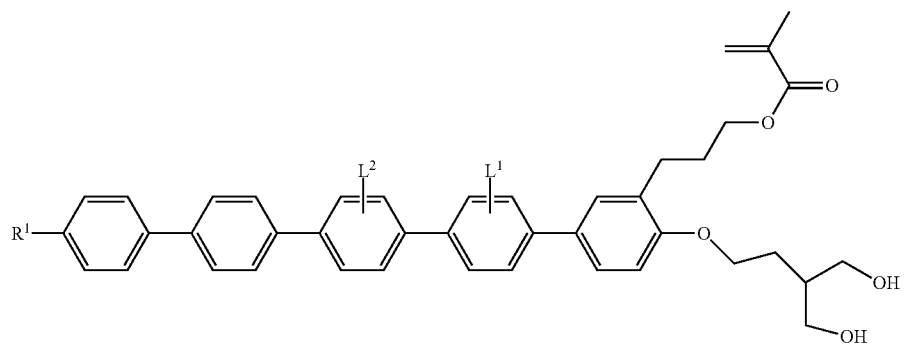
I-50
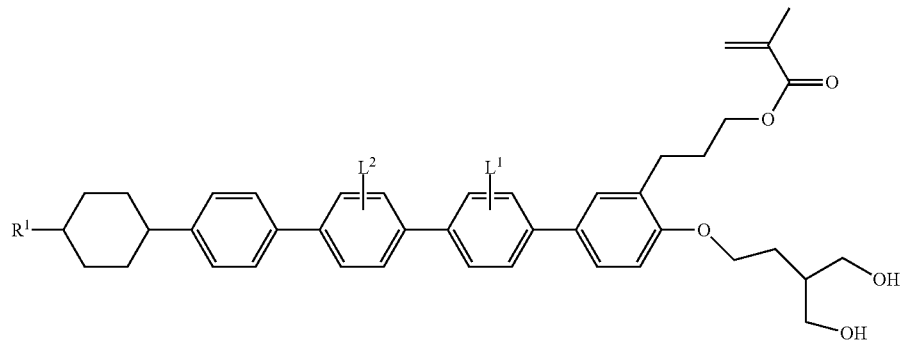
I-51
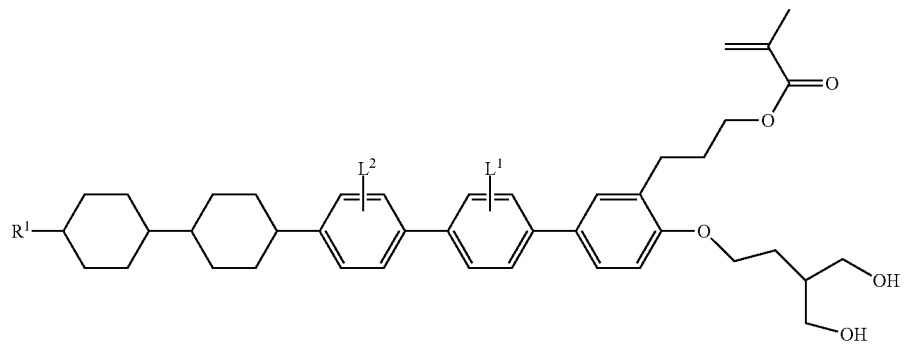

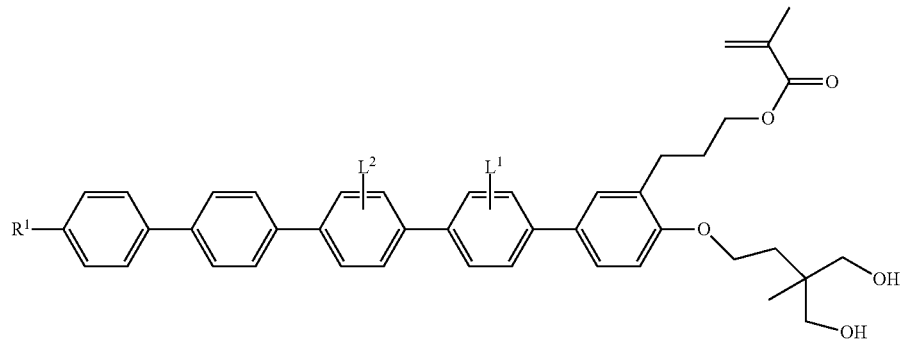
I-52
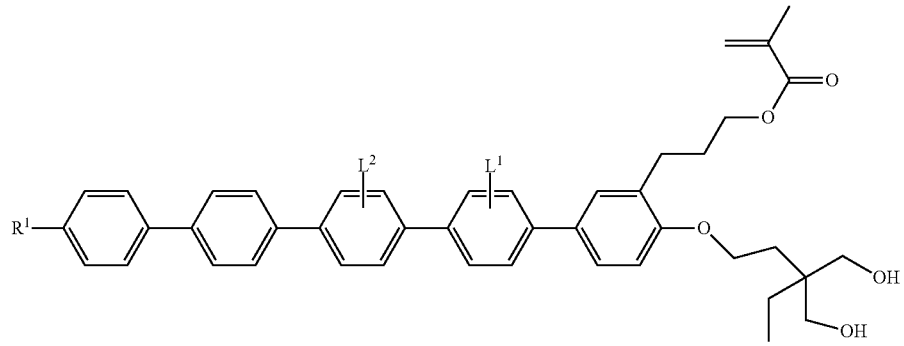
I-53
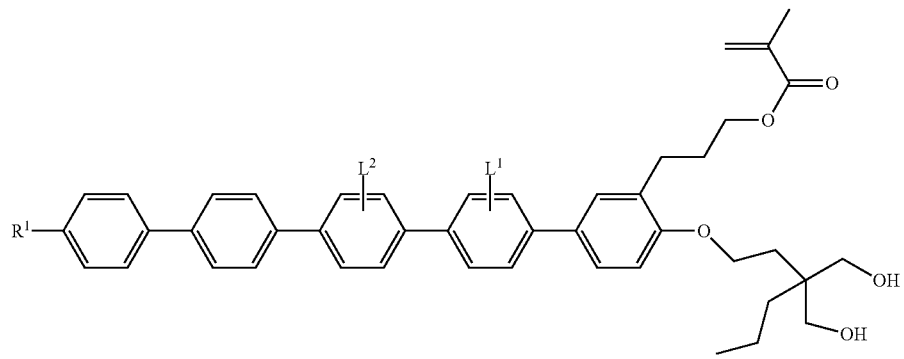
I-54
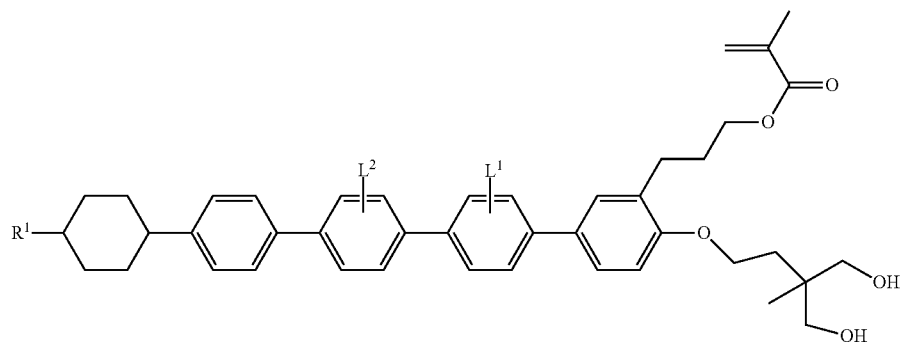
I-55

I-56
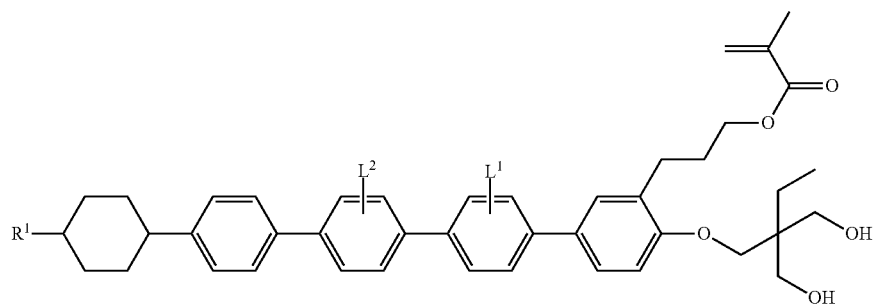
I-57
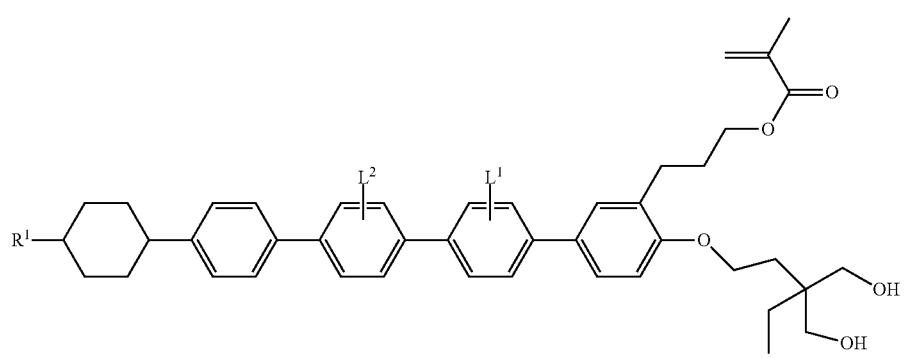
I-58
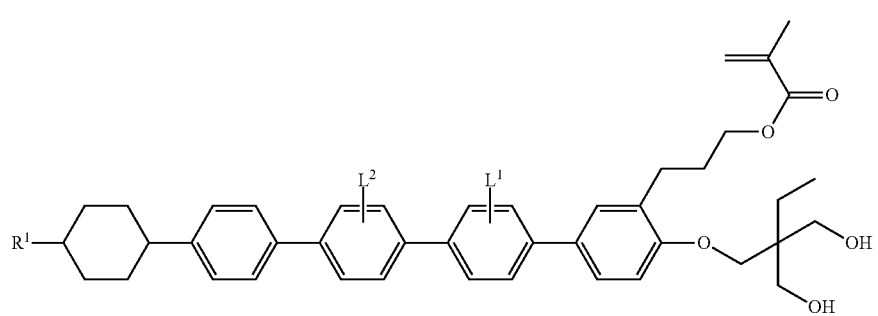
I-59
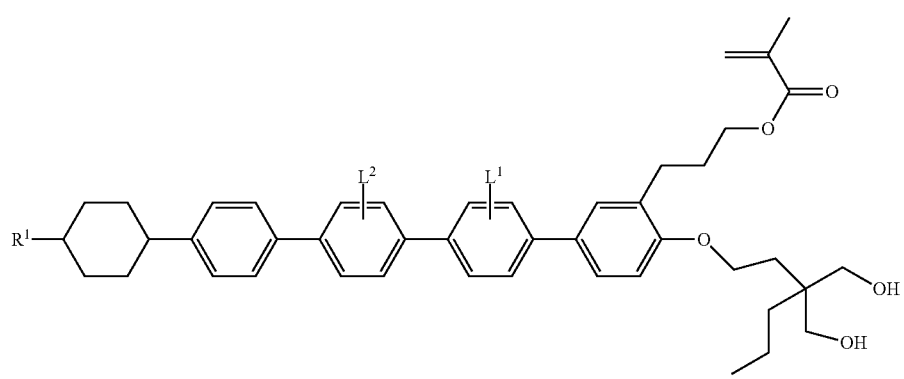
I-60
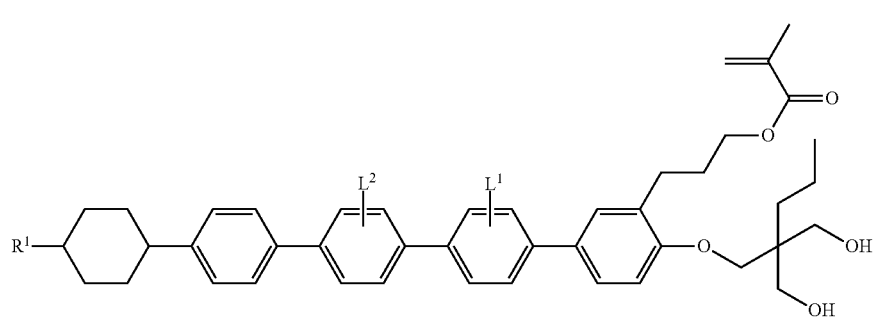

-continued
I-61
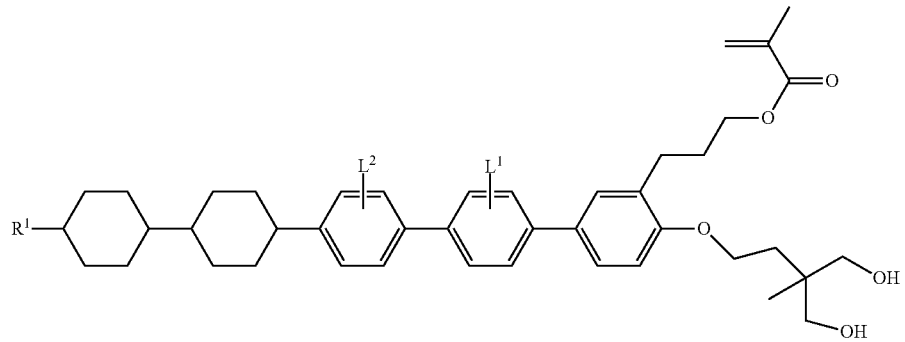
I-62
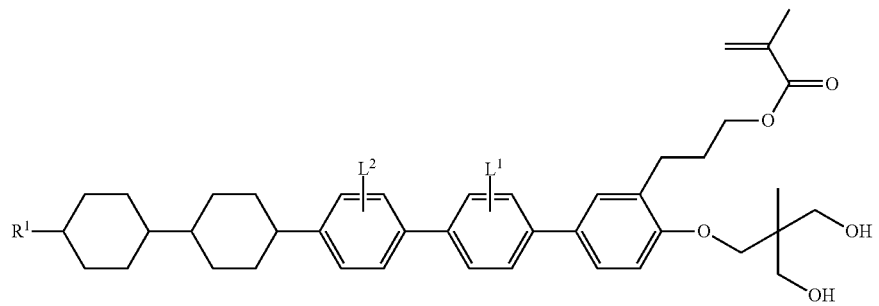
I-63
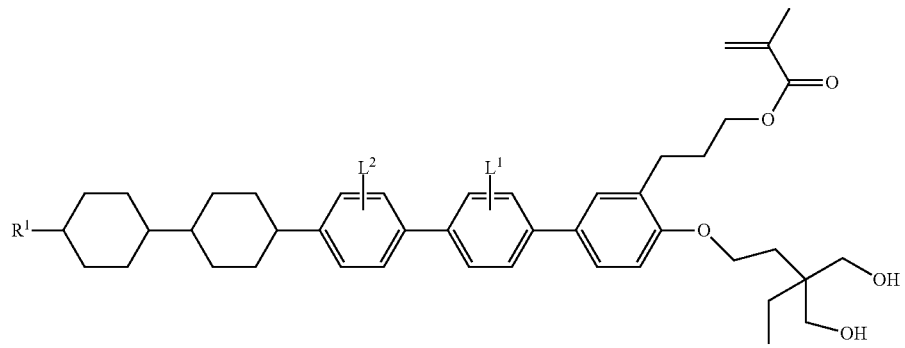
I-64
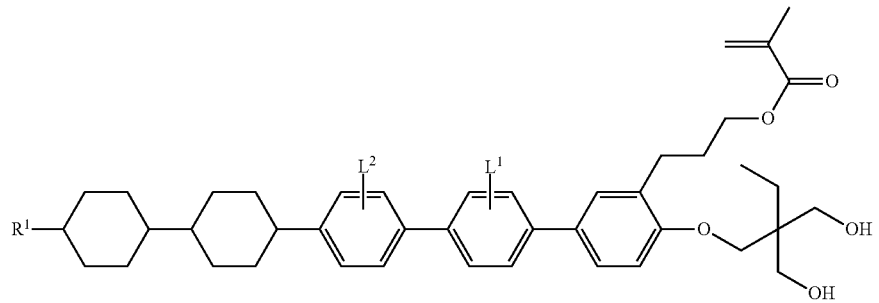

I-65
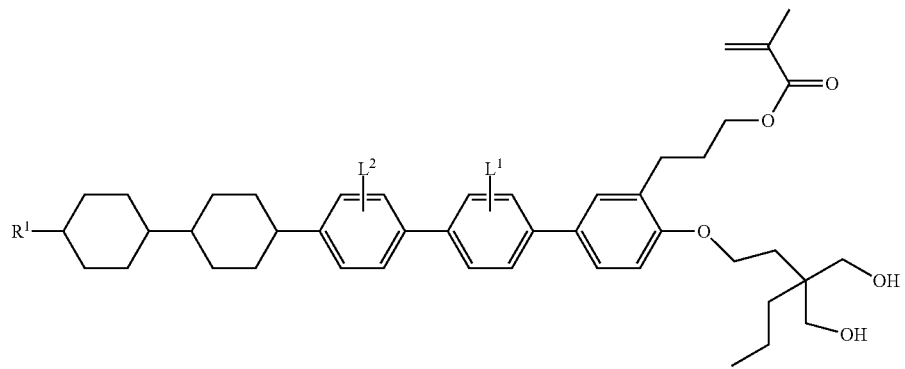
I-66
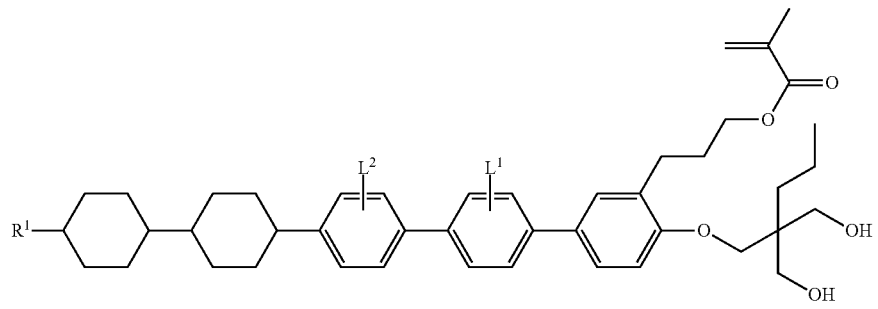
I-67
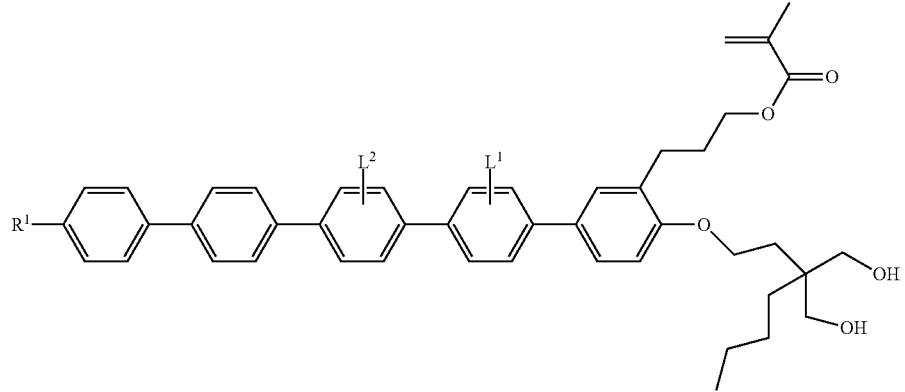
I-68
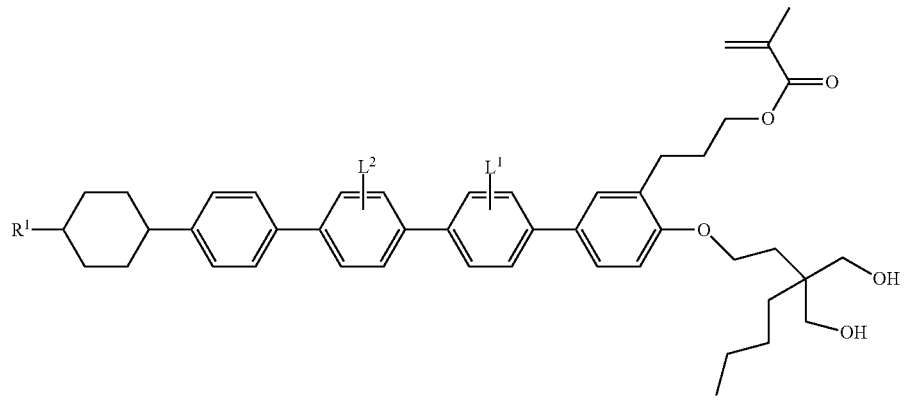

-continued
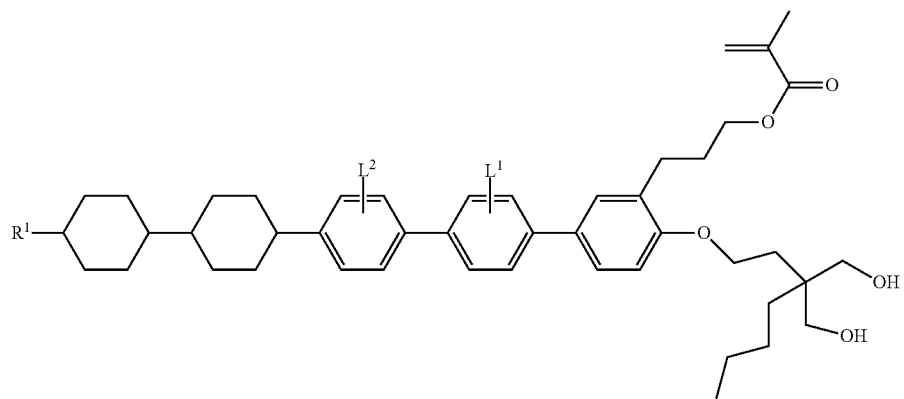
I-69
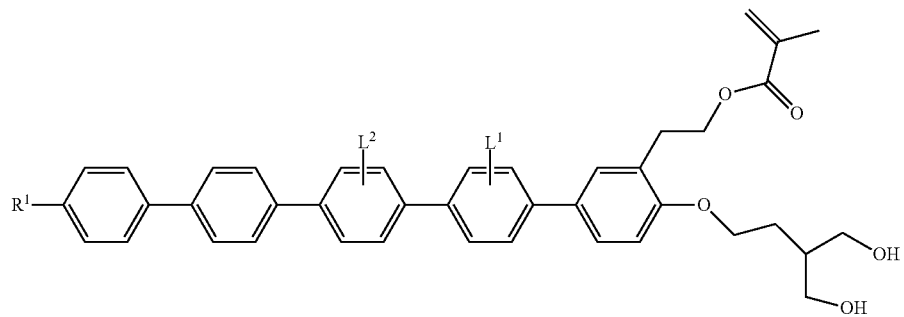
I-70
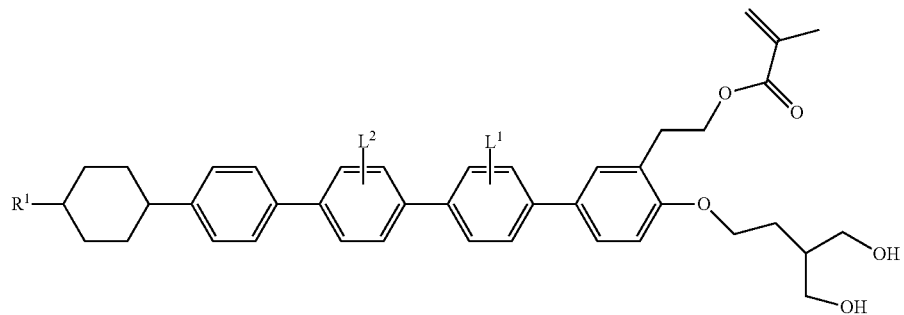
I-71
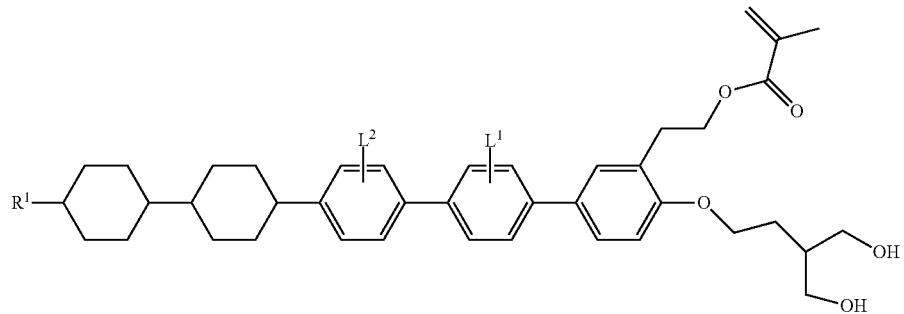
I-72

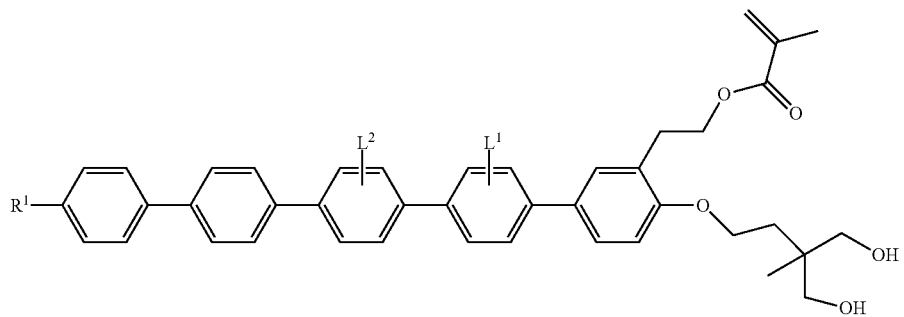
I-73
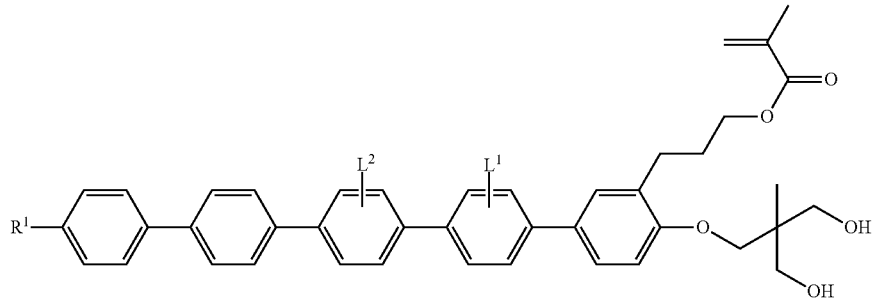
I-74
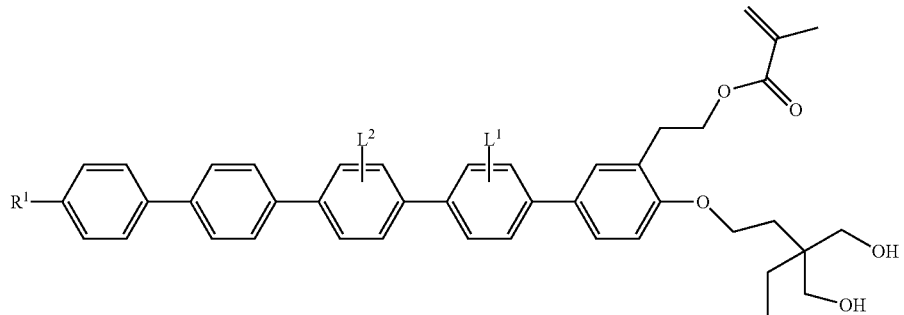
I-75
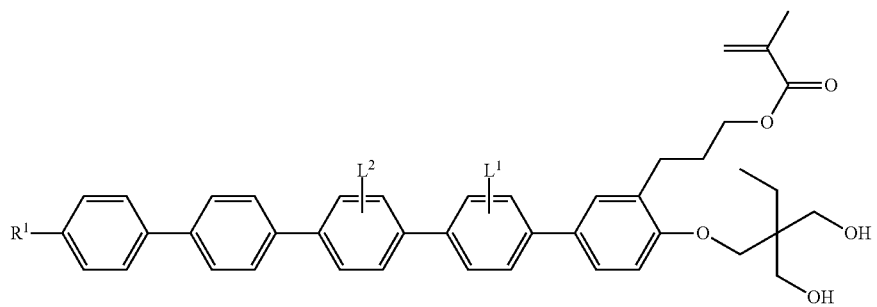
I-76
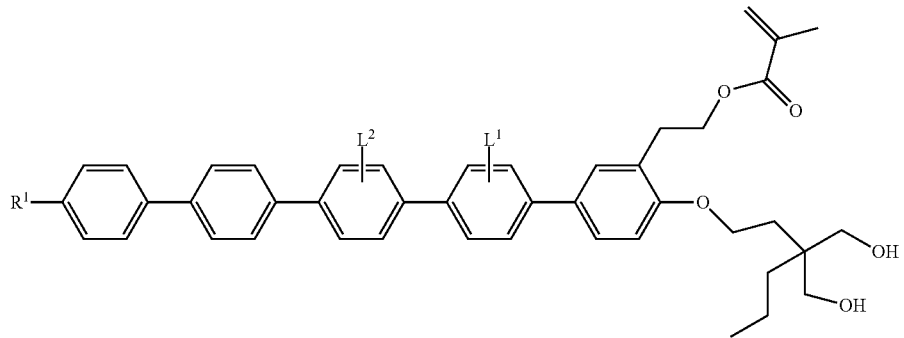
I-77

I-78
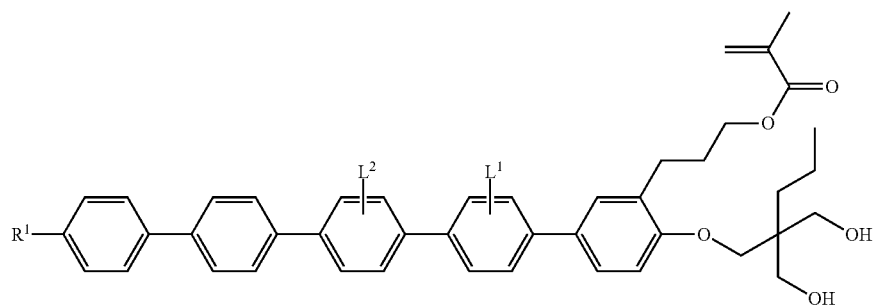
I-79
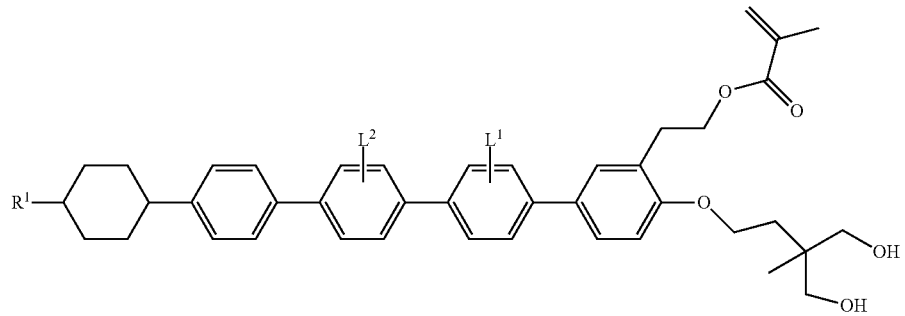
I-80
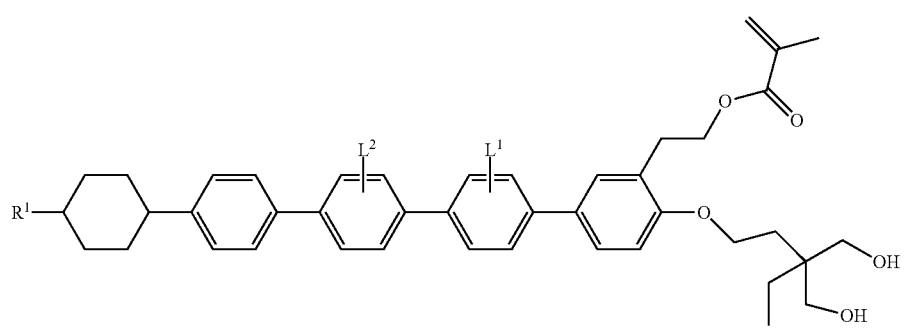
I-81
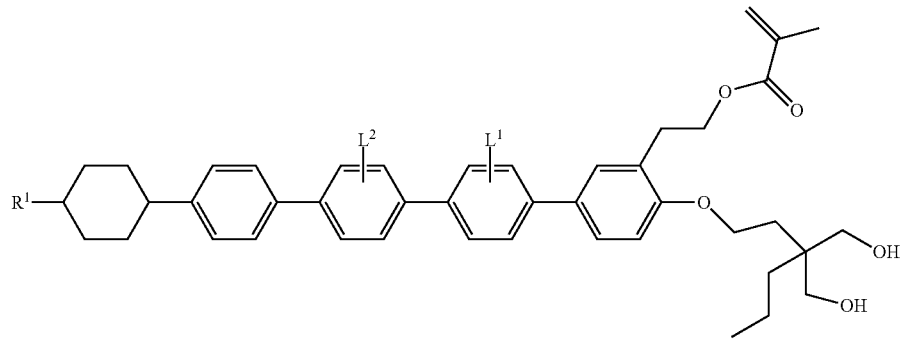
I-82
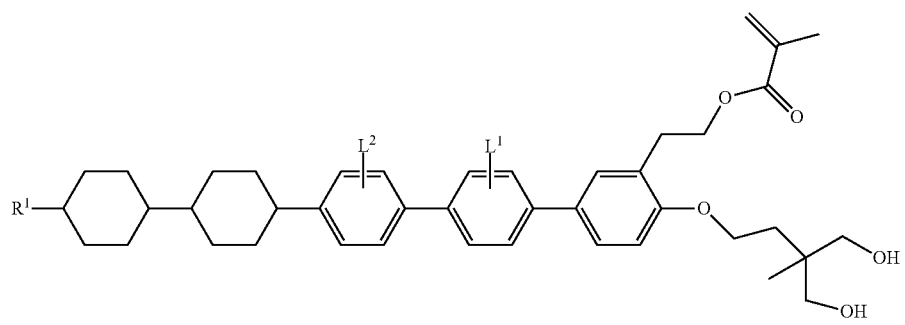

I-83
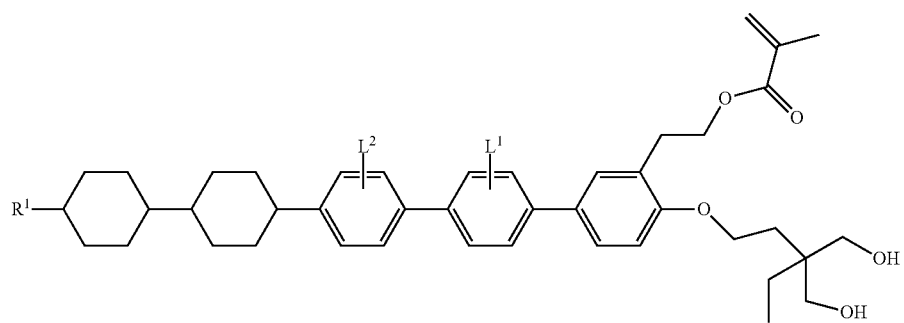
I-84
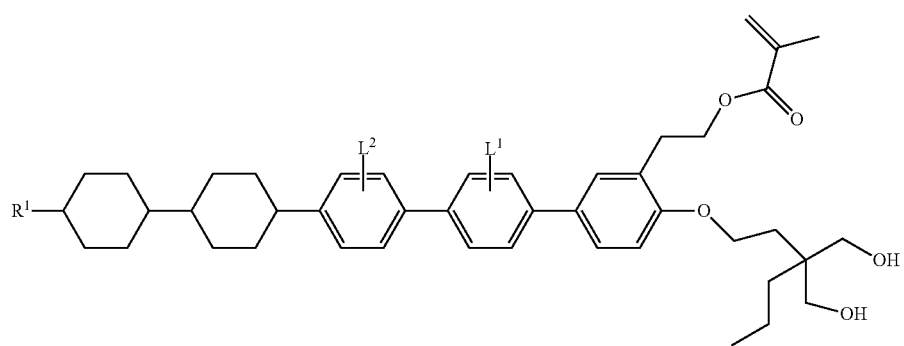
I-85
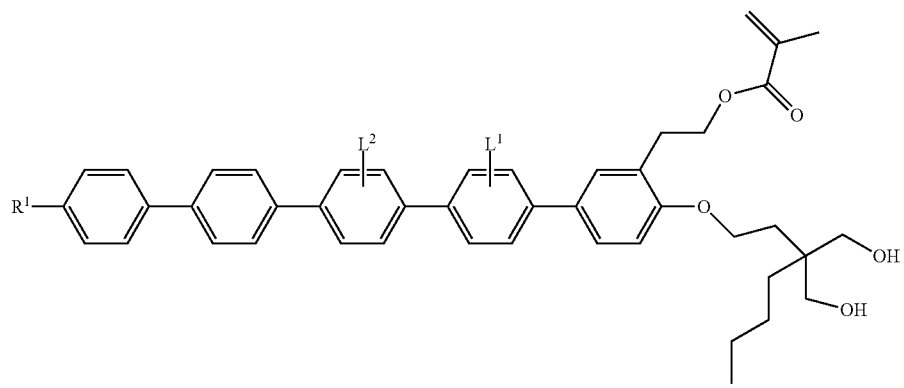
I-86
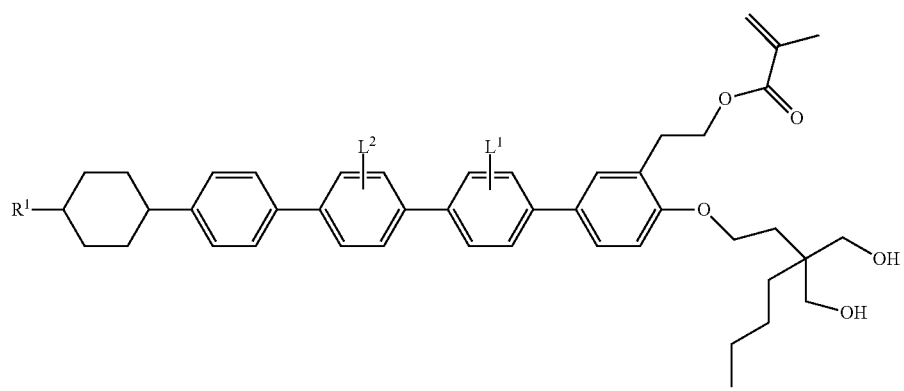

-continued

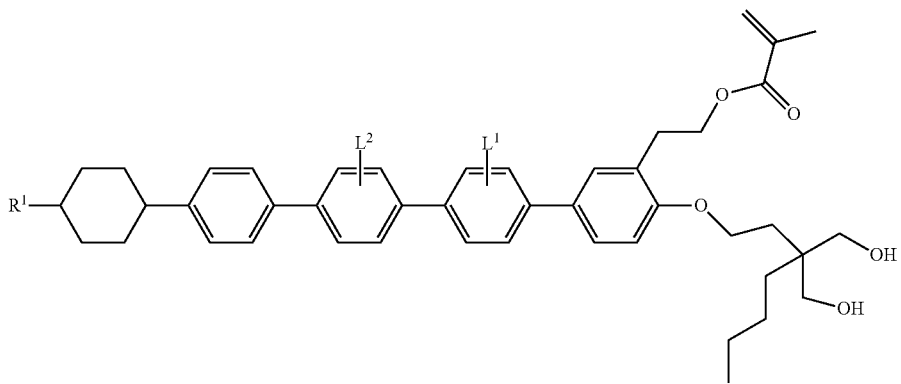
I-87

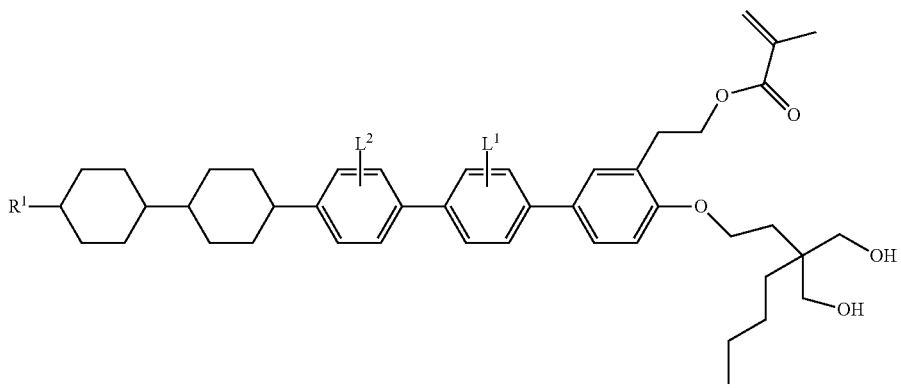
I-88

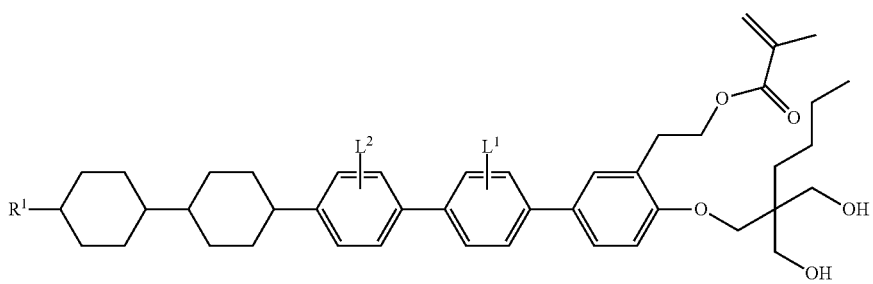
I-89 in which R¹ independently is defined as in formula I, and L¹ and L² independently denote H or adopt a meaning of L as in formula I, and preferably independently L¹ denotes H, —CH₃, —CH₂CH₃, F or Cl, and
L² denotes H, —CH₃, —CH₂CH₃, F or Cl.

Particularly preferably, at least one group from L¹ and L² is not H.

Besides the self-alignment additives of the formula I, the LC medium according to the invention may also comprise further self-alignment additives of the formula K which contain, for example, fewer than five rings. The total concentration of the polymerisable self-alignment additives of the formula I and the further (conventional) self-alignment additives of the formula K together is preferably the values indicated above, i.e., for example, 0.1 to 2.5% by weight.

The further self-alignment additives can have a structure of the formula K, where compounds of the formula I are excluded in formula K:

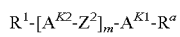   K in which the groups R¹, Z² and R$^a$ independently are defined as for formula I above, m denotes 1, 2 or 3, and in each case independently A$^{K1}$ is defined like A¹ and A$^{K2}$ like A² in formula I, in each case regarding the preferred definitions.

The formula K encompasses polytmerisable and unpolymerisable compounds. The preferred embodiments of the anchor group R$^a$, the elements A², Z², R¹ and the substituents L and -Sp-P, etc., can also be applied to the conventional additives of the formula K.

The preparation of the conventional self-alignment additives is disclosed, for example, in the specification WO 2012/038026, EP 2918658 A2, US 2015/0252265 A1 or WO 2016/015803 A1.

The term "aryl" denotes an aromatic carbon group or a group derived therefrom.

Aryl groups may be monocyclic or polycyclic, i.e. they may contain one ring (such as, for example, phenyl) or two or more fused rings. At least one of the rings here has an aromatic configuration. Heteroaryl groups contain one or more heteroatoms, preferably selected from O, N, S and Se.

Particular preference is given to mono-, bi- or tricyclic aryl groups having 6 to 25 C atoms. Preference is furthermore given to 5-, 6- or 7-membered aryl groups, in which, in addition, one or more CH groups may be replaced by N, S or O in such a way that O atoms and/or S atoms are not linked directly to one another.

Preferred aryl groups are, for example, phenyl, naphthyl, anthracene, phenanthrene, pyrene, dihydropyrene, chrysene, perylene, tetracene, pentacene, benzopyrene, fluorene, indene, indenofluorene, spirobifluorene, etc.

In connection with the present invention, the term "alkyl" denotes an unbranched or branched, saturated, aliphatic hydrocarbon radical having 1 to 15 (i.e. 1, 2, 3, 4, 5, 6, 7, 8, 9, 10, 11, 12, 13, 14 or 15) carbon atoms.

The term "cyclic alkyl" includes alkyl groups which have at least one carbocyclic part, i.e., for example, also cycloalkylalkyl, alkylcycloalkyl and alkyl-cycloalkylalkyl. The carbocyclic groups therein include, for example, cyclopropyl, cyclobutyl, cyclopentyl, bicyclo[1.1.1]pentyl, cyclohexyl, spiro[3.3]-bicycloheptyl, cycloheptyl, cyclooctyl, etc.

In connection with the present invention, the term "fluoroalkyl" denotes an unbranched or branched, saturated or unsaturated, preferably saturated, aliphatic hydrocarbon radical having 1 to 15 (i.e. 1, 2, 3, 4, 5, 6, 7, 8, 9, 10, 11, 12, 13, 14 or 15) carbon atoms which is substituted by one or more fluorine atoms. The radical is preferably perfluorinated.

"Halogen" in connection with the present invention stands for fluorine, chlorine, bromine or iodine, preferably for fluorine or chlorine.

The term "spacer group" or "spacer", generally denoted by "Sp" (or $Sp^{a/c/d/1/2/3}$) herein, is known to the person skilled in the art and is described in the literature, for example in Pure Appl. Chem. 73(5), 888 (2001) and C. Tschierske, G. Pelzl, S. Diele, Angew. Chem. (2004), 116, 6340-6368. In the present disclosure, the term "spacer group" or "spacer" denotes a connecting group, for example an alkylene group, which connects a mesogenic group to a polymerisable group. Whereas the mesogenic group generally contains rings, the spacer group generally contains no ring systems, i.e. is in chain form, where the chain may also be branched. The term chain is applied, for example, to an alkylene group. Substitutions on and in the chain, for example by —O— or —COO—, are generally also included.

The above preferred compounds of the formula I can in principle be prepared by the following illustrative synthetic routes (Schemes 1-3):

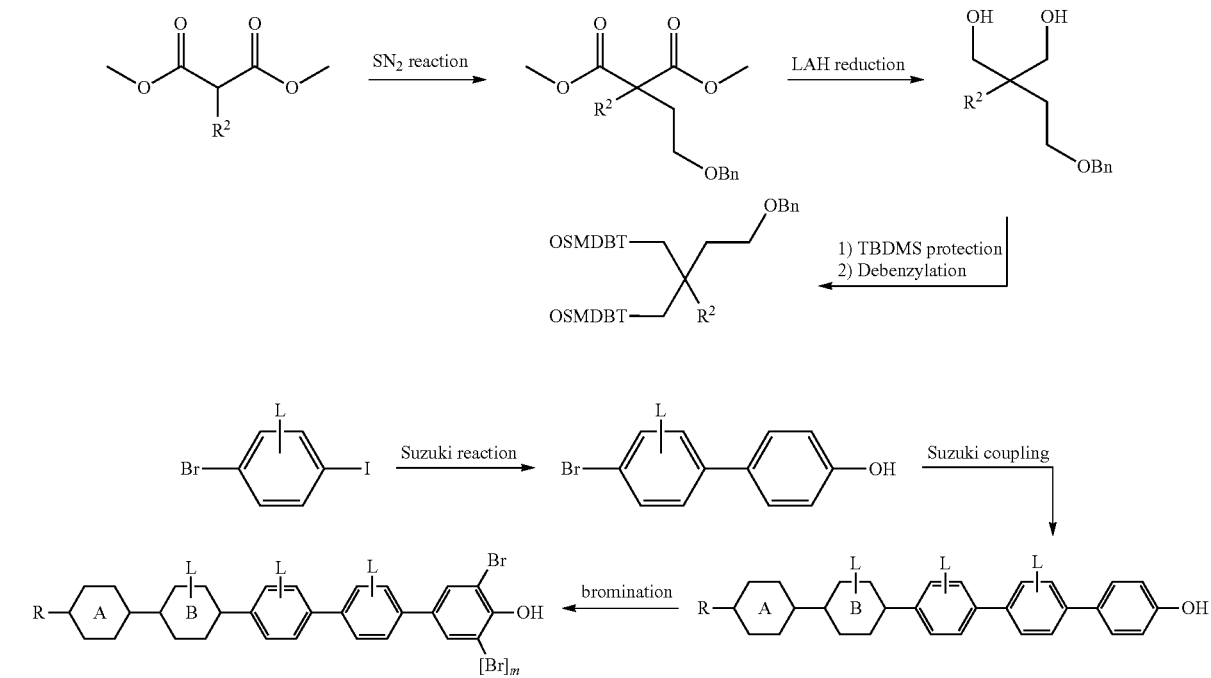

Definitions:
$m = 0, 1$;
ring A, B = aromatic or non-aromatic ring as described under formula I-A;
L = independently of one another, identically or differently, and as described under formula I-A.

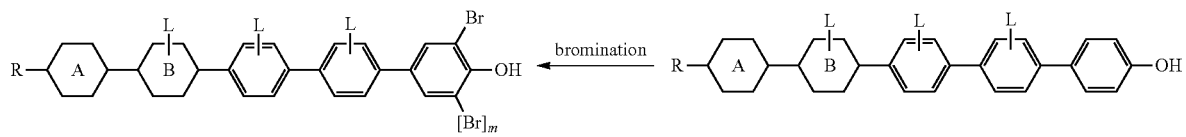

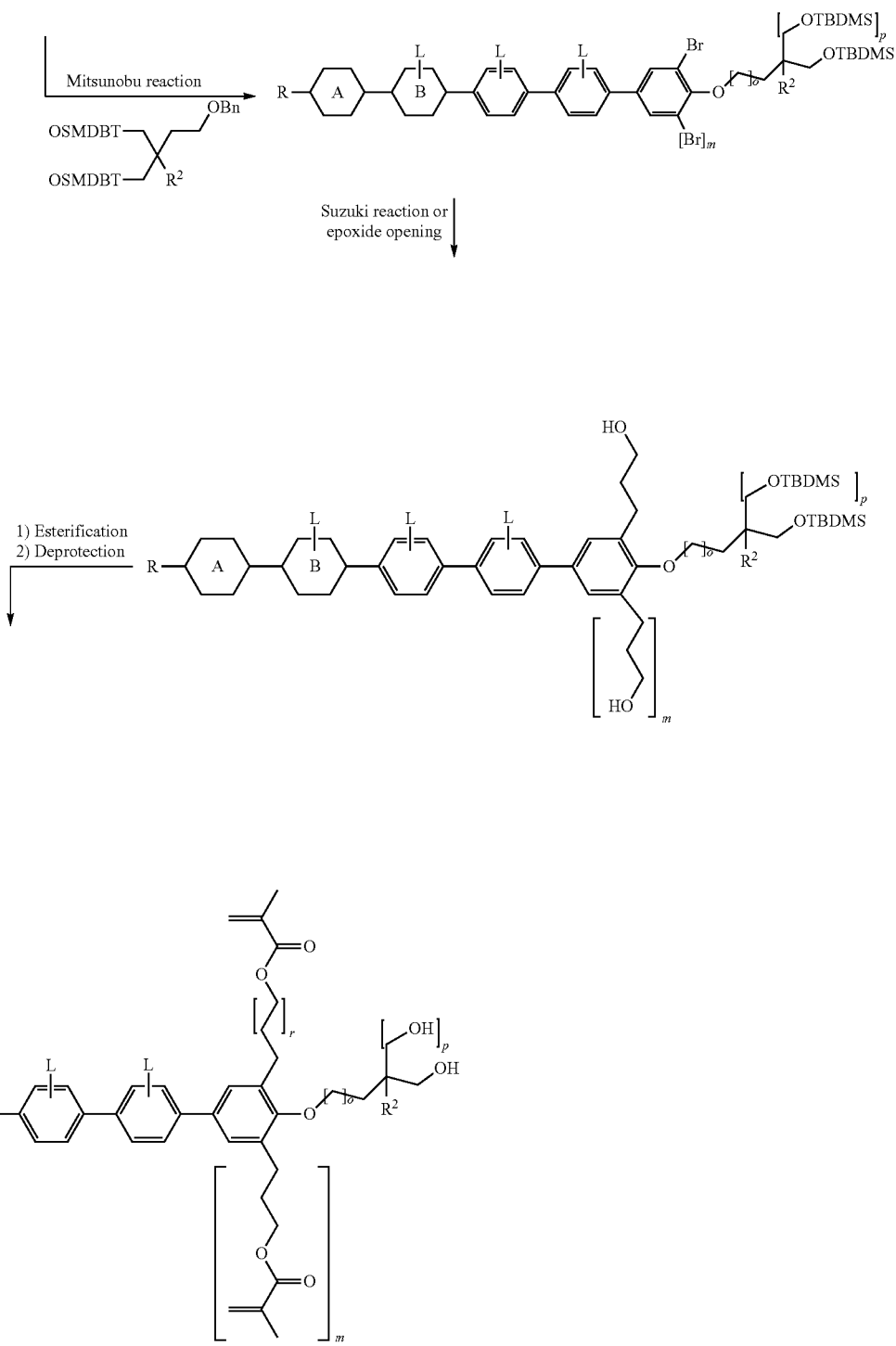
Definitions:
$R^2$ = as described under formula 1;
$o$ = 0, 1, 2, 3;
$p$ = 0, 1, 2 (for $p$ > 1 $R^2$ is not present);
$r$ = 0, 1;
$m$ = 0, 1;
ring A, B = aromatic or non-aromatic ring as described under formula I-A;
L = independently of one another, identically or differently, and as desribed under formula I-A.

Scheme 3.
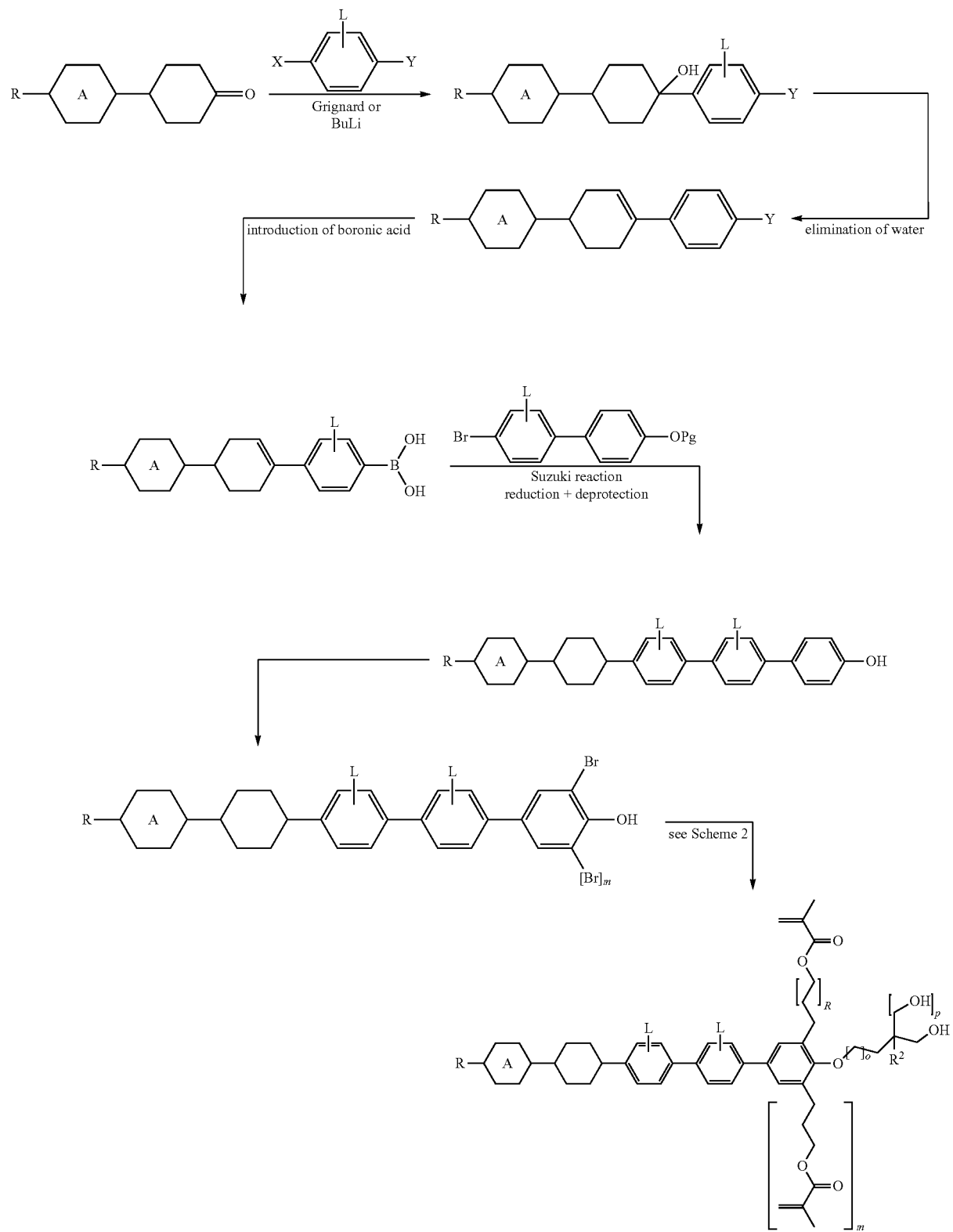
Definitions:
as in Scheme 2 and
Pg = protecting group: e.g.: benzyl.

Besides the compounds of the formula I, the polymerisable component of the LC medium according to the invention preferably comprises further polymerisable or (partially) polymerised compounds. These are preferably conventional polymerisable compounds without an anchor group, preferably mesogenic compounds, in particular those which are suitable for the PS technique. Polymerisable compounds which are preferred for this purpose are the structures indicated below for formula M and the subformulae thereof. The polymer formed therefrom is able to stabilise the alignment of the LC medium, optionally form a passivation layer and optionally generate a pre-tilt.

The present invention also encompasses an LC medium as described above and below which comprises
- 95% by weight or more of a low-molecular-weight, unpolymerisable, liquid-crystalline component, and
- 5% by weight or less of a polymerisable or polymerised component.

The polymerisable component preferably comprises compounds of the formula I or of the formula M or both in variable proportions.

The LC media according to the invention therefore preferably comprise >0 to <5% by weight, particularly preferably 0.05 to 1% by weight and very particularly preferably 0.2 to 1% by weight of polymerisable compounds without an anchor group $R^a$, in particular compounds of the formula M as defined below and the preferred formulae falling thereunder.

The polymerisation of the polymerisable component(s) is carried out together or in part-steps under different polymerisation conditions. The polymerisation is preferably carried out under the action of UV light. In general, the polymerisation is initiated with the aid of a polymerisation initiator and UV light. In the case of the preferred (meth) acrylates, virtually complete polymerisation is achieved in this way. During the polymerisation, a voltage can optionally be applied to the electrodes of the cell or another electric field can be applied in order additionally to influence the alignment of the LC medium.

Particular preference is given to LC media according to the invention which, besides the compounds of the formula I, comprise further polymerisable or (partially) polymerised compounds (without an anchor group) and optionally further self-alignment additives. These further self-alignment additives are preferably those of the formula K, as defined above.

The optionally present further monomers of the polymerisable component of the LC medium are preferably described by the following formula M:

$$P^1\text{-}Sp^1\text{-}A^{2x}\text{-}(Z^1\text{-}A^{1x})_n\text{-}Sp^2\text{-}P^2 \qquad M$$

in which the individual radicals have the following meanings:
$P^1$, $P^2$ each, independently of one another, denote a polymerisable group,
$Sp^1$, $Sp^2$ on each occurrence, identically or differently, denote a spacer group or a single bond,
$A^{1x}, A^{2x}$ each, independently of one another, denote a radical selected from the following groups:
  a) the group consisting of trans-1,4-cyclohexylene, 1,4-cyclohexenylene and 4,4'-bicyclohexylene, in which, in addition, one or more non-adjacent CH$_2$ groups may be replaced by —O— and/or —S— and in which, in addition, one or more H atoms may be replaced by a group $L^X$, or a radical of the formula

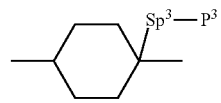

b) the group consisting of 1,4-phenylene and 1,3-phenylene, in which, in addition, one or two CH groups may be replaced by N and in which, in addition, one or more H atoms may be replaced by a group $L^X$ or -Sp$^3$-P,
  c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by $L^X$,
  d) the group consisting of saturated, partially unsaturated or fully unsaturated, and optionally substituted, polycyclic radicals having 5 to 20 cyclic C atoms, one or more of which may, in addition, be replaced by heteroatoms, preferably selected from the group consisting of bicyclo[1.1.1]pentane-1,3-diyl, bicyclo[2.2.2]octane-1,4-diyl, spiro[3.3]heptane-2,6-diyl,

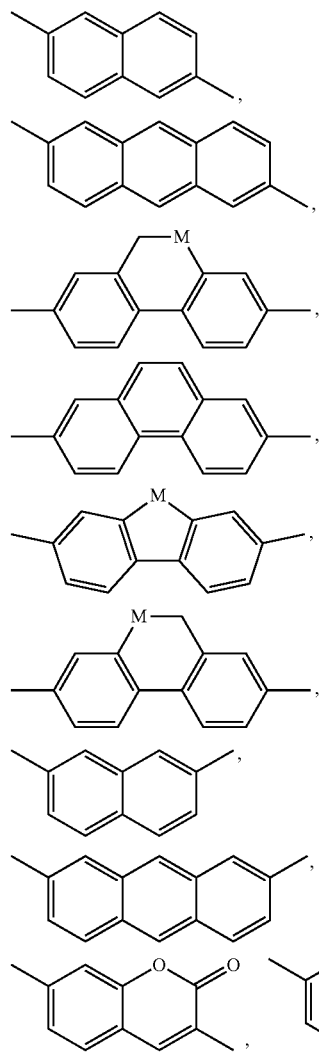

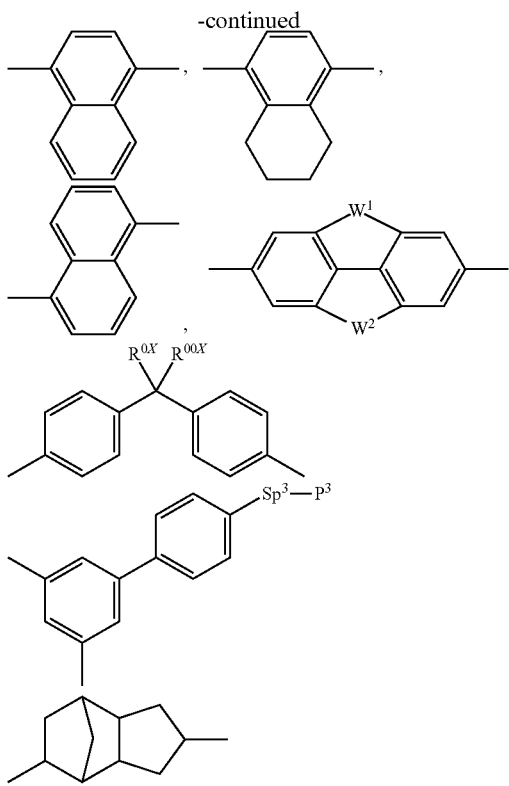

where, in addition, one or more H atoms in these radicals may be replaced by a group $L^X$ or -$Sp^a$-P, and/or one or more double bonds may be replaced by single bonds, and/or one or more CH groups may be replaced by N, $P^3$ denotes a polymerisable group, $Sp^a$ denotes a spacer group, n in formula M denotes 0, 1, 2 or 3, preferably 1 or 2, $Z^1$ in each case, independently of one another, denotes —CO—O—, —O—CO—, —CH$_2$O—, —OCH$_2$—, —CF$_2$O—, —OCF$_2$—, or —(CH$_2$)$_n$—, where n is 2, 3 or 4, —O—, —CO—, —C(R$^c$R$^d$)—, —CH$_2$CF$_2$—, —CF$_2$CF$_2$— or a single bond, $L^X$ on each occurrence, identically or differently, denotes F, Cl, CN, SCN, SF$_5$ or unbranched or branched, in each case optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, $R^{0x}$, $R^{00x}$ each, independently of one another, denote H, F or unbranched or branched alkyl having 1 to 12 C atoms, in which, in addition, one or more H atoms may be replaced by F, M denotes —O—, —S—, —CH$_2$—, —CHY$^1$— or —CY$^1$Y$^2$—, and $Y^1$ and $Y^2$ each, independently of one another, have one of the meanings indicated above for $R^0$ or denote Cl or CN, and preferably H, F, Cl, CN, OCF$_3$ or CF$_3$, $W^1$, $W^2$ each, independently of one another, denote —CH$_2$CH$_2$—, —CH=CH—, —CH$_2$—O—, —O—CH$_2$—, —C(R$^c$R$^d$)— or —O—, $R^c$ and $R^d$ each, independently of one another, denote H or alkyl having 1 to 6 C atoms, preferably H, methyl or ethyl.

where one or more of the groups $P^1$-$Sp^1$-, -$Sp^2$-$P^2$ and -$Sp^3$-$P^3$ may denote a radical $R^{aa}$, with the proviso that at least one of the groups $P^1$-$Sp^1$-, -$Sp^2$-$P^2$ and -$Sp^3$-$P^3$ present does not denote $R^{aa}$, $R^{aa}$ denotes H, F, Cl, CN or unbranched or branched alkyl having 1 to 25 C atoms, in which, in addition, one or more non-adjacent CH$_2$ groups may each be replaced, independently of one another, by C(R$^0$)=C(R$^{00}$)—, —C≡C—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or $P^1$-$Sp^1$-, particularly preferably unbranched or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals contain at least two C atoms and the branched radicals contain at least three C atoms), where the groups —OH, —NH$_2$, —SH, —NHR, —C(O)OH and —CHO are not present in $R^{aa}$.

The polymerisable group P, $P^1$, $P^2$ or $P^3$ in the formulae above and below is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a polymerisable C=C double bond or —C≡C— triple bond, and groups which are suitable for polymerisation with ring opening, such as, for example, oxetane or epoxide groups.

Preferred groups P/$P^1$/$P^2$/$P^3$ are selected from the group consisting of CH$_2$=CW$^1$—CO—O—, CH$_2$=CW$^1$—CO—,

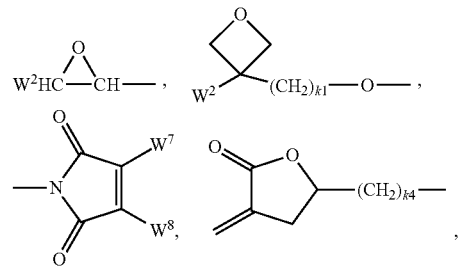

CH$_2$=CW$^2$—O—, CW$^1$=CH—CO—(O)$_{k3}$—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, CH$_2$=CH—(COO)$_{k1}$-Phe-(O)$_{k2}$—, CH$_2$=CH—(CO)$_{k1}$-Phe-(O)$_{k2}$—, Phe-CH=CH—, HOOC— and W$^4$W$^5$W$^6$Si—, in which W$^1$ in groups P/$P^1$/$P^2$/$P^3$ denotes H, F, Cl, CN, CF$_3$, phenyl or alkyl having 1 to 5 C atoms, in particular H, F, Cl or CH$_3$, W$^2$ and W$^3$ each, independently of one another, denote H or alkyl having 1 to 5 C atoms, in particular H, methyl, ethyl or n-propyl, W$^4$, W$^5$ and W$^6$ each, independently of one another, denote Cl, oxaalkyl or oxacarbonylalkyl having 1 to 5 C atoms, W$^7$ and W$^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Particularly preferred groups P/$P^1$/$P^2$/$P^3$ are selected from the group consisting of CH$_2$=CW$^1$—CO—O—, CH$_2$=CW$^1$—CO—,

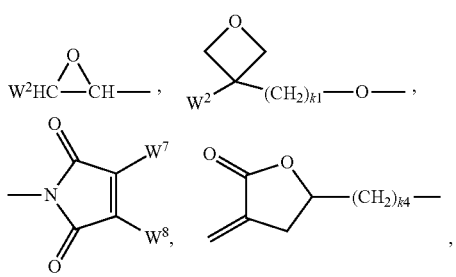

$CH_2=CW^2-O-$, $CW^1=CH-CO-(O)_{k3}-$, $(CH_2=CH)_2CH-OCO-$, $(CH_2=CH-CH_2)_2CH-OCO-$, $(CH_2=CH)_2CH-O-$, $(CH_2=CH-CH_2)_2N-$, $(CH_2=CH-CH_2)_2N-CO-$, $CH_2=CW^1-CO-NH-$, $CH_2=CH-(COO)_{k1}$-Phe-$(O)_{k2}-$, $CH_2=CH-(CO)_{k1}$-Phe-$(O)_{k2}-$, Phe-$CH=CH-$ and $W^4W^5W^6Si-$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups $P/P^1/P^2/P^3$ are selected from the group consisting of $CH_2=CW^1-CO-O-$, in particular $CH_2=CH-CO-O-$, $CH_2=C(CH_3)-CO-O-$ and $CH_2=CF-CO-O-$, furthermore $CH_2=CH-O-$, $(CH_2=CH)_2CH-O-CO-$, $(CH_2=CH)_2CH-O-$,

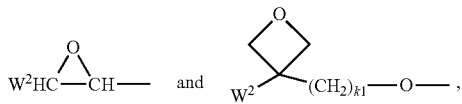

Very particularly preferred groups $P/P^1/P^2/P^3$ are therefore selected from the group consisting of acrylate, methacrylate, ethylacrylate, fluoroacrylate, furthermore vinyloxy, chloroacrylate, oxetane and epoxide groups, and of these in turn preferably an acrylate or methacrylate group.

Preferred spacer groups Sp, $Sp^1$, $Sp^2$ or $Sp^3$ are a single bond or selected from the formula Sp"-X", so that the radical $P^{(1/2)}$-$Sp^{(1/2)}$- conforms to the formula $P^{1/2}$-Sp"-X"— or P-Sp"-X"—, where Sp" denotes alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —Si ($R^{00}R^{000}$)—, —CO—, —CO—O—, —O—CO—, —O—CO—O—, —S—CO—, —CO—S—, —N($R^{00}$)—CO—O—, —O—CO—N($R^{00}$)—, —N($R^{00}$)—CO—N ($R^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N($R^{00}$)—, —N($R^{00}$)—CO—, —N($R^{00}$)—CO—N($R^{00}$)—, —OCH_2—, —CH_2O—, —SCH_2—, —CH_2S—, —CF_2O—, —OCF_2—, —CF_2S—, —SCF_2—, —CF_2CH_2—, —CH_2CF_2—, —CF_2CF_2—, —CH=N—, —N=CH—, —N=N—, —CH=$CR^0$—, —$CY^2$=$CY^3$—, —C≡C—, —CH=CH—CO—O—, —O—CO—CH=CH— or a single bond, $R^0$ in X" in each case independently denotes alkyl having 1 to 12 C atoms, $R^{00}$ in X" and Sp" in each case independently denotes alkyl having 1 to 12 C atoms, $R^{000}$ in X" and Sp" in each case independently denotes H or alkyl having 1 to 12 C atoms, and $Y^2$ and $Y^3$ in X" and Sp" each, independently of one another, denote H, F, Cl or CN.

X" is preferably —O—, —S—, —CO—, —COO—, —OCO—, —O—COO— or a single bond.

Typical spacer groups Sp" are, for example, a single bond, —$(CH_2)_{p1}$—, —O—$(CH_2)_{p1}$—, —$(CH_2CH_2O)_{q1}$—$CH_2CH_2$—, —$CH_2CH_2$—S—$CH_2CH_2$—, or —$(SiR^{00}R^{000}$—O)$_{p1}$—, in which p1 is an integer from 1 to 12, q1 is an integer from 1 to 3, and $R^{00}$ and $R^{000}$ have the meanings indicated above.

Particularly preferred groups -Sp"-X"— are —$(CH_2)_{p1}$—, —$(CH_2)_{p1}$—O—, —$(CH_2)_{p1}$—O—CO—, —$(CH_2)_{p1}$—O—CO—O—, in which p1 and q1 have the meanings indicated above.

Particularly preferred groups Sp" are, for example, in each case unbranched ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

The substances of the formula M generally and preferably do not contain an anchor group, i.e. do not contain a group —OH, —$NH_2$, —SH, —C(O)OH or —CHO.

Suitable and preferred (co)monomers for use in displays according to the invention are selected, for example, from the following formulae:

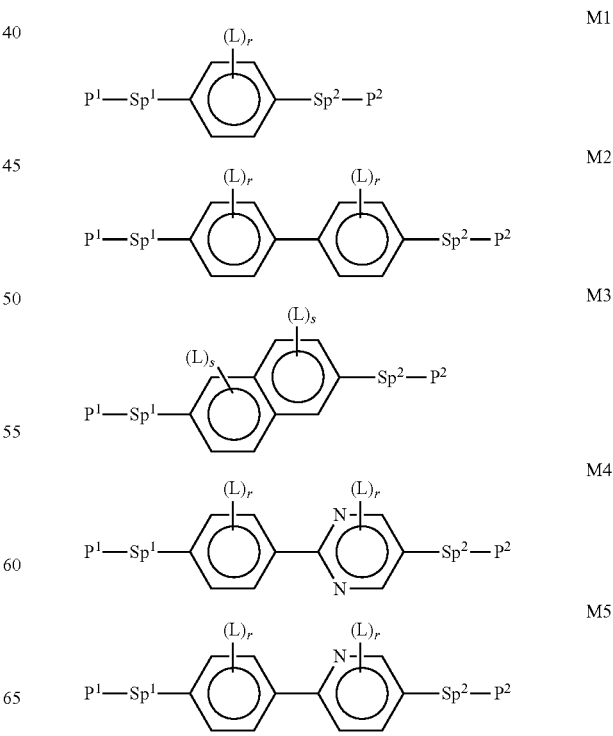

M6
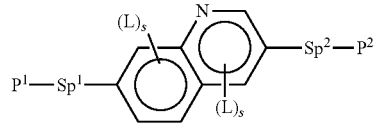
M7
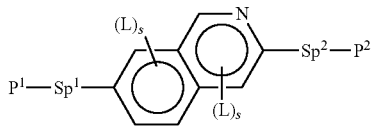
M8
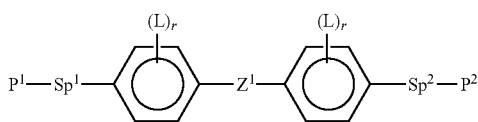
M9
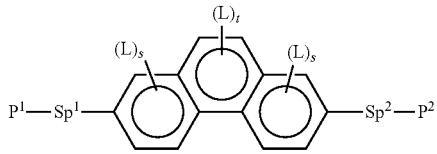
M10
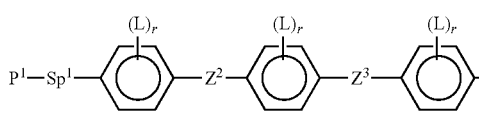
M11
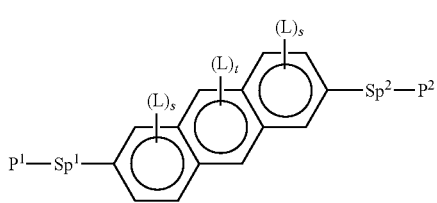
M12
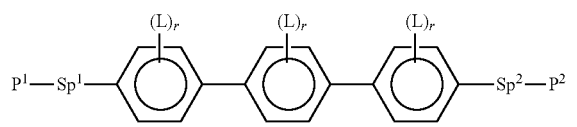
M13
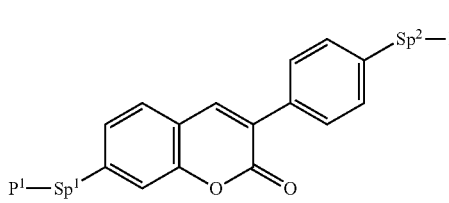
M14
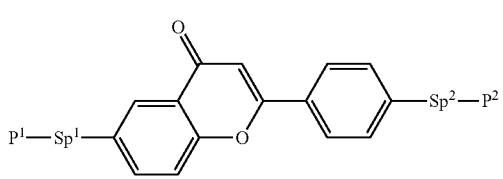
M15
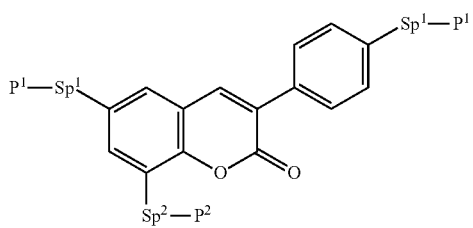
M16
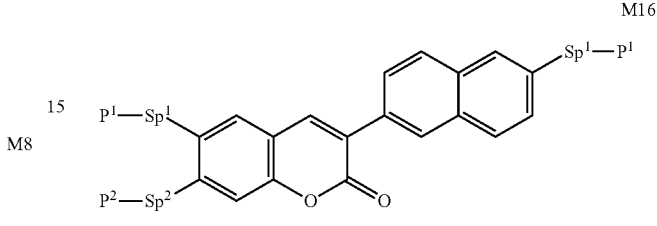
M17
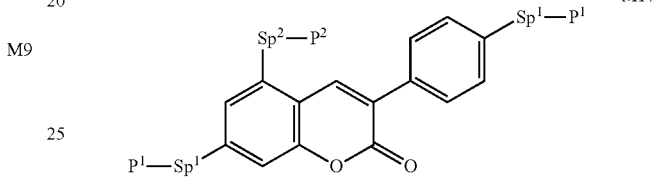
M18
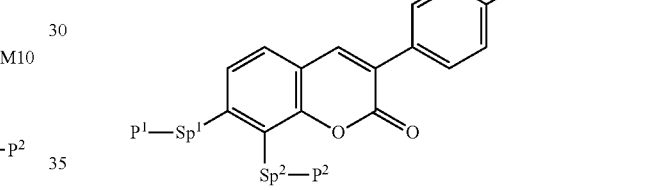
M19
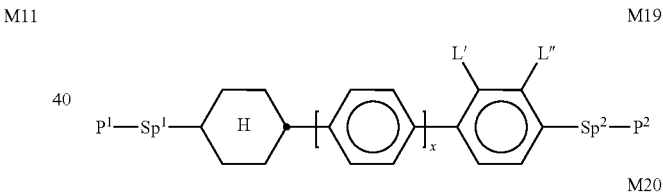
M20
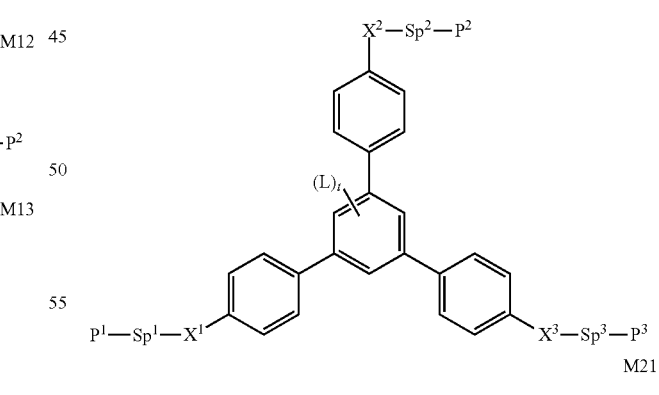
M21
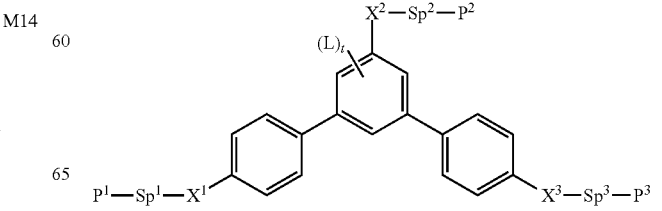

M22 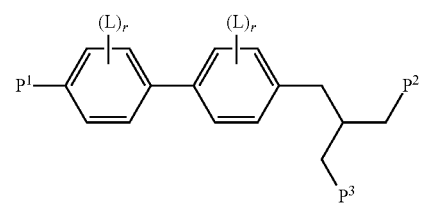

M23 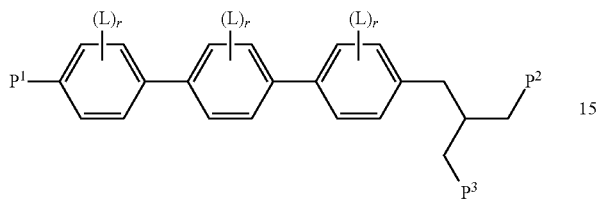

M24 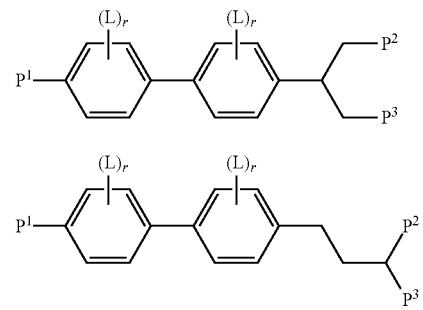

M25

M26 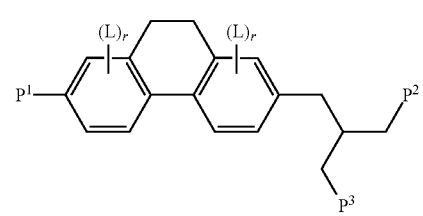

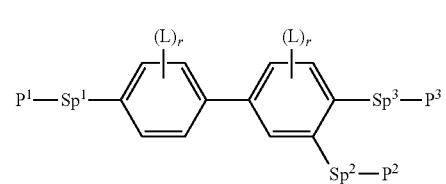

M27 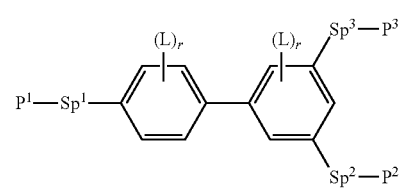

M28 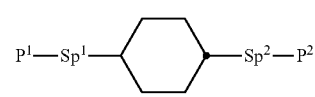

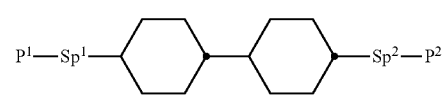

M29 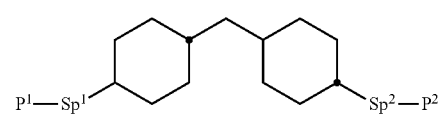

M30

M31

M32 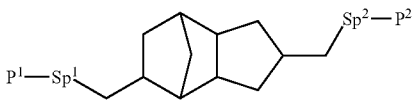

M33 

M34 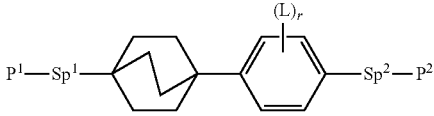

M35 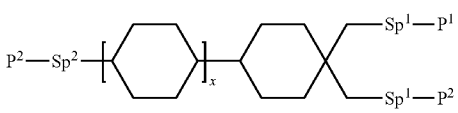

M36 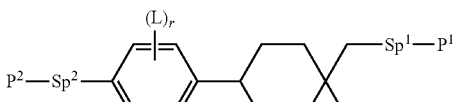

M37 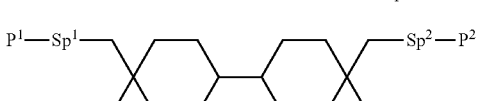

in which the individual radicals have the following meanings:

$P^1$, $P^2$ and $P^3$ each, independently of one another, denote a polymerisable group, preferably having one of the meanings indicated above and below for P, preferably an acrylate, methacrylate, ethylacrylate, fluoroacrylate, oxetane, vinyloxy or epoxide group, $Sp^1$, $Sp^2$ and $Sp^3$ each, independently of one another, denote a single bond or a spacer group, preferably having one of the meanings indicated above and below for formula M, and particularly preferably —(CH$_2$)$_{p1}$—, —(CH$_2$)$_{p1}$—O—, —(CH$_2$)$_{p1}$—CO—O— or —(CH$_2$)$_{p1}$—O—CO—O—, in which p1 is an integer from 1 to 12, and where the bonding to the adjacent ring in the last-mentioned groups takes place via the O atom, where, in addition, one or more of the radicals $P^1$-$Sp^1$-, $P^2$-$Sp^2$- and $P^3$-$Sp^3$- may denote a radical $R^{aa}$, with the proviso that at least one of the radicals $p^1$-$Sp^1$-, $P^2$-$Sp^2$- and $P^3$-$Sp^3$- present does not denote $R^{aa}$, $R^{aa}$ denotes H, F, Cl, CN or unbranched or branched alkyl having 1 to 25 C atoms, in which, in addition, one or more non-adjacent CH$_2$ groups may each be replaced, independently of one another, by C(R$^0$)=C(R$^{00}$)—, —C≡—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or $P^1$-$Sp^1$-, preferably unbranched or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), where —OH, —NH$_2$, —SH, —NHR, —C(O)OH and —CHO are not present in the group $R^{aa}$, R⁰, R⁰⁰ each, independently of one another and on each occurrence identically or differently, denote H or alkyl having 1 to 12 C atoms, $R^y$ and $R^z$ each, independently of one another, denote H, F, CH$_3$ or CF$_3$, $X^1$, $X^2$ and $X^3$ each, independently of one another, denote —CO—O—, O—CO— or a single bond, $Z^1$ in formula M8 denotes —O—, —CO—, —C($R^yR^z$)— or —CF$_2$CF$_2$—, $Z^2$ and $Z^3$ in formula M10 each, independently of one another, denote —CO—O—, —O—CO—, —CH$_2$O—, —OCH$_2$—, —CF$_2$O—, —OCF$_2$— or —(CH$_2$)$_n$—, where n is 2, 3 or 4, L on each occurrence in formulae M1-M37, identically or differently, denotes F, Cl, CN, SCN, SF$_5$ or unbranched or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, x denotes 0 or 1.

In the compounds of the formulae M1 to M37, the ring group

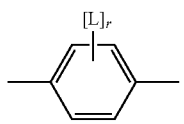

preferably denotes

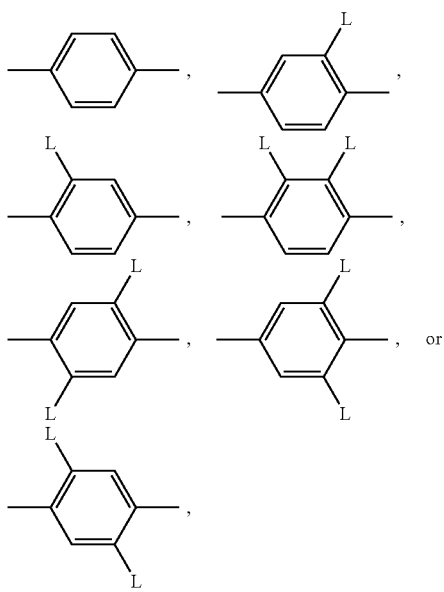

in which L, on each occurrence identically or differently, has one of the above meanings and preferably denotes F, Cl, CN, NO$_2$, CH$_3$, C$_2$H$_5$, C(CH$_3$)$_3$, CH(CH$_3$)$_2$, CH$_2$CH(CH$_3$) C$_2$H$_5$, OCH$_3$, OC$_2$H$_5$, COCH$_3$, COC$_2$H$_5$, COOCH$_3$, COOC$_2$H$_5$, CF$_3$, OCF$_3$, OCHF$_2$, OC$_2$F$_5$ or P-Sp-, particularly preferably F, Cl, CN, CH$_3$, C$_2$H$_5$, OCH$_3$, COCH$_3$, OCF$_3$ or P-Sp-, very particularly preferably F, Cl, CH$_3$, OCH$_3$, COCH$_3$ or OCF$_3$, in particular F or CH$_3$.

The LC medium or the polymerisable component preferably comprises one or more compounds selected from the group of the formulae M1-M28, particularly preferably from the group of the formulae M2-M15, of these particularly preferably from the group of the formulae M2, M3, M9, M14 and M15. The LC medium or the polymerisable component preferably comprises no compounds of the formula M10 in which $Z^2$ and $Z^3$ denote —(CO)O— or —O(CO)—.

Particular preference is thus given, for example, to the polymerisable compounds of the formula:

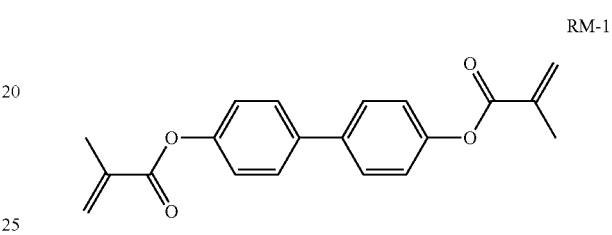

RM-1

For the production of PS displays, the polymerisable compounds are polymerised or crosslinked (if a polymerisable compound contains two or more polymerisable groups) by in-situ polymerisation in the LC medium between the substrates of the LC display, optionally with application of a voltage. The polymerisation can be carried out in one step. It is also possible firstly to carry out the polymerisation with application of a voltage in a first step in order to produce a pretilt angle, and subsequently, in a second polymerisation step, to polymerise or crosslink the compounds which have not fully reacted in the first step without an applied voltage ("end curing").

Suitable and preferred polymerisation methods are, for example, thermal or photopolymerisation, preferably photopolymerisation, in particular UV photo-polymerisation. One or more initiators can optionally also be added here. Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocure1173® (Ciba AG). If an initiator is employed, its proportion is preferably 0.001 to 5% by weight, particularly preferably 0.001 to 1% by weight.

The polymerisable component or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of the RMs or the polymerisable component, is preferably 10-10,000 ppm, particularly preferably 50-500 ppm.

Besides the self-alignment additives described above and the optional polymerisable compounds (M) described above, the LC media for use in the LC displays according to the invention comprise a low-molecular-weight, unpolymerisable component (LC mixture, "host mixture") comprising one or more, preferably two or more, low-molecular-weight (i.e. monomeric or unpolymerised, unpolymerisable) compounds. The latter are stable or unreactive with respect to a polymerisation reaction under the conditions used for the polymerisation of the polymerisable compounds. In principle, any dielectrically negative or positive LC mixture which is suitable for use in conventional VA and VA-IPS displays is suitable as host mixture. The proportion of the host mixture for liquid-crystal displays is generally 95% by weight or more, preferably 97% by weight or more Suitable LC mixtures are known to the person skilled in the art and are described in the literature. LC media for VA displays having negative dielectric anisotropy are described, for example, in EP 1 378 557 A1 or WO 2013/004372.

Suitable LC mixtures having positive dielectric anisotropy which are suitable for LCDs and especially for IPS displays are known, for example, from JP 07-181 439 (A), EP 0 667 555, EP 0 673 986, DE 195 09 410, DE 195 28 106, DE 195 28 107, WO 96/23 851 and WO 96/28 521.

Preferred embodiments of the liquid-crystalline medium having negative dielectric anisotropy according to the invention are indicated below:

The LC medium preferably additionally comprises one or more compounds selected from the group of the compounds of the formulae A, B and C, A
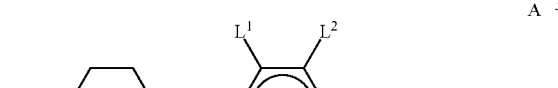

B
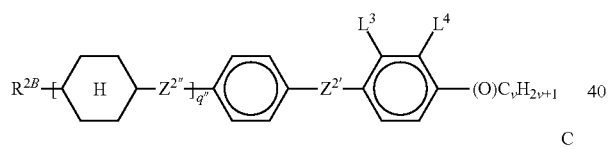

C
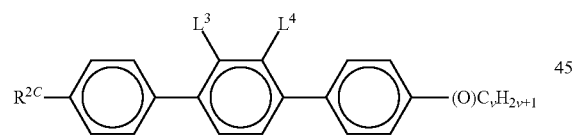

in which
$R^{2A}$, $R^{2B}$ and $R^{2C}$ each, independently of one another, denote H, an alkyl radical having up to 15 C atoms which is unsubstituted, monosubstituted by CN or $CF_3$ or at least monosubstituted by halogen, where, in addition, one or more $CH_2$ groups in these radicals may be replaced by —O—, —S—,

—C≡C—, —CH=CH—, —$CF_2$O—, —O$CF_2$—, —OC—O— or —O—CO— in such a way that O atoms are not linked directly to one another,
$L^{1-4}$ in formulae A, B and C, in each case, independently of one another, denote F, Cl, $CF_3$ or $CHF_2$, $Z^{2"}$ and $Z^{2'}$ each, independently of one another, denote a single bond, —$CH_2CH_2$—, —CH=CH—, —$CF_2$O—, —O$CF_2$—, —$CH_2$O—, —O$CH_2$—, —COO—, —OCO—, —$C_2F_4$—, —CF=CF—, —CH=CH$CH_2$O—, p denotes 1 or 2, preferably 1, q" denotes 0 or 1, (O) denotes —O— or a single bond, and v denotes 1 to 6.

In the compounds of the formulae A and B, $Z^2$ can have identical or different meanings. In the compounds of the formula B, $Z^2$ and $Z^{2'}$ can have identical or different meanings. In the compounds of the formulae A, B and C, $R^{2A}$, $R^{2B}$ and $R^{2C}$ each preferably denote alkyl having 1-6 C atoms, in particular $CH_3$, $C_2H_5$, n-$C_3H_7$, n-$C_4H_9$, n-$C_5H_{11}$.

In the compounds of the formulae A and B, $L^1$, $L^2$, $L^3$ and $L^4$ preferably denote $L^1=L^2=F$ and $L^3=L^4=F$, furthermore $L^1=F$ and $L^2=Cl$, $L^1=Cl$ and $L^2=F$, $L^3=F$ and $L^4=Cl$, $L^3=Cl$ and $L^4=F$. $Z^2$ and $Z^{2'}$ in the formulae A and B preferably each, independently of one another, denote a single bond, furthermore a —$C_2H_4$— bridge.

If $Z^2$=—$C_2H_4$— in the formula B, $Z^{2'}$ is preferably a single bond, or if $Z^{2'}$=—$C_2H_4$—, $Z^2$ is preferably a single bond. In the compounds of the formulae A and B, (O)$C_vH_{2v+1}$ preferably denotes O$C_vH_{2v+1}$, furthermore $C_vH_{2v+1}$. In the compounds of the formula C, (O)$C_vH_{2v+1}$ preferably denotes $C_vH_{2v+1}$. In the compounds of the formula C, $L^3$ and $L^4$ preferably each denote F.

Preferred compounds of the formulae A, B and C are, for example:

A-1
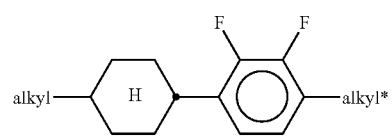

A-2
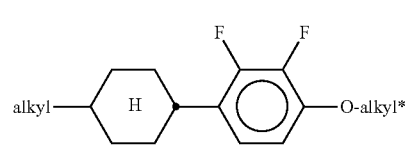

A-7
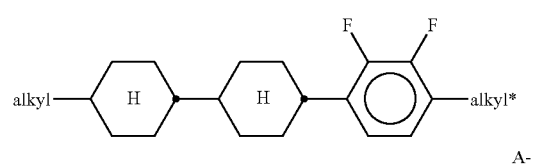

A-8
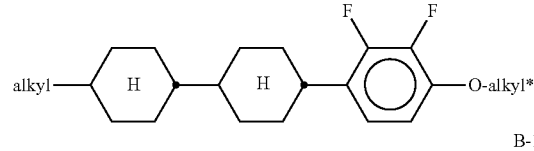

B-1
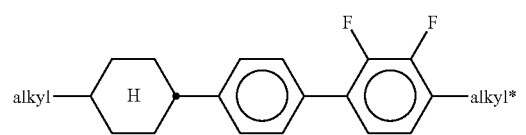

-continued

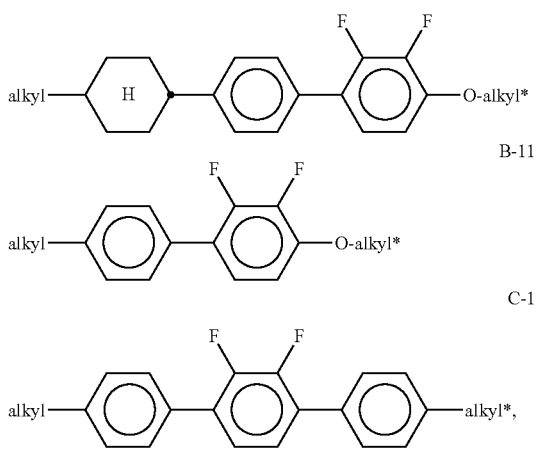

in which alkyl and alkyl* each, independently of one another, denote an unbranched alkyl radical having 1-6 C atoms.

The LC medium preferably additionally comprises one or more compounds of the formula D,

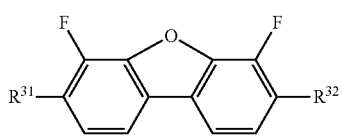

in which
$R^{31}$, $R^{32}$, independently of one another, denote an unsubstituted alkyl radical having 1 to 7 C atoms, preferably an n-alkyl radical, particularly preferably having 2 to 5 C atoms, or an unsubstituted alkoxy radical having 2 to 7 C atoms, particularly preferably having 2 to 5 C atoms, where preferably at least one of the radicals $R^{31}$ and $R^{32}$ denotes alkoxy. The LC medium preferably has a Δε of −1.5 to −8.0, in particular of −2.5 to −6.0.

In a further preferred embodiment, the medium comprises one or more compounds of the formulae D-1 to D-3

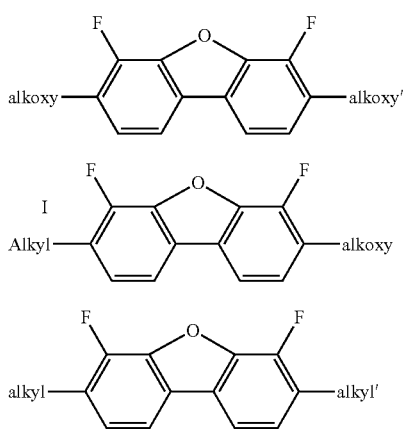

in which
alkyl, alkyl' denote alkyl having 1 to 7 C atoms, preferably having 2-5 C atoms, and
alkoxy, alkoxy denote alkoxy having 1 to 7 C atoms, preferably having 2 to 5 C atoms.

The medium preferably comprises one or more compounds of the formula E:

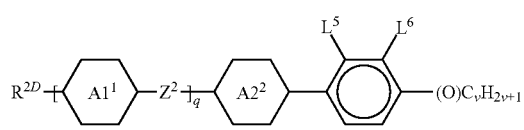

in which
$A1^1$, $A2^2$ independently denote a ring group selected from the formulae

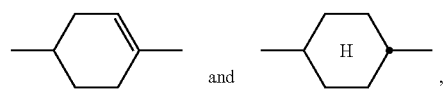

where formula D contains at least one group

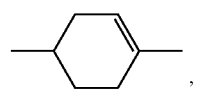

$R^{2D}$ independently denotes H, an alkyl radical having up to 15 C atoms which is unsubstituted, monosubstituted by CN or $CF_3$ or at least monosubstituted by halogen, where, in addition, one or more $CH_2$ groups in these radicals may be replaced by —O—, —S—,

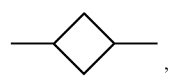

—C≡—, —$CF_2$O—, —O$CF_2$—, —OC—O— or —O—CO— in such a way that O atoms are not linked directly to one another,
$L^5$, $L^6$ in each case, independently of one another, denote F, Cl, $CF_3$ or $CHF_2$,
$Z^2$ of formula E independently denotes a single bond, —$CH_2CH_2$—, —CH=CH—, —$CF_2$O—, —O$CF_2$—, —$CH_2$O—, —O$CH_2$—, —COO—, —OCO—, —$C_2F_4$—, —CF=CF— or —CH=CH$CH_2$O—,
q denotes 0 or 1,
(O) denotes —O— or a single bond, and
v denotes 1 to 6.

The values of the birefringence Δn in the liquid-crystal mixture are generally between 0.07 and 0.16, preferably between 0.08 and 0.12. The rotational viscosity $γ_1$ at 20° C. before the polymerisation is preferably ≤165 mPa·s, in particular ≤140 mPa·s.

Preferred embodiments of the liquid-crystalline medium according to the invention having negative or positive dielectric anisotropy are indicated below:

LC medium which additionally comprises one or more compounds of the formulae II and/or III:

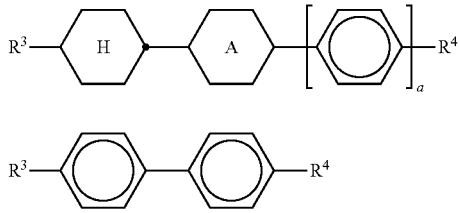

in which ring A denotes 1,4-phenylene or trans-1,4-cyclohexylene, a is 0 or 1,

R³ in formulae II and III, in each case, independently of one another, denotes alkyl having 1 to 9 C atoms or alkenyl having 2 to 9 C atoms, preferably alkenyl having 2 to 9 C atoms, and R⁴ in formulae II and III, in each case, independently of one another, denotes an unsubstituted or halogenated alkyl radical having 1 to 12 C atoms, where, in addition, one or two non-adjacent CH₂ groups may be replaced by —O—, —CH=CH—, —CH=CF—, —(CO)—, —O(CO)— or —(CO)O— in such a way that O atoms are not linked directly to one another, and preferably denotes alkyl having 1 to 12 C atoms or alkenyl having 2 to 9 C atoms.

The compounds of the formula II are preferably selected from the group consisting of the following formulae:

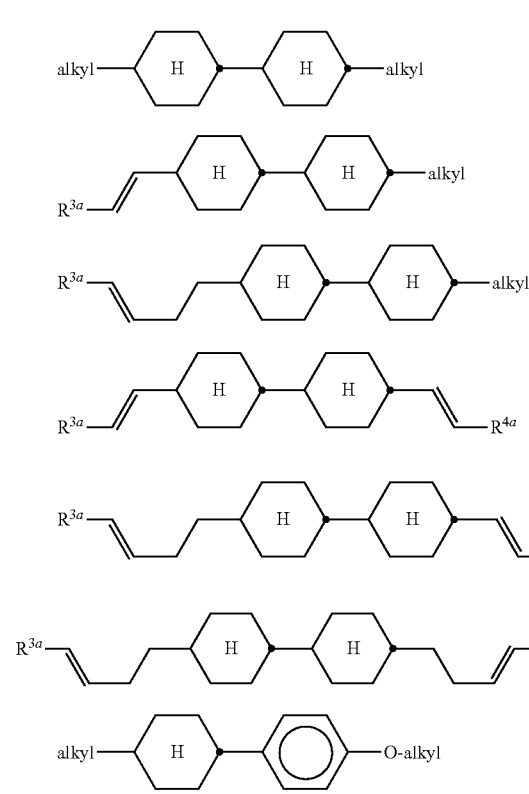

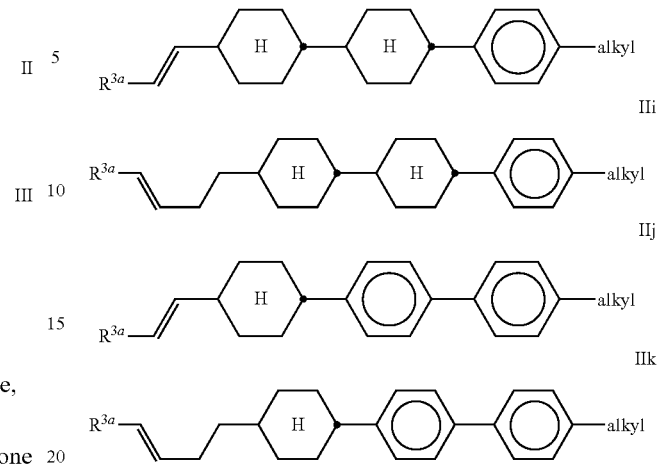

in which $R^{3a}$ and $R^{4a}$ each, independently of one another, denote H, CH₃, C₂H₅ or C₃H₇, and "alkyl" in each case indeendently denotes an unbranched alkyl group having 1 to 8, preferably 1, 2, 3, 4 or 5, C atoms. Particular preference is given to compounds of the formulae IIa, IIb, IIg and IIh, in particular those in which $R^{3a}$ denotes H or CH₃, preferably H, and compounds of the formula IId, in particular those in which $R^{3a}$ and $R^{4a}$ denote H, CH₃ or C₂H₅.

Preferred embodiments of the liquid-crystalline medium according to the invention having positive dielectric anisotropy are given below:

The LC medium preferably comprises one or more compounds of the formulae IV and V:

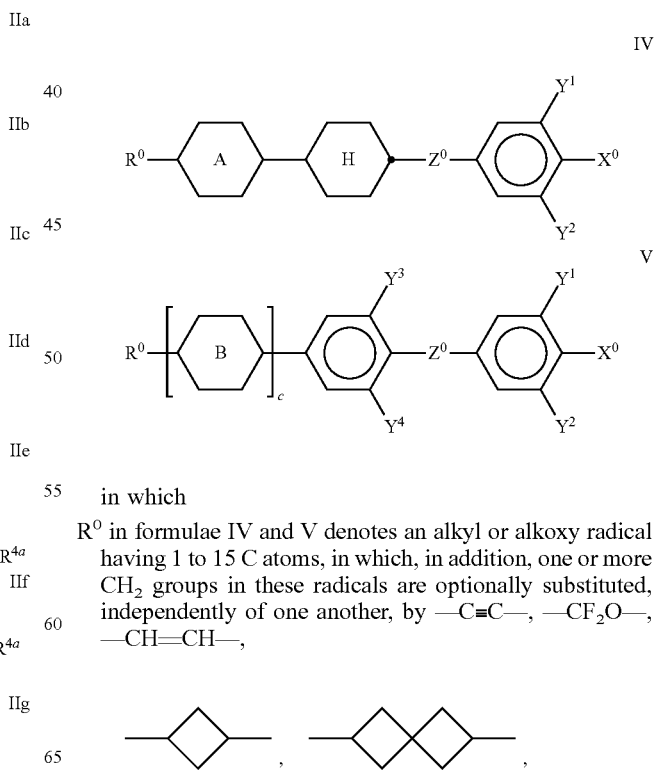

in which

R⁰ in formulae IV and V denotes an alkyl or alkoxy radical having 1 to 15 C atoms, in which, in addition, one or more CH₂ groups in these radicals are optionally substituted, independently of one another, by —C≡C—, —CF₂O—, —CH=CH—, —O—, —(CO)O— or —O(CO)— in such a way that O atoms are not linked directly to one another, and in which, in addition, one or more H atoms may optionally be replaced by halogen, ring A in formula IV denotes

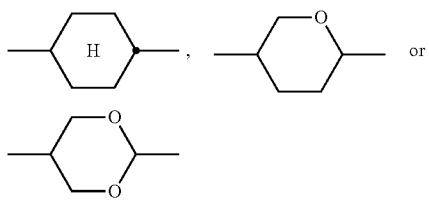

ring B in formula V, independently of one another, denotes 1,4-phenylene, optionally substituted by one or two F or Cl,

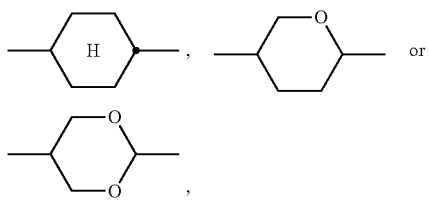

$X^0$ in formulae IV and V denotes F, Cl, CN, $SF_5$, SCN, NCS, a halogenated alkyl group, a halogenated alkenyl group, a halogenated alkoxy group or a halogenated alkenyloxy group, each having up to 6 C atoms, $Y^{1-4}$ in formulae IV and V, in each case, independently of one another, denote H or F, $Z^0$ in formulae IV and V denotes —$CF_2O$—, —(CO)O— or a single bond, and c denotes 0, 1 or 2, preferably 1 or 2,

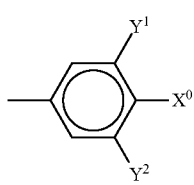

preferably denotes

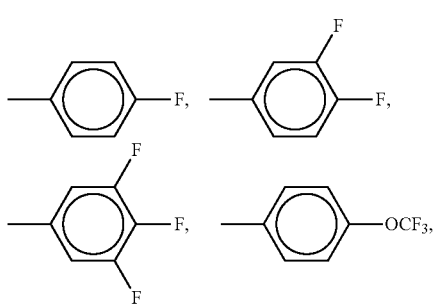

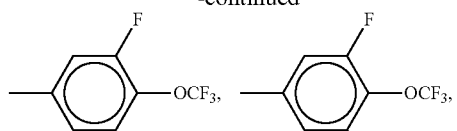

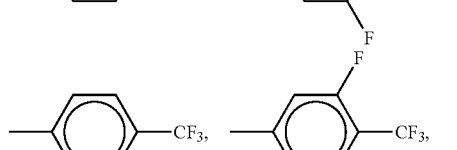

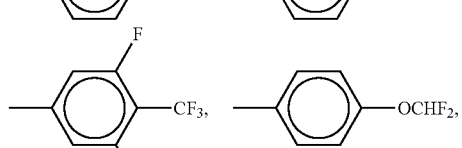

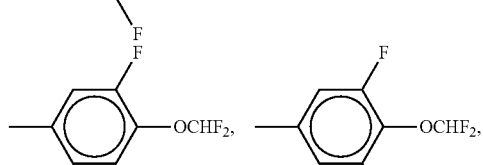

$R^0$ in formulae IV and V preferably denotes unbranched alkyl or alkenyl having 2 to 7 C atoms, $X^0$ in formulae IV and V preferably denotes F, $OCF_3$, Cl or $CF_3$, in particular F.

The nematic phase of the dielectrically negative or positive LC medium in accordance with the invention preferably has a nematic phase in a temperature range from 10° C. or less to 60° C. or more, particularly preferably from 0 or less to 70° C. or more.

For the purposes of the present application, the two formulae for substituted benzene rings

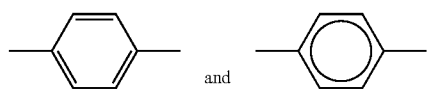

are equivalent. 1,4-substituted cyclohexane is represented by

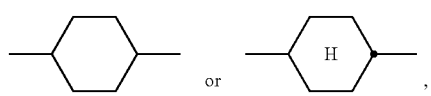

which is preferably in the 1,4-trans-configuration.

A phenylene ring of the formula

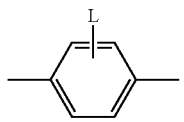

which is substituted by the group L is substituted by a group L at precisely one position as desired. Correspondingly, the substituent $(L)_r$ stands for a number r of substituents L at various free positions.

In the present invention and in particular in the following examples, the structures of the mesogenic compounds are indicated by abbreviations, which are also called acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote unbranched alkyl or alkenyl respectively, preferably 1-E-alkenyl, in each case having n, m or l C atoms respectively. Table A shows the codes used for the ring elements of the core structures of the compounds, while Table B shows the linking groups. Table C indicates the meanings of the codes for the end groups of the left-hand or right-hand side. The acronyms are composed of the codes for the ring elements with optional linking groups, followed by a first hyphen and the codes for the left-hand end group, and a second hyphen and the codes for the right-hand end group. Table D shows illustrative structures of compounds with their respective abbreviations.

TABLE A

| Ring elements | |
|---|---|
| C | cyclohexane |
| D | 1,3-dioxane |
| A | tetrahydropyran |
| G | 2-fluoro-phenylene |
| U | 2,3-difluoro-phenylene |
| M | pyrimidine |
| N | pyridine |
| Y | 2,3-difluoro-phenylene |
| P(F, Cl)Y | 2-fluoro-3-chloro-phenylene |
| Np | naphthalene |
| P | phenylene |
| Dl | 1,3-dioxane |
| Al | tetrahydropyran |
| Gl | 3-fluoro-phenylene |
| Ul | 2,3,4-trifluoro-phenylene |
| Ml | pyrimidine |
| Nl | pyridine |

TABLE A-continued
| Ring elements | |
|---|---|
| P(Cl, F)Y | 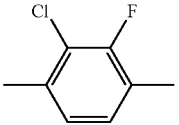 |
| dH | 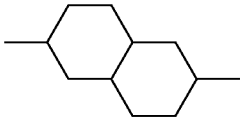 |
| n3f | 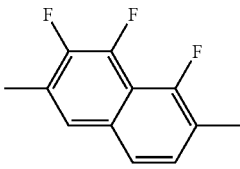 |
| tH | 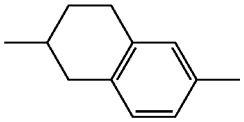 |
| tH2f | 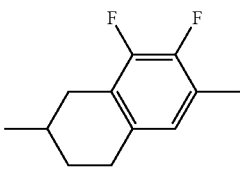 |
| o2f | 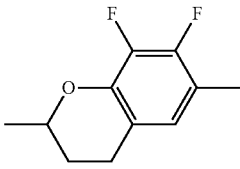 |
| dh | 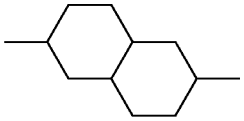 |
| K | 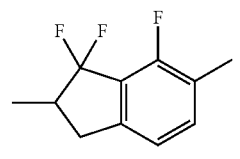 |
| L |  |
| F | 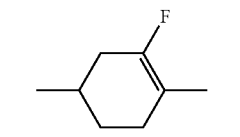 |
TABLE A-continued
| Ring elements | |
|---|---|
| Nf | 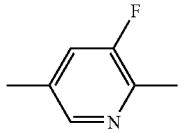 |
| n3fl | 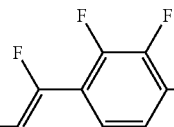 |
| tHl | 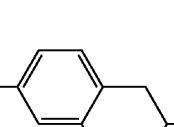 |
| tH2fl | 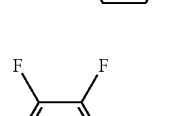 |
| o2fl | 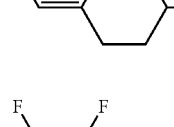 |
| B | 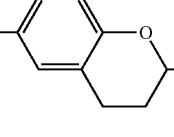 |
| Kl | 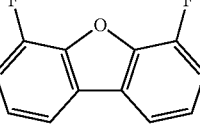 |
| Li | 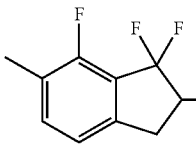 |
| Fl | 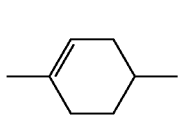 |

TABLE A-continued

Ring elements

Nfl

[Structure: 3-fluoro-2,5-dimethylpyridine ring]

TABLE B

Bridging members

| | | | | |
|---|---|---|---|---|
| E | —$CH_2$—$CH_2$— | | | |
| V | —CH=CH— | | | |
| T | —C≡C— | | | |
| W | —$CF_2$—$CF_2$— | | | |
| B | —CF=CF— | | | |
| Z | —CO—O— | ZI | —O—CO— |
| X | —CF=CH— | XI | —CH=CF— |
| O | —$CH_2$—O— | OI | —O—$CH_2$— |
| Q | —$CF_2$—O— | QI | —O—$CF_2$— |

TABLE C

End groups

| On the left individually or in combination | | On the right individually or in combination | |
|---|---|---|---|
| -n- | $C_nH_{2n+1}$— | -n | —$C_nH_{2n+1}$ |
| -nO- | $C_nH_{2n+1}$—O— | -nO | —O—$C_nH_{2n+1}$ |
| -V- | $CH_2$=CH— | -V | —CH=$CH_2$ |
| -nV- | $C_nH_{2n+1}$—CH=CH— | -nV | —$C_nH_{2n}$—CH=$CH_2$ |
| -Vn- | $CH_2$=CH—$C_nH_{2n}$— | -Vn | —CH=CH—$C_nH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |
| -TO- | $CF_3O$— | -OT | —$OCF_3$ |
| -A- | H—C≡C— | -A | —C≡C—H |
| -nA- | $C_nH_{2n+1}$—C≡C— | -An | —C≡C—$C_nH_{2n+1}$ |
| -NA- | N≡C—C≡C— | -AN | —C≡C—C≡N |
| | | -OXF | —O—CH=CF2 |

| On the left only in combination | | On the right only in combination | |
|---|---|---|---|
| -...n...- | —$C_nH_{2n}$— | -...n... | —$C_nH_{2n}$— |
| -...M...- | —CFH— | -...M... | —CFH— |
| -...D...- | —$CF_2$— | -...D... | —$CF_2$— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— |
| | | -...X... | —CH=CF— | in which n and m are each integers and the three dots "..." are placeholders for other abbreviations from this table.

The following table shows illustrative structures together with their respective abbreviations. These are shown in order to demonstrate the meaning of the rules for the abbreviations. Besides the compounds of the formula I, the mixtures according to the invention preferably comprise one or more compounds of the compounds mentioned below.

The following abbreviations are used:
(n, m and z, independently of one another, in each case an integer, preferably 1 to 6).

TABLE D

Illustrative structures

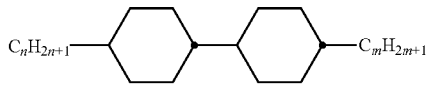

CC-n-m

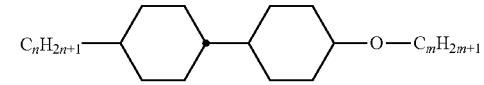

CC-n-Om

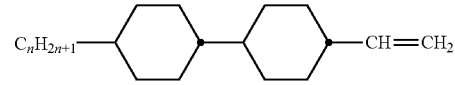

CC-n-V

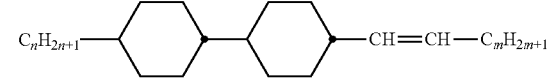

CC-n-Vm

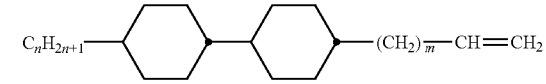

CC-n-mV

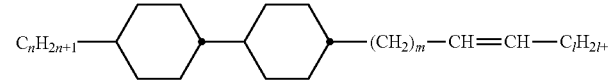

CC-n-mVl

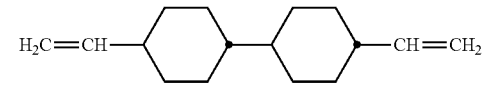

CC-V-V

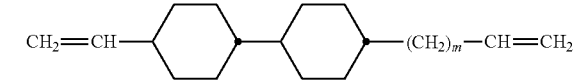

CC-V-mV

TABLE D-continued
Illustrative structures
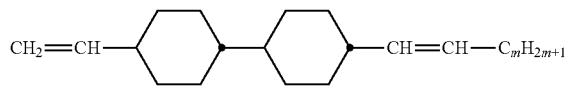
CC-V-Vm
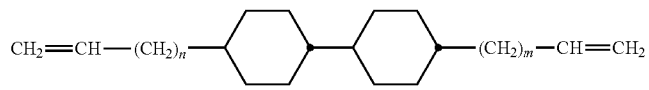
CC-Vn-mV
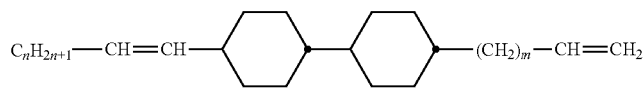
CC-nV-Vm
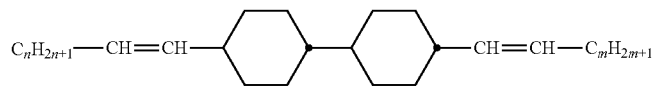
CC-nV-Vm
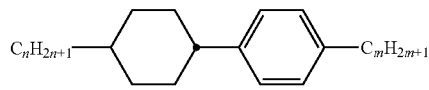
CP-n-m
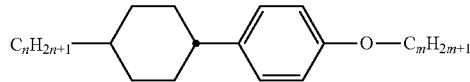
CP-n-Om
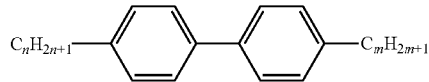
PP-n-m
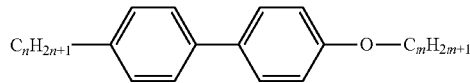
PP-n-Om
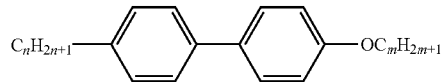
PP-n-Om
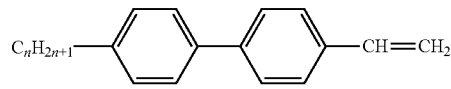
PP-n-V TABLE D-continued
Illustrative structures
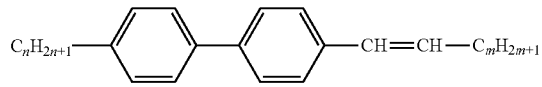
PP-n-Vm
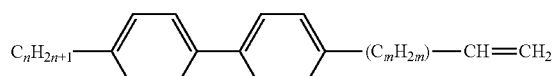
PP-n-mV
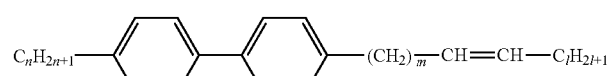
PP-n-mVl
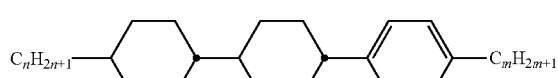
CCP-n-m
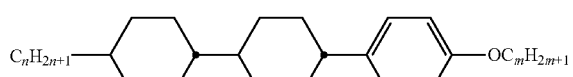
CCP-n-Om
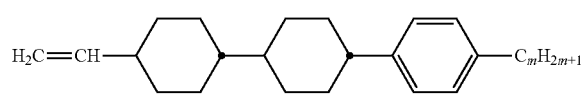
CCP-V-m
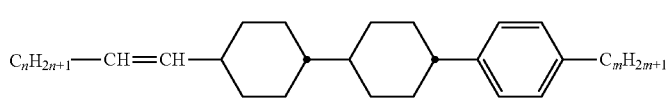
CCP-nV-m
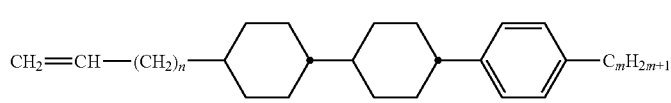
CCP-Vn-m
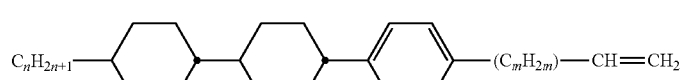
CCP-n-mV TABLE D-continued
Illustrative structures
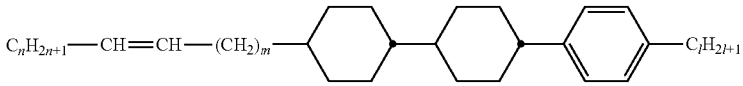
CCP-nVm-l
CPP-n-m
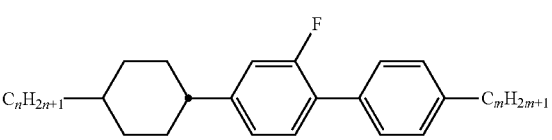
CGP-n-m
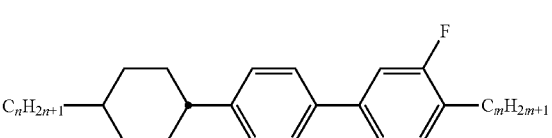
CPG-n-m
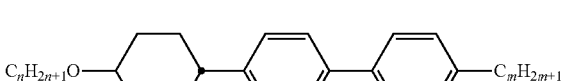
CPP-nO-m
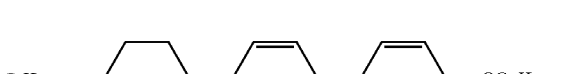
CPP-n-Om
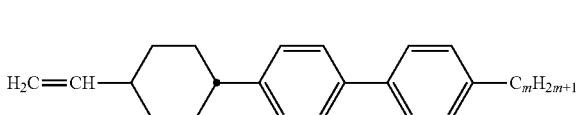
CPP-V-m
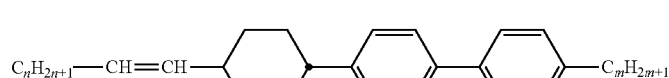
CPP-nV-m
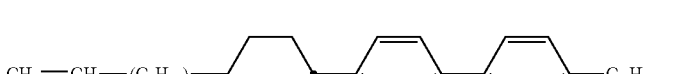
CPP-Vn-m TABLE D-continued
Illustrative structures
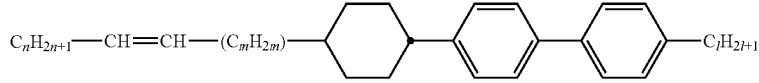
CPP-nVm-l
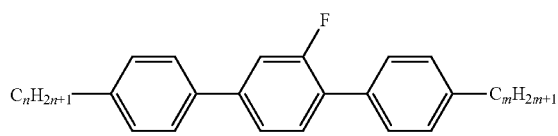
PGP-n-m
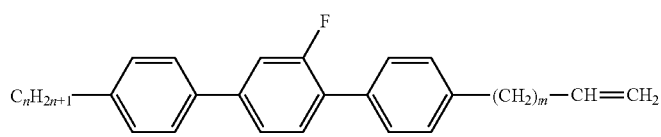
PGP-n-mV
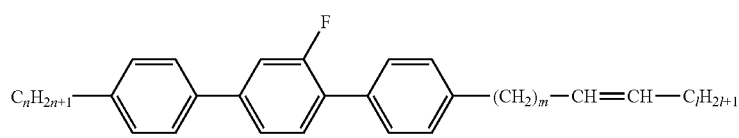
PGP-n-mVl
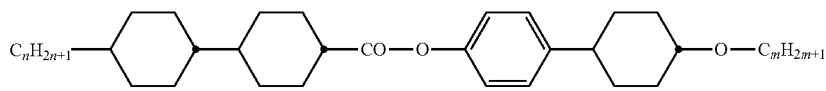
CCZPC-n-m
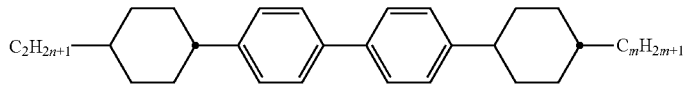
CPPC-n-m
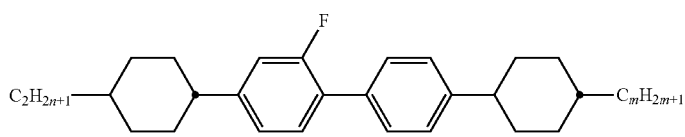
CGPC-n-m
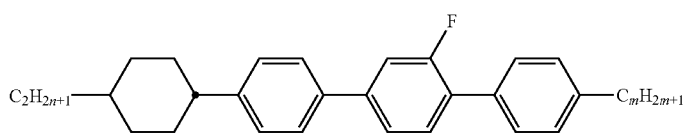
CPGP-n-m TABLE D-continued
Illustrative structures
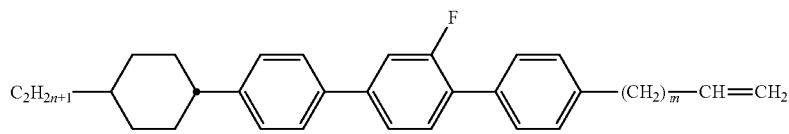
CPGP-n-mV
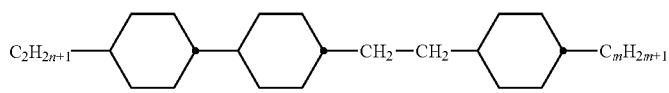
CCEC-n-m
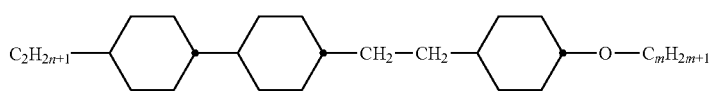
CCEC-n-Om
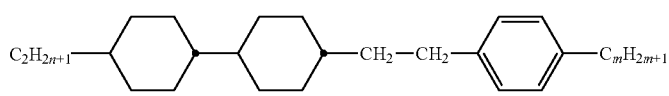
CCEP-n-m
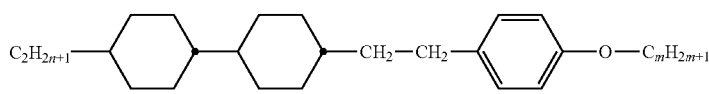
CCEP-n-Om
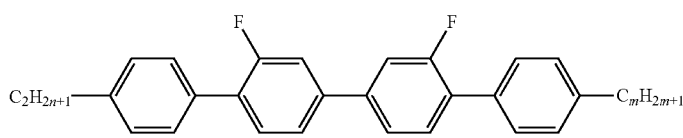
PGIGP-n-m
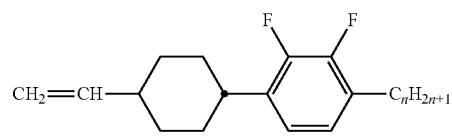
CY-V-n
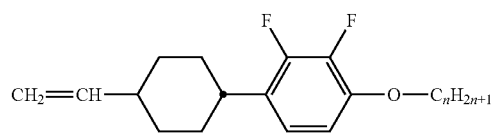
CY-V-On TABLE D-continued
Illustrative structures
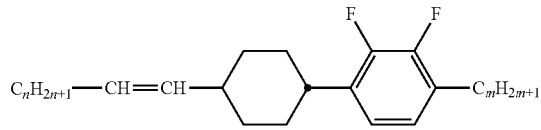
CY-nV-m
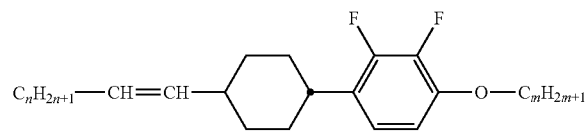
CY-nV-Om
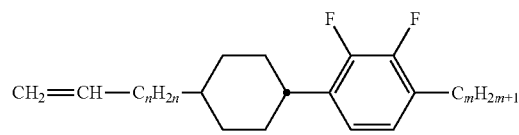
CY-Vn-m
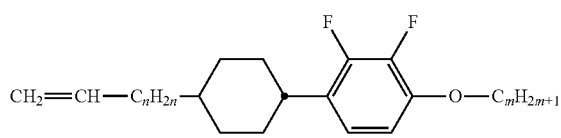
CY-Vn-Om
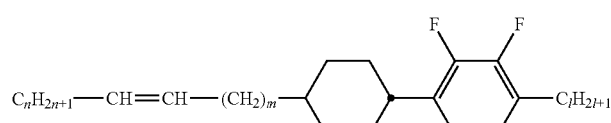
CY-nVm-l
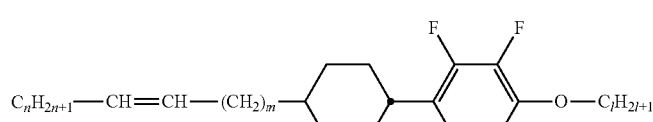
CY-nVm-Ol
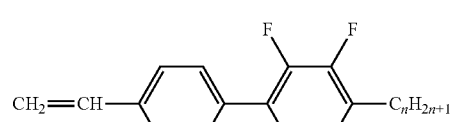
PY-V-n TABLE D-continued
Illustrative structures
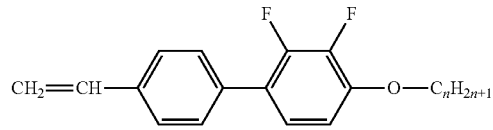
PY-V-On
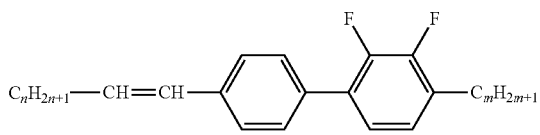
PY-nV-m
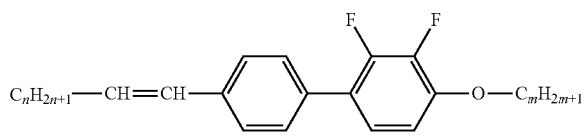
PY-nV-Om
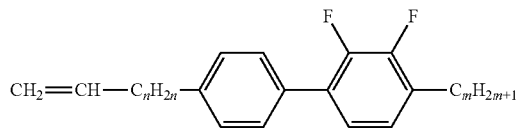
PY-Vn-m
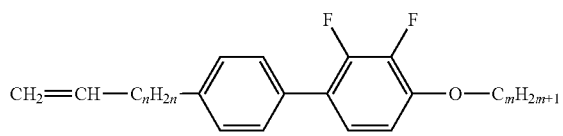
PY-Vn-Om
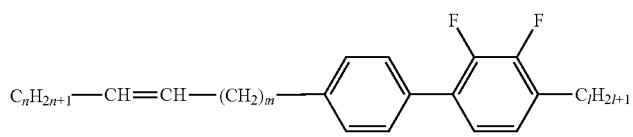
PY-nV-m-l
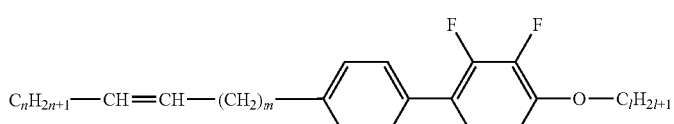
PY-nV-m-Ol TABLE D-continued
Illustrative structures
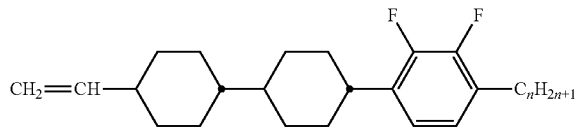
CCY-V-n
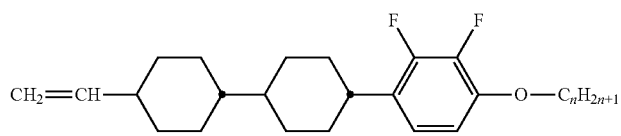
CCY-V-On
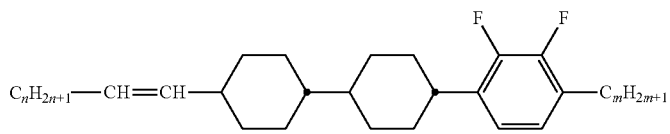
CCY-nV-m
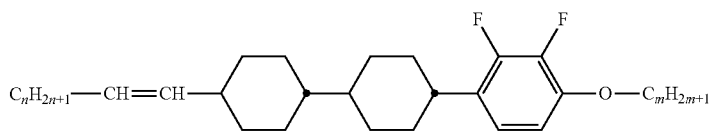
CCCY-nV-Om
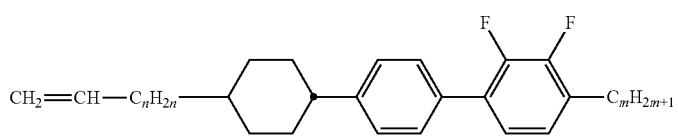
CCY-Vn-m
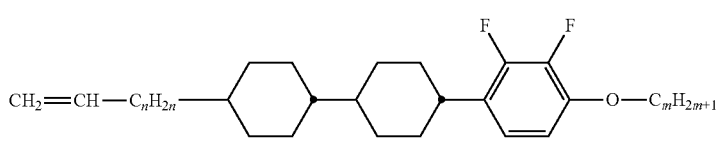
CCY-Vn-Om
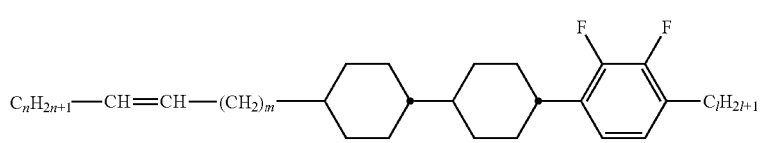
CCY-nVm-l TABLE D-continued
Illustrative structures
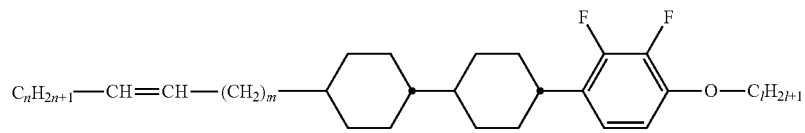
CCY-nVm-Ol
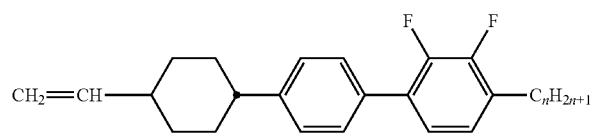
CPY-V-n
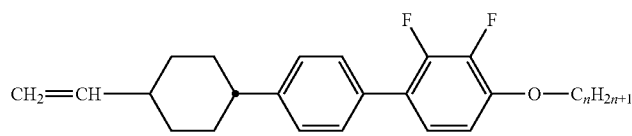
CPY-V-On
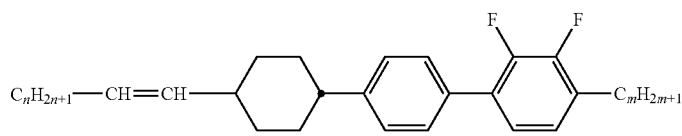
CPY-nV-m
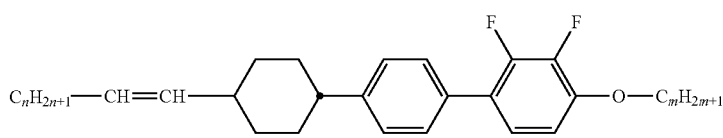
CPY-nV-Om
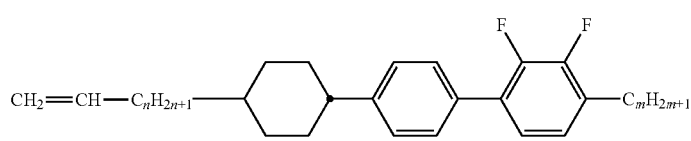
CPY-Vn-m
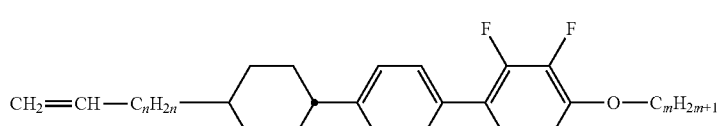
CPY-Vn-Om TABLE D-continued
Illustrative structures
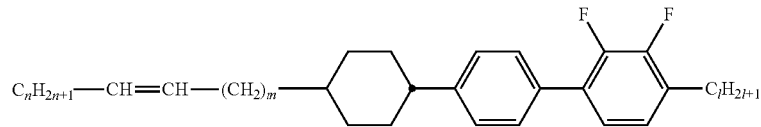
CPY-nVm-l
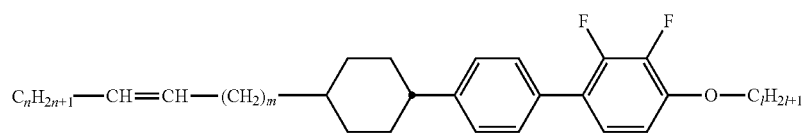
CPY-nVm-Ol
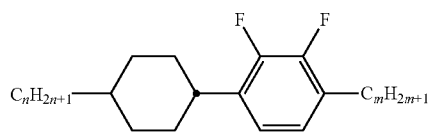
CY-n-m
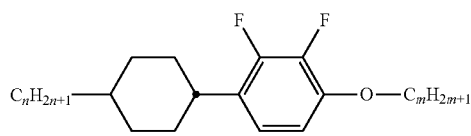
CY-n-Om
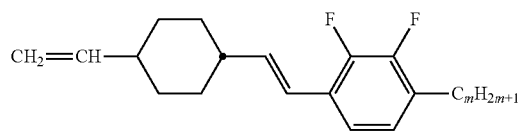
CVY-n-m
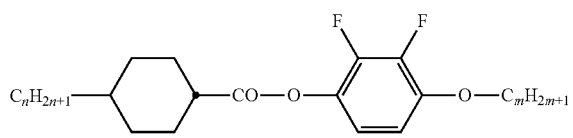
CZY-n-Om
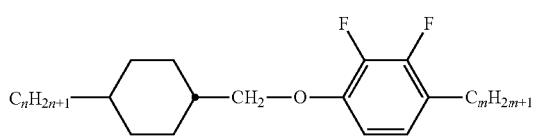
COY-n-m TABLE D-continued
Illustrative structures
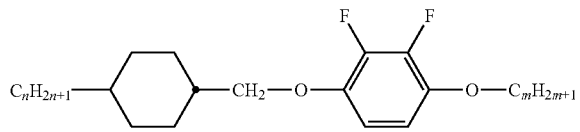
COY-n-Om
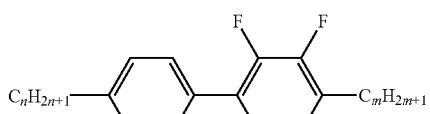
PY-n-m
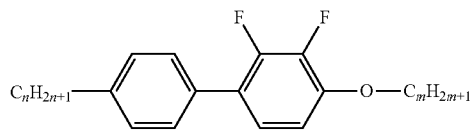
PY-n-Om
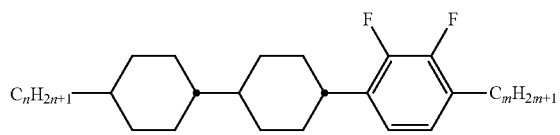
CCY-n-m
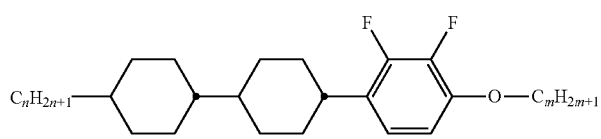
CCY-n-Om
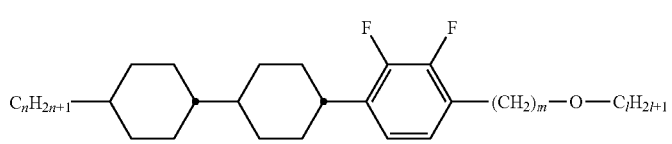
CCY-n-mOl
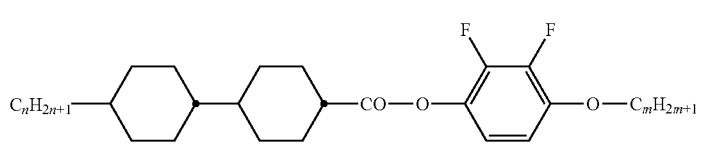
CCZY-n-Om TABLE D-continued
Illustrative structures
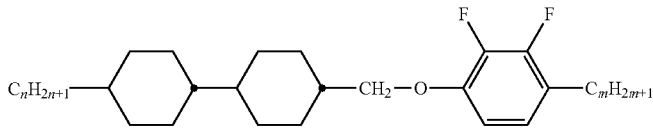
CCOY-n-m
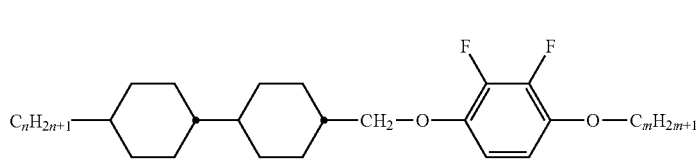
CCOY-n-Om
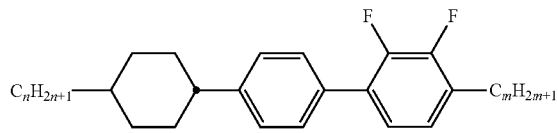
CPY-n-m
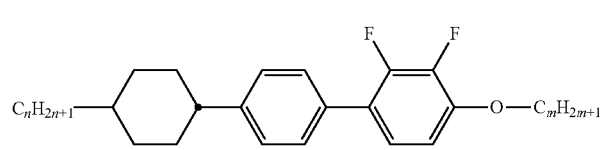
CPY-n-Om
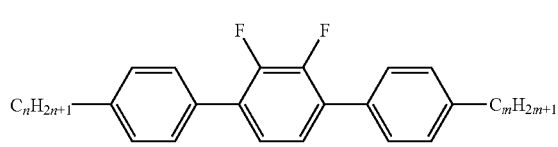
PYP-n-m
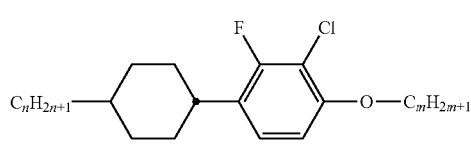
CP(F,Cl)-n-Om
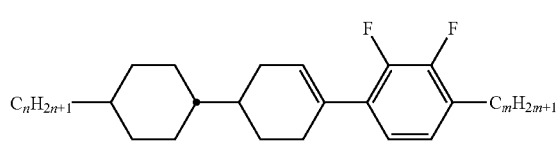
CLY-n-m TABLE D-continued
Illustrative structures
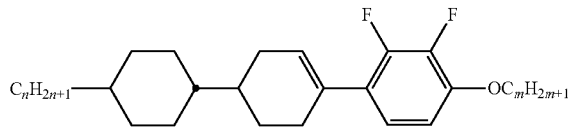
CLY-n-Om
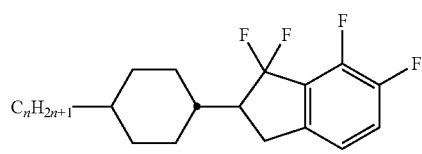
CK-n-F
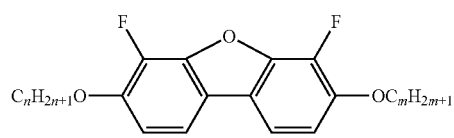
B-nO-Om
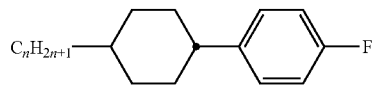
CP-n-F
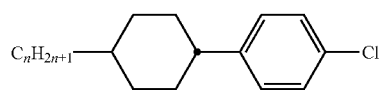
CP-n-CL
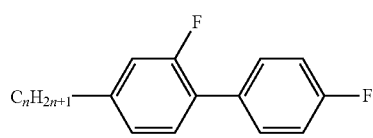
GP-n-F
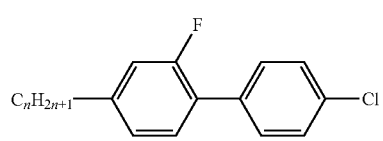
GP-n-CL
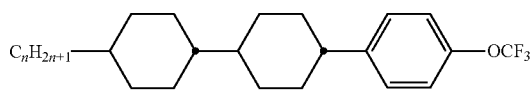
CCP-n-OT TABLE D-continued
Illustrative structures
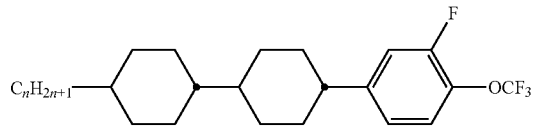
CCG-n-OT
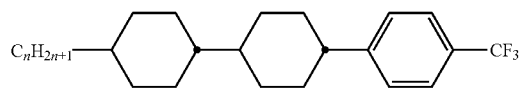
CCP-n-T
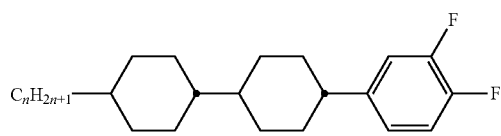
CCG-n-F
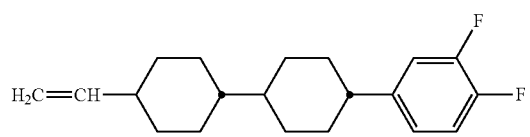
CCG-V-F
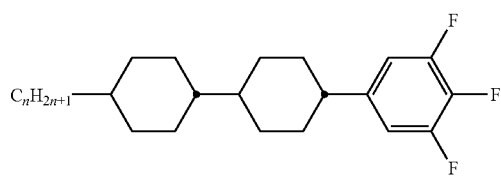
CCU-n-F
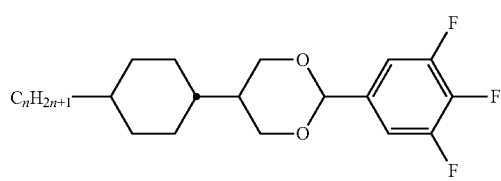
CDU-n-F
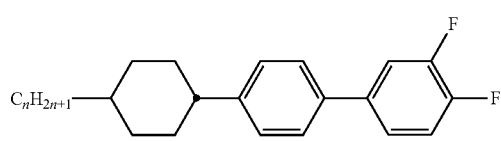
CPG-n-F TABLE D-continued
Illustrative structures
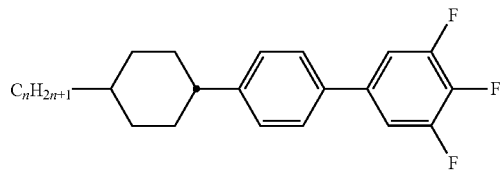
CPU-n-F
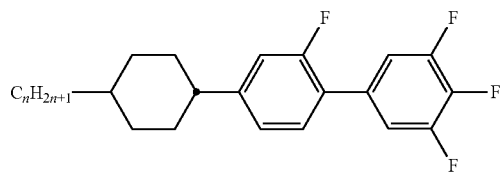
CGU-n-F
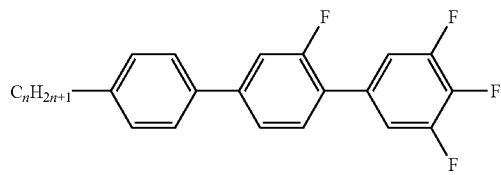
PGU-n-F
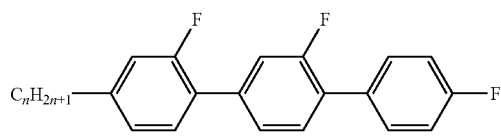
GGP-n-F
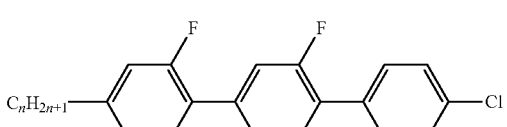
GGP-n-CL
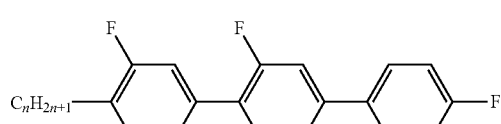
PGIGI-n-F
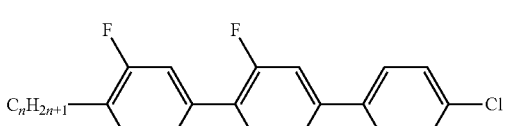
PGIGI-n-CL TABLE D-continued
Illustrative structures
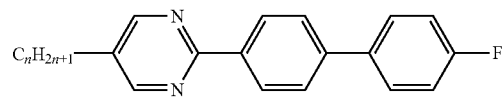
MPP-n-F
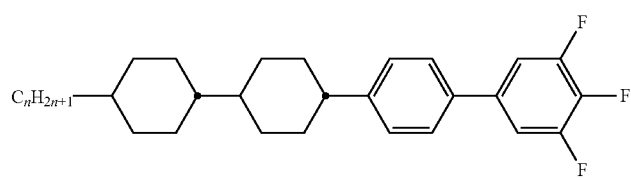
CCPU-n-F
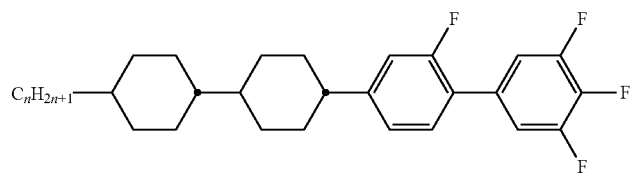
CCGU-n-F
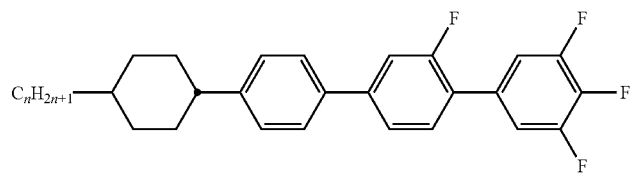
CPGU-n-F
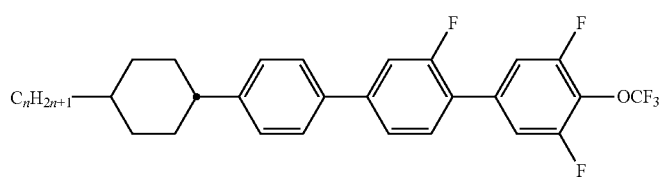
CPGU-n-OT
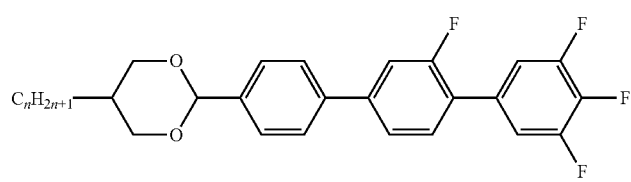
DPGU-n-F TABLE D-continued
Illustrative structures
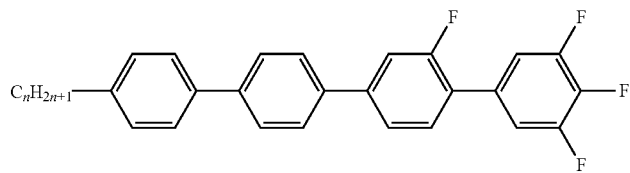
PPGU-n-F
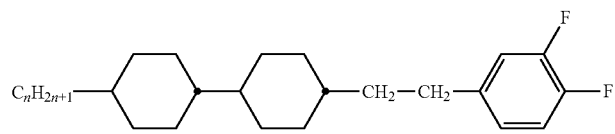
CCEG-n-F
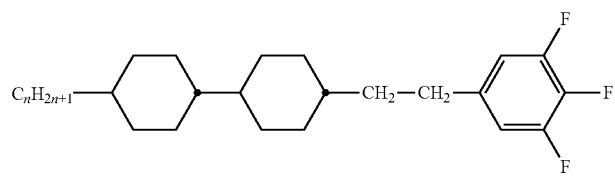
CCEU-n-F
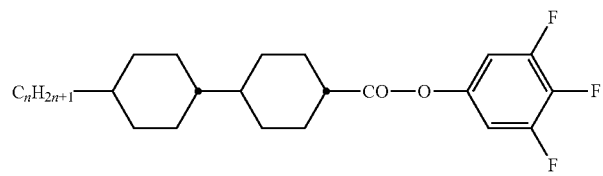
CCZU-n-F
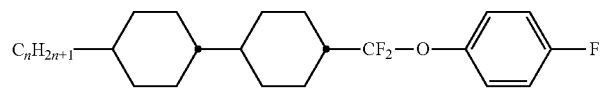
CCQP-n-F
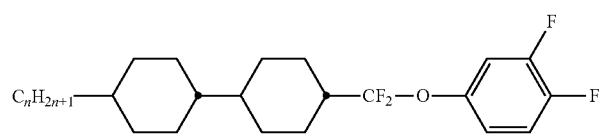
CCQG-n-F
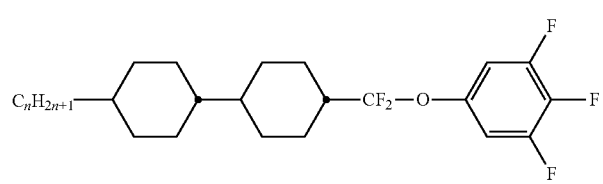
CCQU-n-F TABLE D-continued
Illustrative structures
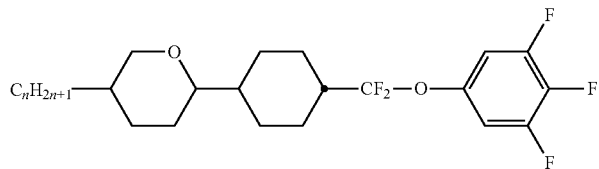
ACQU-n-F
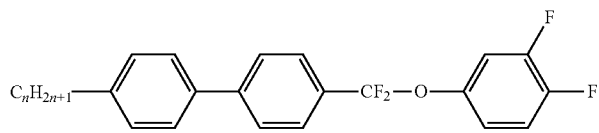
PPQG-n-F
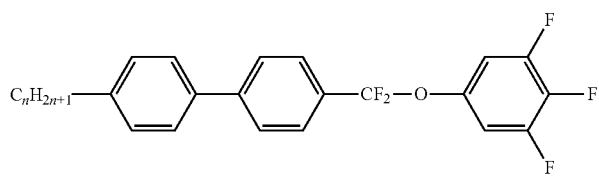
PPQU-n-F
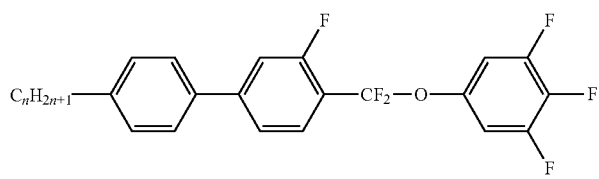
PGQU-n-F
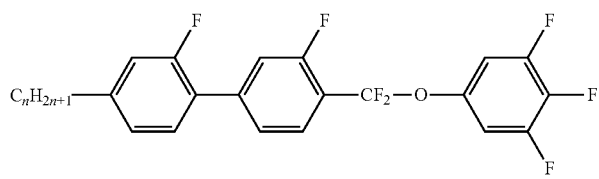
GGQU-n-F
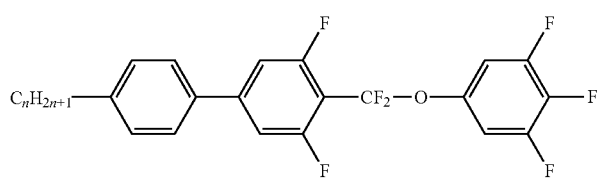
PUQU-n-F TABLE D-continued
Illustrative structures
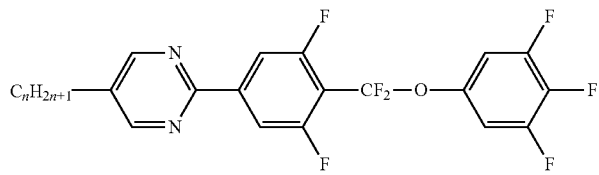
MUQU-n-F
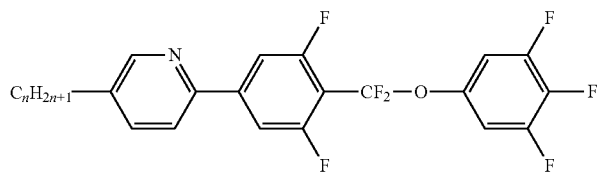
NUQU-n-F
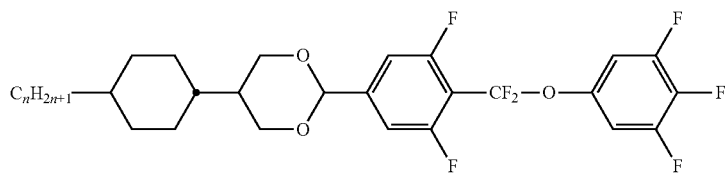
CDUQU-n-F
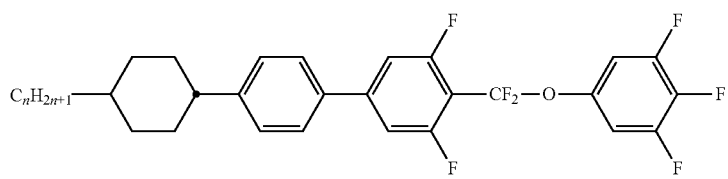
CPUQU-n-F
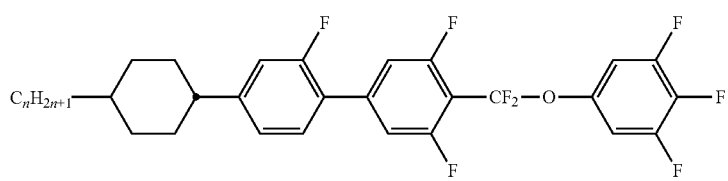
CGUQU-n-F
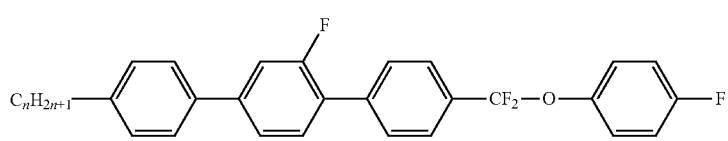
PGPQP-n-F

TABLE D-continued
Illustrative structures
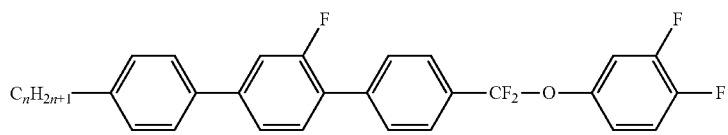
PGPQG-n-F
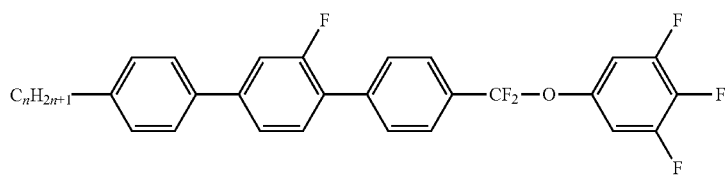
PGPQU-n-F
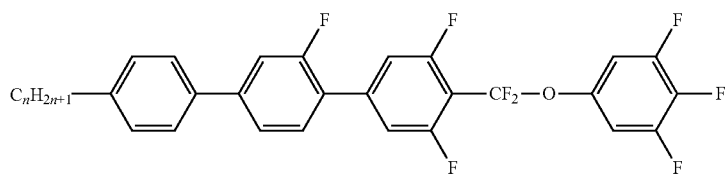
PGUQU-n-F
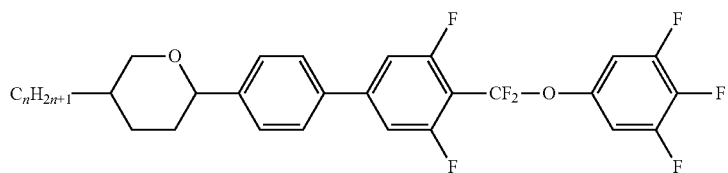
APUQU-n-F
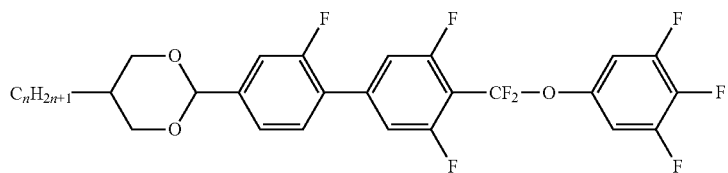
DGUQU-n-F
TABLE E
Table E shows possible chiral dopants which can be added to the LC media according to the invention.
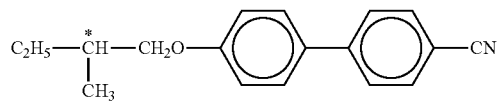
C 15

TABLE E-continued
Table E shows possible chiral dopants which can be added to the LC media according to the invention.
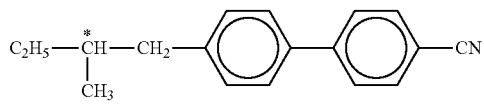
CB 15
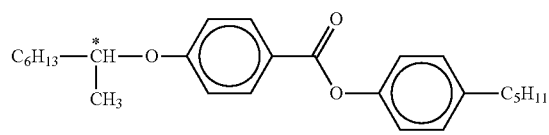
CM 21
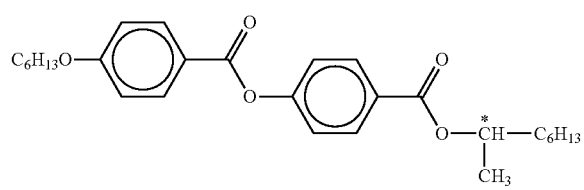
R/S-811
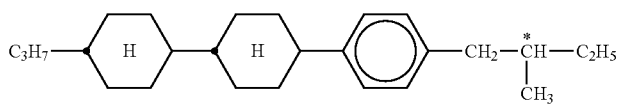
CM 44
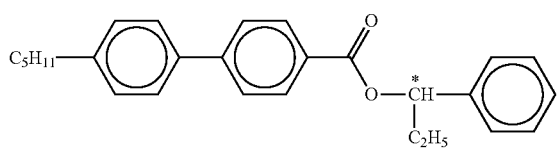
CM 45
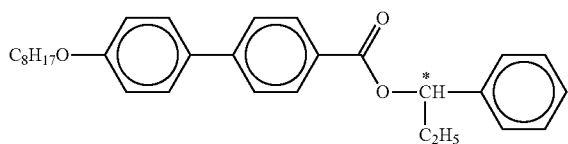
CM 47
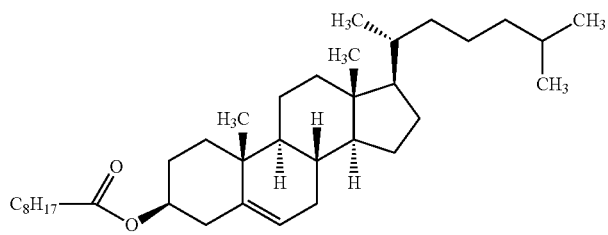
CN TABLE E-continued
Table E shows possible chiral dopants which can be added to the LC media according to the invention.
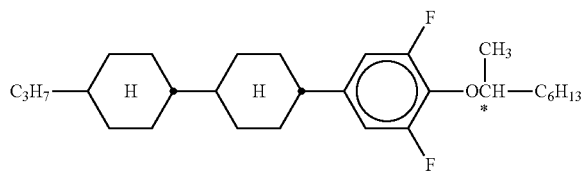
R/S-2011
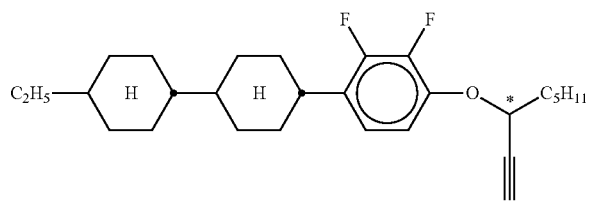
R/S-3011
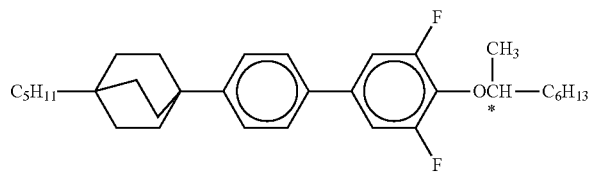
R/S-4011
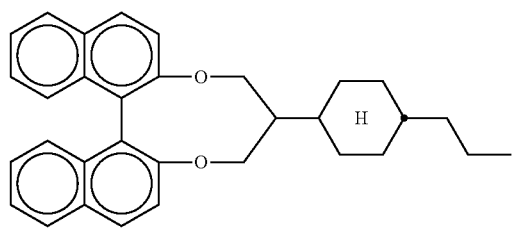
R/S-5011
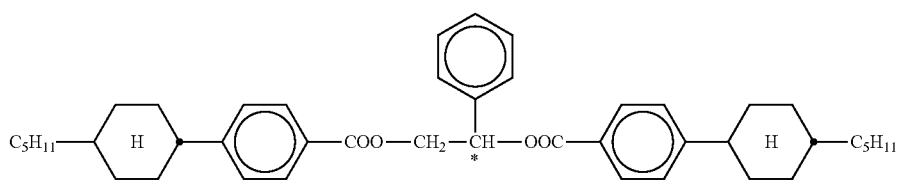
R/S-1011

The LC media optionally comprise 0 to 10% by weight, in particular 0.01 to 5% by weight, particularly preferably 0.1 to 3% by weight, of dopants, preferably selected from the group consisting of compounds from Table E.

TABLE F

Table F indicates possible stabilisers which can be added to the LC media according to the invention.
(n here denotes an integer from 1 to 12, preferably 1, 2, 3, 4, 5, 6, 7 or 8,
terminal methyl groups are not shown).

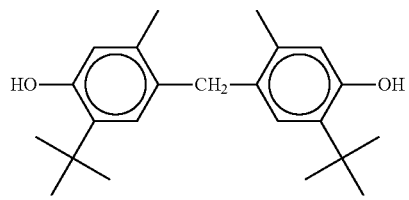

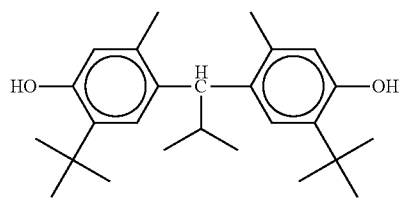

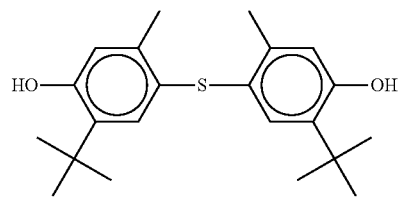

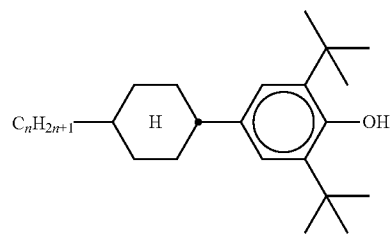

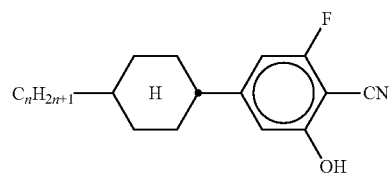

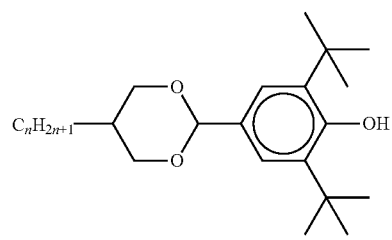

TABLE F-continued
Table F indicates possible stabilisers which can be added to the LC media according to the invention.
(n here denotes an integer from 1 to 12, preferably 1, 2, 3, 4, 5, 6, 7 or 8,
terminal methyl groups are not shown).
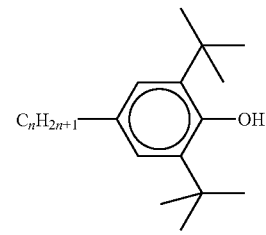
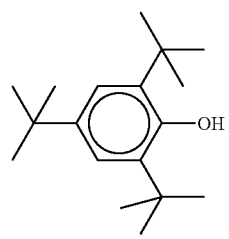
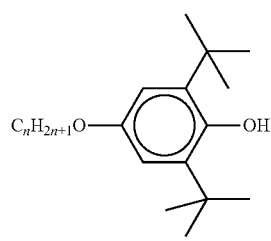
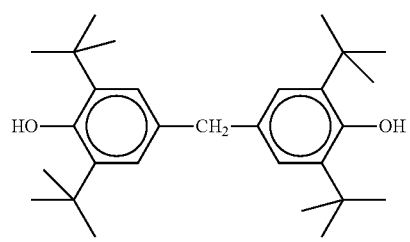
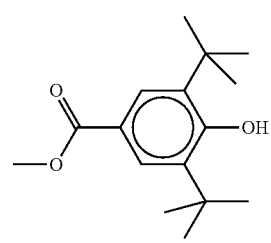
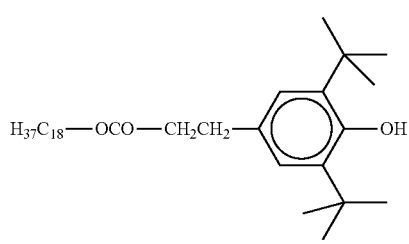

TABLE F-continued
Table F indicates possible stabilisers which can be added to the LC media according to the invention.
(n here denotes an integer from 1 to 12, preferably 1, 2, 3, 4, 5, 6, 7 or 8,
terminal methyl groups are not shown).
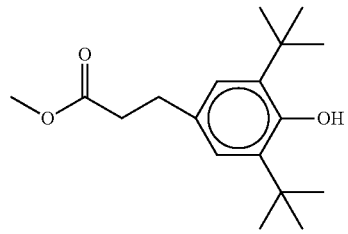
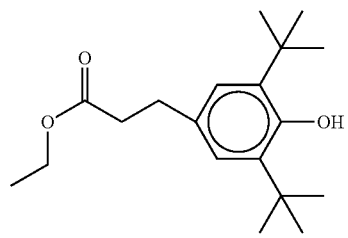
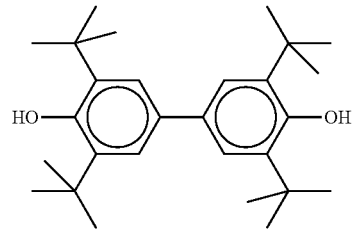
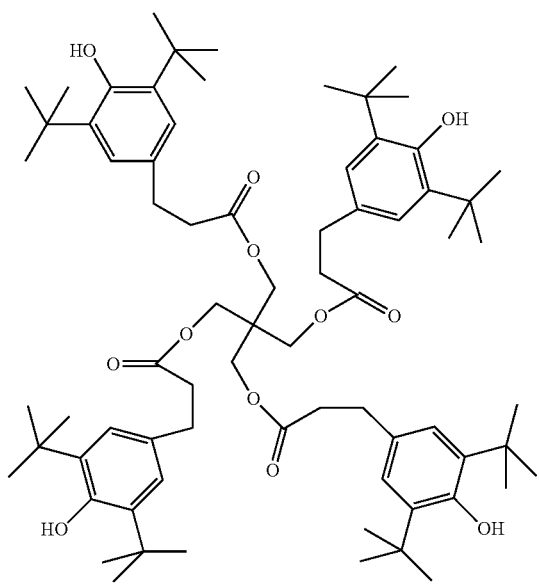 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]

TABLE F-continued
Table F indicates possible stabilisers which can be added to the LC media according to the invention.
(n here denotes an integer from 1 to 12, preferably 1, 2, 3, 4, 5, 6, 7 or 8,
terminal methyl groups are not shown).
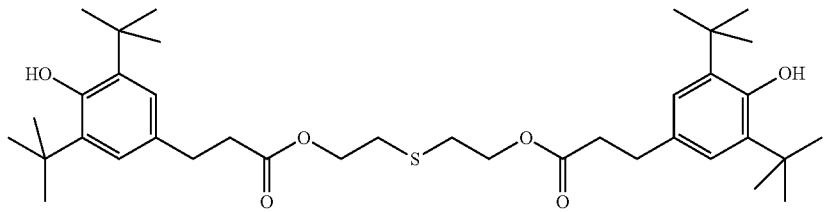 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
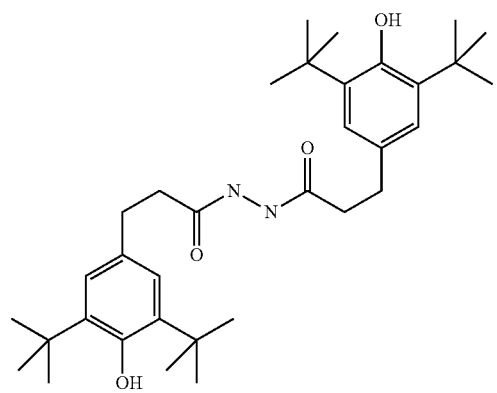 [SMILES: CC(C)(C)c1cc(CCC(=O)NNC(=O)CCc2cc(C(C)(C)C)c(O)c(C(C)(C)C)c2)cc(C(C)(C)C)c1O]
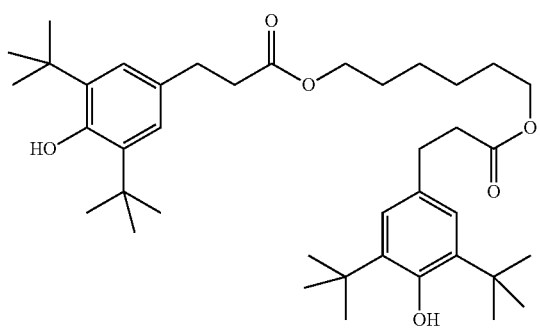 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
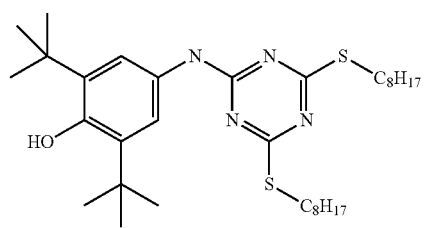

TABLE F-continued
Table F indicates possible stabilisers which can be added to the LC media according to the invention.
(n here denotes an integer from 1 to 12, preferably 1, 2, 3, 4, 5, 6, 7 or 8,
terminal methyl groups are not shown).
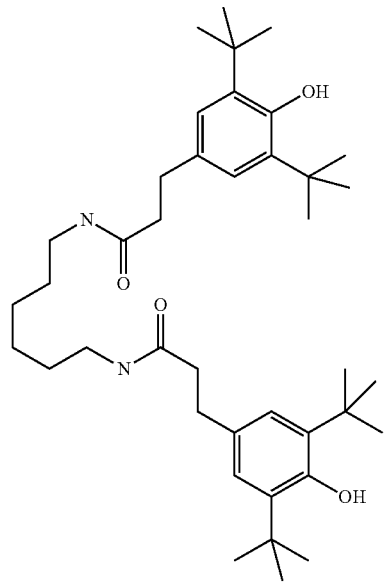 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
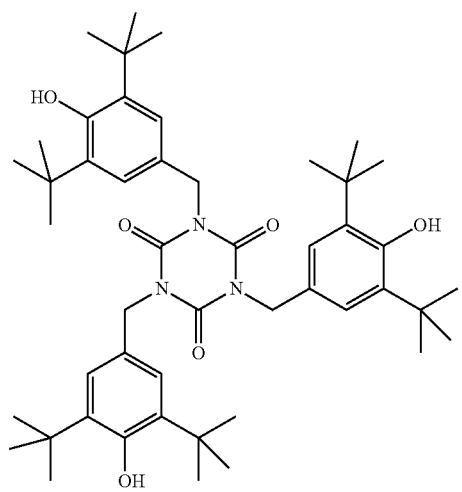 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
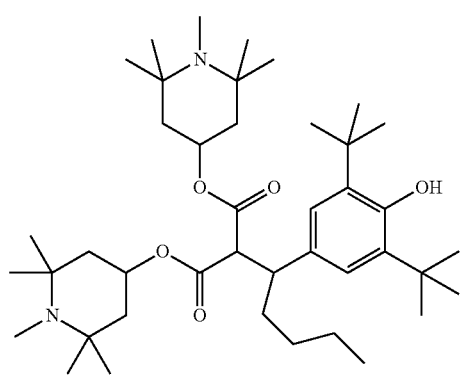 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE F-continued
Table F indicates possible stabilisers which can be added to the LC media according to the invention.
(n here denotes an integer from 1 to 12, preferably 1, 2, 3, 4, 5, 6, 7 or 8,
terminal methyl groups are not shown).
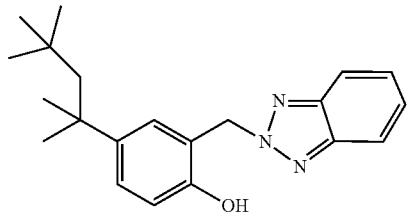 [SMILES: CC(C)(C)CC(C)(C)c1ccc(O)c(Cn2nc3ccccc3n2)c1]
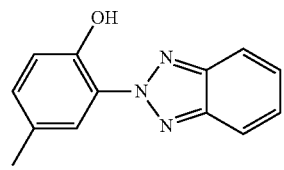 [SMILES: Cc1ccc(O)c(-n2nc3ccccc3n2)c1]
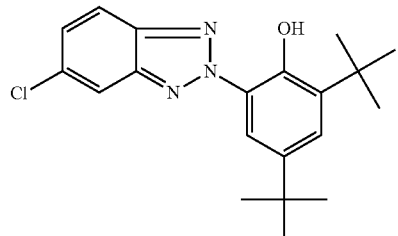
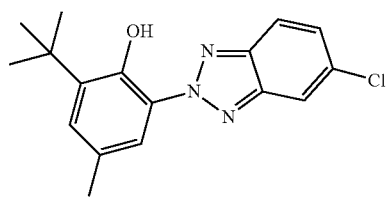 [SMILES: Cc1cc(-n2nc3ccc(Cl)cc3n2)c(O)c(C(C)(C)C)c1]
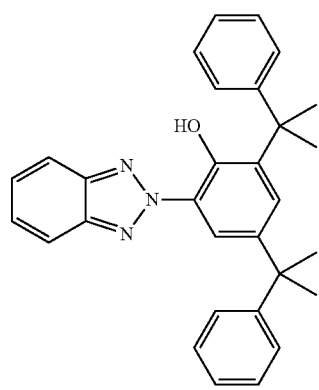 [SMILES: CC(C)(c1ccccc1)c1cc(-n2nc3ccccc3n2)c(O)c(C(C)(C)c2ccccc2)c1]
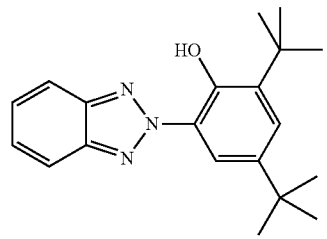 [SMILES: CC(C)(C)c1cc(-n2nc3ccccc3n2)c(O)c(C(C)(C)C)c1]

TABLE F-continued
Table F indicates possible stabilisers which can be added to the LC media according to the invention.
(n here denotes an integer from 1 to 12, preferably 1, 2, 3, 4, 5, 6, 7 or 8,
terminal methyl groups are not shown).
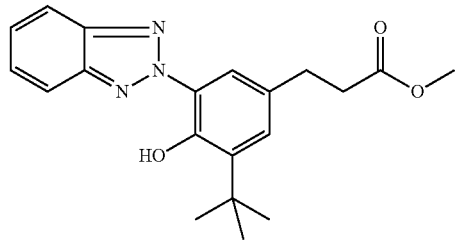 [SMILES: COC(=O)CCc1cc(-n2nc3ccccc3n2)c(O)c(C(C)(C)C)c1]
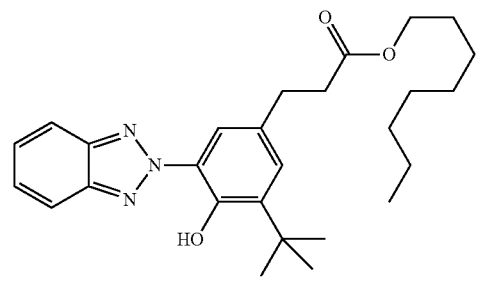 [SMILES: CCCCCCCCOC(=O)CCc1cc(-n2nc3ccccc3n2)c(O)c(C(C)(C)C)c1]
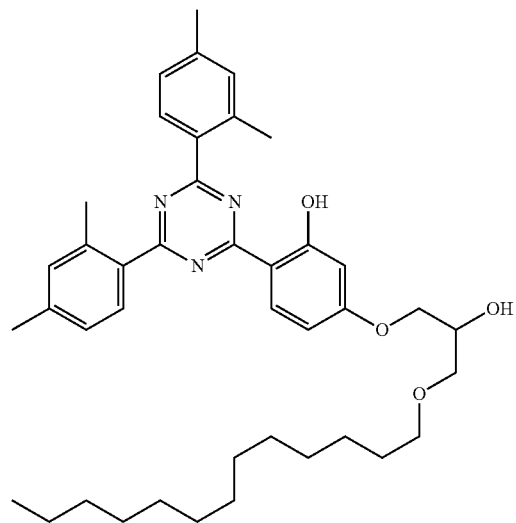 [SMILES: CCCCCCCCCCCCCOCC(O)COc1ccc(-c2nc(-c3ccc(C)cc3C)nc(-c3ccc(C)cc3C)n2)c(O)c1]

TABLE F-continued
Table F indicates possible stabilisers which can be added to the LC media according to the invention.
(n here denotes an integer from 1 to 12, preferably 1, 2, 3, 4, 5, 6, 7 or 8,
terminal methyl groups are not shown).
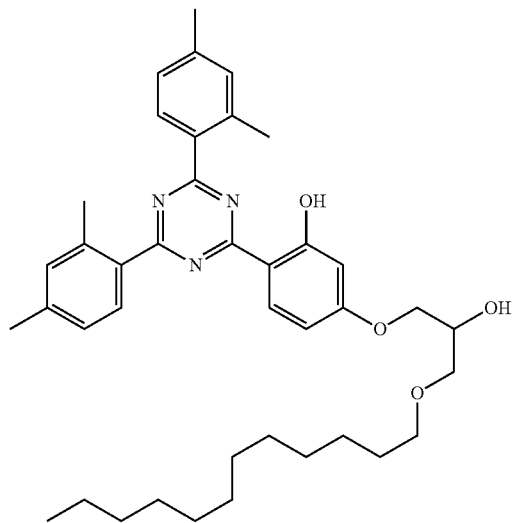 [SMILES: CCCCCCCCCCCCOCC(O)COc1ccc(-c2nc(-c3ccc(C)cc3C)nc(-c3ccc(C)cc3C)n2)c(O)c1]
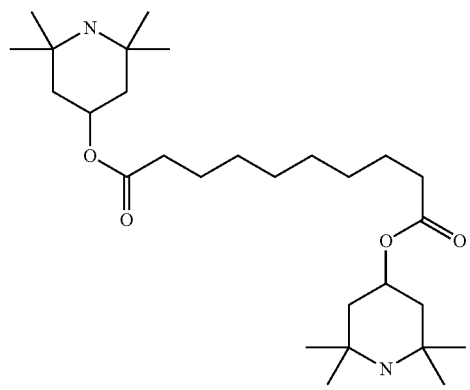
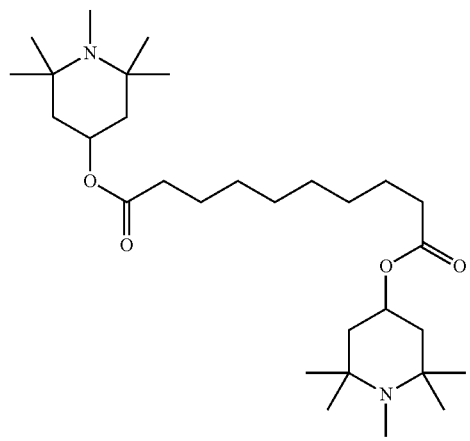

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table F.

TABLE G

Table G shows illustrative compounds which can preferably be used as polymerisable compounds in the LC media in accordance with the present invention.

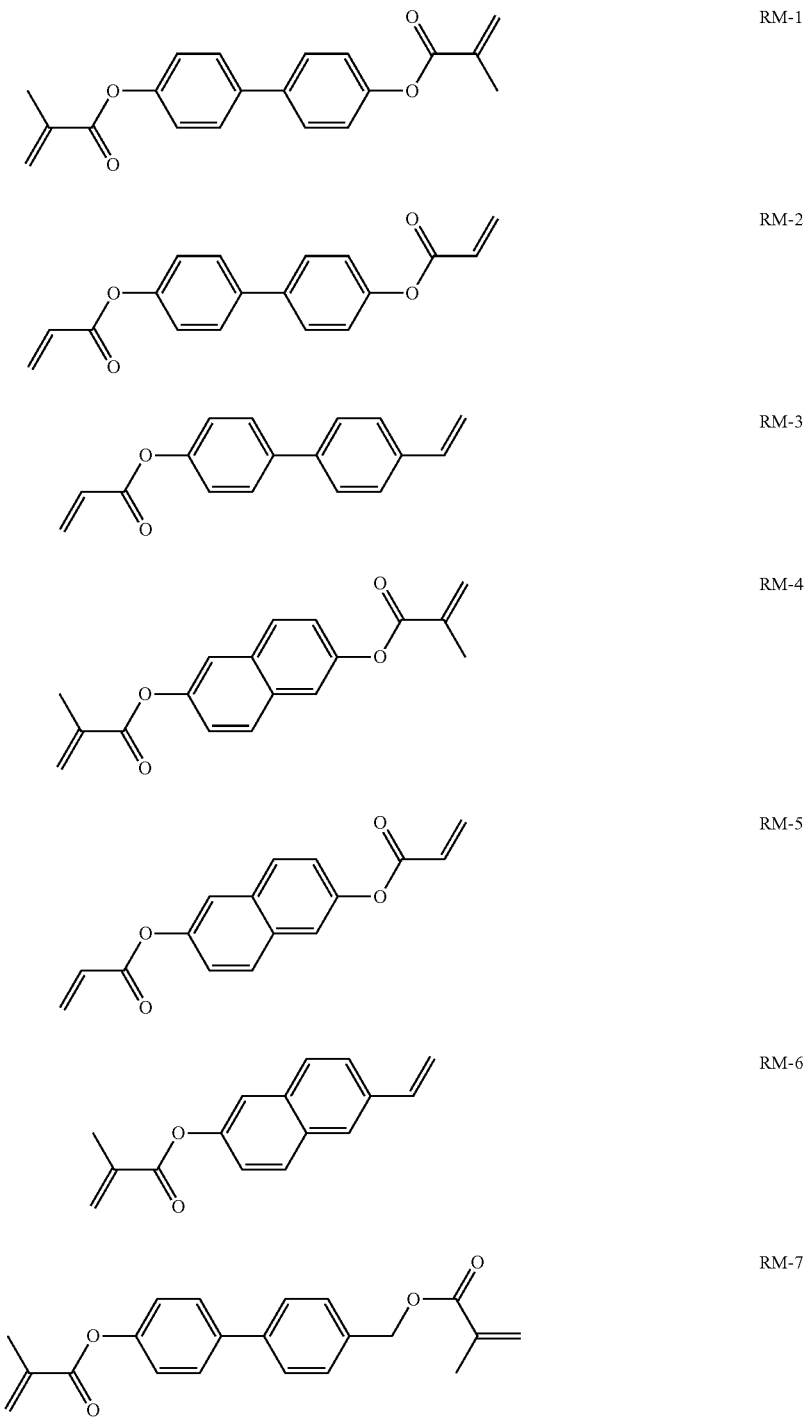

TABLE G-continued
Table G shows illustrative compounds which can preferably be used as polymerisable compounds in the LC media in accordance with the present invention.
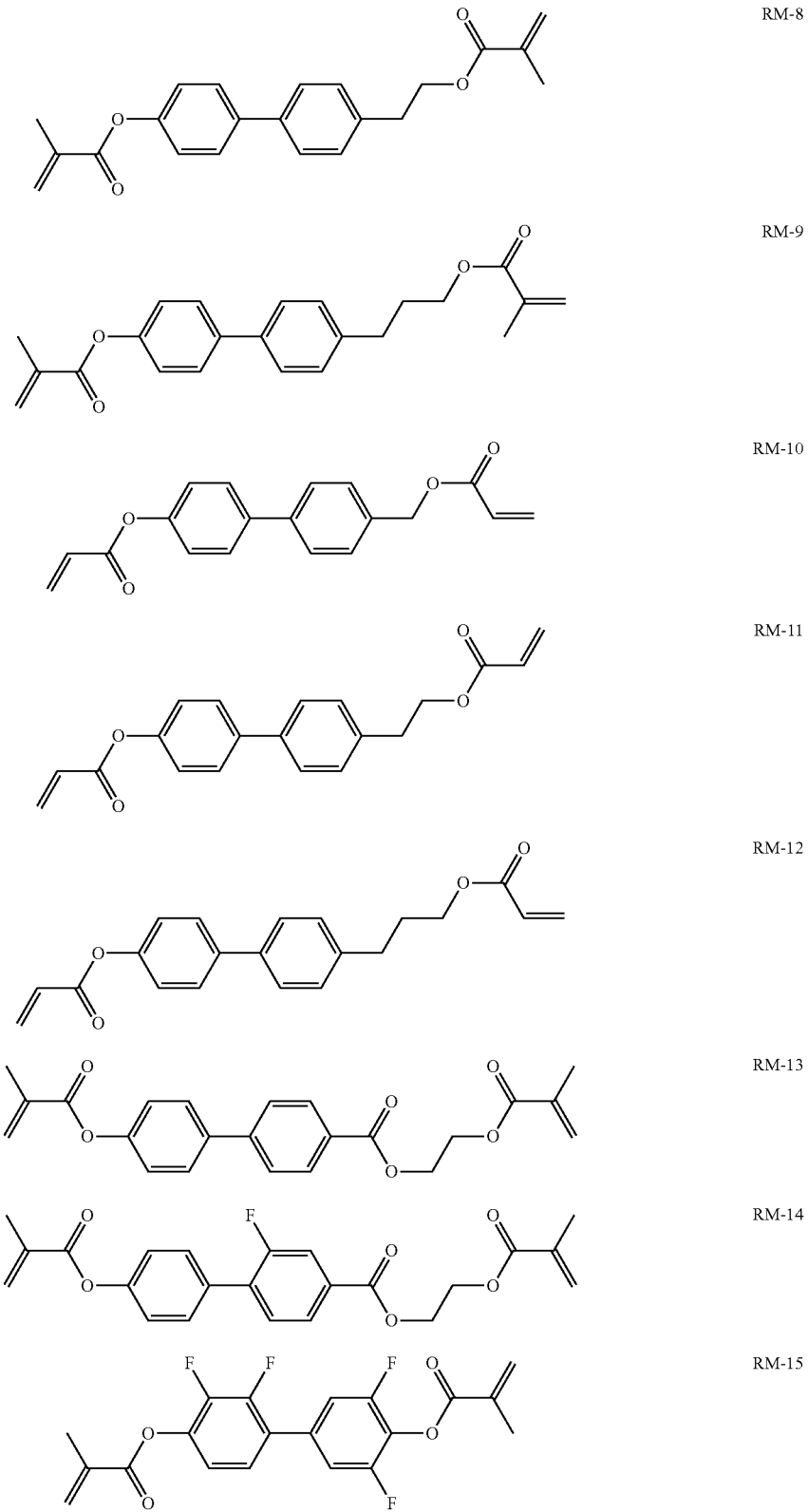
RM-8
RM-9
RM-10
RM-11
RM-12
RM-13
RM-14
RM-15

TABLE G-continued
Table G shows illustrative compounds which can preferably be used as polymerisable compounds in the LC media in accordance with the present invention.
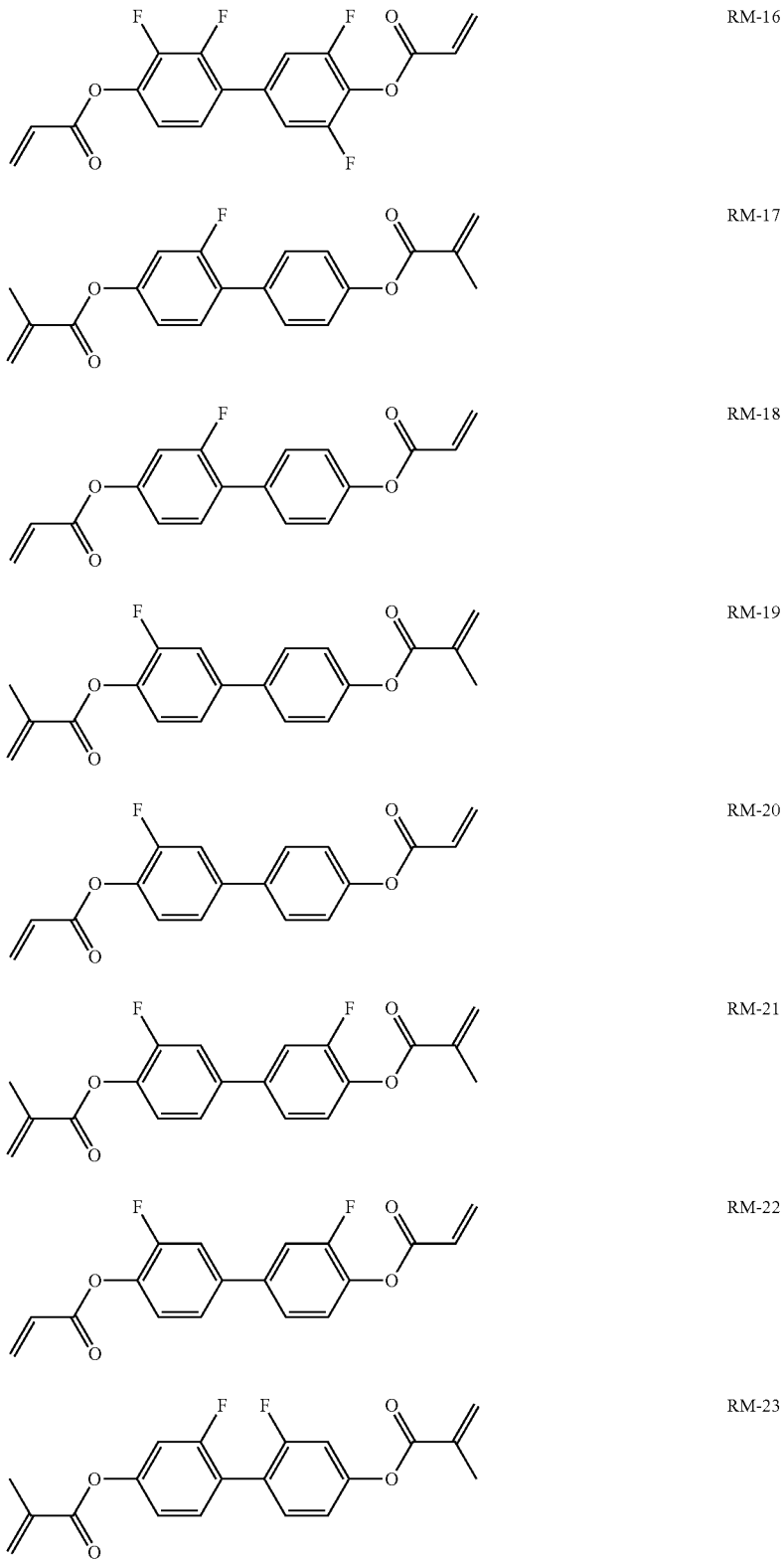

TABLE G-continued
Table G shows illustrative compounds which can preferably be used as polymerisable compounds in the LC media in accordance with the present invention.
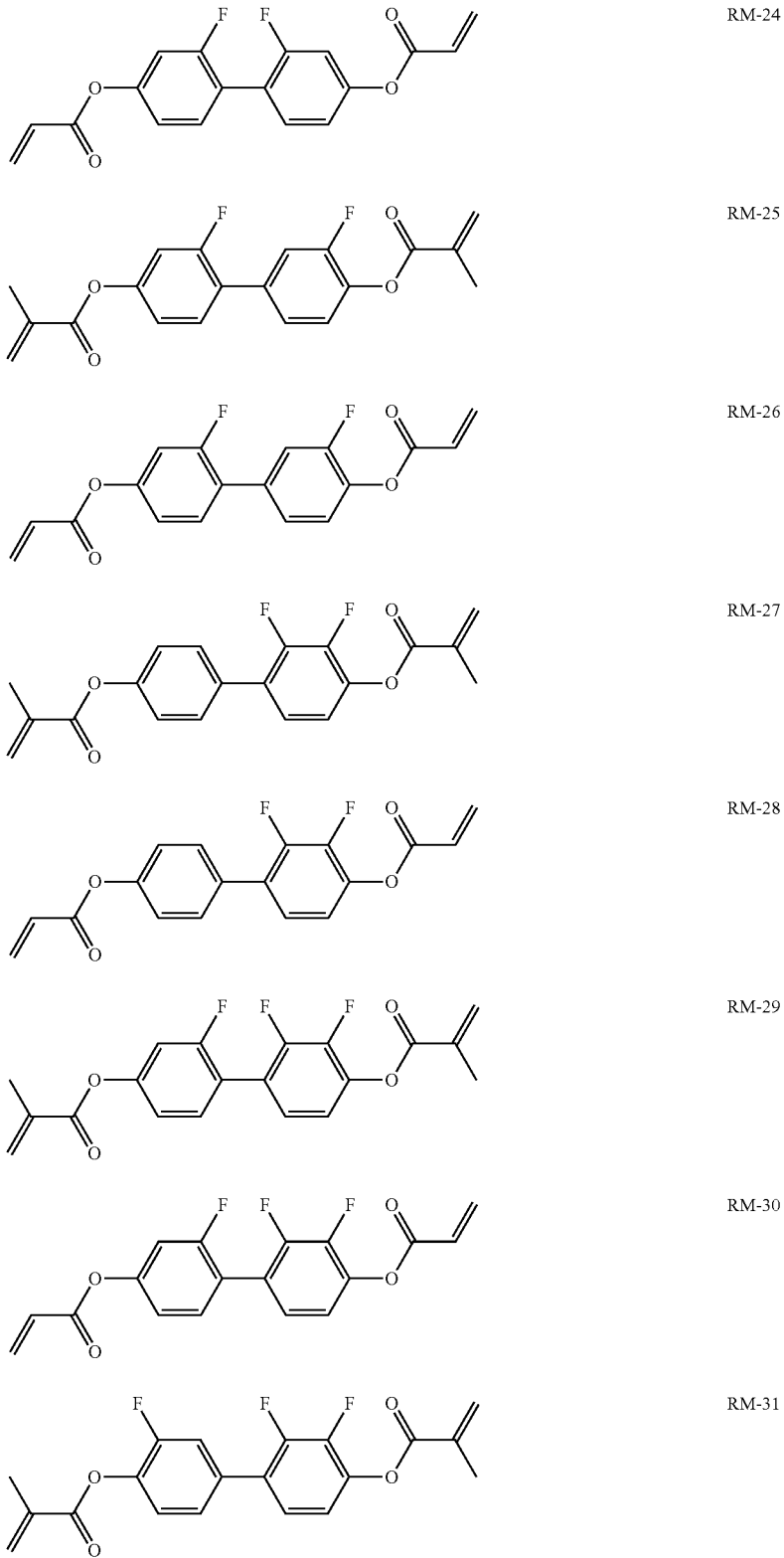

TABLE G-continued
Table G shows illustrative compounds which can preferably be used as polymerisable compounds in the LC media in accordance with the present invention.
| | |
|---|---|
| 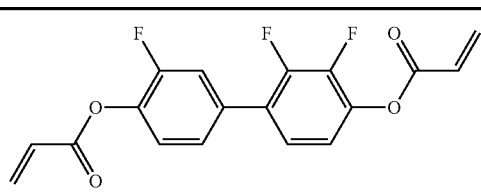 | RM-32 |
| 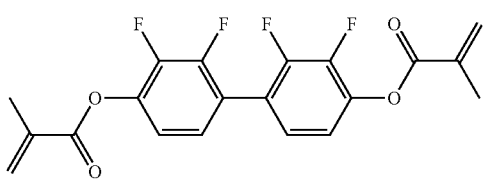 [SMILES: C=C(C)C(=O)Oc1ccc(-c2ccc(OC(=O)C(=C)C)c(F)c2F)c(F)c1F] | RM-33 |
| 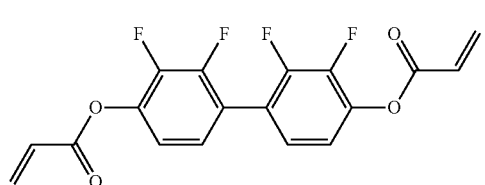 | RM-34 |
| 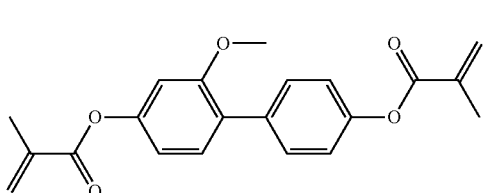 | RM-35 |
| 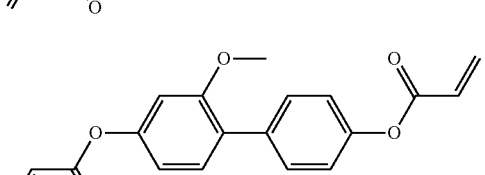 | RM-36 |
| 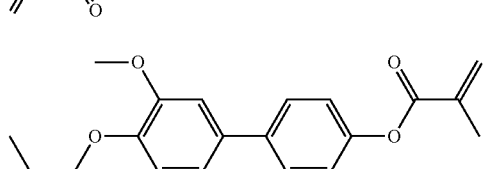 | RM-37 |
| 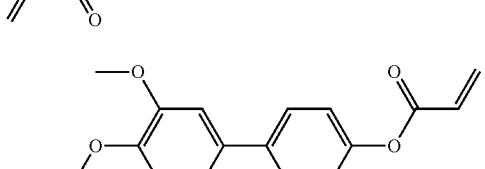 | RM-38 |
| 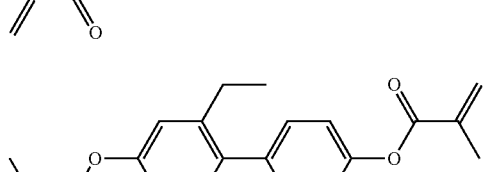 | RM-39 |

TABLE G-continued
Table G shows illustrative compounds which can preferably be used as polymerisable compounds in the LC media in accordance with the present invention.
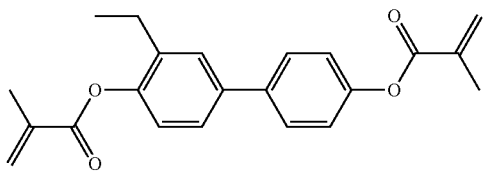 [SMILES: C=C(C)C(=O)Oc1ccc(-c2ccc(OC(=O)C(=C)C)c(CC)c2)cc1]
RM-40
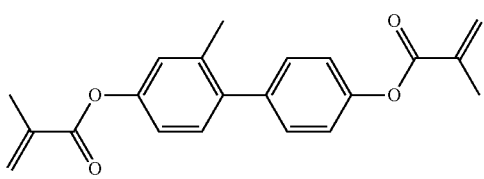 [SMILES: C=C(C)C(=O)Oc1ccc(-c2ccc(OC(=O)C(=C)C)cc2C)cc1]
RM-41
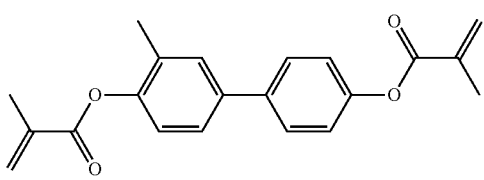 [SMILES: C=C(C)C(=O)Oc1ccc(-c2ccc(OC(=O)C(=C)C)c(C)c2)cc1]
RM-42
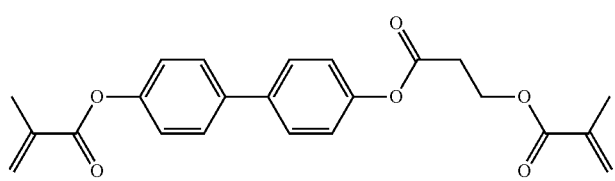
RM-43
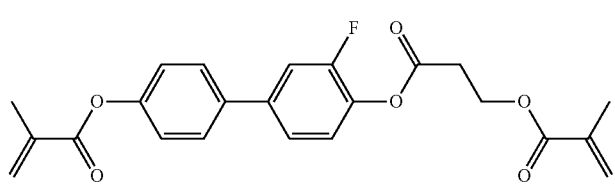 [SMILES: C=C(C)C(=O)OCCC(=O)Oc1ccc(-c2ccc(OC(=O)C(=C)C)cc2)cc1F]
RM-44
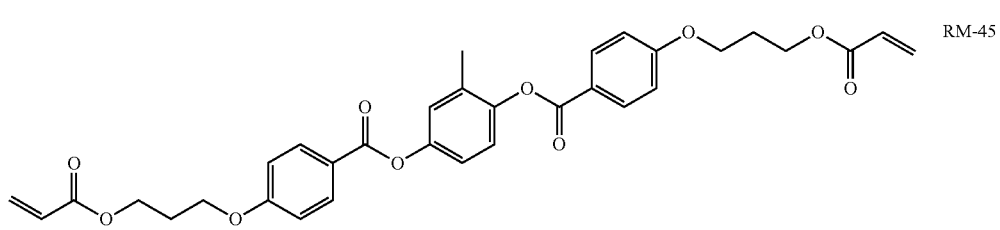
RM-45
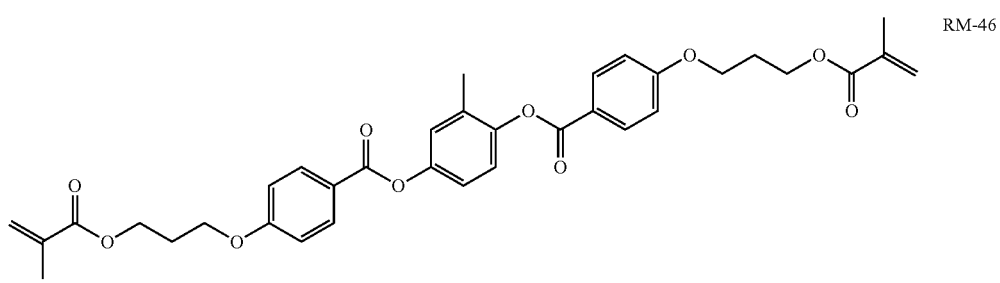
RM-46

TABLE G-continued
Table G shows illustrative compounds which can preferably be used as polymerisable compounds in the LC media in accordance with the present invention.
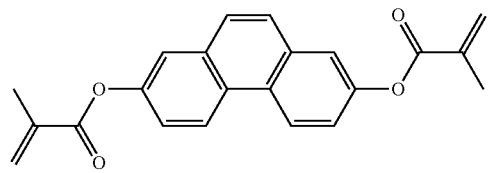 [SMILES: C=C(C)C(=O)Oc1ccc2c(ccc3cc(OC(=O)C(=C)C)ccc32)c1] RM-47
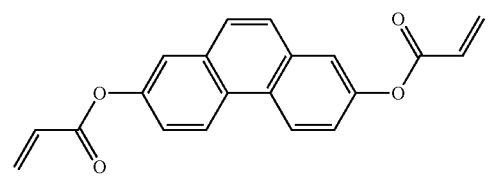 [SMILES: C=CC(=O)Oc1ccc2c(ccc3cc(OC(=O)C=C)ccc32)c1] RM-48
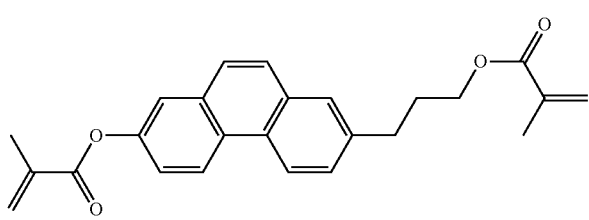 [SMILES: C=C(C)C(=O)OCCCc1ccc2c(ccc3cc(OC(=O)C(=C)C)ccc32)c1] RM-49
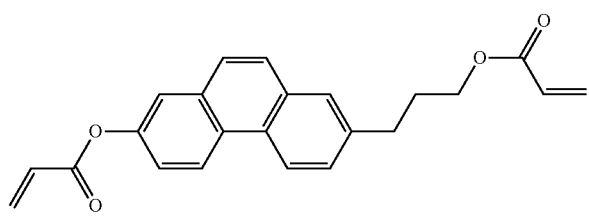 [SMILES: C=CC(=O)OCCCc1ccc2c(ccc3cc(OC(=O)C=C)ccc32)c1] RM-50
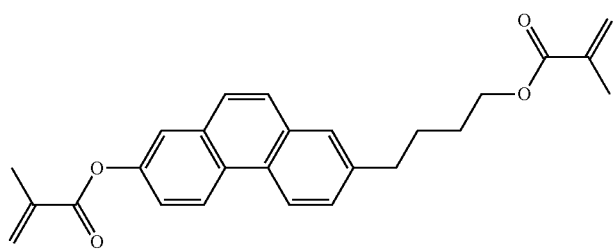 [SMILES: C=C(C)C(=O)OCCCCc1ccc2c(ccc3cc(OC(=O)C(=C)C)ccc32)c1] RM-51
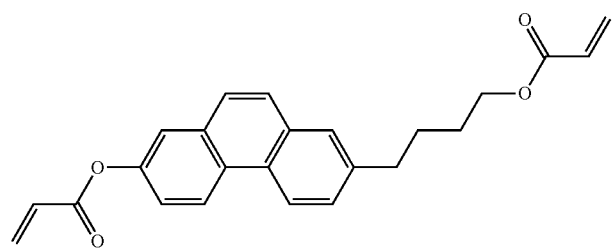 [SMILES: C=CC(=O)OCCCCc1ccc2c(ccc3cc(OC(=O)C=C)ccc32)c1] RM-52
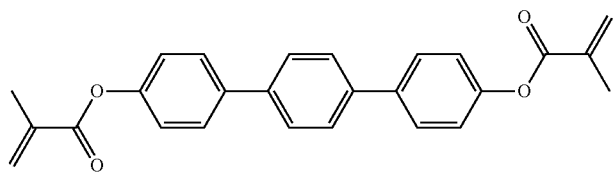 [SMILES: C=C(C)C(=O)Oc1ccc(-c2ccc(-c3ccc(OC(=O)C(=C)C)cc3)cc2)cc1] RM-53

TABLE G-continued
Table G shows illustrative compounds which can preferably be used as polymerisable compounds in the LC media in accordance with the present invention.
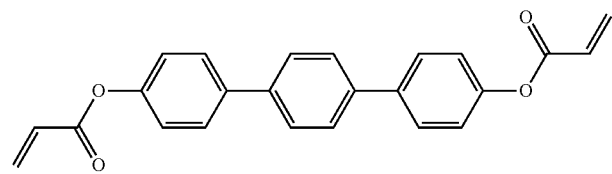 [SMILES: C=CC(=O)Oc1ccc(-c2ccc(-c3ccc(OC(=O)C=C)cc3)cc2)cc1]
RM-54
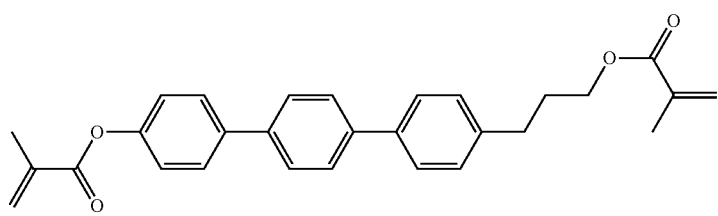 [SMILES: C=C(C)C(=O)OCCCc1ccc(-c2ccc(-c3ccc(OC(=O)C(=C)C)cc3)cc2)cc1]
RM-55
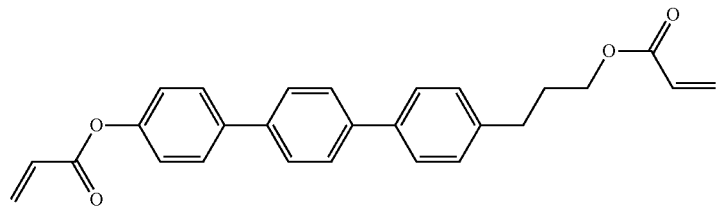
RM-56
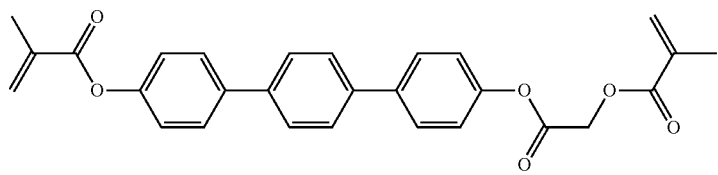 [SMILES: C=C(C)C(=O)OCC(=O)Oc1ccc(-c2ccc(-c3ccc(OC(=O)C(=C)C)cc3)cc2)cc1]
RM-57
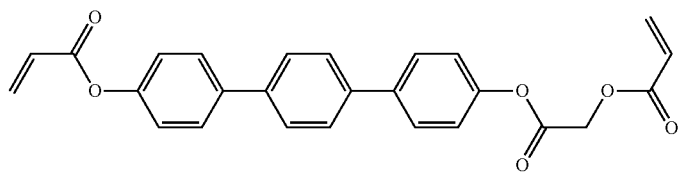 [SMILES: C=CC(=O)OCC(=O)Oc1ccc(-c2ccc(-c3ccc(OC(=O)C=C)cc3)cc2)cc1]
RM-58
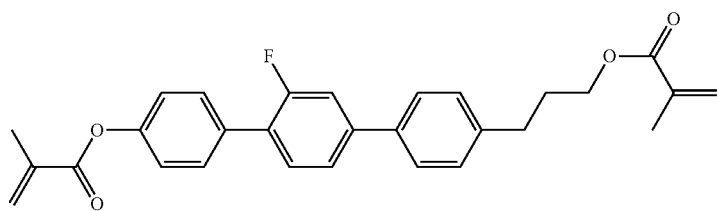 [SMILES: C=C(C)C(=O)OCCCc1ccc(-c2ccc(-c3ccc(OC(=O)C(=C)C)cc3)c(F)c2)cc1]
RM-59
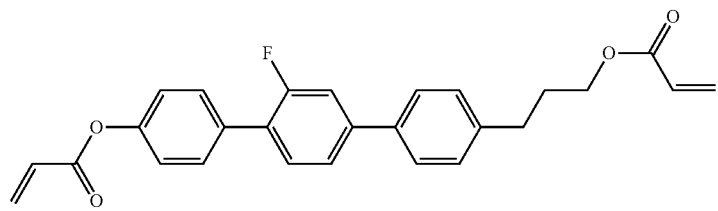 [SMILES: C=CC(=O)OCCCc1ccc(-c2ccc(-c3ccc(OC(=O)C=C)cc3)c(F)c2)cc1]
RM-60

TABLE G-continued
Table G shows illustrative compounds which can preferably be used as polymerisable compounds in the LC media in accordance with the present invention.
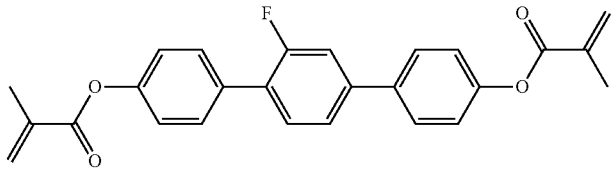 [SMILES: C=C(C)C(=O)Oc1ccc(-c2ccc(-c3ccc(OC(=O)C(=C)C)cc3)c(F)c2)cc1] RM-61
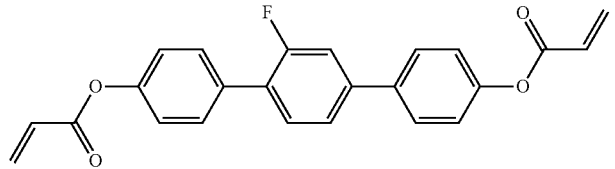 [SMILES: C=CC(=O)Oc1ccc(-c2ccc(-c3ccc(OC(=O)C=C)cc3)c(F)c2)cc1] RM-62
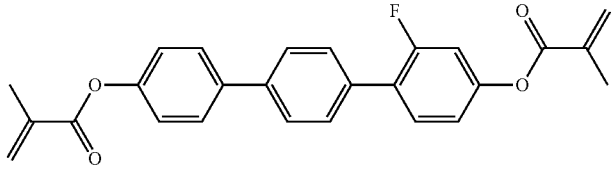 [SMILES: C=C(C)C(=O)Oc1ccc(-c2ccc(-c3ccc(OC(=O)C(=C)C)cc3F)cc2)cc1] RM-63
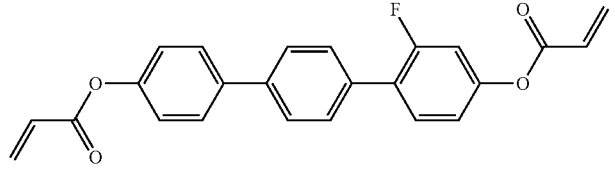 [SMILES: C=CC(=O)Oc1ccc(-c2ccc(-c3ccc(OC(=O)C=C)cc3F)cc2)cc1] RM-64
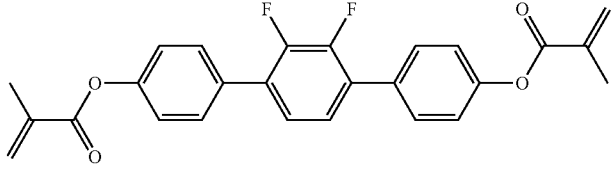 [SMILES: C=C(C)C(=O)Oc1ccc(-c2ccc(-c3ccc(OC(=O)C(=C)C)cc3)c(F)c2F)cc1] RM-65
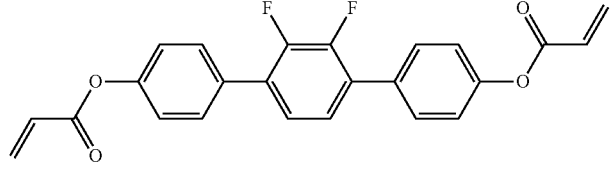 [SMILES: C=CC(=O)Oc1ccc(-c2ccc(-c3ccc(OC(=O)C=C)cc3)c(F)c2F)cc1] RM-66
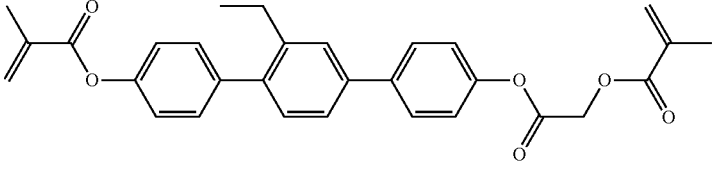 RM-67
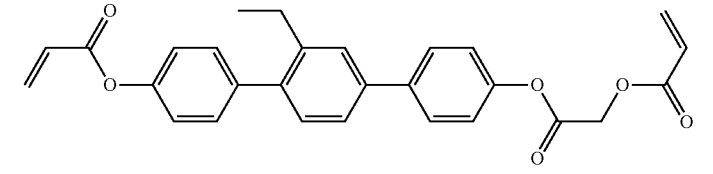 [SMILES: C=CC(=O)OCC(=O)Oc1ccc(-c2ccc(-c3ccc(OC(=O)C=C)cc3)c(CC)c2)cc1] RM-68

TABLE G-continued
Table G shows illustrative compounds which can preferably be used as polymerisable compounds in the LC media in accordance with the present invention.
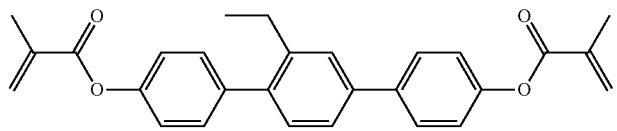 [SMILES: C=C(C)C(=O)Oc1ccc(-c2ccc(-c3ccc(OC(=O)C(=C)C)cc3)c(CC)c2)cc1] RM-69
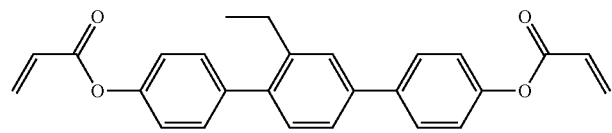 [SMILES: C=CC(=O)Oc1ccc(-c2ccc(-c3ccc(OC(=O)C=C)cc3)c(CC)c2)cc1] RM-70
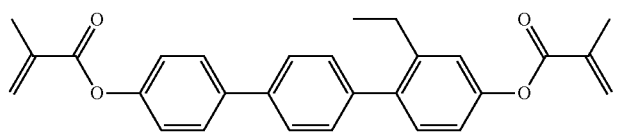 [SMILES: C=C(C)C(=O)Oc1ccc(-c2ccc(-c3ccc(OC(=O)C(=C)C)cc3CC)cc2)cc1] RM-71
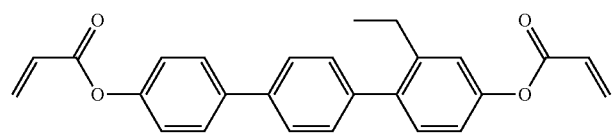 [SMILES: C=CC(=O)Oc1ccc(-c2ccc(-c3ccc(OC(=O)C=C)cc3CC)cc2)cc1] RM-72
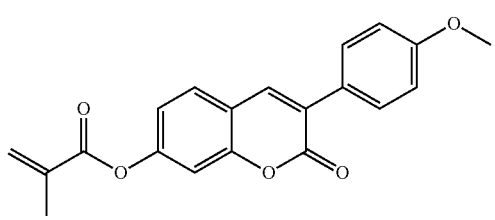 [SMILES: C=C(C)C(=O)Oc1ccc2cc(-c3ccc(OC)cc3)c(=O)oc2c1] RM-73
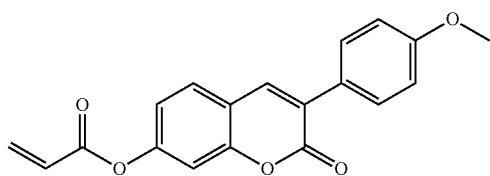 [SMILES: C=CC(=O)Oc1ccc2cc(-c3ccc(OC)cc3)c(=O)oc2c1] RM-74
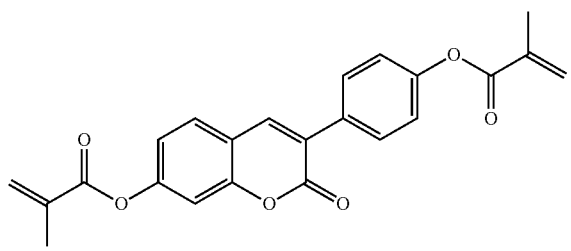 [SMILES: C=C(C)C(=O)Oc1ccc(-c2cc3ccc(OC(=O)C(=C)C)cc3oc2=O)cc1] RM-75
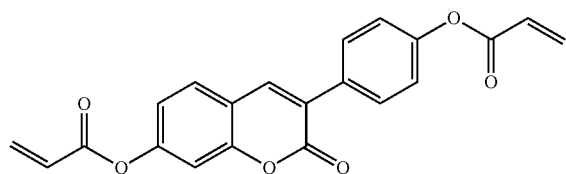 [SMILES: C=CC(=O)Oc1ccc(-c2cc3ccc(OC(=O)C=C)cc3oc2=O)cc1] RM-76

TABLE G-continued
Table G shows illustrative compounds which can preferably be used as polymerisable compounds in the LC media in accordance with the present invention.
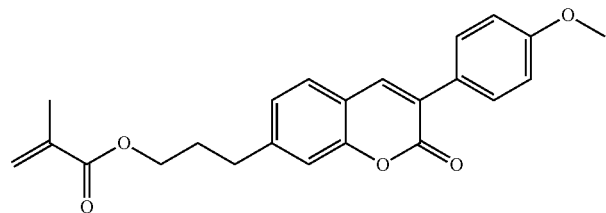 [SMILES: C=C(C)C(=O)OCCCc1ccc2cc(-c3ccc(OC)cc3)c(=O)oc2c1]
RM-77
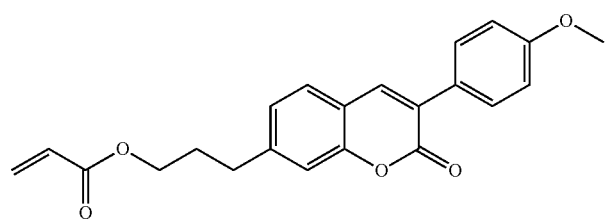 [SMILES: C=CC(=O)OCCCc1ccc2cc(-c3ccc(OC)cc3)c(=O)oc2c1]
RM-78
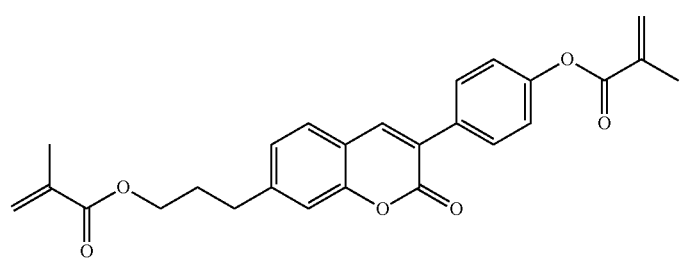 [SMILES: C=C(C)C(=O)OCCCc1ccc2cc(-c3ccc(OC(=O)C(=C)C)cc3)c(=O)oc2c1]
RM-79
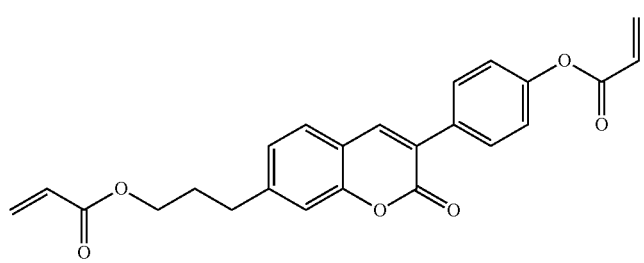 [SMILES: C=CC(=O)OCCCc1ccc2cc(-c3ccc(OC(=O)C=C)cc3)c(=O)oc2c1]
RM-80
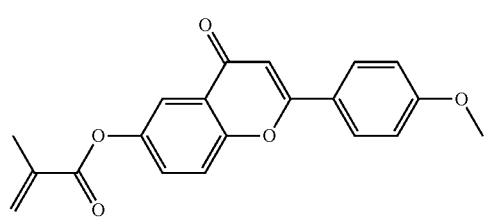 [SMILES: C=C(C)C(=O)Oc1ccc2oc(-c3ccc(OC)cc3)cc(=O)c2c1]
RM-81
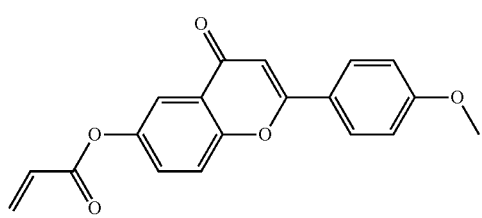 [SMILES: C=CC(=O)Oc1ccc2oc(-c3ccc(OC)cc3)cc(=O)c2c1]
RM-82

TABLE G-continued
Table G shows illustrative compounds which can preferably be used as polymerisable compounds in the LC media in accordance with the present invention.
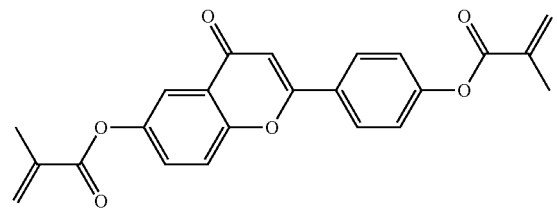 [SMILES: C=C(C)C(=O)Oc1ccc(-c2cc(=O)c3cc(OC(=O)C(=C)C)ccc3o2)cc1]
RM-83
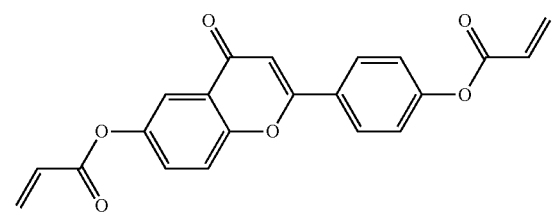 [SMILES: C=CC(=O)Oc1ccc(-c2cc(=O)c3cc(OC(=O)C=C)ccc3o2)cc1]
RM-84
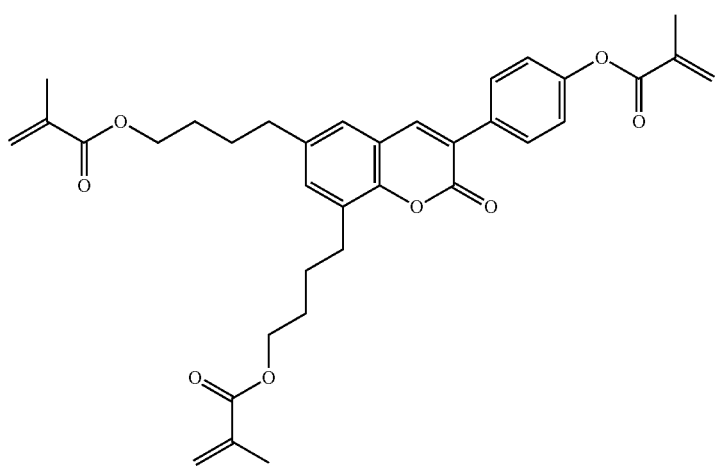 [SMILES: C=C(C)C(=O)OCCCCc1cc(CCCCOC(=O)C(=C)C)c2oc(=O)c(-c3ccc(OC(=O)C(=C)C)cc3)cc2c1]
RM-85
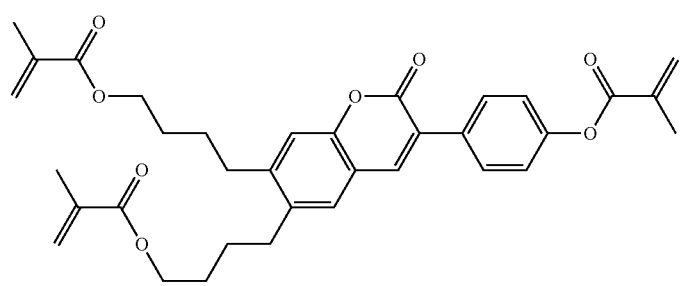 [SMILES: C=C(C)C(=O)OCCCCc1cc2cc(-c3ccc(OC(=O)C(=C)C)cc3)c(=O)oc2cc1CCCCOC(=O)C(=C)C]
RM-86
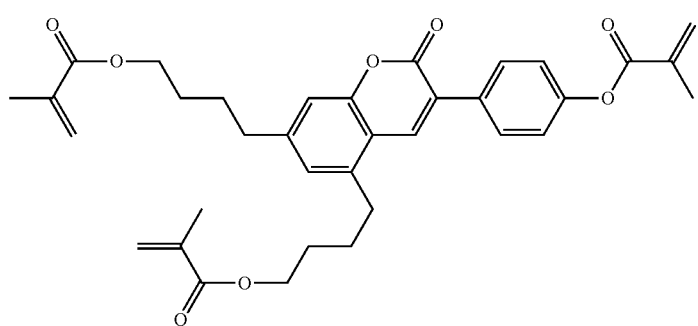 [SMILES: C=C(C)C(=O)OCCCCc1cc(CCCCOC(=O)C(=C)C)c2cc(-c3ccc(OC(=O)C(=C)C)cc3)c(=O)oc2c1]
RM-87

TABLE G-continued
Table G shows illustrative compounds which can preferably be used as polymerisable compounds in the LC media in accordance with the present invention.
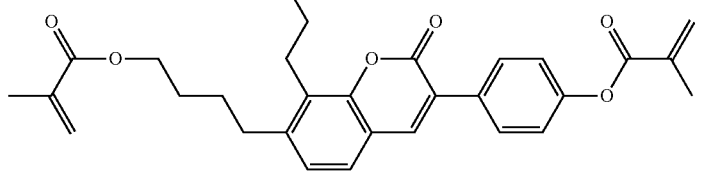
RM-88
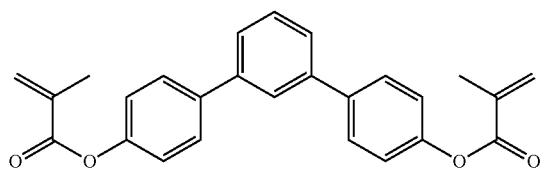 [SMILES: C=C(C)C(=O)Oc1ccc(-c2cccc(-c3ccc(OC(=O)C(=C)C)cc3)c2)cc1]
RM-89
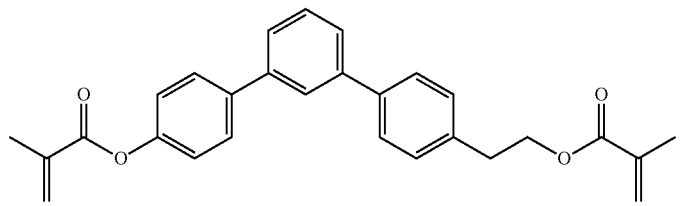 [SMILES: C=C(C)C(=O)OCCc1ccc(-c2cccc(-c3ccc(OC(=O)C(=C)C)cc3)c2)cc1]
RM-90
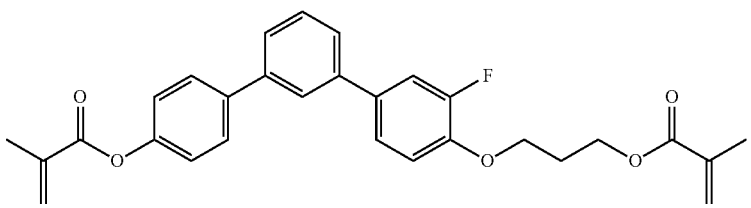 [SMILES: C=C(C)C(=O)OCCCOc1ccc(-c2cccc(-c3ccc(OC(=O)C(=C)C)cc3)c2)cc1F]
RM-91
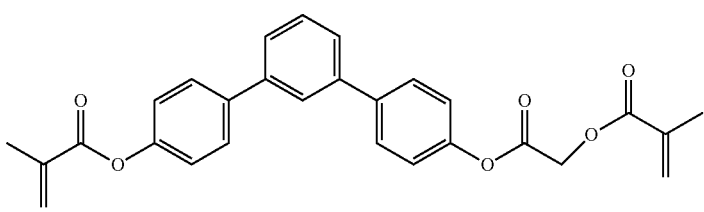 [SMILES: C=C(C)C(=O)OCC(=O)Oc1ccc(-c2cccc(-c3ccc(OC(=O)C(=C)C)cc3)c2)cc1]
RM-92
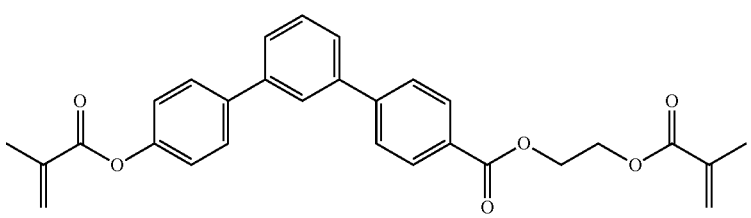 [SMILES: C=C(C)C(=O)OCCOC(=O)c1ccc(-c2cccc(-c3ccc(OC(=O)C(=C)C)cc3)c2)cc1]
RM-93

TABLE G-continued
Table G shows illustrative compounds which can preferably be used as polymerisable compounds in the LC media in accordance with the present invention.
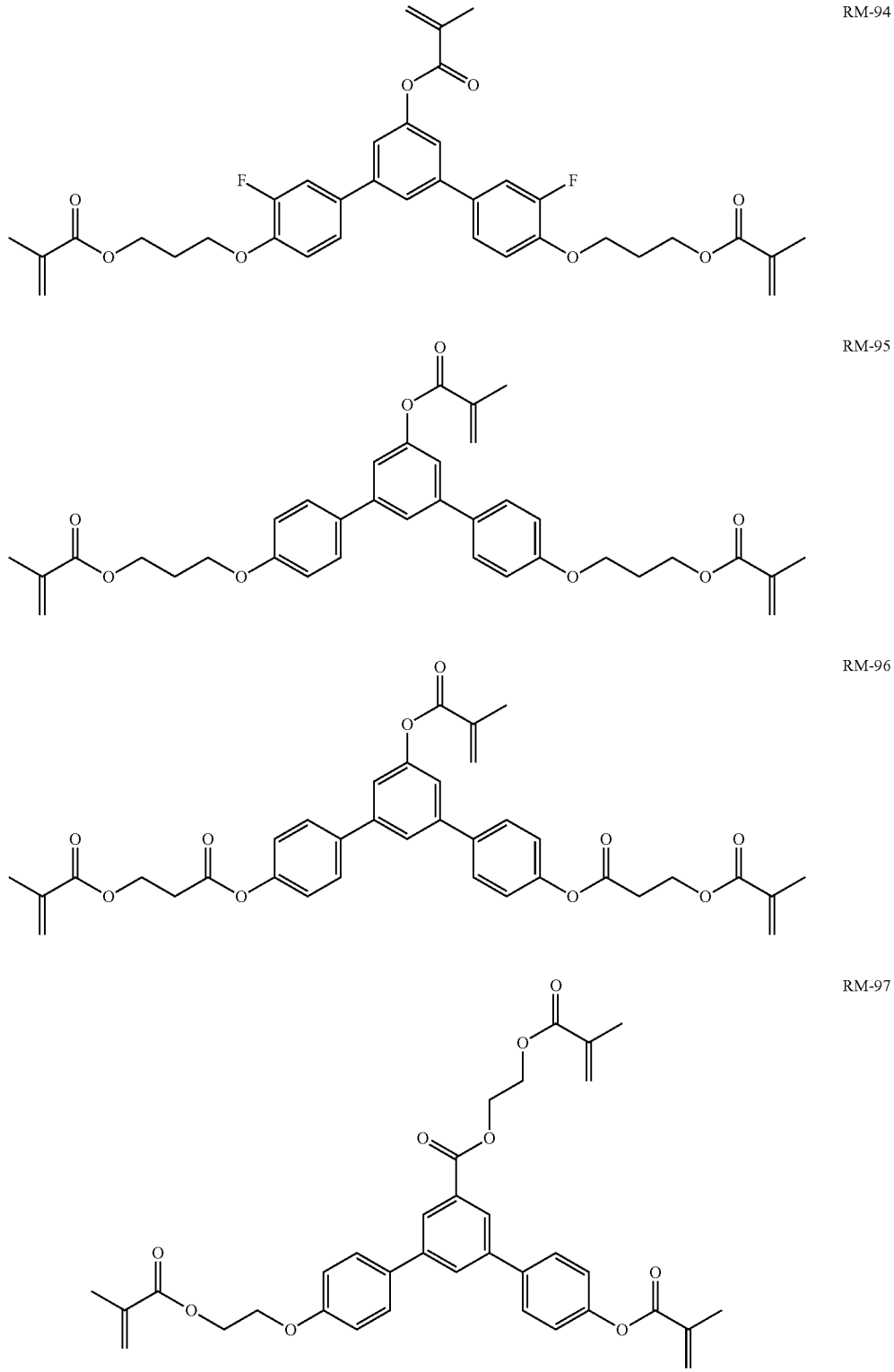
RM-94
RM-95
RM-96
RM-97

TABLE G-continued
Table G shows illustrative compounds which can preferably be used as polymerisable compounds in the LC media in accordance with the present invention.
RM-98
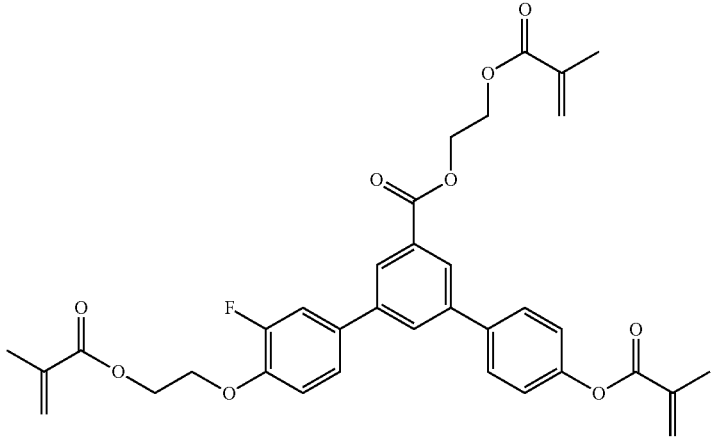 [SMILES: C=C(C)C(=O)OCCOC(=O)c1cc(-c2ccc(OC(=O)C(=C)C)cc2)cc(-c2ccc(OCCOC(=O)C(=C)C)c(F)c2)c1]
RM-99
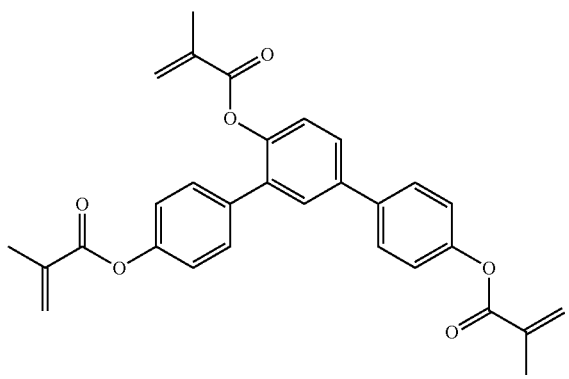 [SMILES: C=C(C)C(=O)Oc1ccc(-c2ccc(OC(=O)C(=C)C)c(-c3ccc(OC(=O)C(=C)C)cc3)c2)cc1]
RM-100
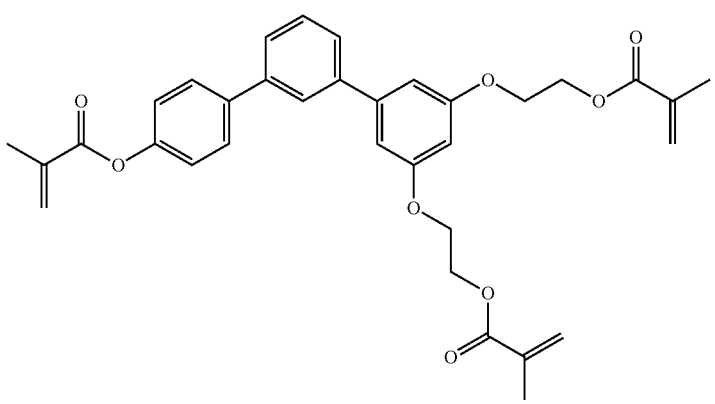 [SMILES: C=C(C)C(=O)OCCOc1cc(OCCOC(=O)C(=C)C)cc(-c2cccc(-c3ccc(OC(=O)C(=C)C)cc3)c2)c1]

TABLE G-continued
Table G shows illustrative compounds which can preferably be used as polymerisable compounds in the LC media in accordance with the present invention.
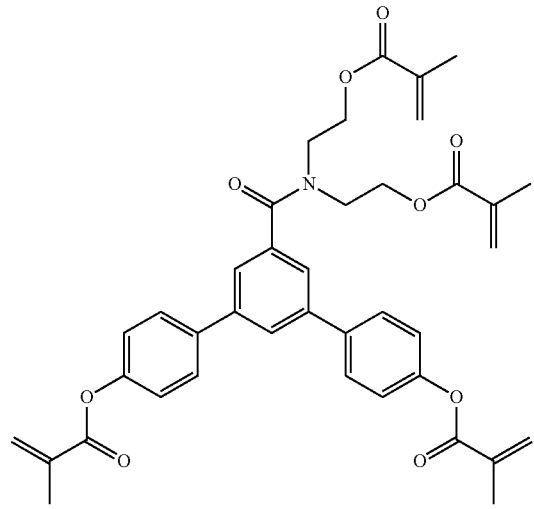 [SMILES: C=C(C)C(=O)OCCN(CCOC(=O)C(=C)C)C(=O)c1cc(-c2ccc(OC(=O)C(=C)C)cc2)cc(-c2ccc(OC(=O)C(=C)C)cc2)c1]
RM-101
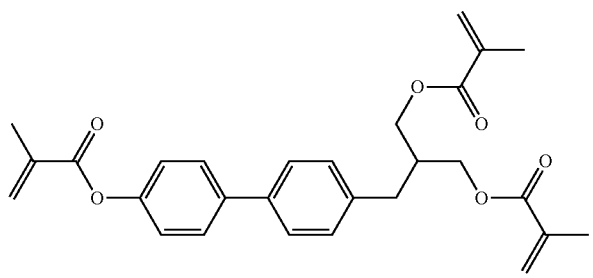 [SMILES: C=C(C)C(=O)OCC(COC(=O)C(=C)C)Cc1ccc(-c2ccc(OC(=O)C(=C)C)cc2)cc1]
RM-102
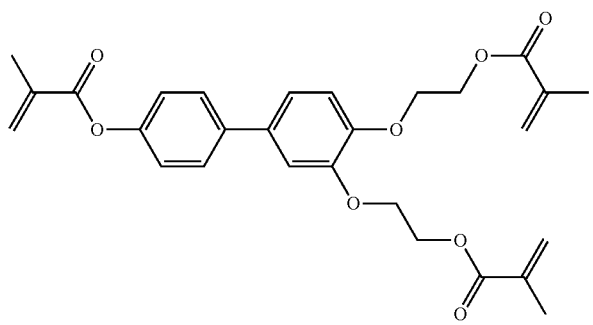 [SMILES: C=C(C)C(=O)OCCOc1ccc(-c2ccc(OC(=O)C(=C)C)cc2)cc1OCCOC(=O)C(=C)C]
RM-103
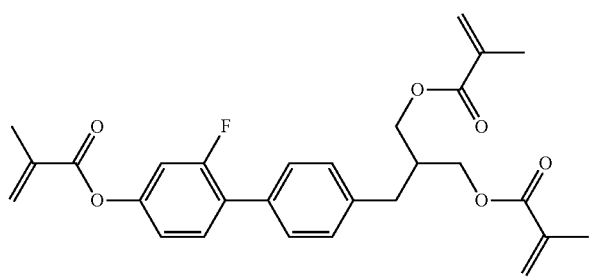 [SMILES: C=C(C)C(=O)OCC(COC(=O)C(=C)C)Cc1ccc(-c2ccc(OC(=O)C(=C)C)cc2F)cc1]
RM-104

TABLE G-continued
Table G shows illustrative compounds which can preferably be used as polymerisable compounds in the LC media in accordance with the present invention.
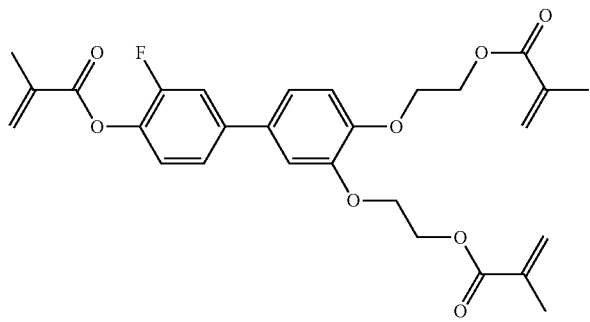 [SMILES: C=C(C)C(=O)OCCOc1ccc(-c2ccc(OC(=O)C(=C)C)c(F)c2)cc1OCCOC(=O)C(=C)C]
RM-105
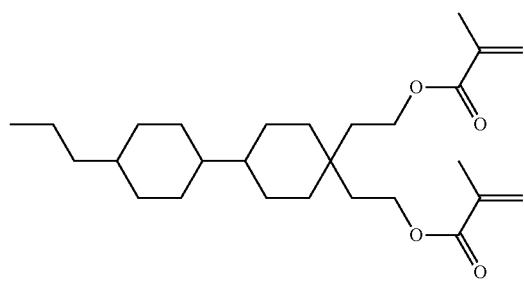 [SMILES: C=C(C)C(=O)OCCC1(CCOC(=O)C(=C)C)CCC(C2CCC(CCC)CC2)CC1]
RM-106
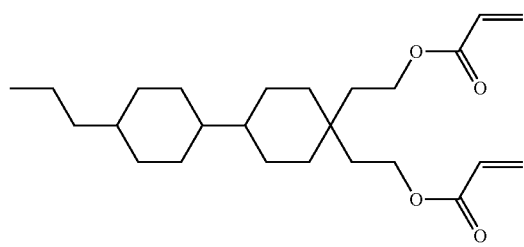 [SMILES: C=CC(=O)OCCC1(CCOC(=O)C=C)CCC(C2CCC(CCC)CC2)CC1]
RM-107
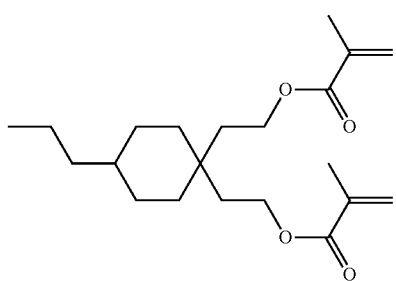 [SMILES: C=C(C)C(=O)OCCC1(CCOC(=O)C(=C)C)CCC(CCC)CC1]
RM-108
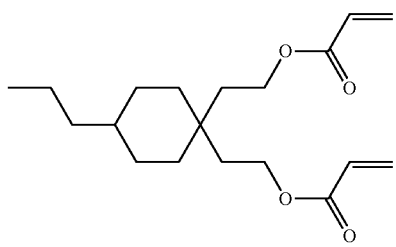 [SMILES: C=CC(=O)OCCC1(CCOC(=O)C=C)CCC(CCC)CC1]
RM-109
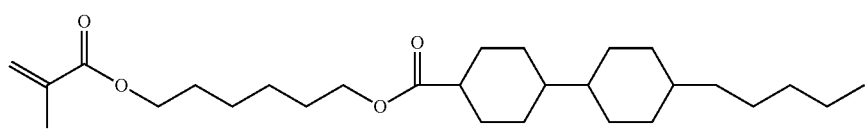 [SMILES: C=C(C)C(=O)OCCCCCCOC(=O)C1CCC(C2CCC(CCCCC)CC2)CC1]
RM-110

TABLE G-continued
Table G shows illustrative compounds which can preferably be used as polymerisable compounds in the LC media in accordance with the present invention.
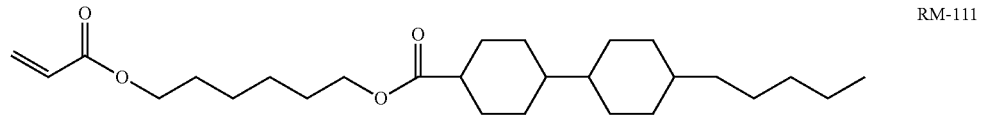
RM-111
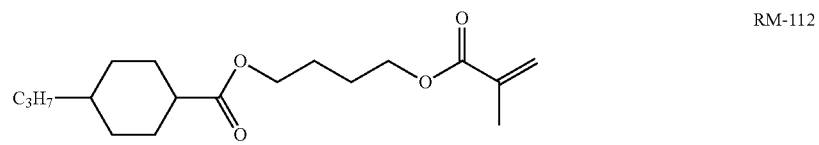
RM-112
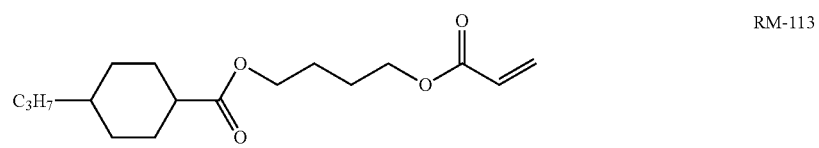
RM-113
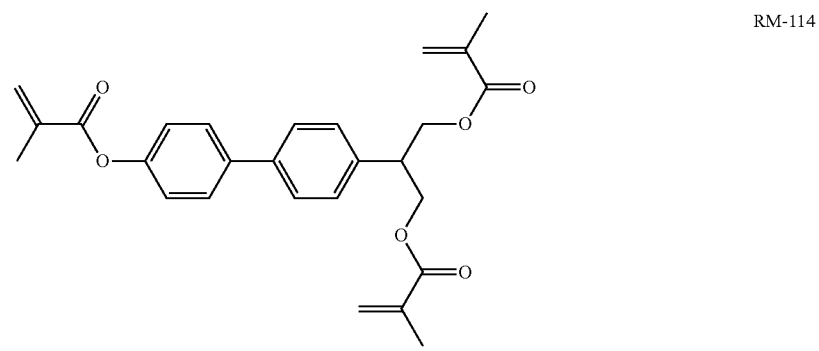
RM-114
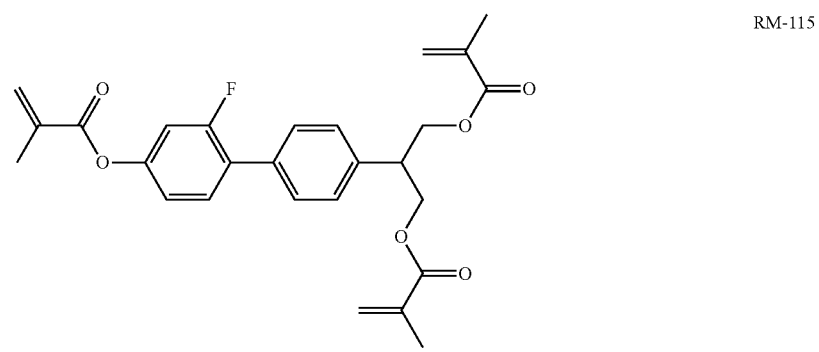
RM-115
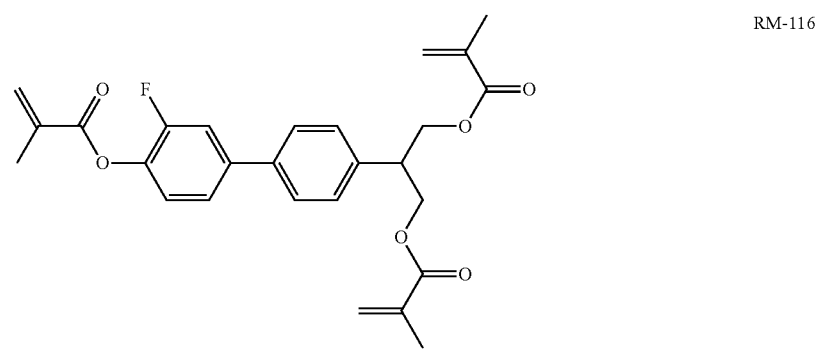
RM-116

TABLE G-continued
Table G shows illustrative compounds which can preferably be used as polymerisable compounds in the LC media in accordance with the present invention.
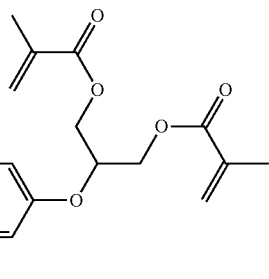
RM-117
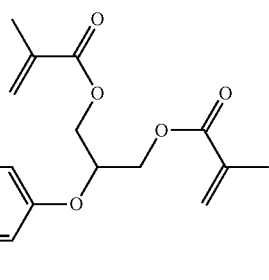
RM-118
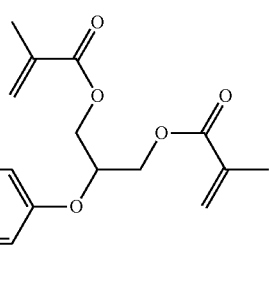
RM-119
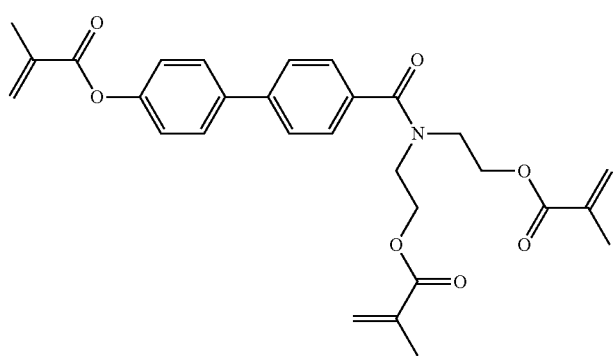 [SMILES: C=C(C)C(=O)OCCN(CCOC(=O)C(=C)C)C(=O)c1ccc(-c2ccc(OC(=O)C(=C)C)cc2)cc1]
RM-120
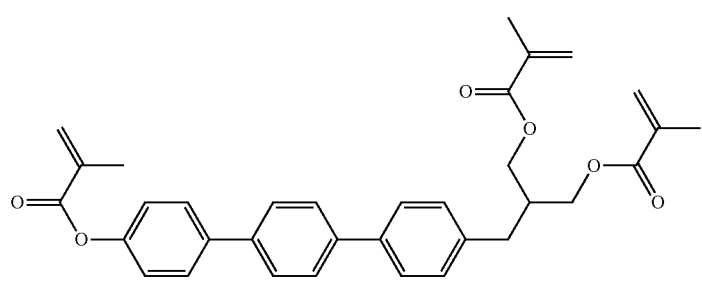 [SMILES: C=C(C)C(=O)OCC(COC(=O)C(=C)C)Cc1ccc(-c2ccc(-c3ccc(OC(=O)C(=C)C)cc3)cc2)cc1]
RM-121

TABLE G-continued
Table G shows illustrative compounds which can preferably be used as polymerisable compounds in the LC media in accordance with the present invention.
RM-122
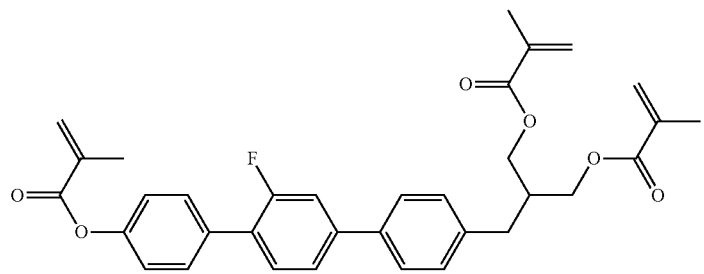 [SMILES: C=C(C)C(=O)OCC(COC(=O)C(=C)C)Cc1ccc(-c2ccc(-c3ccc(OC(=O)C(=C)C)cc3)c(F)c2)cc1]
RM-123
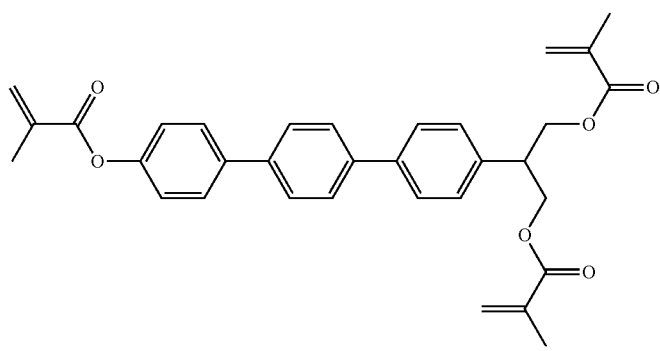 [SMILES: C=C(C)C(=O)OCC(COC(=O)C(=C)C)c1ccc(-c2ccc(-c3ccc(OC(=O)C(=C)C)cc3)cc2)cc1]
RM-124
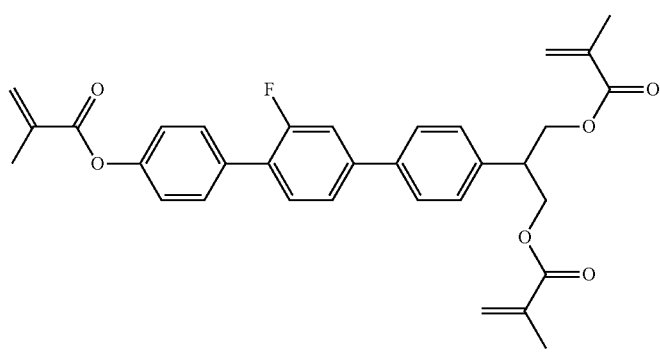 [SMILES: C=C(C)C(=O)OCC(COC(=O)C(=C)C)c1ccc(-c2ccc(-c3ccc(OC(=O)C(=C)C)cc3)c(F)c2)cc1]
RM-125
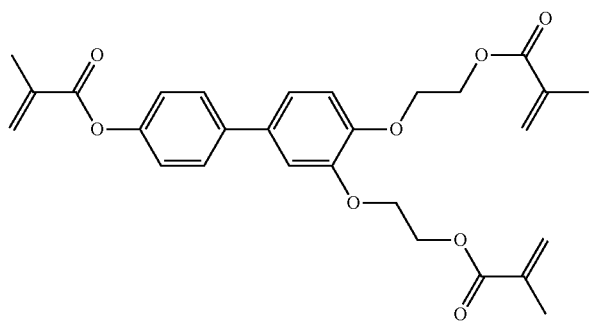 [SMILES: C=C(C)C(=O)OCCOc1ccc(-c2ccc(OC(=O)C(=C)C)cc2)cc1OCCOC(=O)C(=C)C]

TABLE G-continued
Table G shows illustrative compounds which can preferably be used as polymerisable compounds in the LC media in accordance with the present invention.
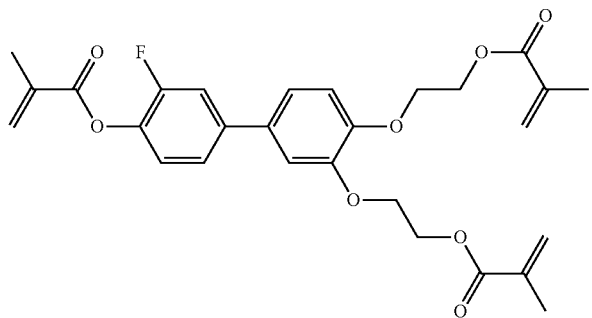 [SMILES: C=C(C)C(=O)OCCOc1ccc(-c2ccc(OC(=O)C(=C)C)c(F)c2)cc1OCCOC(=O)C(=C)C]
RM-126
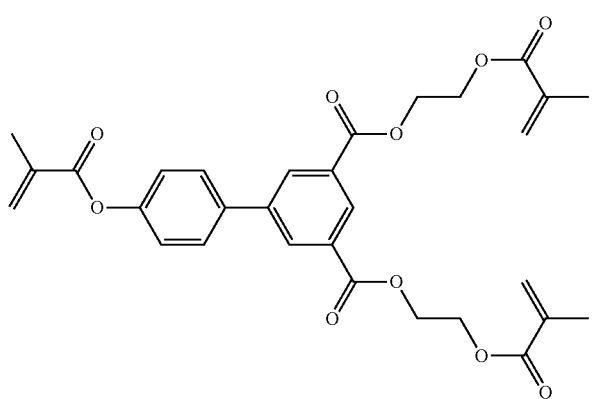 [SMILES: C=C(C)C(=O)OCCOC(=O)c1cc(C(=O)OCCOC(=O)C(=C)C)cc(-c2ccc(OC(=O)C(=C)C)cc2)c1]
RM-127
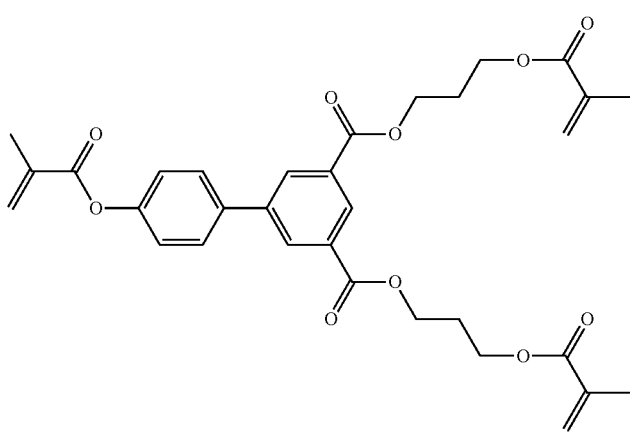 [SMILES: C=C(C)C(=O)OCCCOC(=O)c1cc(C(=O)OCCCOC(=O)C(=C)C)cc(-c2ccc(OC(=O)C(=C)C)cc2)c1]
RM-128
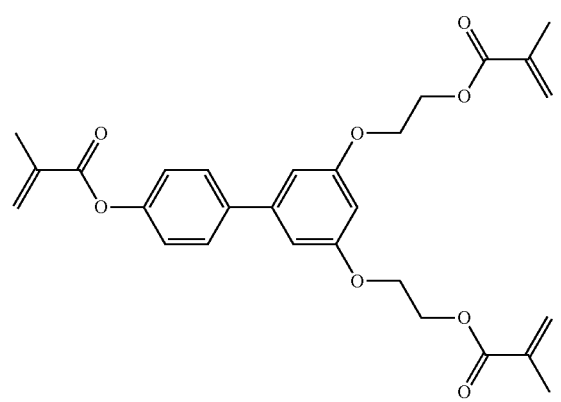 [SMILES: C=C(C)C(=O)OCCOc1cc(OCCOC(=O)C(=C)C)cc(-c2ccc(OC(=O)C(=C)C)cc2)c1]
RM-129

TABLE G-continued
Table G shows illustrative compounds which can preferably be used as polymerisable compounds in the LC media in accordance with the present invention.
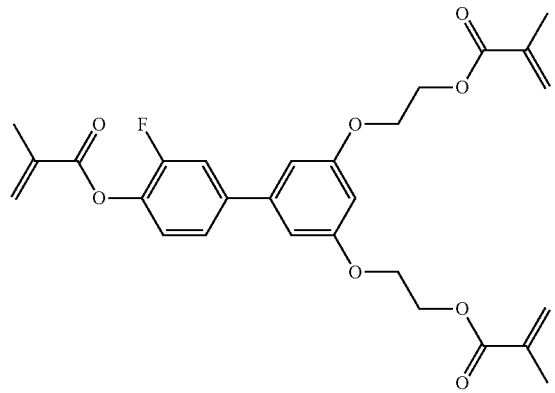 [SMILES: C=C(C)C(=O)OCCOc1cc(OCCOC(=O)C(=C)C)cc(-c2ccc(OC(=O)C(=C)C)c(F)c2)c1]
RM-130
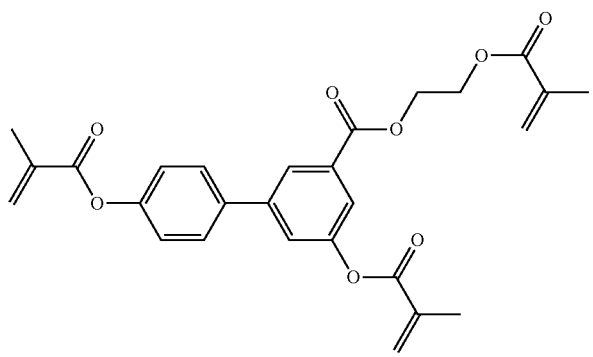 [SMILES: C=C(C)C(=O)OCCOC(=O)c1cc(OC(=O)C(=C)C)cc(-c2ccc(OC(=O)C(=C)C)cc2)c1]
RM-131
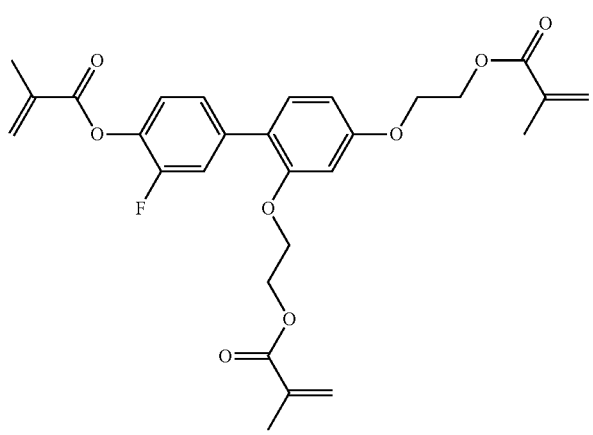 [SMILES: C=C(C)C(=O)OCCOc1ccc(-c2ccc(OC(=O)C(=C)C)c(F)c2)c(OCCOC(=O)C(=C)C)c1]
RM-132

TABLE G-continued
Table G shows illustrative compounds which can preferably be used as polymerisable compounds in the LC media in accordance with the present invention.
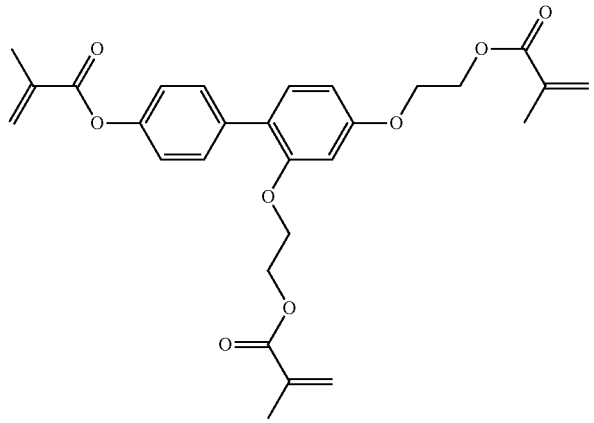 [SMILES: C=C(C)C(=O)OCCOc1ccc(-c2ccc(OC(=O)C(=C)C)cc2)c(OCCOC(=O)C(=C)C)c1] RM-133
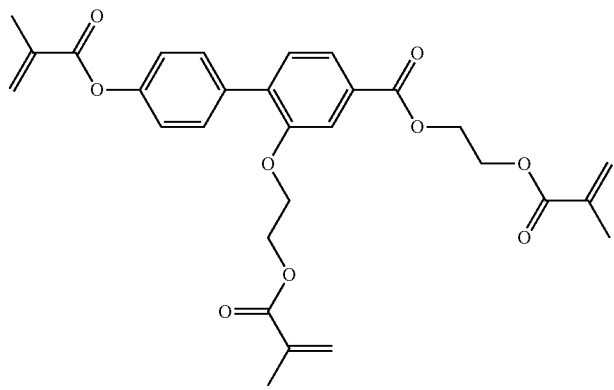 [SMILES: C=C(C)C(=O)OCCOC(=O)c1ccc(-c2ccc(OC(=O)C(=C)C)cc2)c(OCCOC(=O)C(=C)C)c1] RM-134
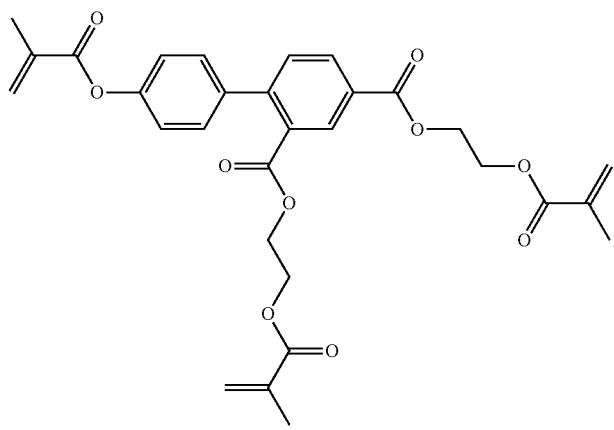 [SMILES: C=C(C)C(=O)OCCOC(=O)c1ccc(-c2ccc(OC(=O)C(=C)C)cc2)c(C(=O)OCCOC(=O)C(=C)C)c1] RM-135
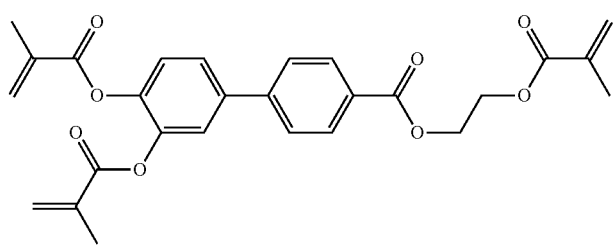 [SMILES: C=C(C)C(=O)OCCOC(=O)c1ccc(-c2ccc(OC(=O)C(=C)C)c(OC(=O)C(=C)C)c2)cc1] RM-136

TABLE G-continued
Table G shows illustrative compounds which can preferably be used as polymerisable compounds in the LC media in accordance with the present invention.
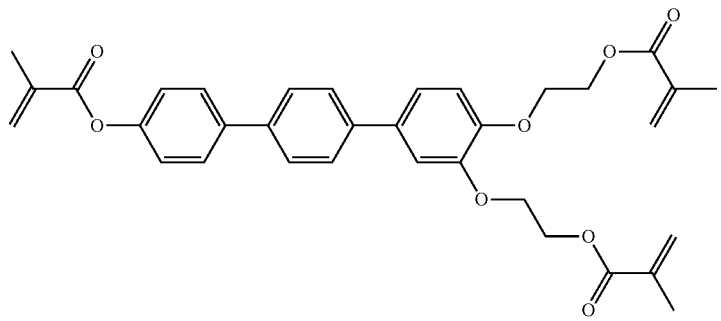 [SMILES: C=C(C)C(=O)OCCOc1ccc(-c2ccc(-c3ccc(OC(=O)C(=C)C)cc3)cc2)cc1OCCOC(=O)C(=C)C]
RM-137
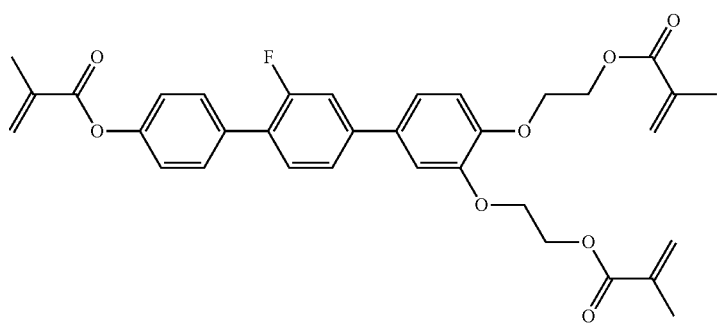 [SMILES: C=C(C)C(=O)OCCOc1ccc(-c2ccc(-c3ccc(OC(=O)C(=C)C)cc3)c(F)c2)cc1OCCOC(=O)C(=C)C]
RM-138
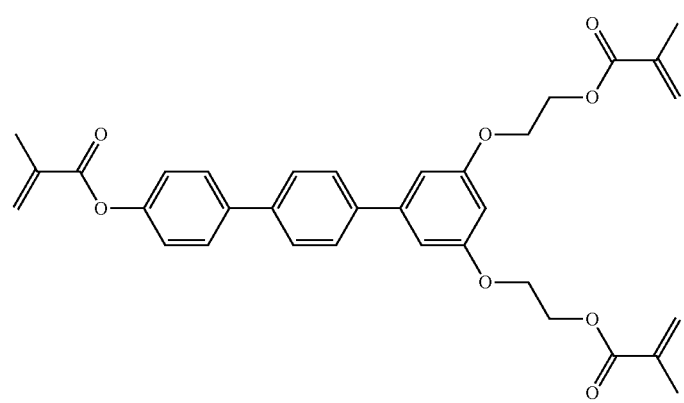 [SMILES: C=C(C)C(=O)OCCOc1cc(OCCOC(=O)C(=C)C)cc(-c2ccc(-c3ccc(OC(=O)C(=C)C)cc3)cc2)c1]
RM-139
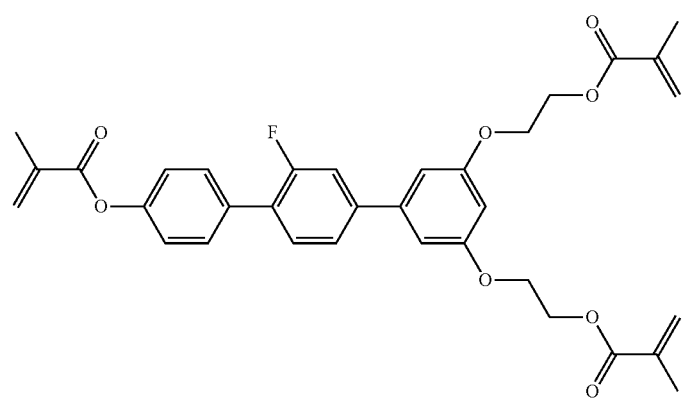 [SMILES: C=C(C)C(=O)OCCOc1cc(OCCOC(=O)C(=C)C)cc(-c2ccc(-c3ccc(OC(=O)C(=C)C)cc3)c(F)c2)c1]
RM-140

TABLE G-continued
Table G shows illustrative compounds which can preferably be used as polymerisable compounds in the LC media in accordance with the present invention.
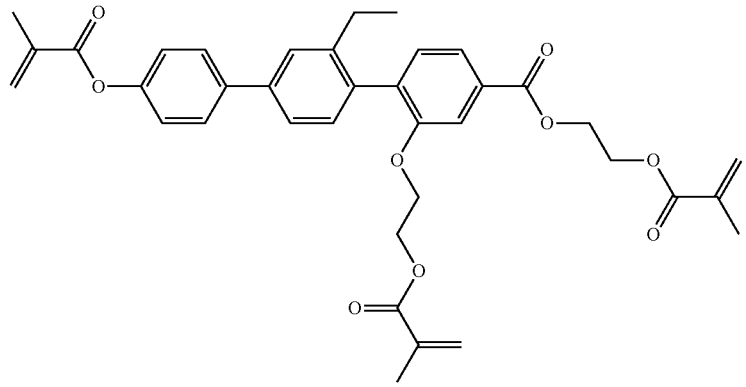 [SMILES: C=C(C)C(=O)OCCOC(=O)c1ccc(-c2ccc(-c3ccc(OC(=O)C(=C)C)cc3)cc2CC)c(OCCOC(=O)C(=C)C)c1]
RM-141
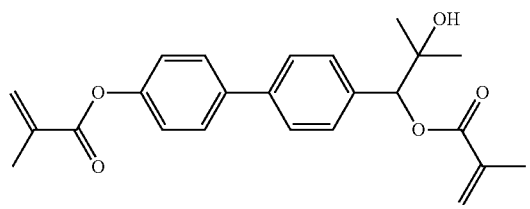 [SMILES: C=C(C)C(=O)Oc1ccc(-c2ccc(C(OC(=O)C(=C)C)C(C)(C)O)cc2)cc1]
RM-142
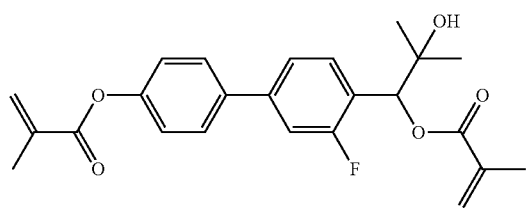 [SMILES: C=C(C)C(=O)Oc1ccc(-c2ccc(C(OC(=O)C(=C)C)C(C)(C)O)c(F)c2)cc1]
RM-143
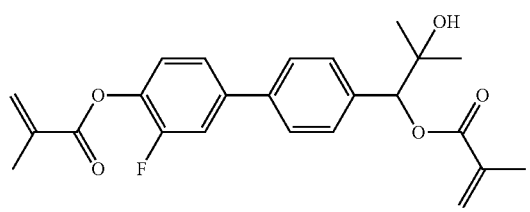 [SMILES: C=C(C)C(=O)Oc1ccc(-c2ccc(C(OC(=O)C(=C)C)C(C)(C)O)cc2)cc1F]
RM-144

In a preferred embodiment of the present invention, the mesogenic media comprise one or more compounds selected from the group of the compounds from Table G.

In the present application, the term "compounds", also written as "compound(s)", denotes, unless explicitly indicated otherwise, both one and also a plurality of compounds. Conversely, the term "compound" generally also encompasses a plurality of compounds, if this is possible according to the definition and is not indicated otherwise. The same applies to the terms LC media and LC medium. The term "component" in each case encompasses one or more substances, compounds and/or particles.

In addition, the following abbreviations and symbols are used:

$n_e$ extraordinary refractive index at 20° C. and 589 nm,
$n_o$ ordinary refractive index at 20° C. and 589 nm,
$\Delta n$ optical anisotropy at 20° C. and 589 nm,
$\varepsilon_\perp$ dielectric permittivity perpendicular to the director at 20° C. and 1 kHz,
$\varepsilon_\parallel$ dielectric permittivity parallel to the director at 20° C. and 1 kHz,
$\Delta\varepsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN]
$V_0$ capacitive threshold (Freedericks threshold) at 20° C. [V].

Unless explicitly noted otherwise, all concentrations in the present application are quoted in percent by weight and relate to the corresponding mixture as a whole, comprising all solid or liquid-crystalline components, without solvents.

All physical properties are and have been determined in accordance with "Merck Liquid Crystals, Physical Properties of Liquid Crystals", Status November 1997, Merck KGaA, Germany, and apply for a temperature of 20° C., and $\Delta n$ is determined at 589 nm and $\Delta\varepsilon$ at 1 kHz, unless explicitly indicated otherwise in each case.

The polymerisable compounds are polymerised in the display or test cell by irradiation with UVA light (usually 365 nm) of defined intensity for a prespecified time, with a voltage optionally being applied to the display at the same time (usually 10 to 30 V alternating current, 1 kHz). In the examples, unless indicated otherwise, a 100 mW/cm² mercury vapour lamp is used, and the intensity is measured using a standard UV meter (Ushio UNI meter) fitted with a 320 nm (optionally 340 nm) band-pass filter.

The following examples explain the present invention without being intended to restrict it in any way. However, the physical properties make clear to the person skilled in the art what properties can be achieved and in what ranges they can be modified. In particular, the combination of the various properties which can preferably be achieved is thus well defined for the person skilled in the art.

Further combinations of the embodiments and variants of the invention in accordance with the description also arise from the claims.

EXAMPLES

The compounds employed, if not commercially available, are synthesised by standard laboratory procedures. The LC media originate from Merck KGaA, Germany.

A) Synthesis Examples

Example 1

Step 1: Synthesis of Intermediate 5 (Boronic Acid)

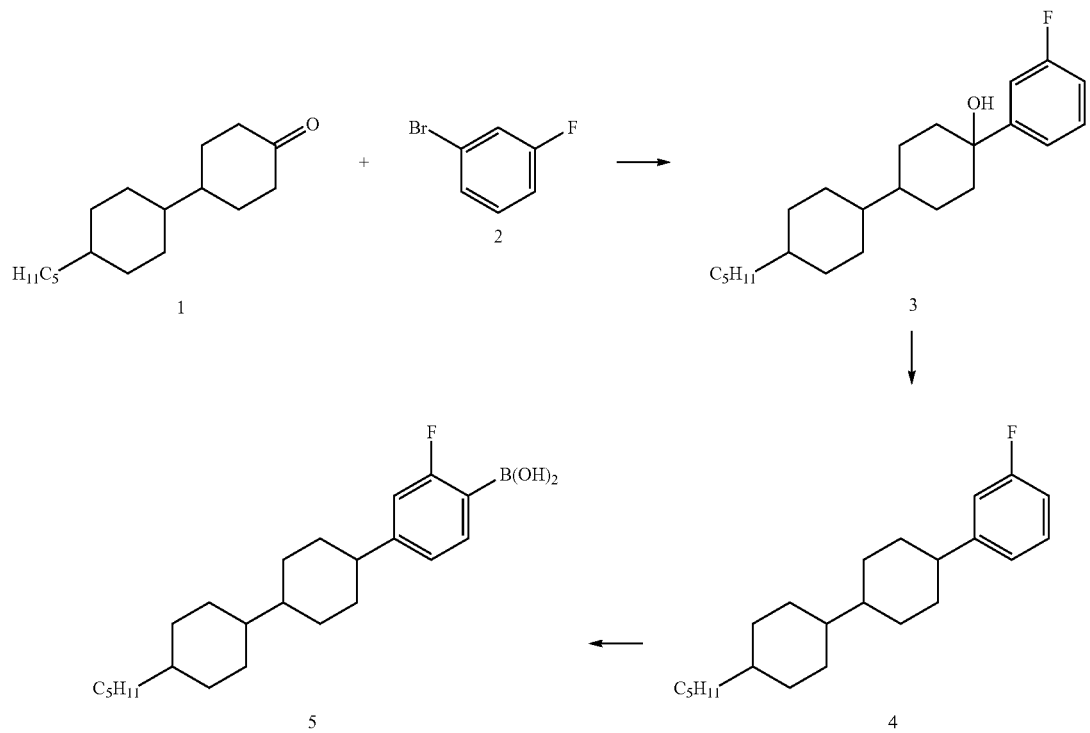

9.7 g (0.4 mol) of magnesium are covered with 40 ml of THF, and both are heated to 50° C. About 10% of a solution of the bromo-aromatic compound 2 (69.9 g, 0.4 mol) in 100 ml of THF are then added dropwise. After the reaction has initiated, 2 is metered in at such a rate that the mixture boils continuously. When the addition is complete, the mixture is allowed to cool to 65° C., and 100 g (0.4 mol) of ketone 1 dissolved in 100 ml of THF are added dropwise. Work-up gives 128.3 g of the alcohol 3, which is dissolved in 800 ml of toluene without further purification and, after addition of 3.2 g of p-toluenesulfonic acid hydrate, is boiled under reflux for 2 h. Work-up gives 98 g of crude olefin, which is converted into 4 by catalytic hydrogenation.

71.7 g (217 mmol) of 4 are dissolved in 200 ml of THF and cooled to −70° C. 170 ml (0.239 mol) of a 1.4 molar solution of s-butyllithium in hexane are then added dropwise at this temperature. When the addition is complete, the mixture is stirred at −70° C. for a further hour, and a solution of 28.3 ml (0.249 mol) of trimethyl borate in 100 ml of THF is subsequently added dropwise. Work-up and crystallisation from heptane gives 65.8 g of boronic acid 5.

Step 2: Synthesis of Intermediate 8

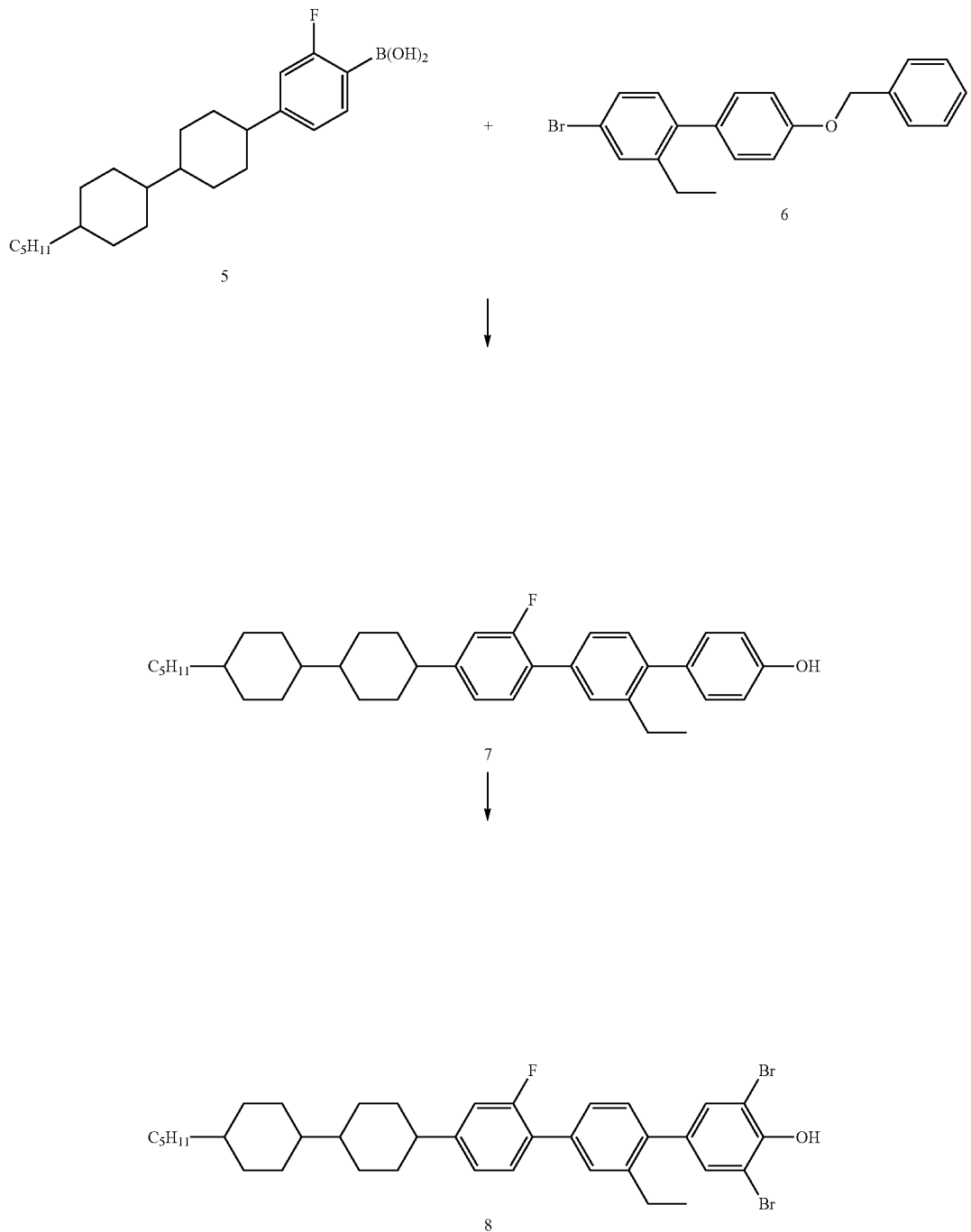

65.2 g (172 mmol) of boronic acid 5, 63 g (172 mmol) of bromide 6, 5.95 g (5.1 mmol) of tetrakis(triphenylphosphino)palladium(0) and 47.3 g of sodium carbonate are suspended in 53 ml of ethanol, 360 ml of toluene and 170 ml of water and heated to reflux. Work-up gives 90.0 g of colourless solid, which is hydrogenated in 1.8 l of tetrahydrofuran over 30 g of palladium on carbon (5%). The crude product is recrystallised from heptane/toluene (1:1), giving 55 g of phenol 7.

40 g (76 mmol) of 7 are presented in 500 ml of tetrahydrofuran, 2 ml of diisopropylamine are added, and 27.0 g (152 mmol) of N-bromosuccinimide are added in portions at −5° C. The mixture is stirred at 0° C. for one hour and then allowed to come to RT. Work-up gives 56.8 g of dibromide 8.

Step 3: Synthesis of Intermediate 11

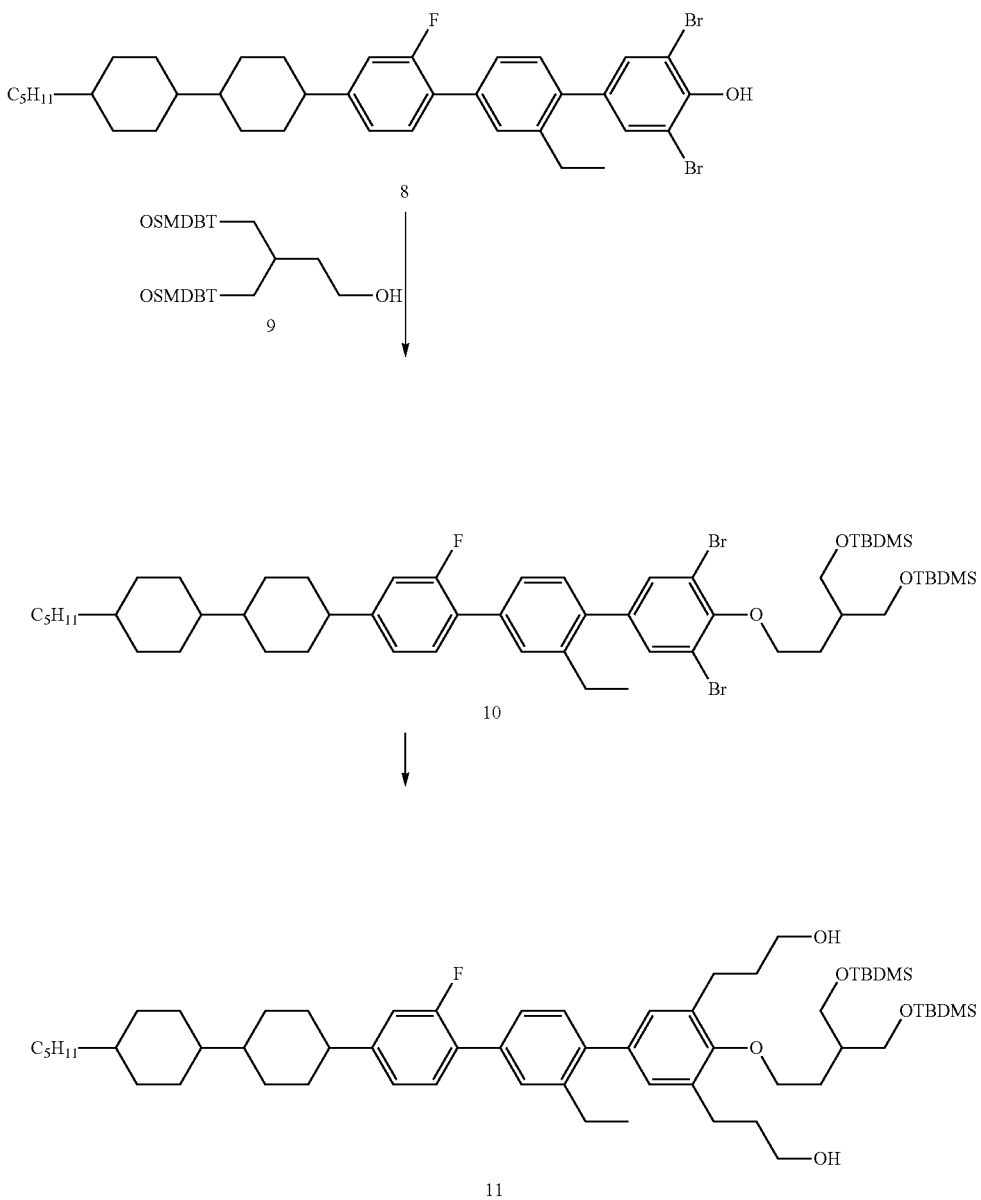

15 g (21.9 mmol) of 8 and 9.2 g (26.3 mmol) of 9 are dissolved in 120 ml of tetrahydrofuran with 6.9 g (26.3 mmol) of triphenylphosphine, and 5.5 ml (26.3 mmol) of diisopropyl azodicarboxylate are added dropwise at RT. The mixture is stirred overnight at RT. Work-up gives 11.7 g of 10 as a white, wax-like solid.

11.7 g (11.5 mmol) of 10 are mixed with 6.2 g (43.8 mmol) of 2-butoxy-1,2-oxaborolane, 14 g of potassium phosphate, 26.1 mg (0.115 mmol) of palladium acetate, 113.2 mg (0.230 mmol) of Ruphos (CAS 787618-22-8), 35 ml of water and 170 ml of tetrahydrofuran and heated under reflux for 3 h. Work-up gives 8.9 g of 11 as a white, wax-like substance.

Step 4: Synthesis of the Final Compound 12 (Self-Alignment Additive No. 2)

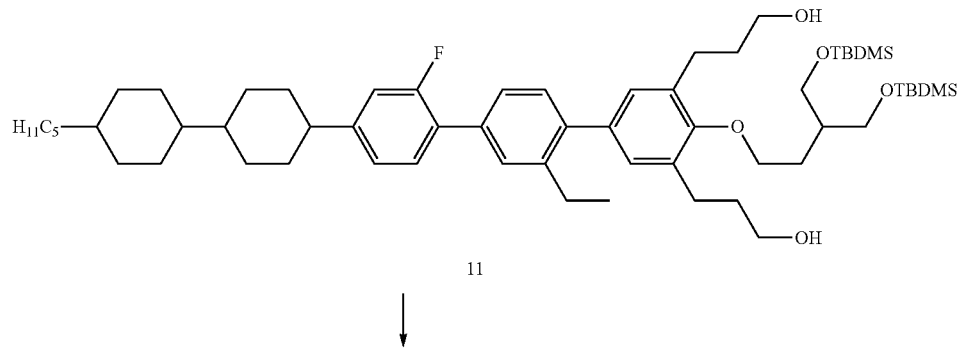

11

↓

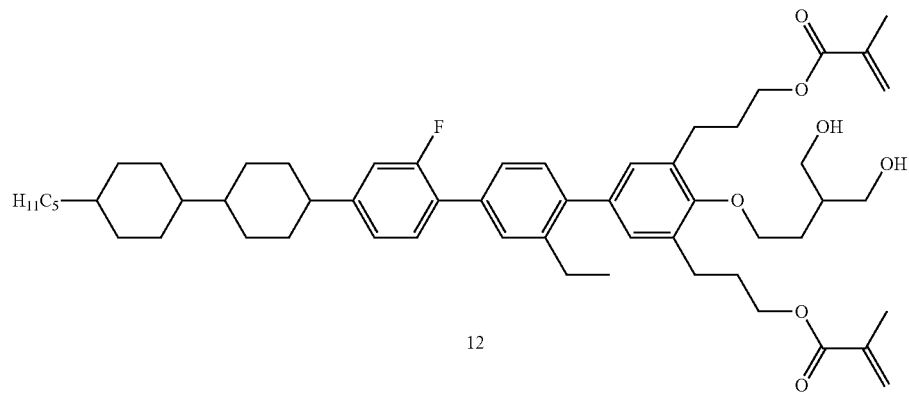

12

8.9 g (9.1 mmol) of 11, 3.9 ml (45.7 mmol) of methacrylic acid and 223 mg (1.8 mmol) of DMAP are dissolved in 90 ml of dichloromethane, and 7.9 ml (45.7 mmol) of EDC (1-[3-(dimethylamino)propyl]-3-ethylcarbodiimide hydrochloride) are added dropwise at 5° C. The mixture is left to stir overnight at RT and subjected to conventional work-up. The crude product. (6.2 g) is dissolved in 50 ml of tetrahydrofuran, and 8.3 ml (16.8 mmol) of 2 molar hydrochloric acid are added at 5° C. The mixture is then left to stir overnight at RT and subjected to conventional work-up. Crystallisation from heptane gives 3.0 g of 12 as a white powder of melting point 72° C.

Phases glass transition temperature (Tg) −26° C., melting point 72° C.

$^1$H NMR (700 MHz, chloroform-d) δ 7.41-7.36 (m, 2H), 7.03 (s, 2H), 7.01 (dd, J=12.0, 1.7 Hz, 1H), 6.10 (s, 2H), 5.56 (q, J=1.7 Hz, 2H), 4.24 (t, J=6.7 Hz, 4H), 3.95-3.89 (m, 4H), 3.80 (dd, J=10.8, 6.7 Hz, 2H), 2.77-2.72 (m, 4H), 2.69 (s, 1H), 2.63 (q, J=7.6 Hz, 2H), 2.49 (tt, J=12.1, 3.5 Hz, 1H), 2.12 (qq, J=10.7, 6.5, 5.4 Hz, 1H), 2.07-2.00 (m, 4H), 2.00-1.95 (m, 2H), 1.94 (s, 6H), 1.87 (q, J=6.3 Hz, 4H), 1.81-1.72 (m, 4H), 1.49-1.41 (m, 2H), 1.34-1.27 (m, 4H), 1.27-1.21 (m, 2H), 1.21-1.05 (m, 10H), 1.01 (qd, J=12.0, 2.8 Hz, 2H), 0.88 (q, J=8.9, 8.1 Hz, 5H).

The following compounds can be prepared analogously by the synthesis described:

Example 2

Self-Alignment Additive No. 1

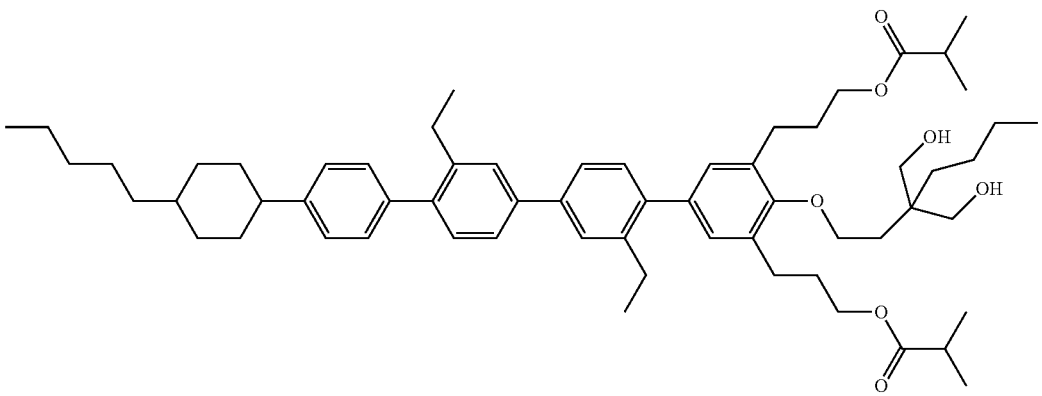 [SMILES: CCCCCC1CCC(c2ccc(-c3ccc(-c4ccc(-c5cc(CCCOC(=O)C(C)C)c(OCCC(CO)(CO)CCCC)c(CCCOC(=O)C(C)C)c5)c(CC)c4)cc3CC)cc2)CC1]

Phases glass transition temperature (Tg) −9° C., melting point 80° C.

$^1$H NMR (500 MHz, chloroform-d) δ 7.57 (d, J=1.9 Hz, 2H), 7.50 (dd, J=7.8, 1.9 Hz, 2H), 7.38-7.20 (m, 6H), 7.07 (s, 2H), 6.13 (t, J=1.3 Hz, 2H), 5.58 (p, J=1.7 Hz, 2H), 4.26 (t, J=6.5 Hz, 4H), 3.99 (t, J=6.3 Hz, 2H), 3.71 (s, 4H), 2.96-2.63 (m, 9H), 2.55 (tt, J=12.1, 3.4 Hz, 1H), 2.17-1.84 (m, 16H), 1.53 (qd, J=12.8, 3.2 Hz, 3H), 1.41-1.01 (m, 23H), 0.93 (dt, J=8.7, 7.0 Hz, 6H).

Example 3

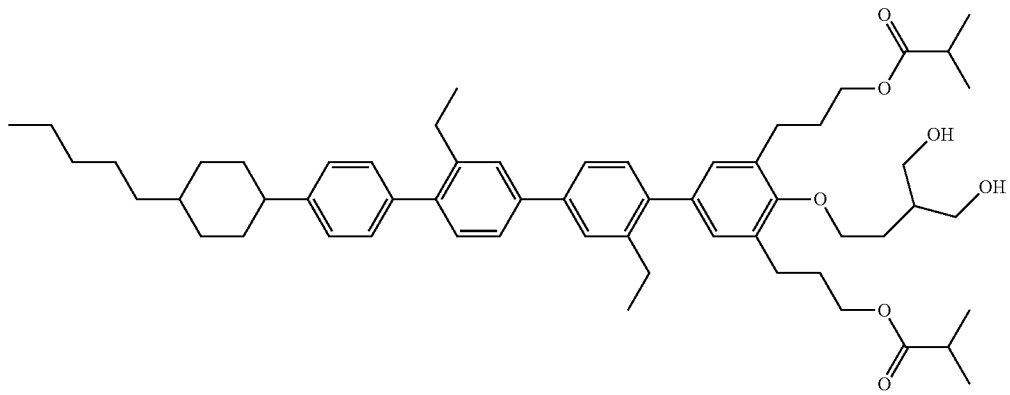 [SMILES: CCCCCC1CCC(c2ccc(-c3ccc(-c4ccc(-c5cc(CCCOC(=O)C(C)C)c(OCCC(CO)CO)c(CCCOC(=O)C(C)C)c5)c(CC)c4)cc3CC)cc2)CC1]

Phases: glass transition temperature (Tg) −17° C. melting point 65° C. ¹H NMR (500 MHz, chloroform-d) δ 7.58 (d, J=1.8 Hz, 2H), 7.51 (dd, J=7.9, 2.0 Hz, 2H), 7.36-7.21 (m, 6H), 7.07 (s, 2H), 6.14 (s, 2H), 5.59 (q, J=1.7 Hz, 2H), 4.28 (t, J=6.6 Hz, 4H), 3.95 (dt, J=10.4, 5.3 Hz, 4H), 3.84 (dd, J=10.8, 6.7 Hz, 2H), 2.86-2.60 (m, 10H), 2.56 (tt, J=12.1, 3.4 Hz, 1H), 2.15 (tt, J=6.5, 4.2 Hz, 1H), 2.11-2.04 (m, 4H), 2.03-1.85 (m, 12H), 1.54 (qd, J=12.8, 3.3 Hz, 3H), 1.32 (dddd, J=26.7, 15.0, 8.8, 6.3 Hz, 9H), 1.20 (td, J=7.5, 4.6 Hz, 6H), 1.11 (qd, J=13.1, 3.3 Hz, 2H), 0.93 (t, J=7.0 Hz, 3H).

Example 4

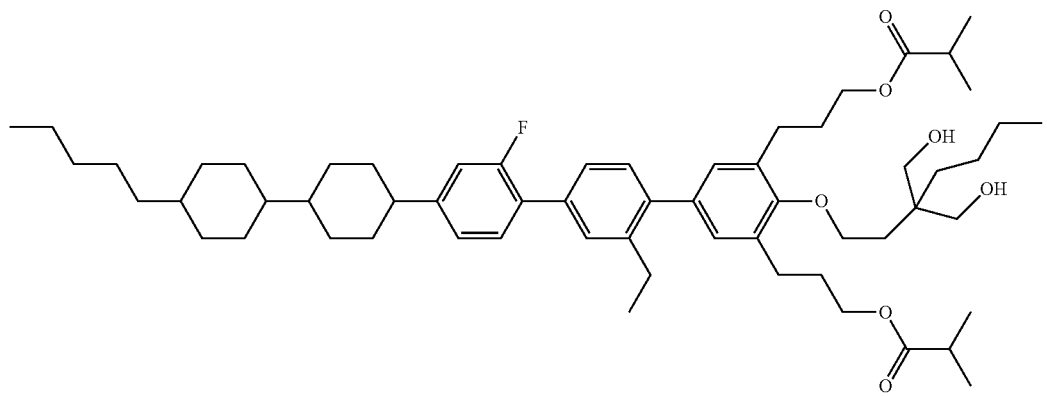 [SMILES: CCCCCC1CCC(C2CCC(c3ccc(-c4ccc(-c5cc(CCCOC(=O)C(C)C)c(OCCC(CO)(CO)CCCC)c(CCCOC(=O)C(C)C)c5)c(CC)c4)c(F)c3)CC2)CC1]

Phases: glass transition temperature (Tg) −20° C., melting point 71° C., nematic-isotropic phase transition 120.0° C.

¹H NMR (500 MHz, chloroform-d) δ 7.49 (d, J=1.6 Hz, 1H), 7.41 (ddd, J=8.0, 5.0, 3.1 Hz, 2H), 7.25 (d, J=7.9 Hz, 1H), 7.12-6.99 (m, 4H), 6.13 (t, J=1.3 Hz, 2H), 5.58 (p, J=1.6 Hz, 2H), 4.26 (t, J=6.5 Hz, 4H), 3.99 (t, J=6.3 Hz, 2H), 3.71 (s, 4H), 2.90-2.70 (m, 5H), 2.66 (q, J=7.6 Hz, 2H), 2.57-2.48 (m, 1H), 2.12-1.94 (m, 13H), 1.90 (d, J=9.1 Hz, 2H), 1.85-1.74 (m, 4H), 1.48 (q, J=12.1 Hz, 2H), 1.32 (ddt, J=23.3, 9.4, 6.4 Hz, 12H), 1.23-1.13 (m, 9H), 1.06 (dtd, J=23.8, 13.2, 11.3, 2.4 Hz, 3H), 0.93 (dt, J=16.1, 7.0 Hz, 8H).

Example 5

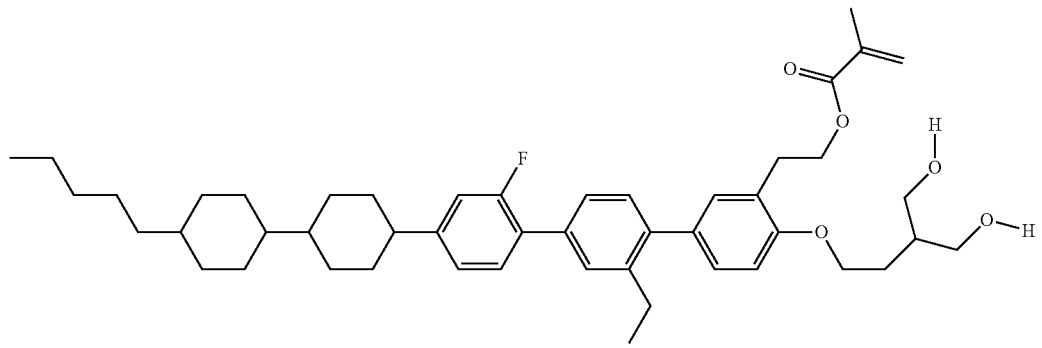 [SMILES: C=C(C)C(=O)OCCc1cc(-c2ccc(-c3ccc(C4CCC(C5CCC(CCCCC)CC5)CC4)cc3F)cc2CC)ccc1OCCC(CO)CO]

$^1$H NMR (500 MHz, chloroform-d) δ 7.46 (t, J=1.7 Hz, 1H), 7.39 (t, J=8.0 Hz, 2H), 7.23-7.12 (m, 3H), 7.06 (dd, J=8.0, 1.7 Hz, 1H), 7.01 (dd, J=12.1, 1.7 Hz, 1H), 6.89 (d, J=8.3 Hz, 1H), 6.08 (dd, J=1.7, 1.0 Hz, 1H), 5.54 (p, J=1.6 Hz, 1H), 4.41 (t, J=7.2 Hz, 2H), 4.12 (t, J=5.9 Hz, 2H), 3.90 (dd, J=10.8, 4.1 Hz, 2H), 3.79 (dd, J=10.8, 6.8 Hz, 2H), 3.04 (t, J=7.2 Hz, 2H), 2.64 (q, J=7.5 Hz, 2H), 2.50 (qd, J=8.6, 7.6, 3.0 Hz, 3H), 2.14 (tdd, J=6.8, 5.4, 2.8 Hz, 1H), 1.97 (dd, J=12.9, 3.3 Hz, 2H), 1.93-1.83 (m, 7H), 1.82-1.70 (m, 4H), 1.51-1.39 (m, 2H), 1.35-1.20 (m, 6H), 1.20-0.95 (m, 12H), 0.88 (q, J=7.0 Hz, 5H).
Example 6
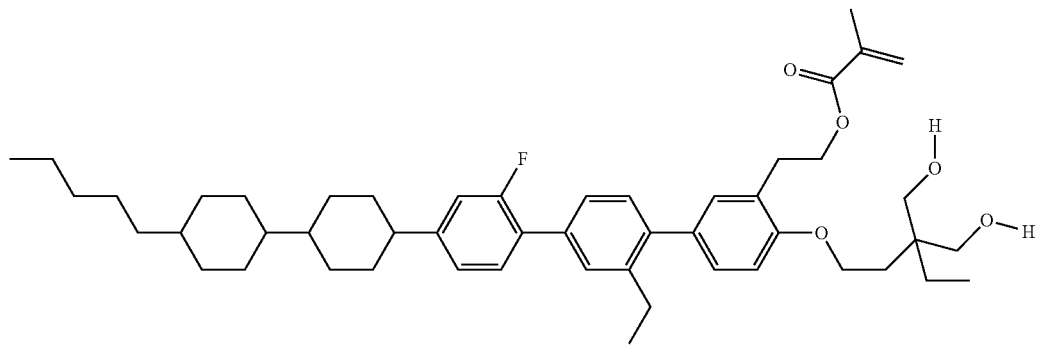 [SMILES: C=C(C)C(=O)OCCc1cc(-c2ccc(-c3ccc(C4CCC(C5CCC(CCCCC)CC5)CC4)cc3F)cc2CC)ccc1OCCC(CC)(CO)CO]
$^1$H NMR (500 MHz, chloroform-d) δ 7.49 (s, 1H), 7.42 (t, J=7.9 Hz, 2H), 7.26-7.16 (m, 3H), 7.09 (dd, J=8.0, 1.6 Hz, 1H), 7.04 (dd, J=12.0, 1.6 Hz, 1H), 6.96 (d, J=8.3 Hz, 1H), 6.11 (s, 1H), 5.56 (t, J=1.7 Hz, 1H), 4.42 (t, J=7.1 Hz, 2H), 4.18 (t, J=6.2 Hz, 2H), 3.93-3.48 (m, 4H), 3.06 (t, J=7.1 Hz, 2H), 2.83-2.12 (m, 5H), 2.08-1.96 (m, 4H), 1.96-1.84 (m, 5H), 1.84-1.69 (m, 4H), 1.54-1.38 (m, 4H), 1.38-0.98 (m, 19H), 0.92 (dq, J=14.9, 7.6 Hz, 8H).
Further Examples
Synthesis Analogous to Example 1
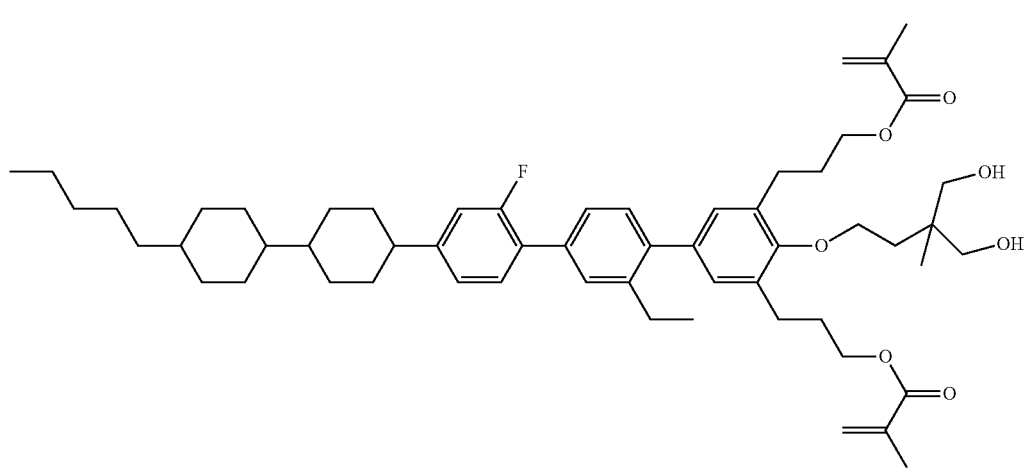
7

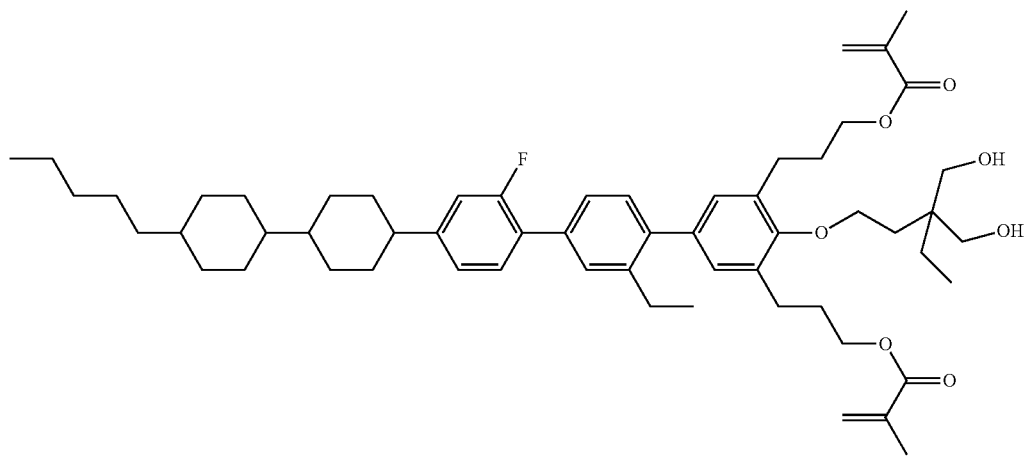
8
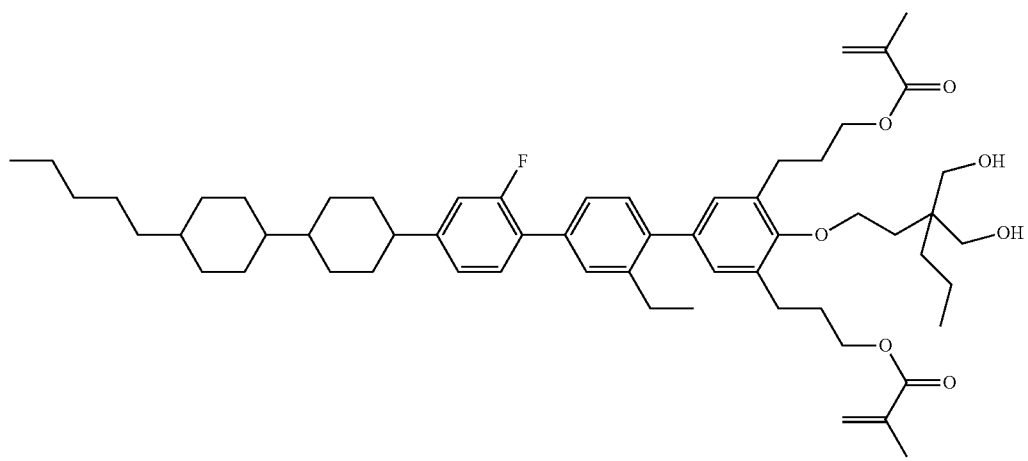
9
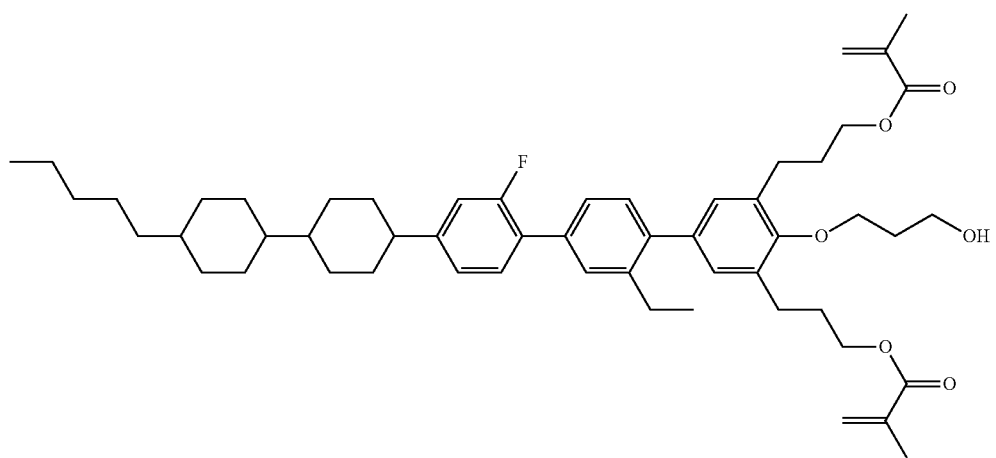
10

-continued
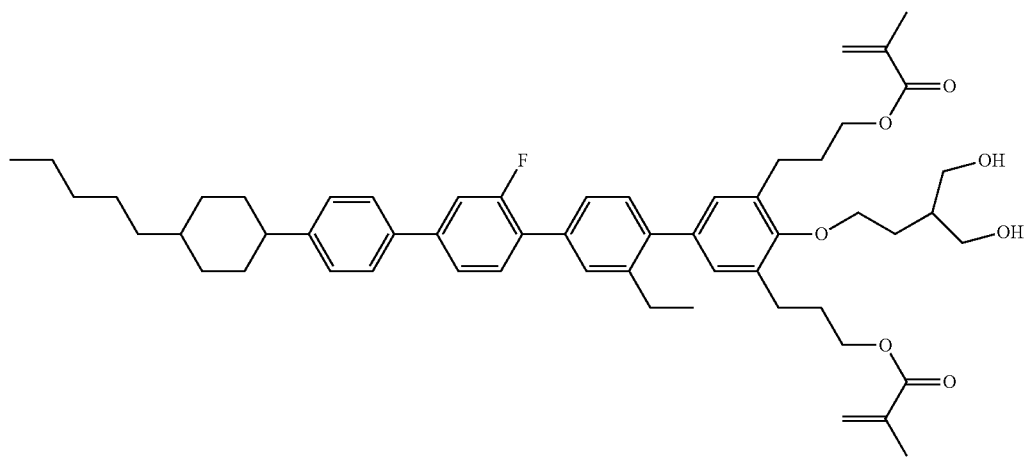
11
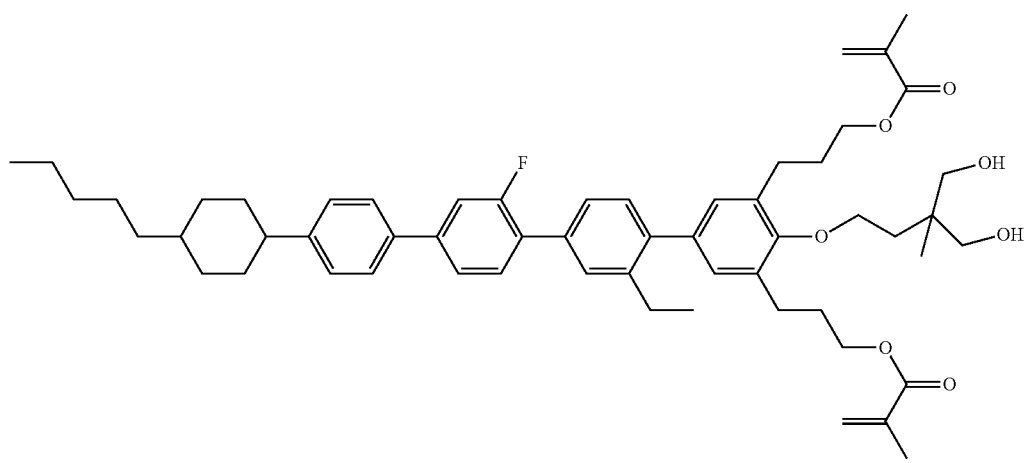
12
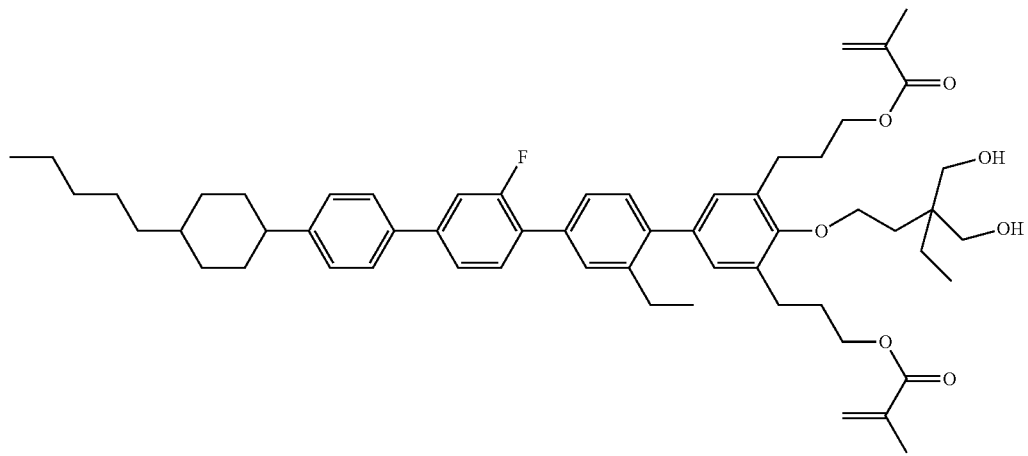
13

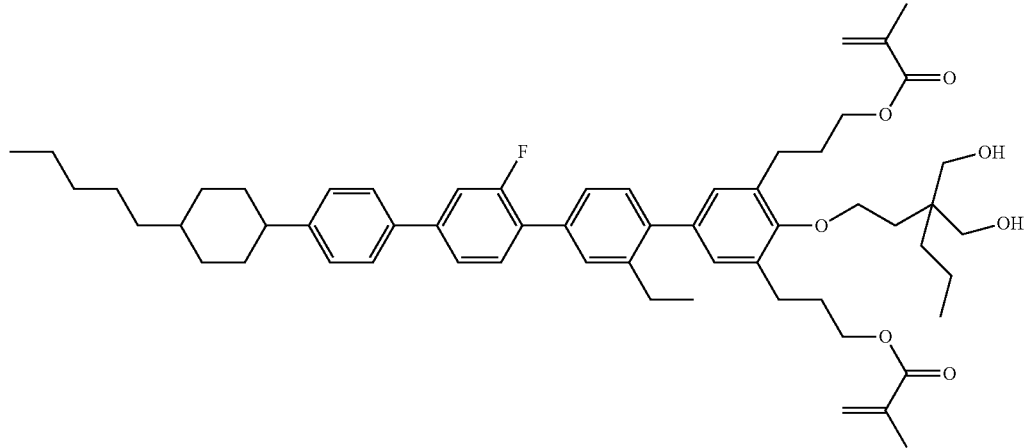
14
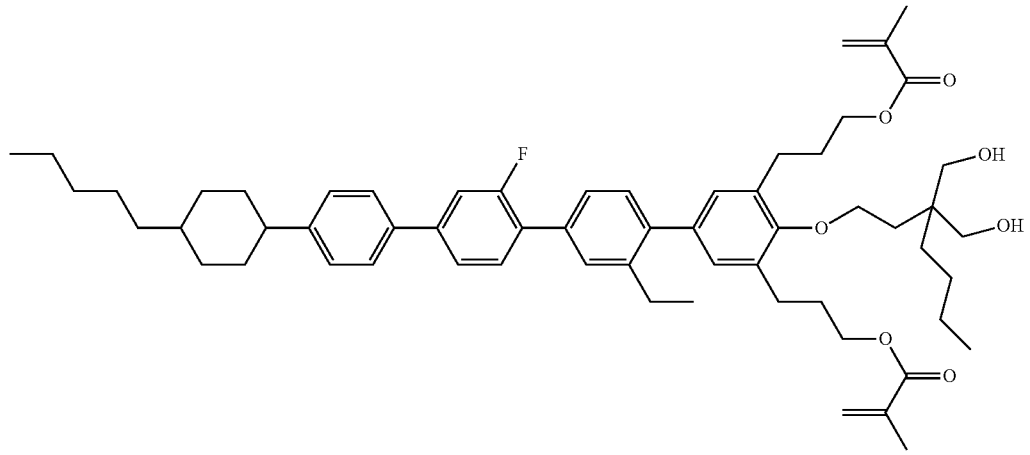
15
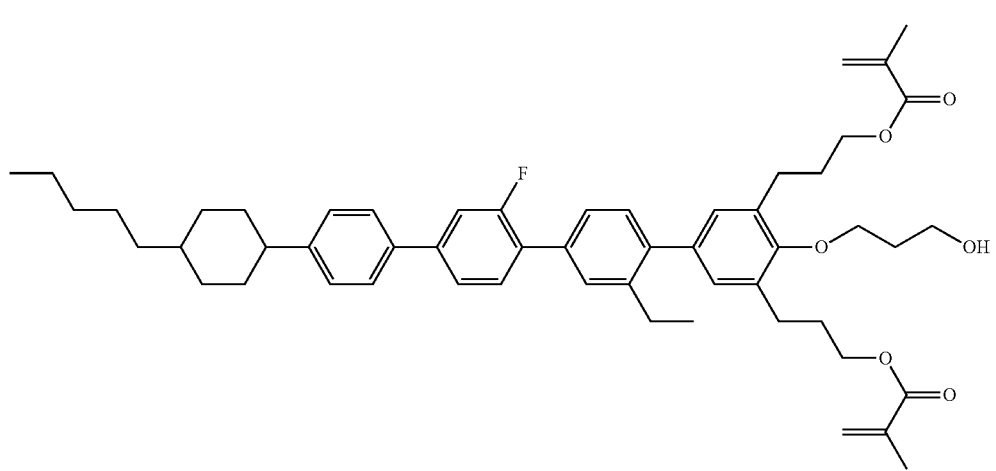
16

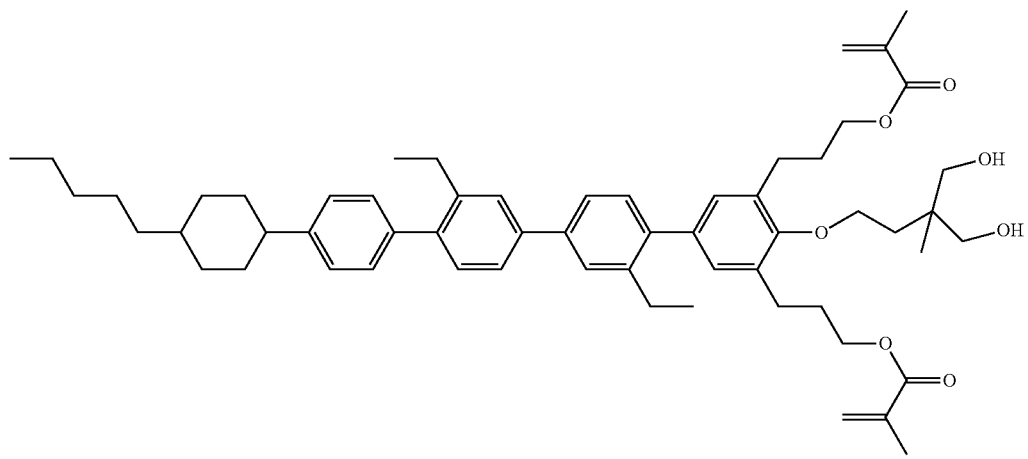
17
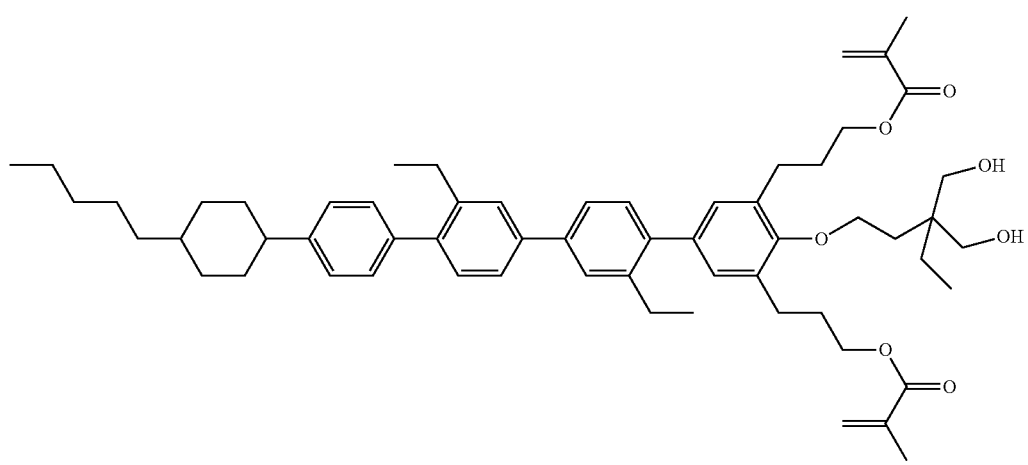
18
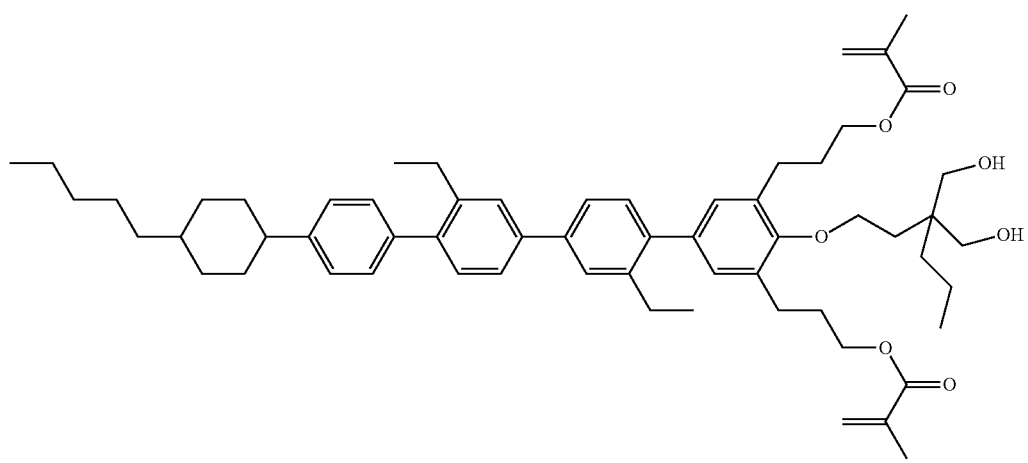
19

-continued
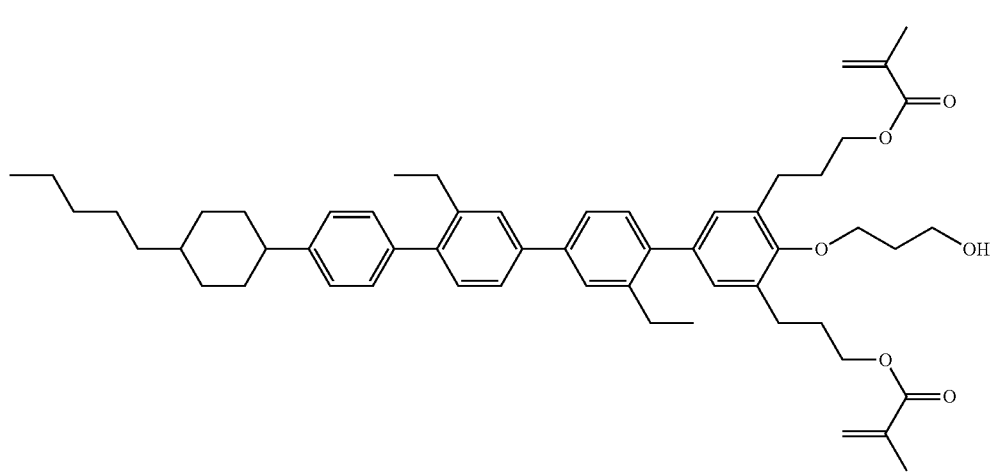
20
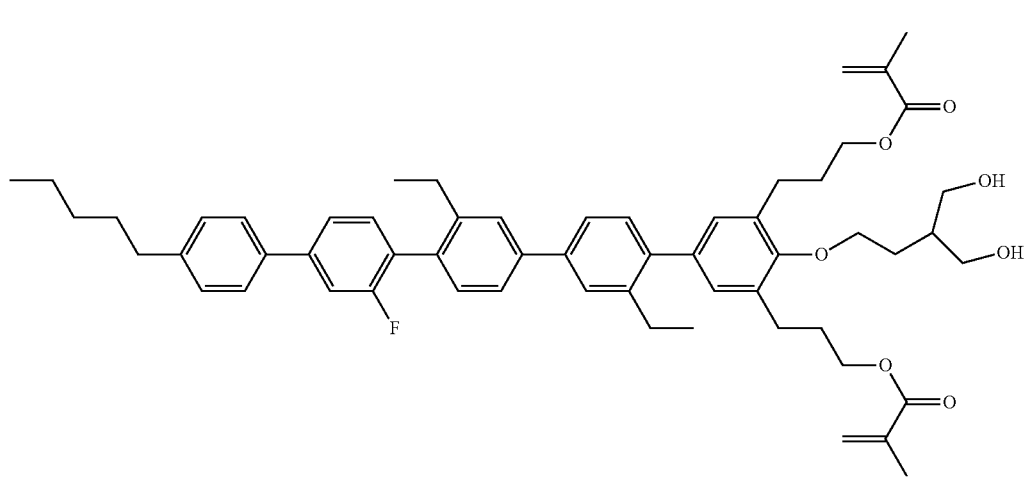
21
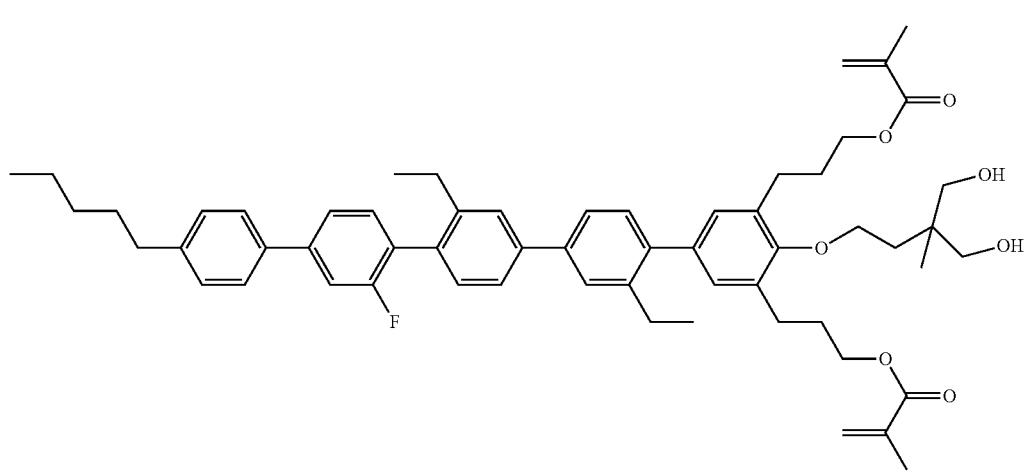
22

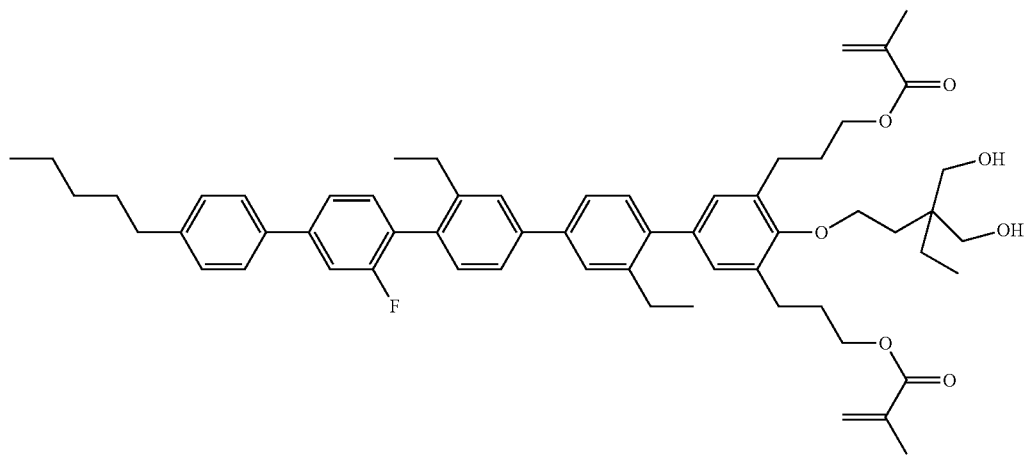
23
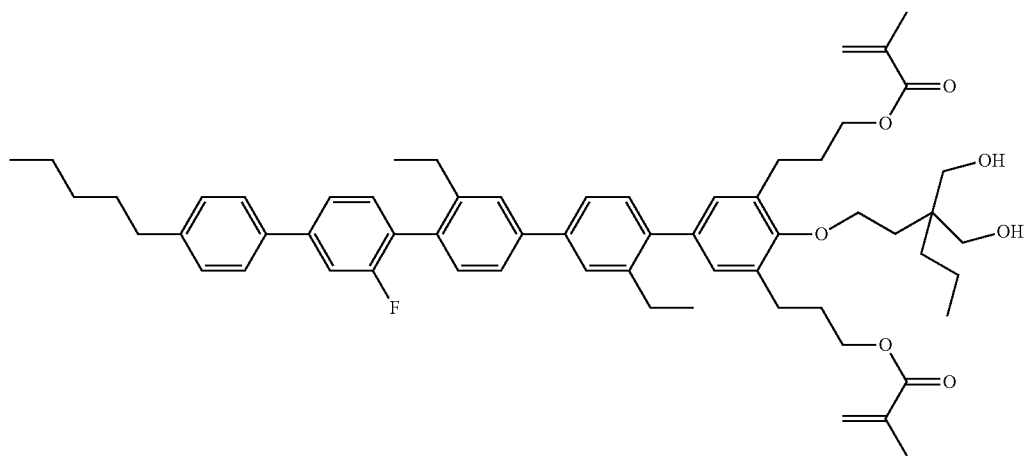
24
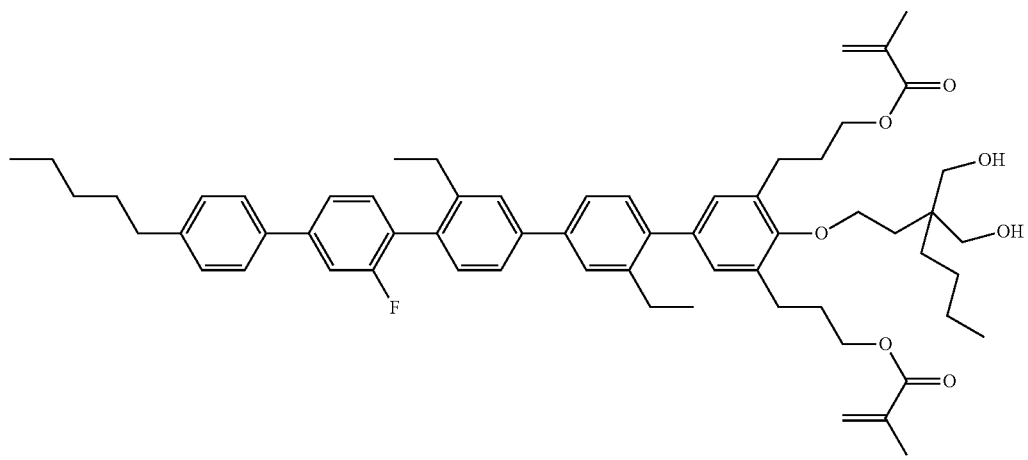
25

-continued
26
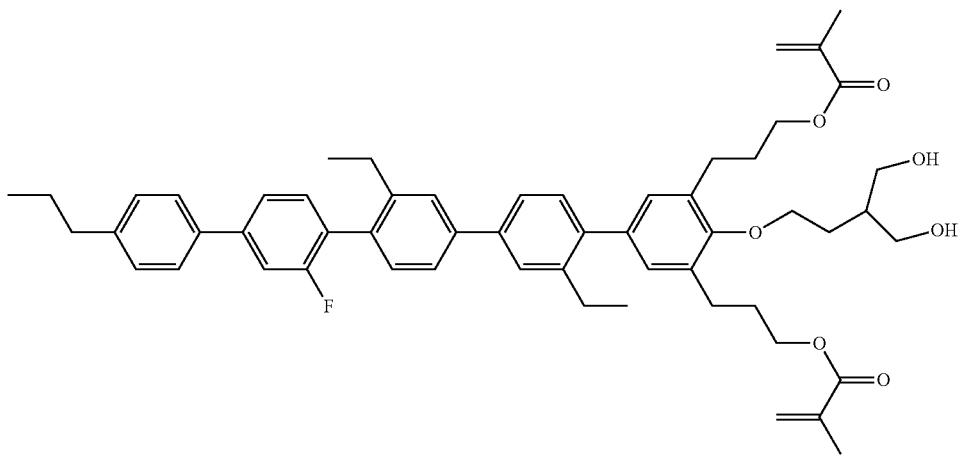
27
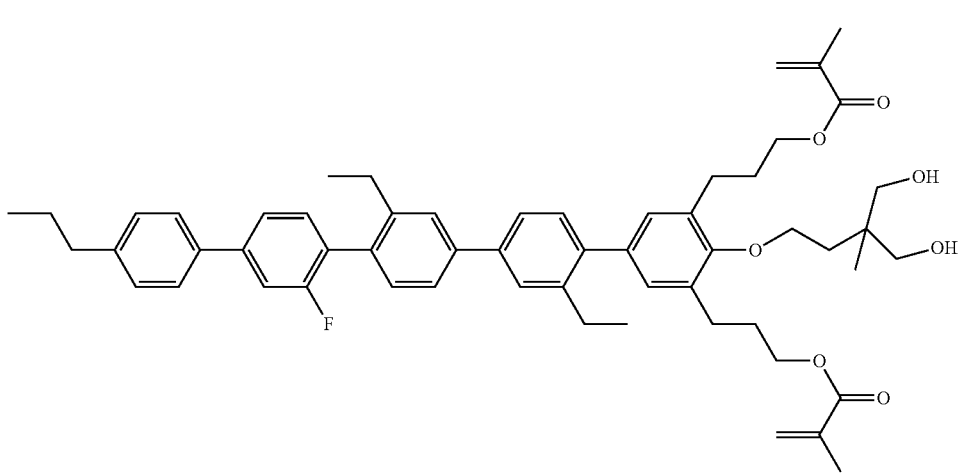
28
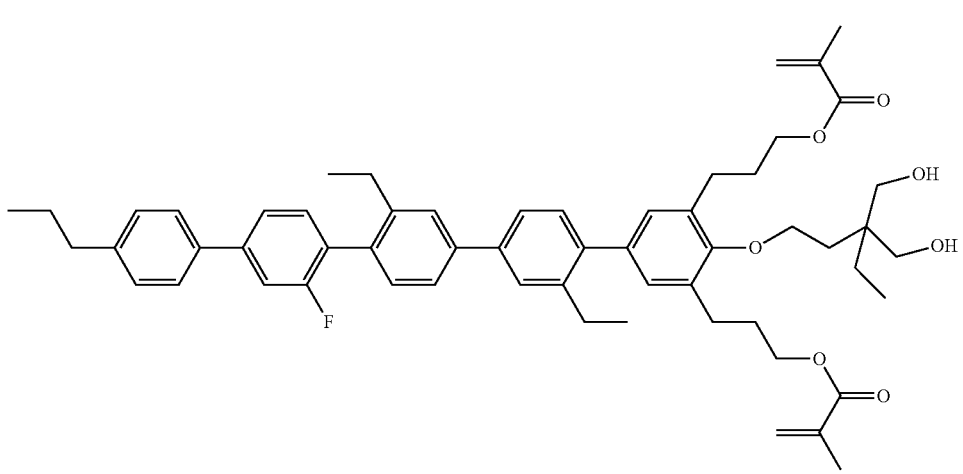

-continued
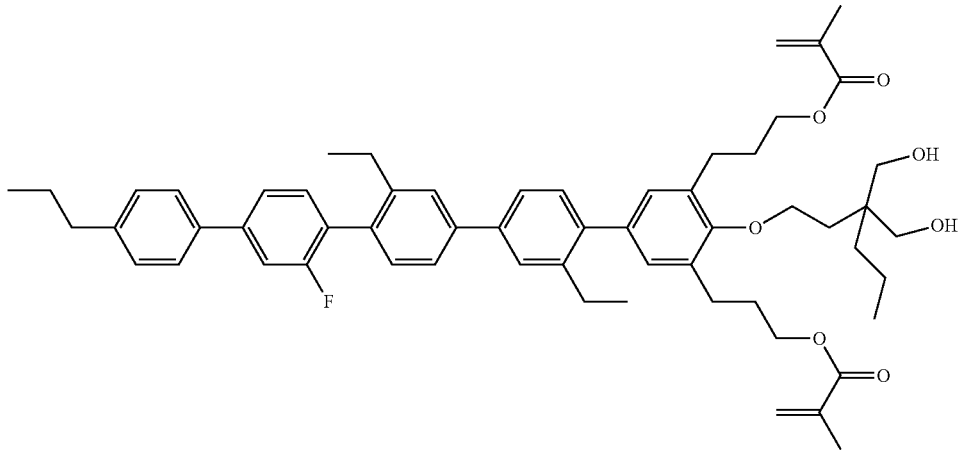
29
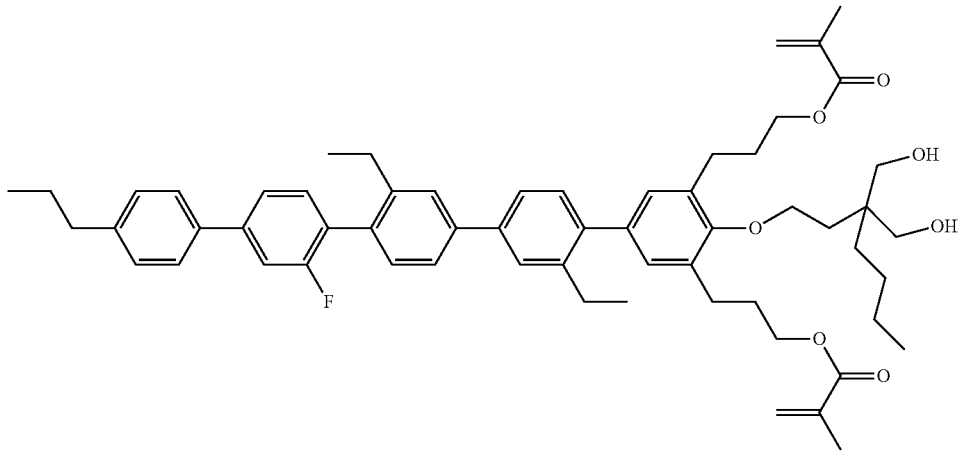
30
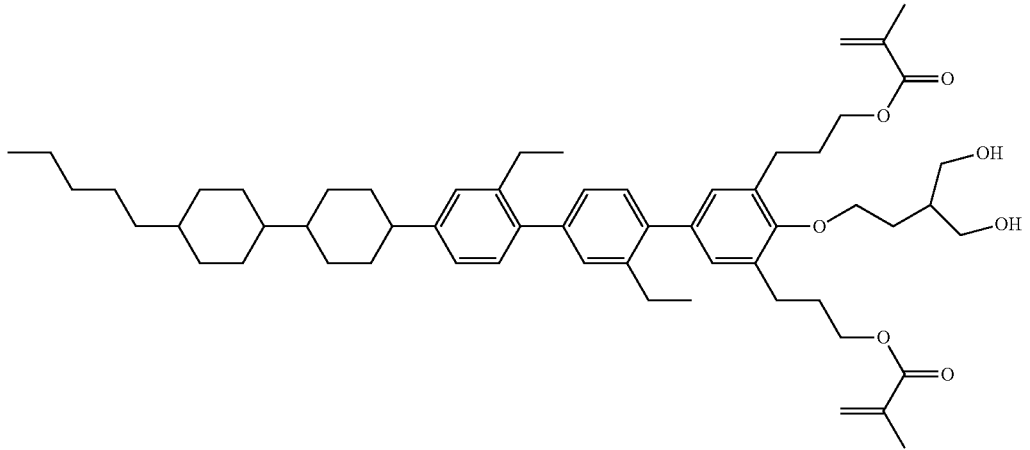
31

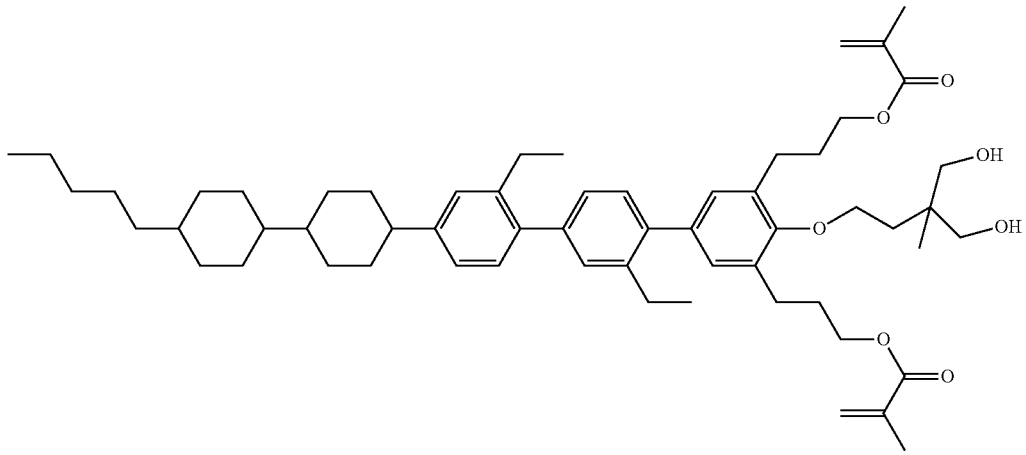
32
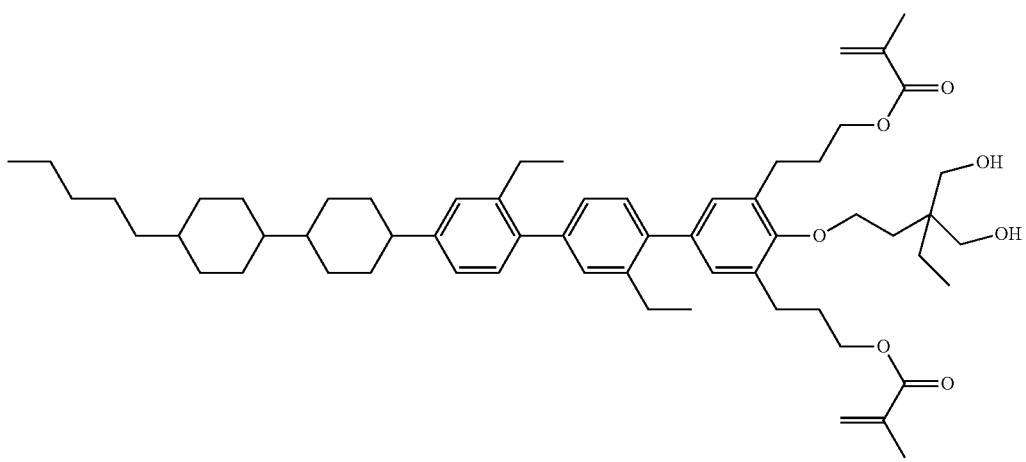
33
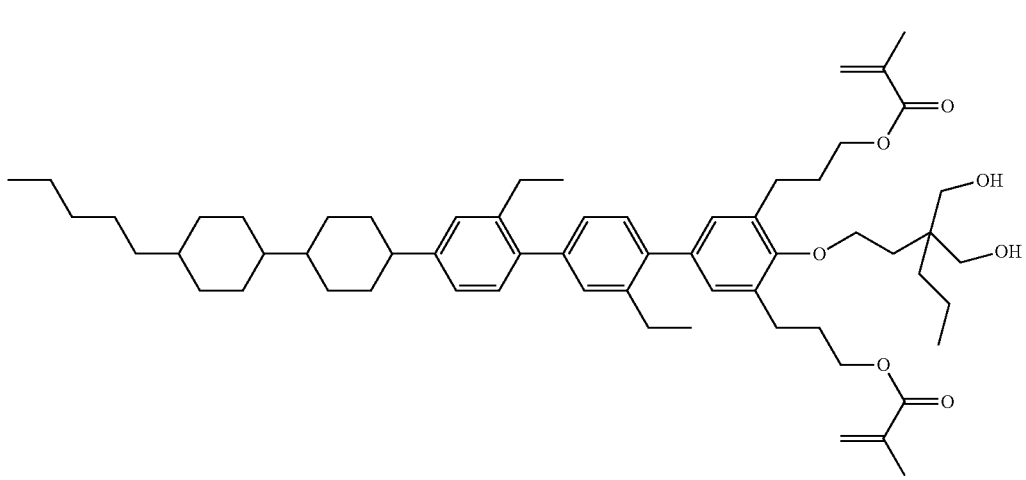
34

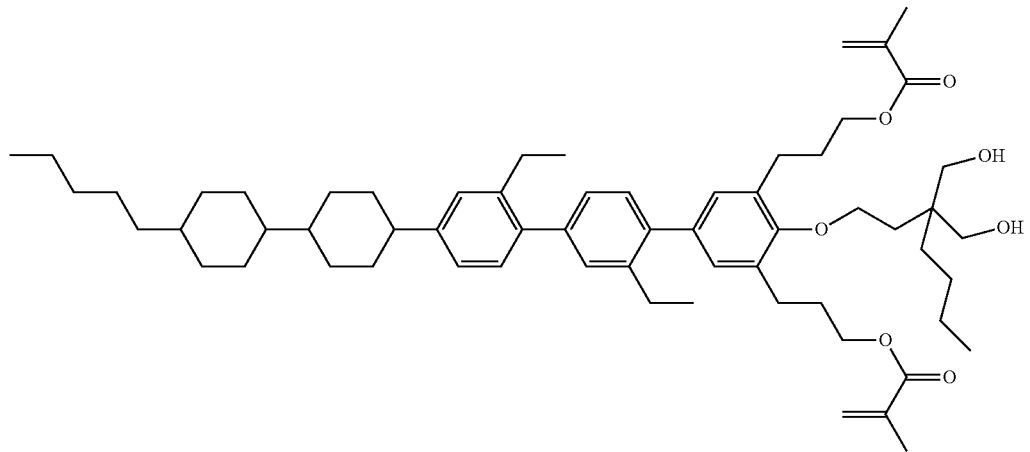
35
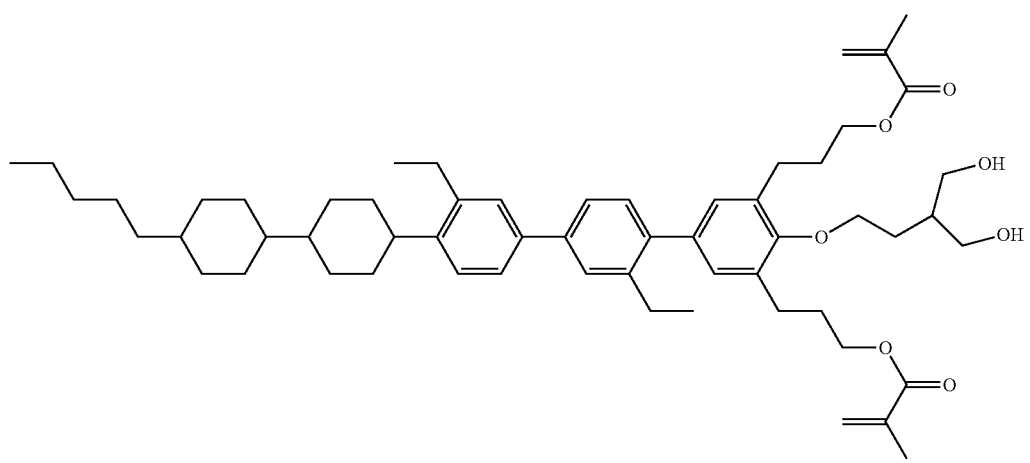
36
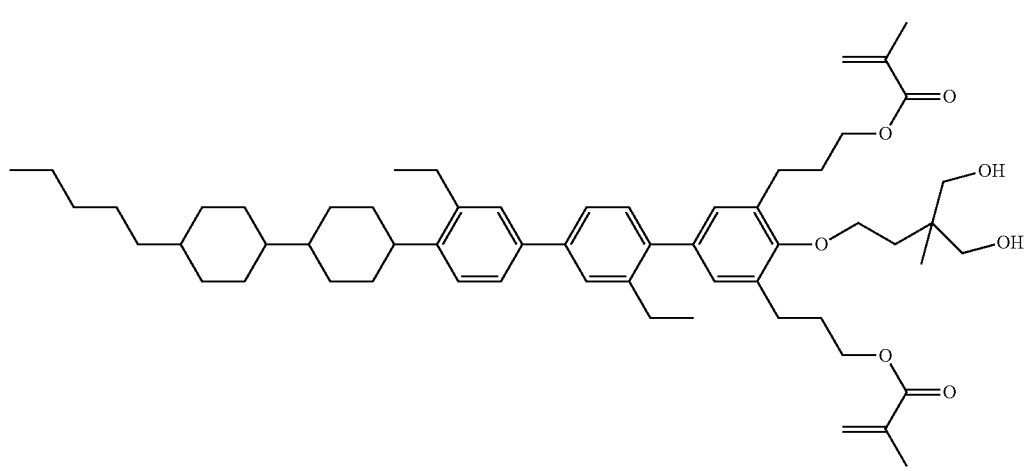
37

-continued
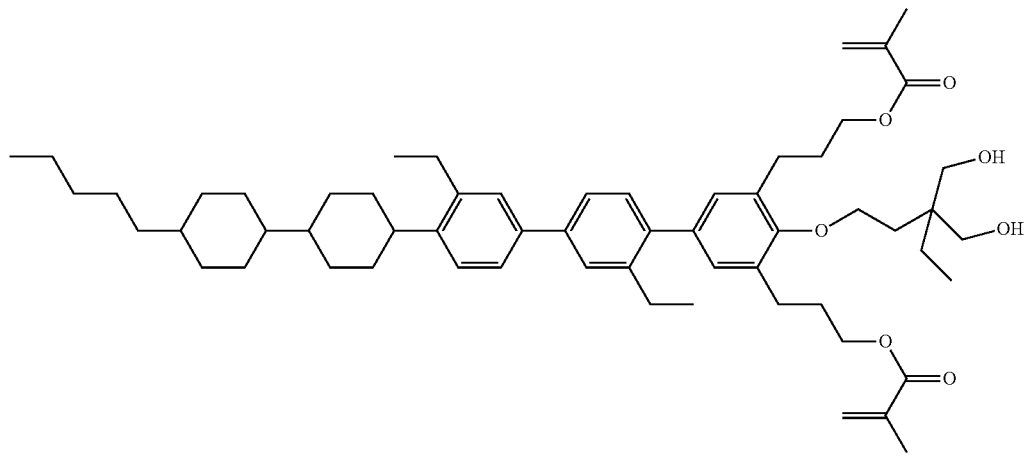
38
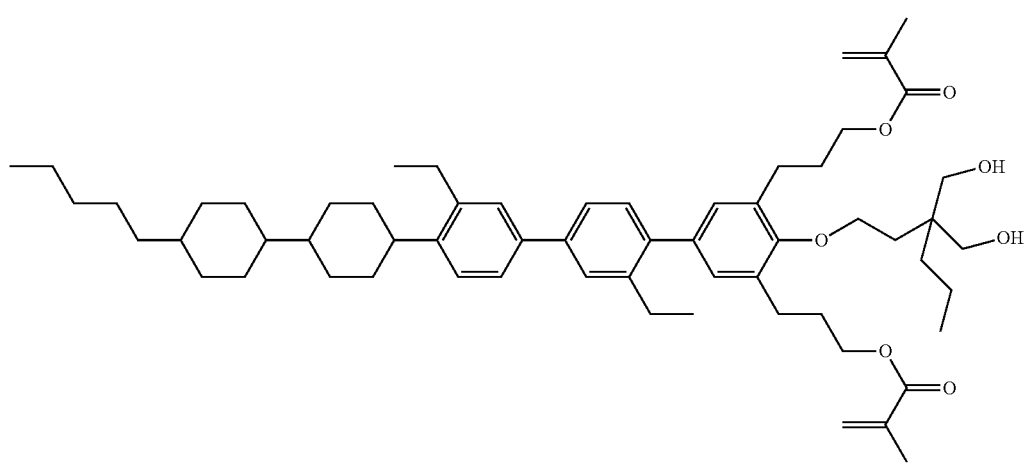
39
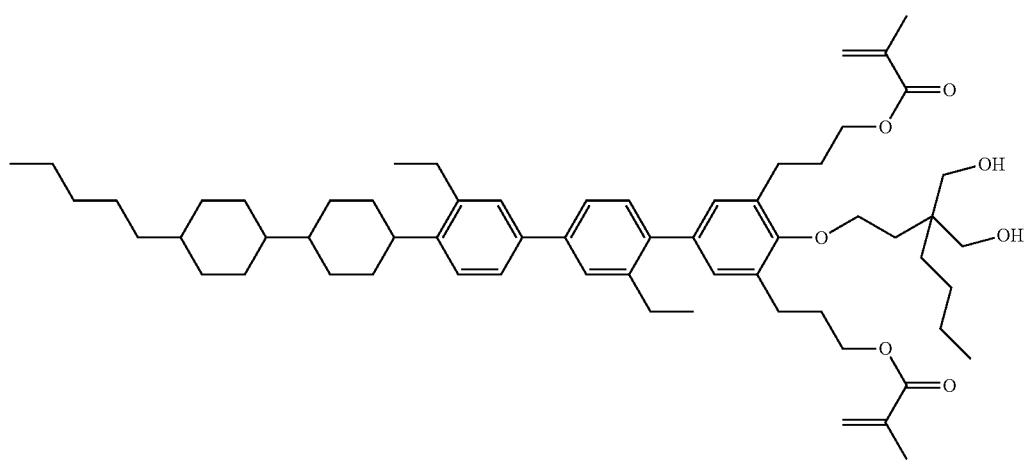
40

-continued
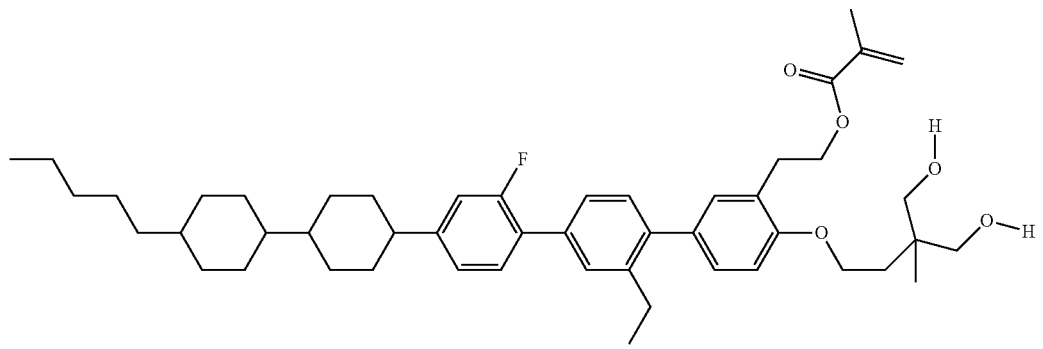
41
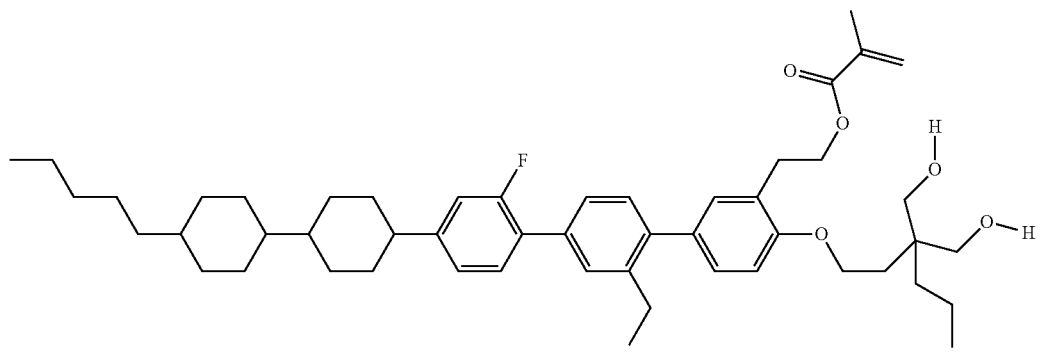
42
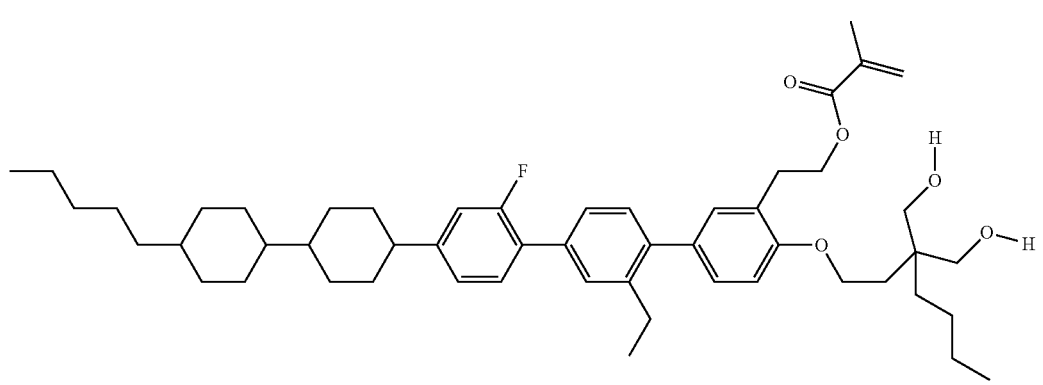
43
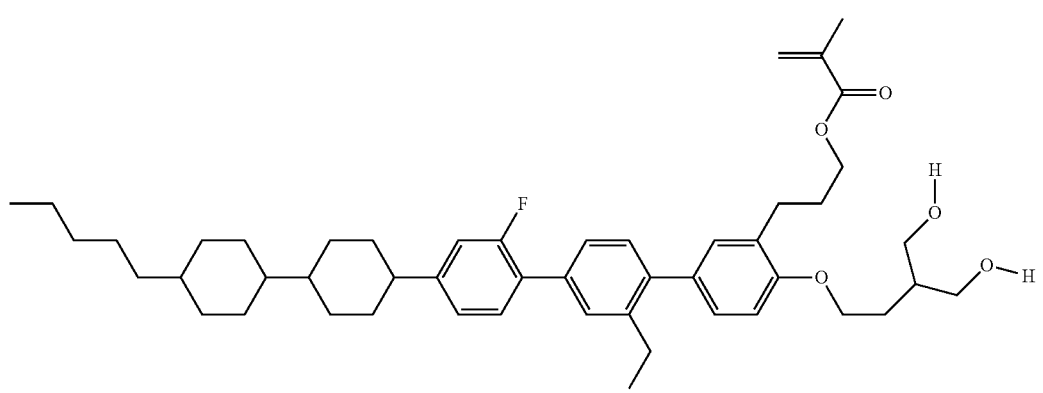
44

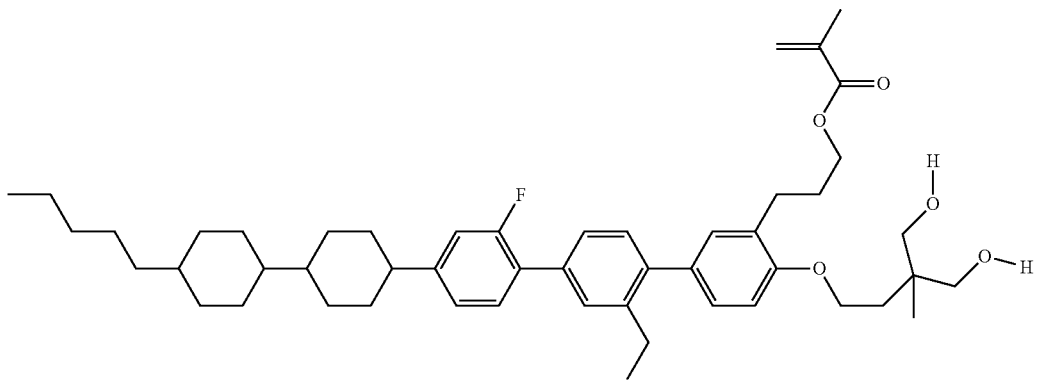
45
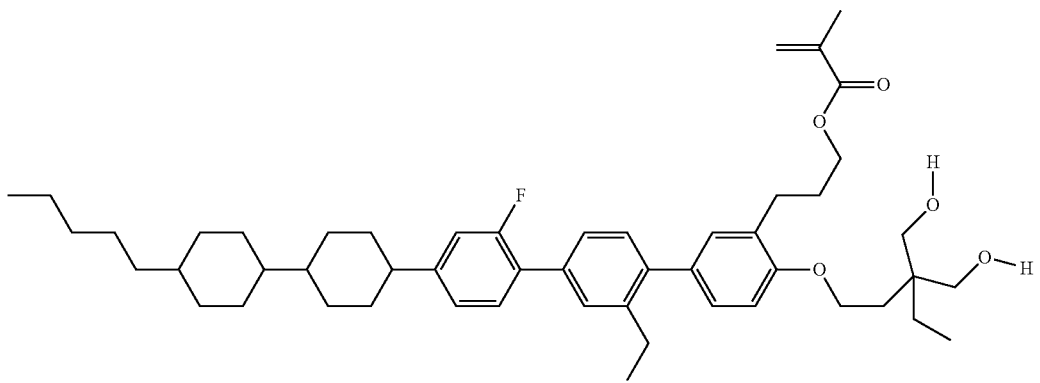
46
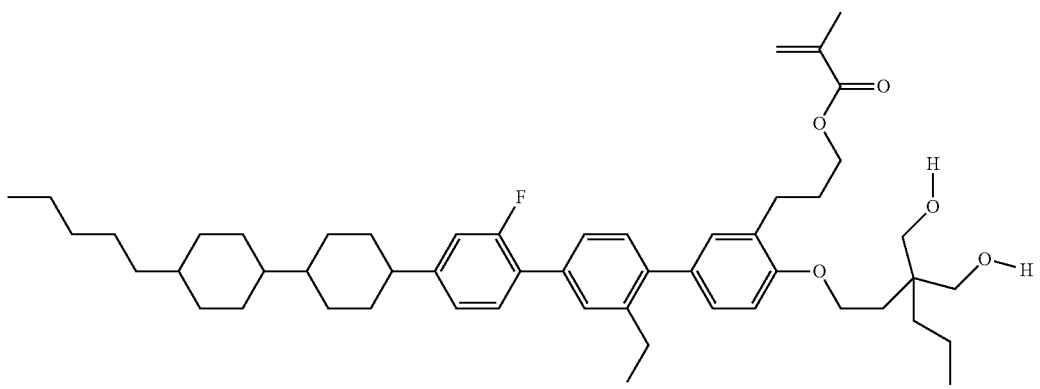
47
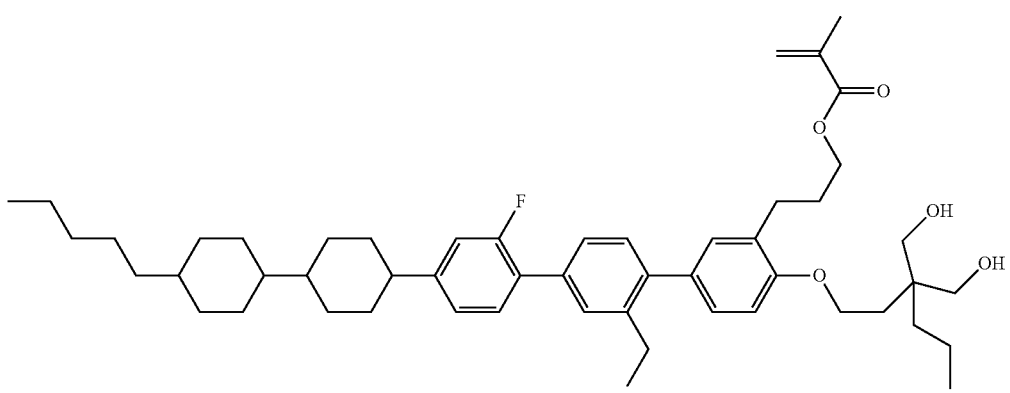
48

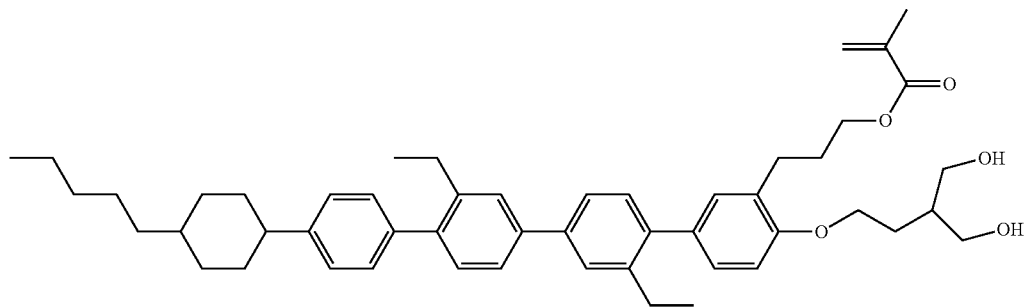
49
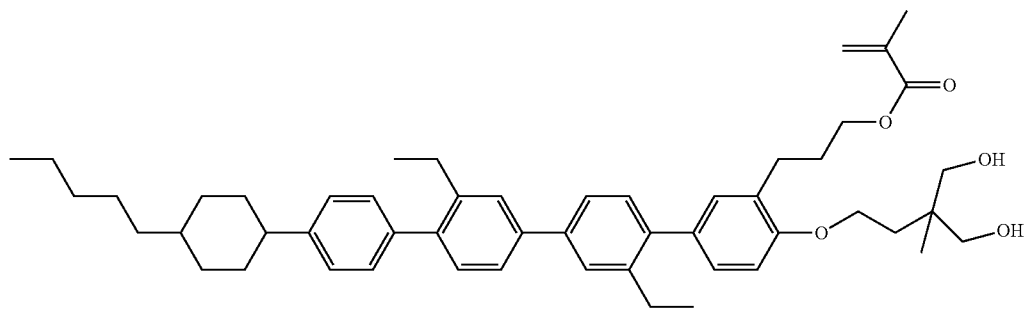
50
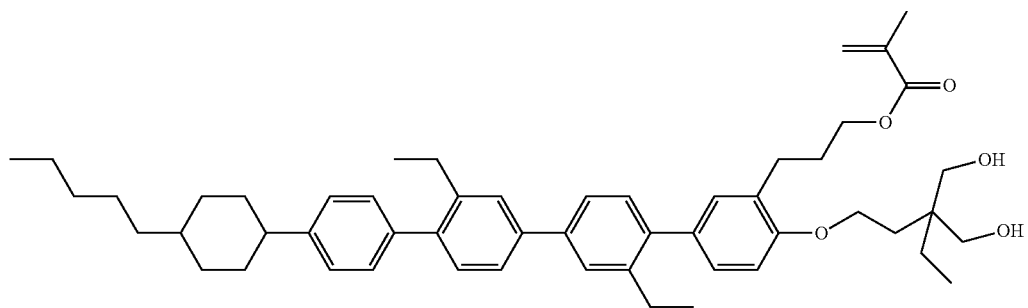
51
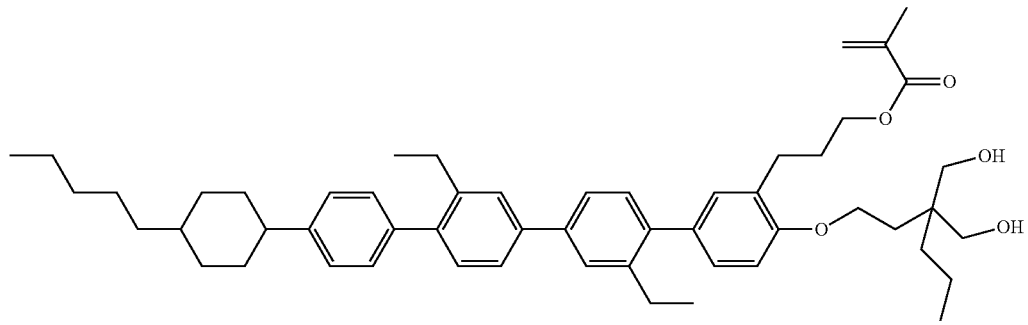
52
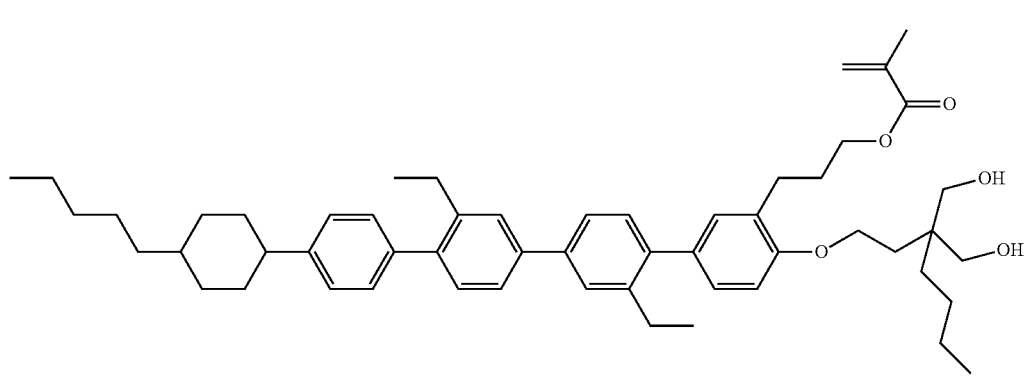
53

54
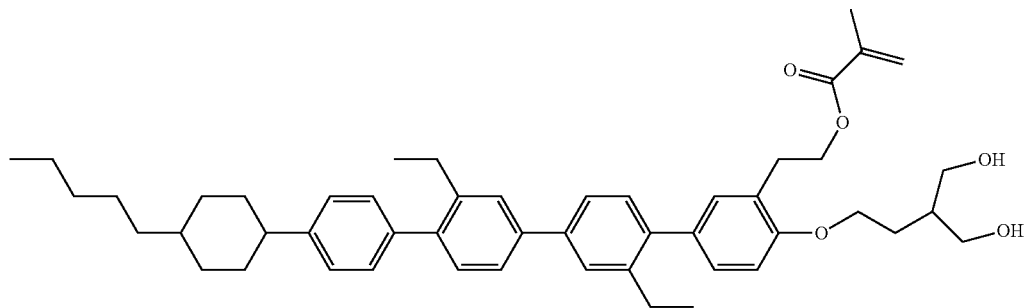
55
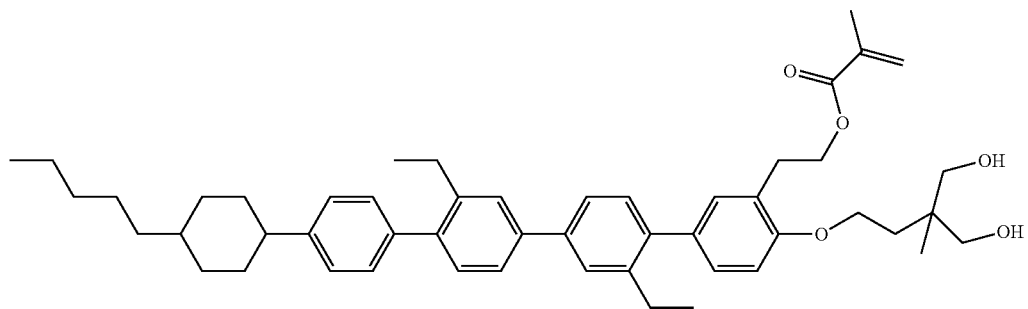
56
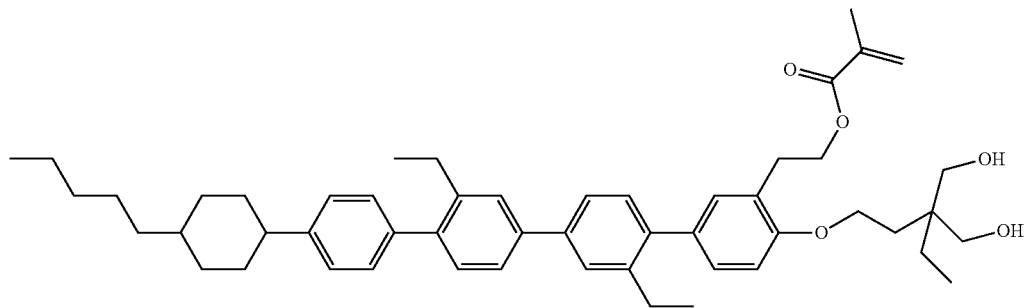
57
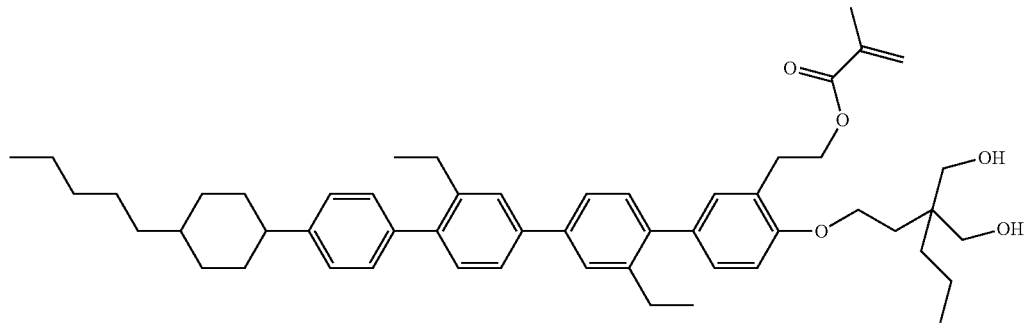
58
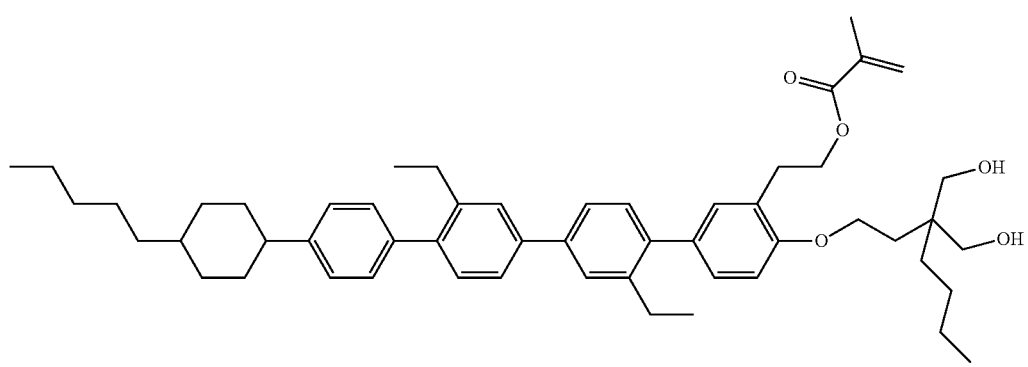

-continued
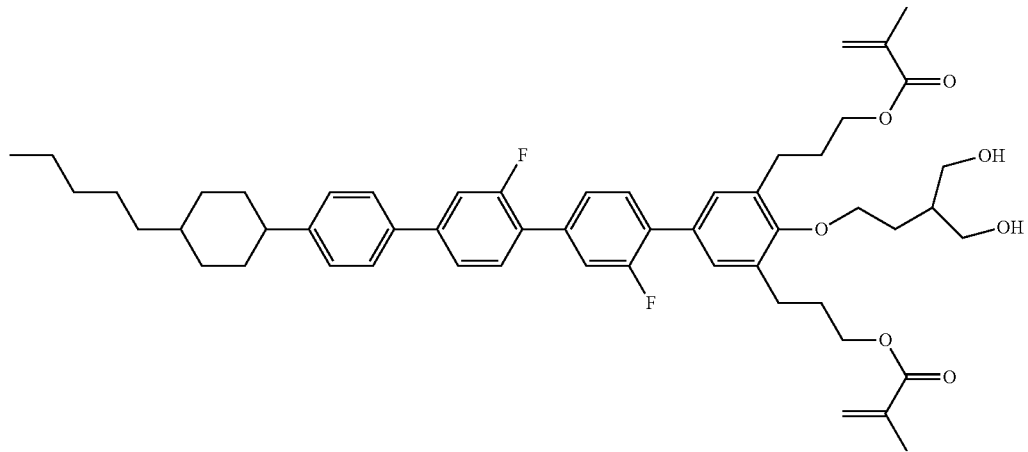
59
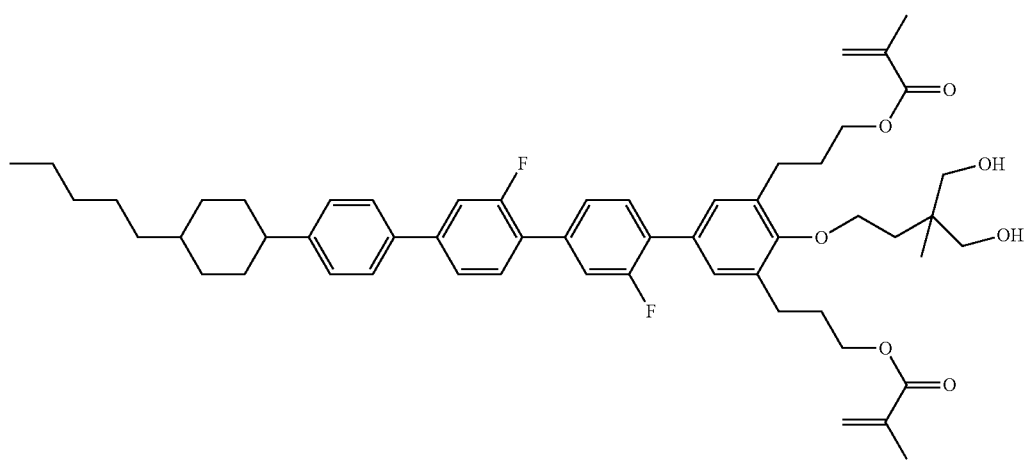
60
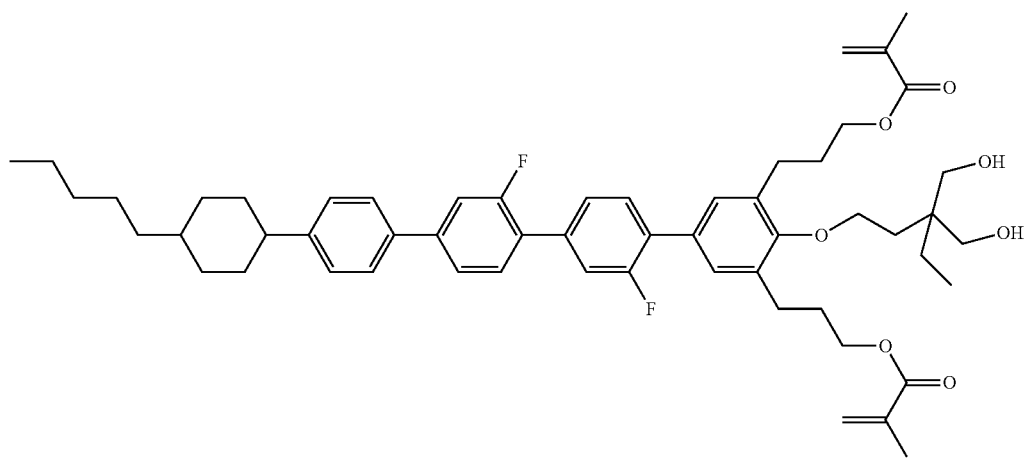
61

-continued
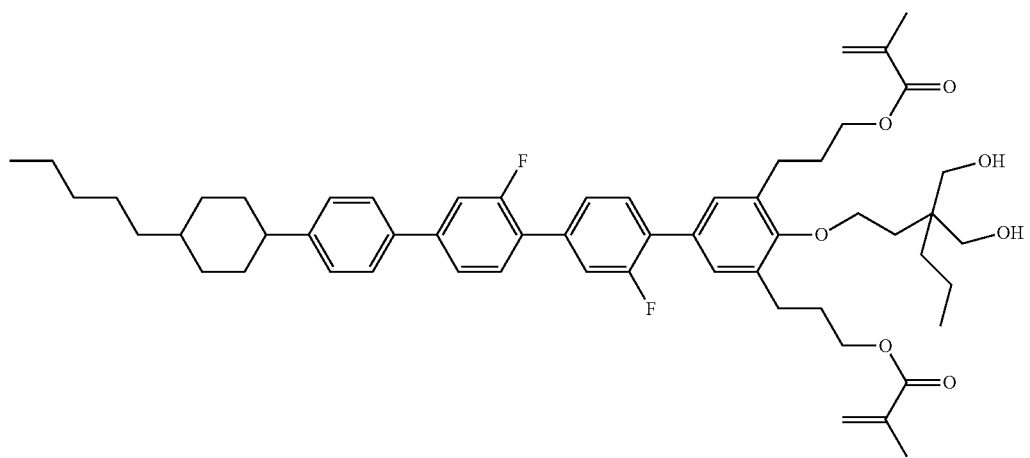
62
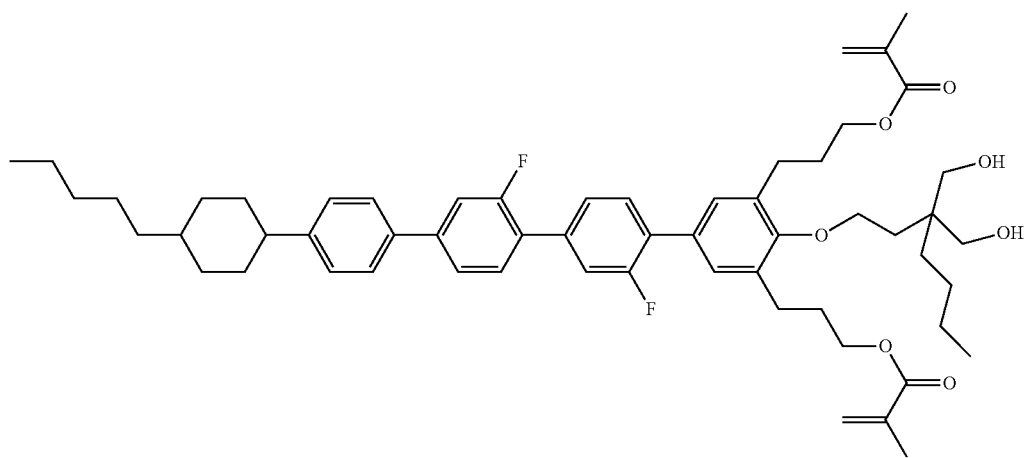
63
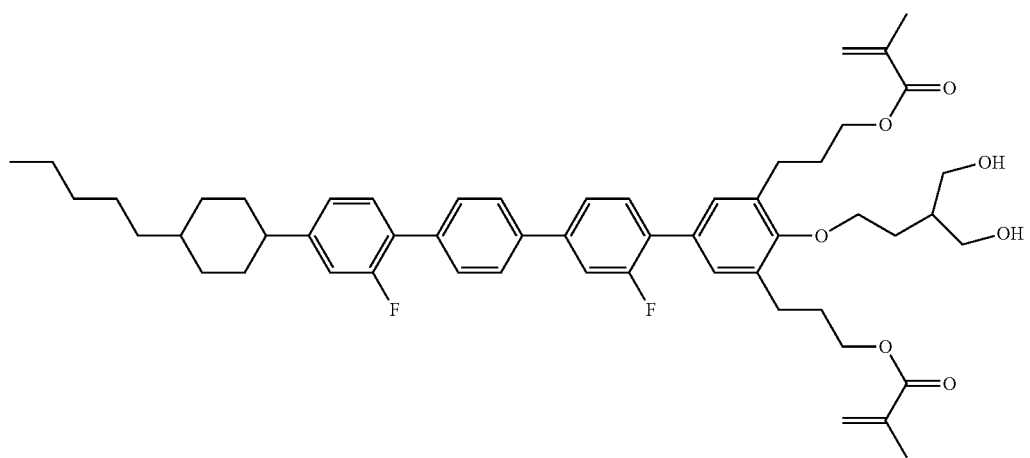
64

65
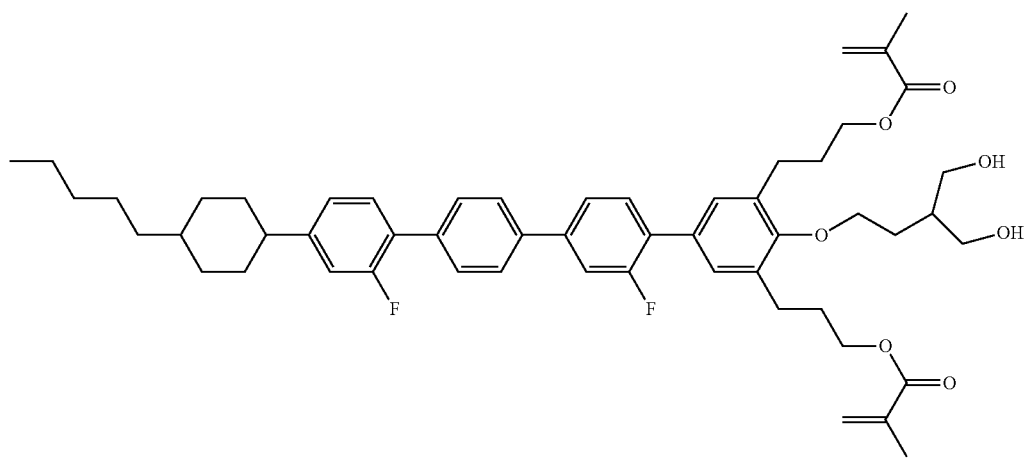
66
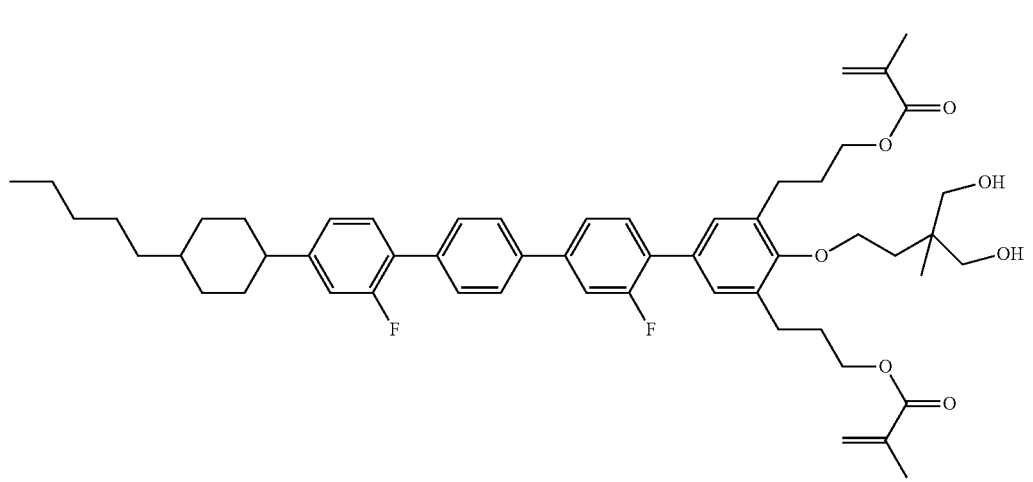
67
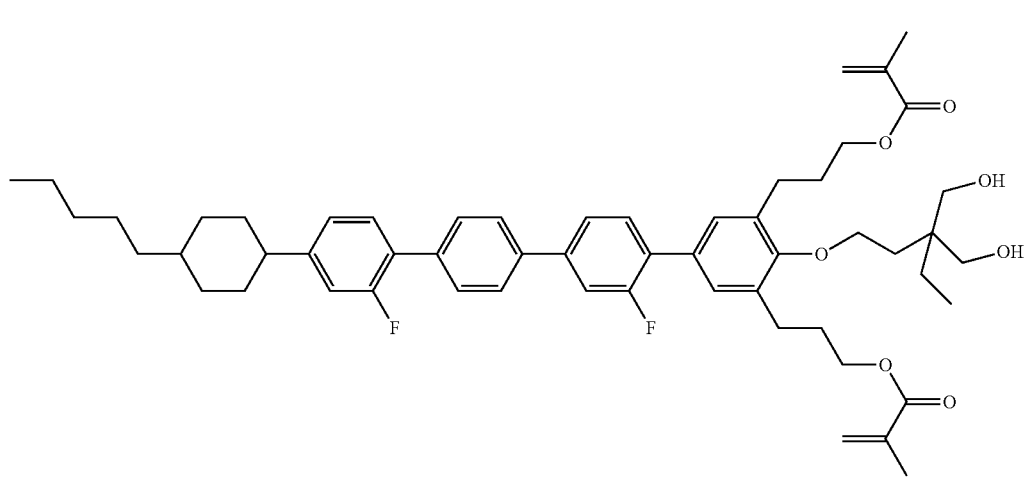

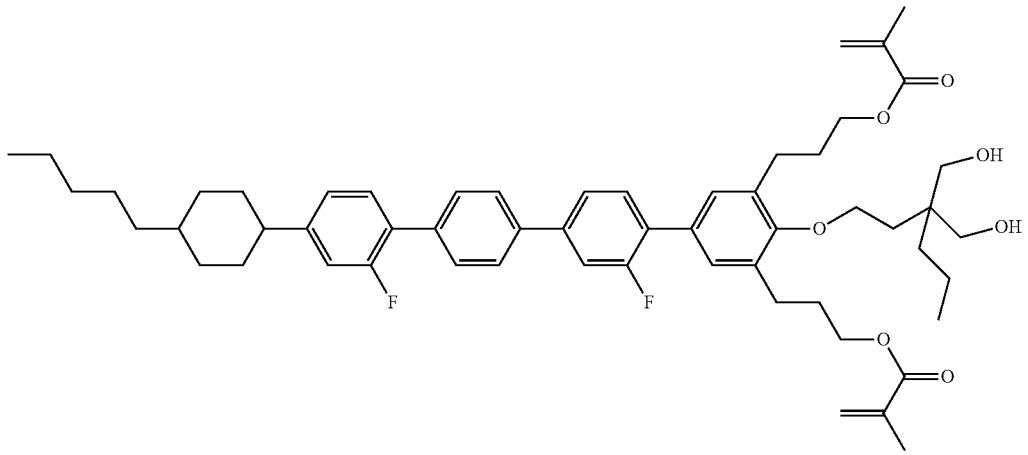
68
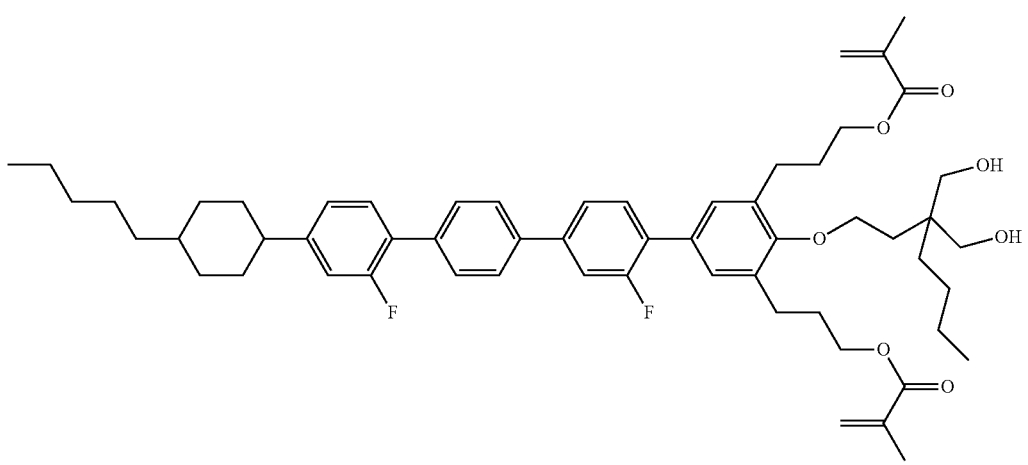
69
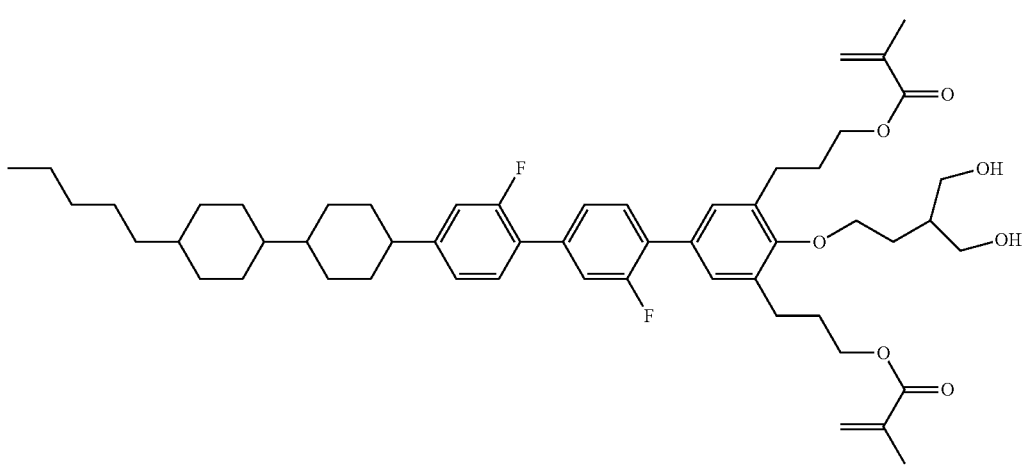
70

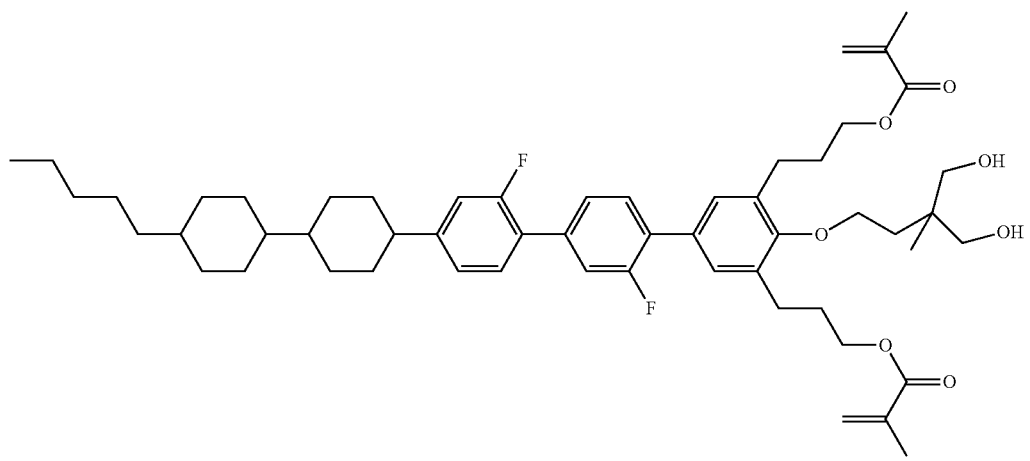
71
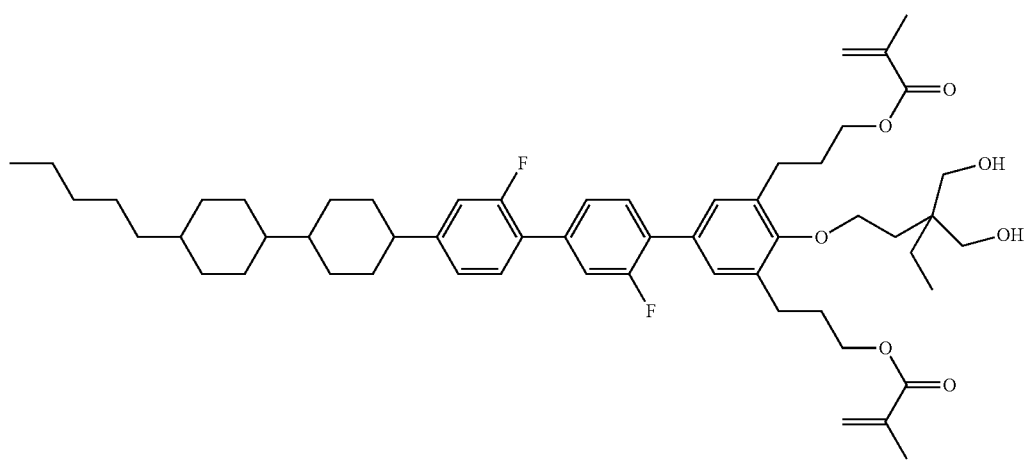
72
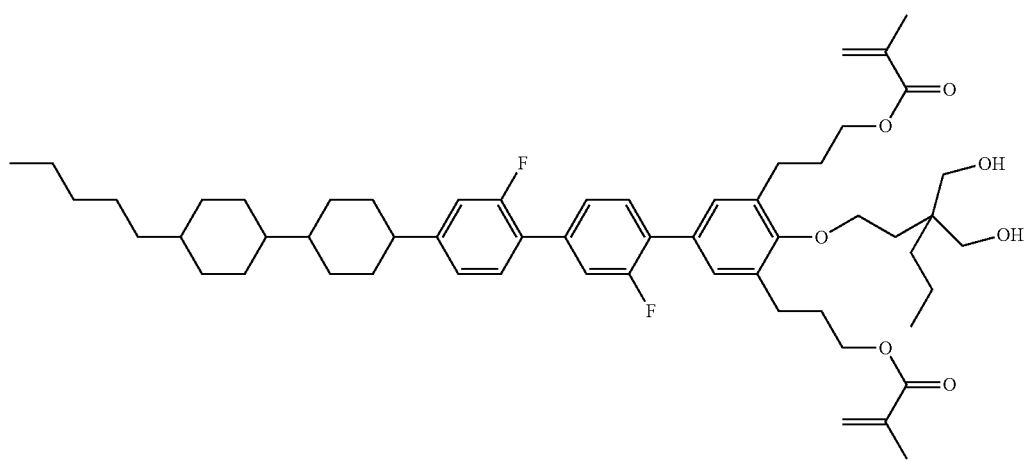
73

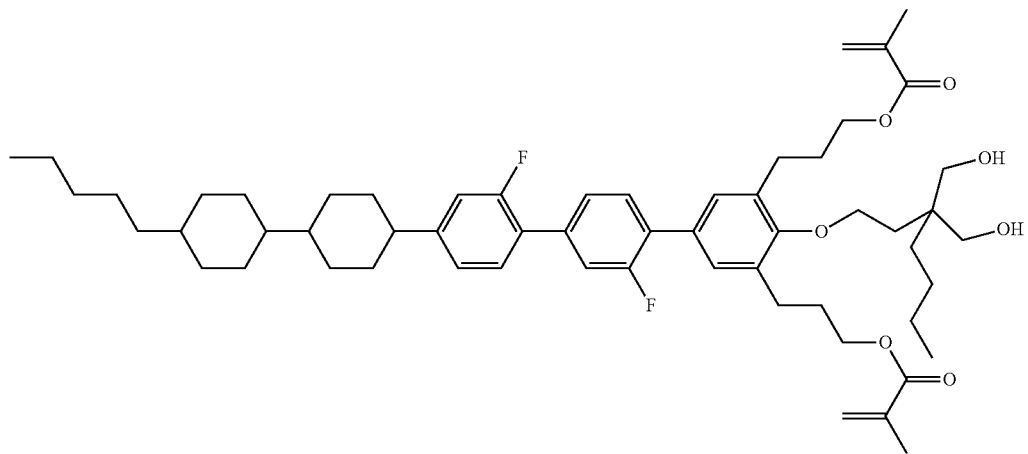
74
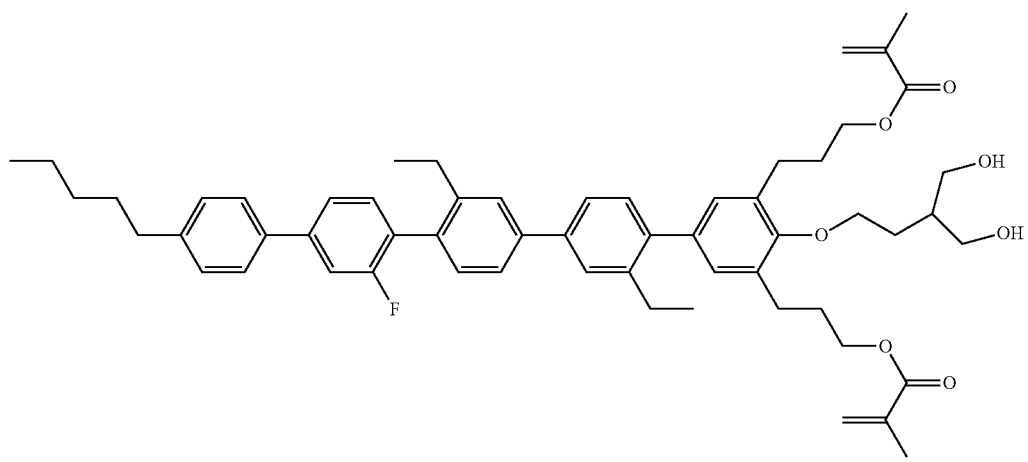
75
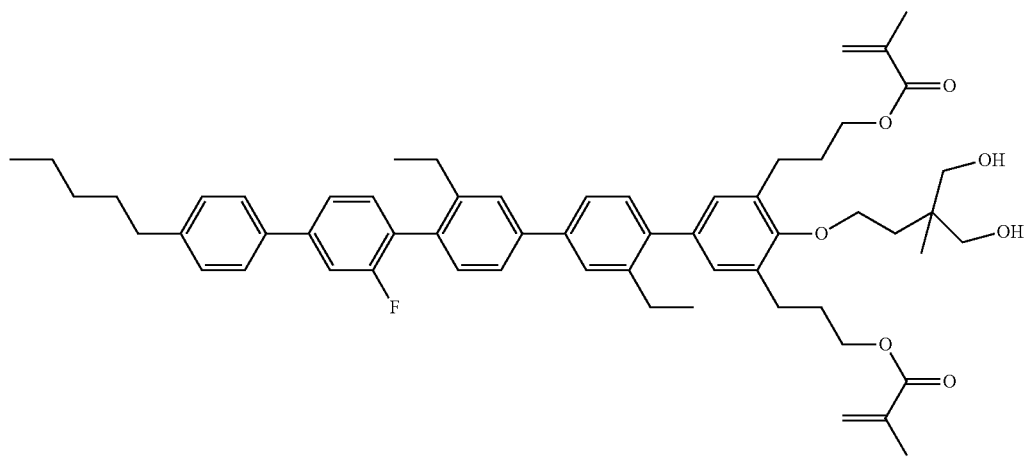
76

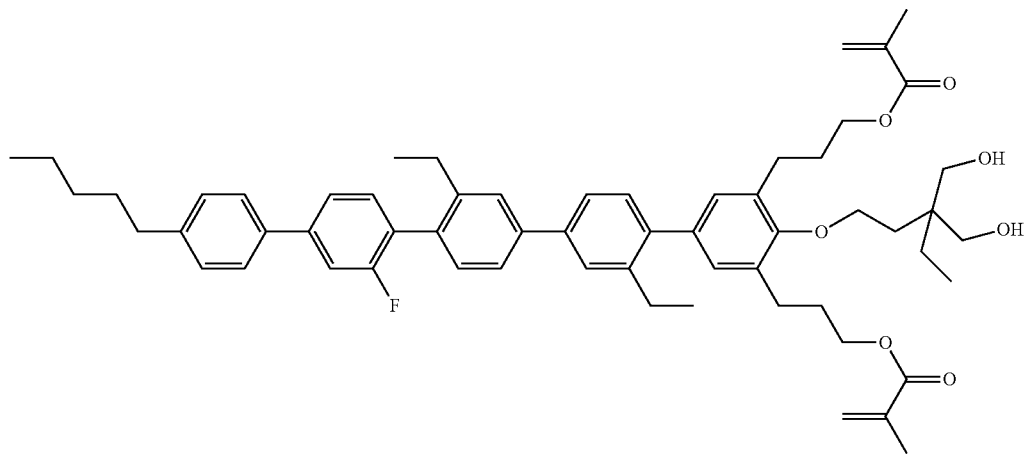
77
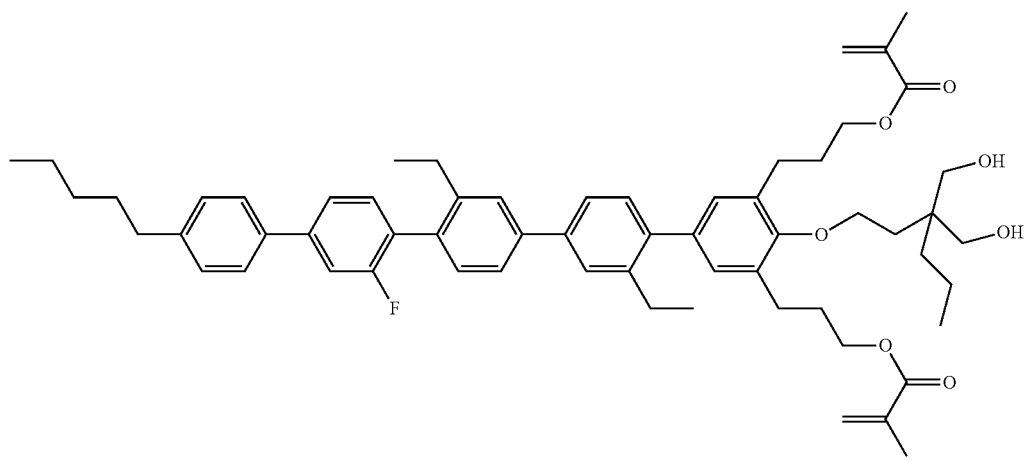
78
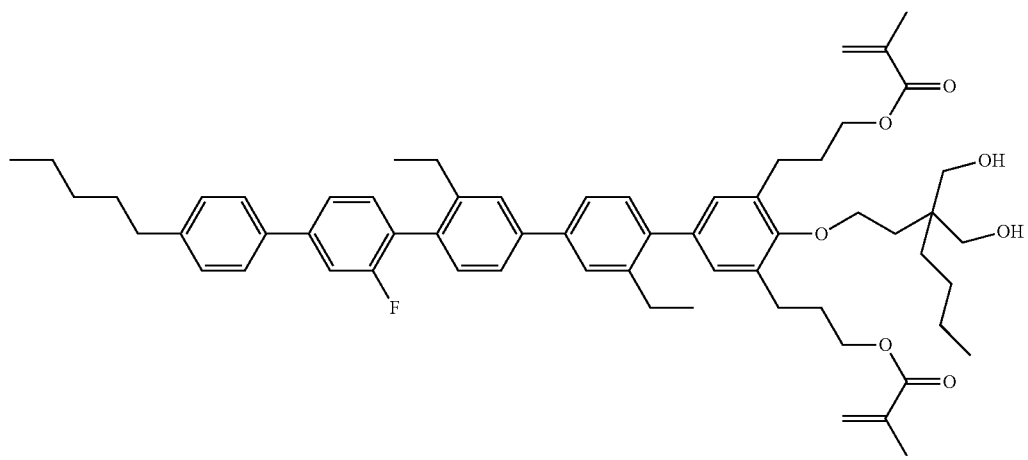
79

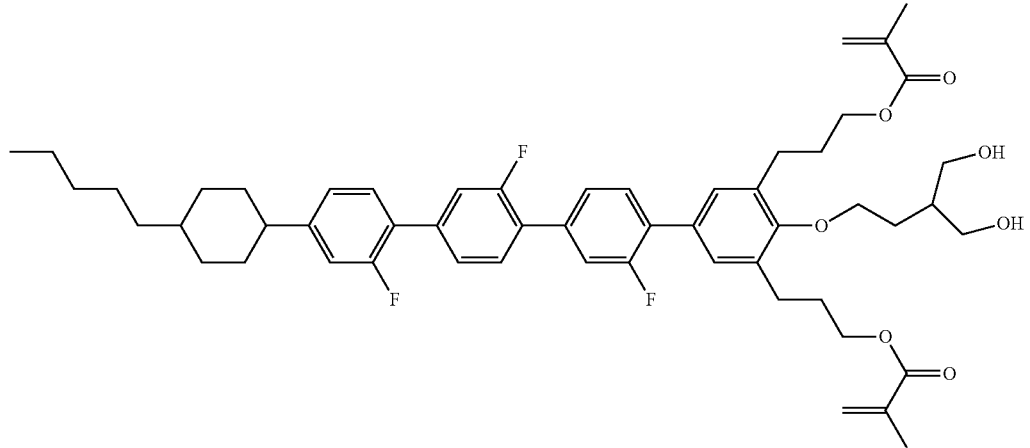
80
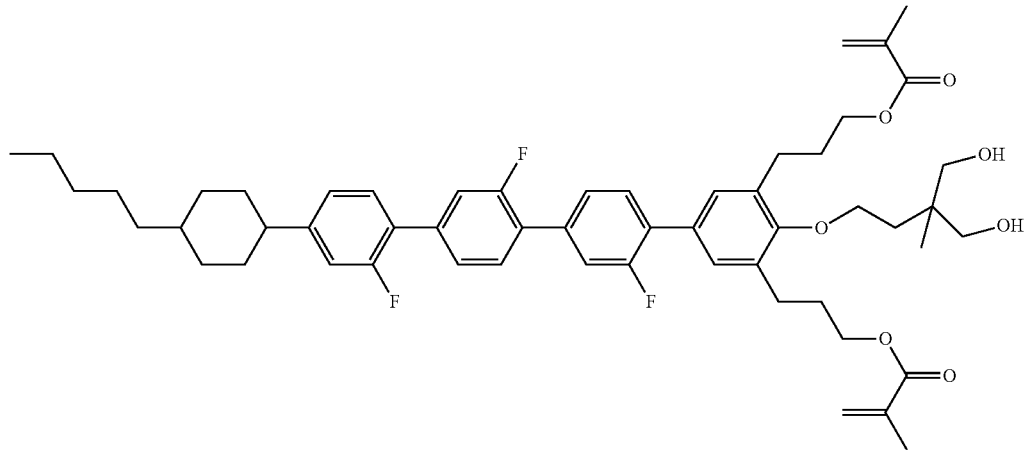
81
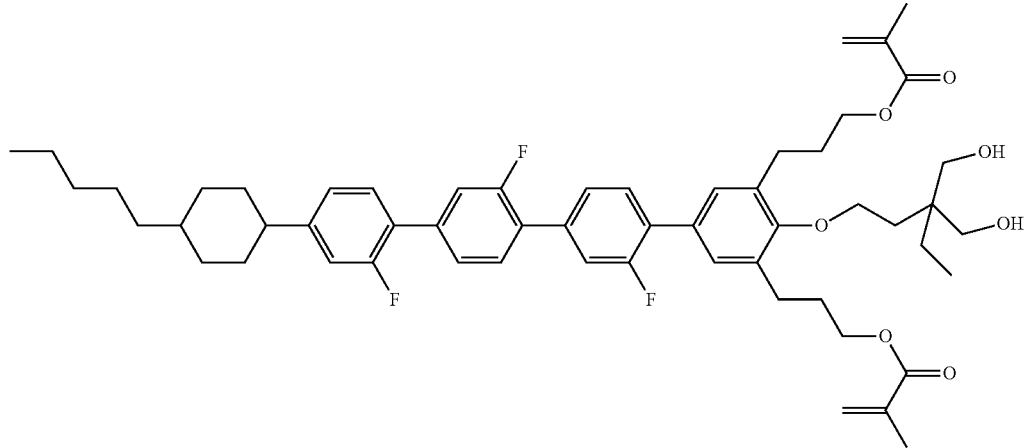
82

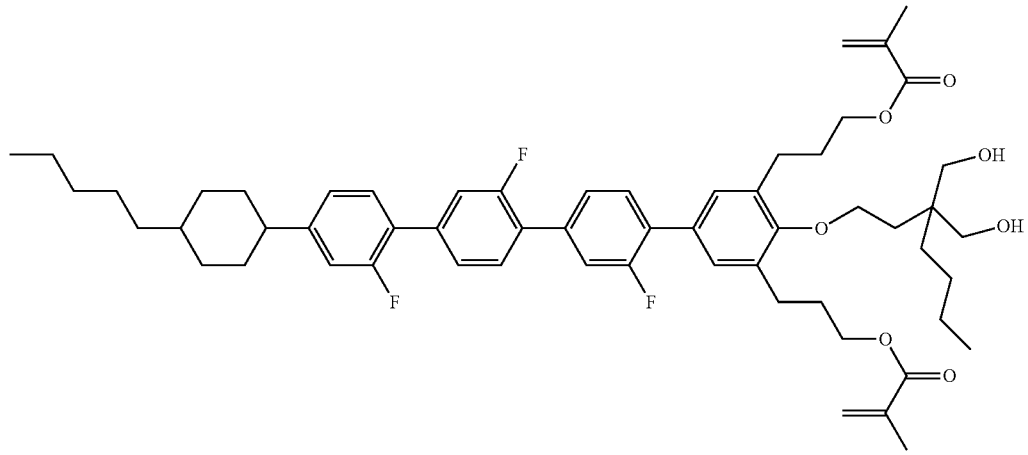
83
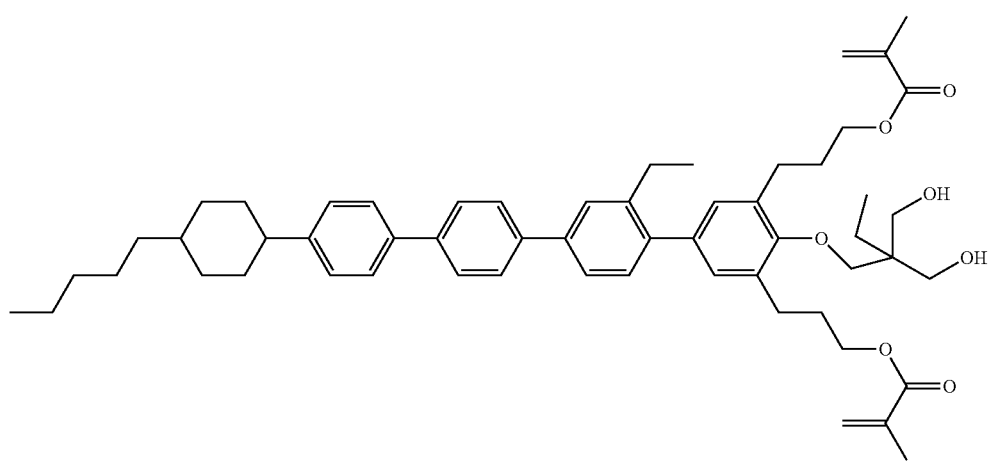
84
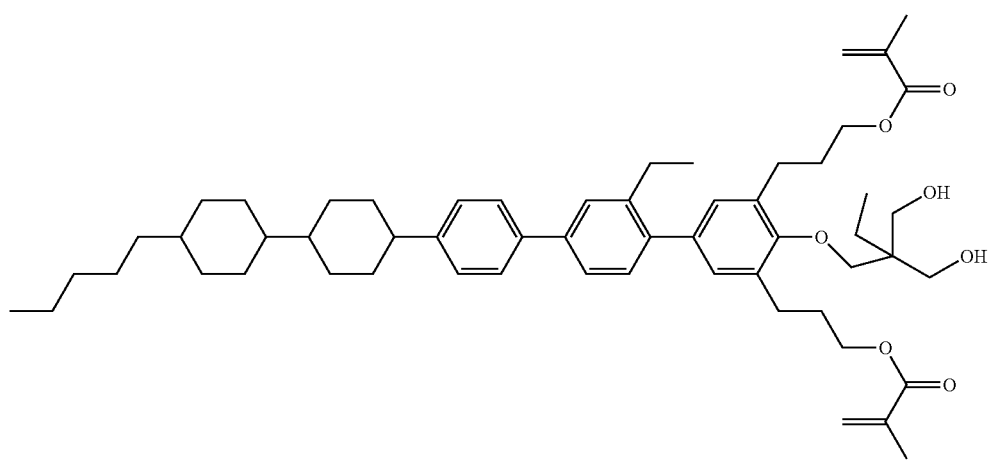
85

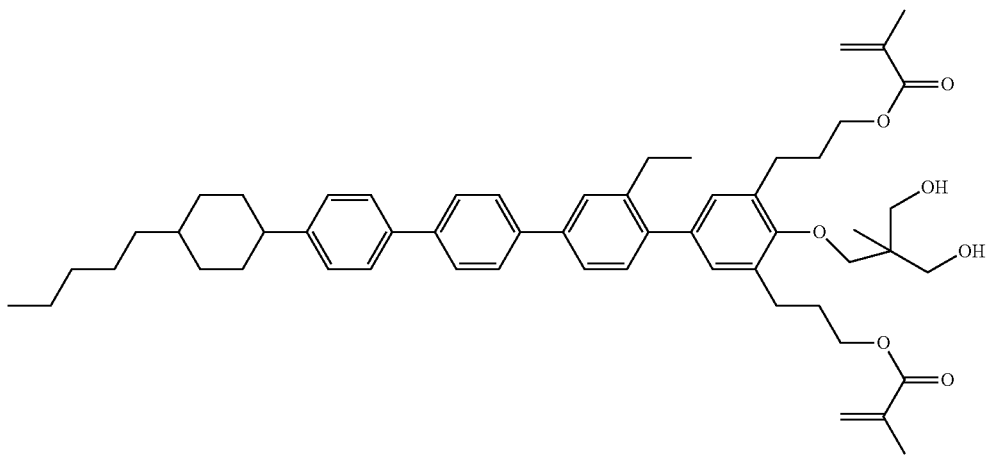
86
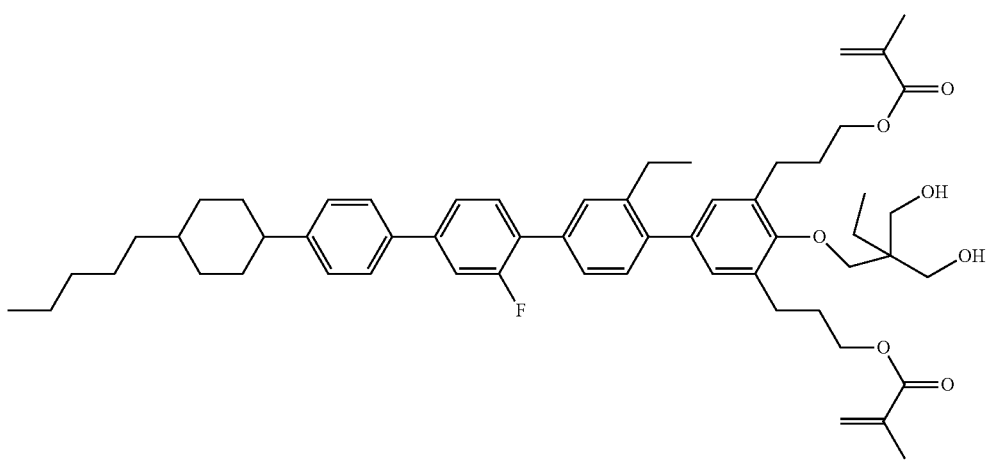
87
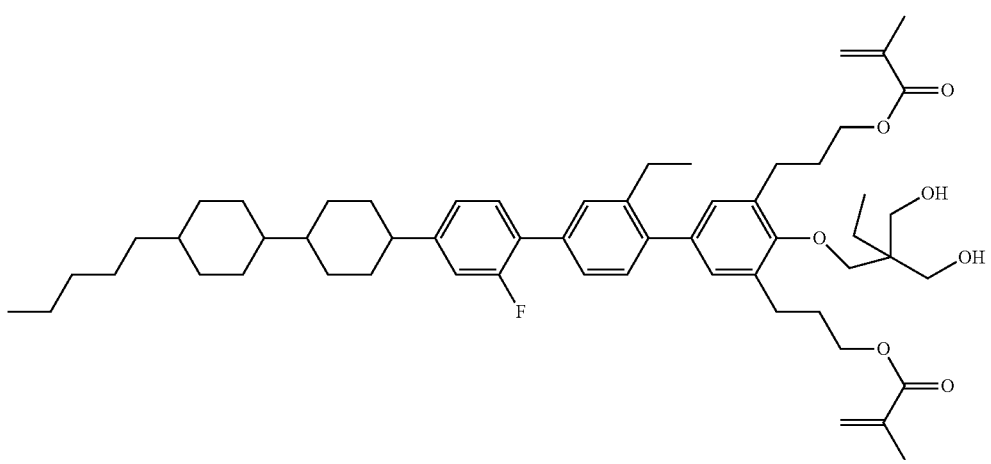
88

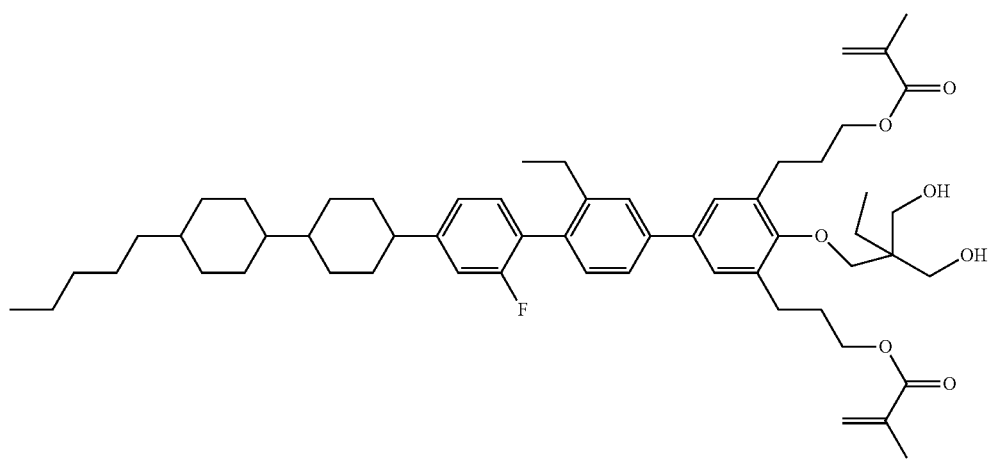
89
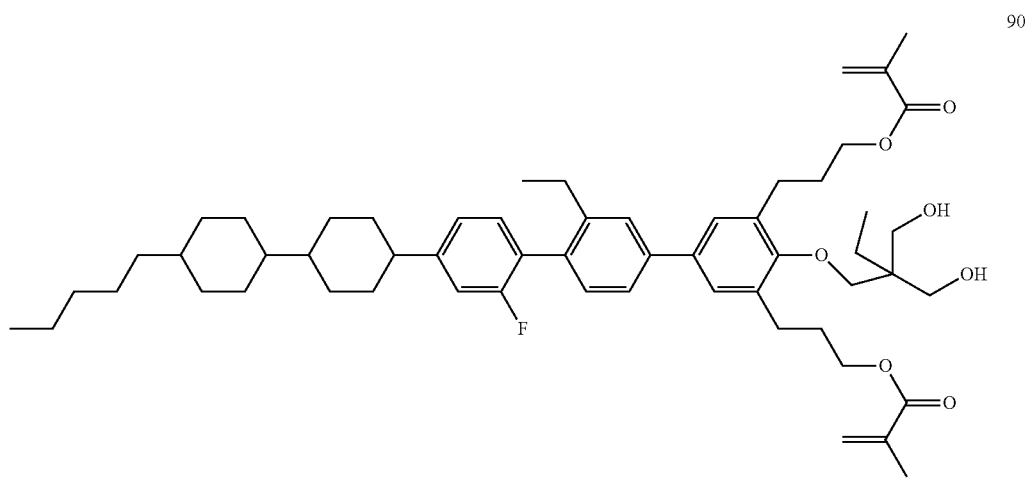
90
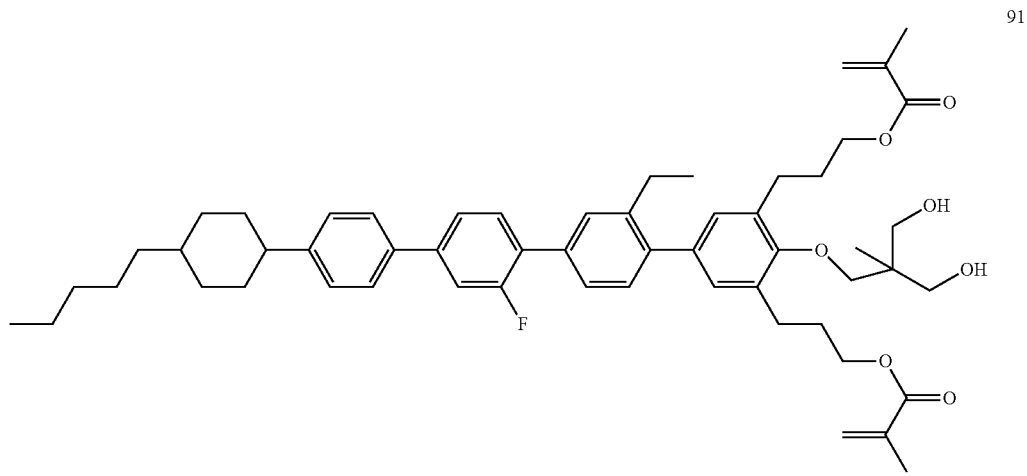
91

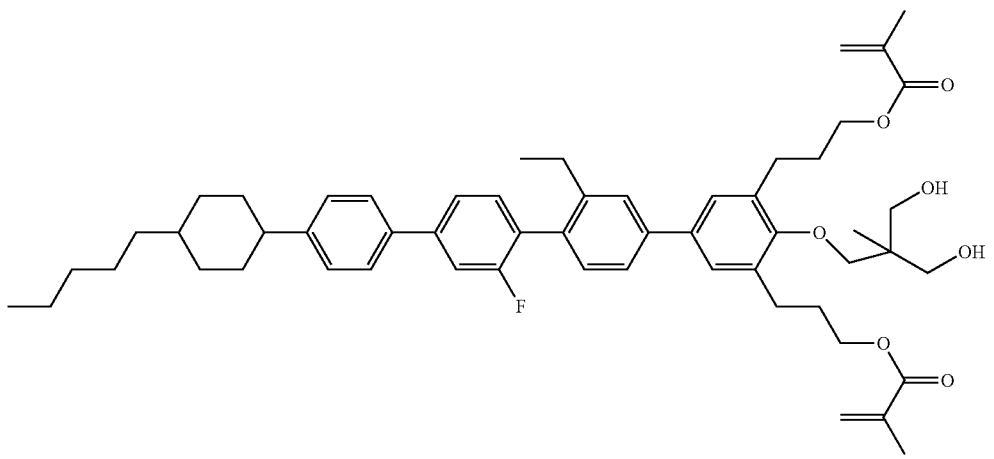
92
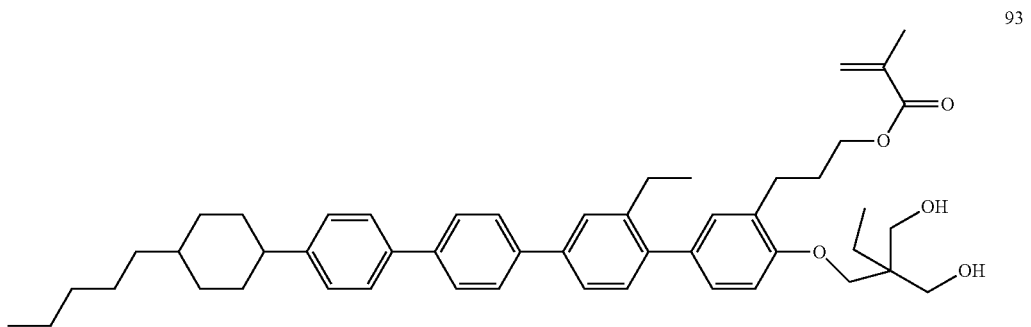
93
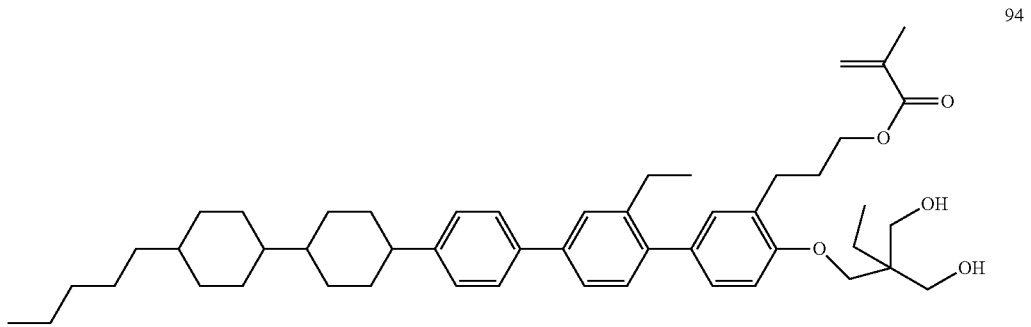
94
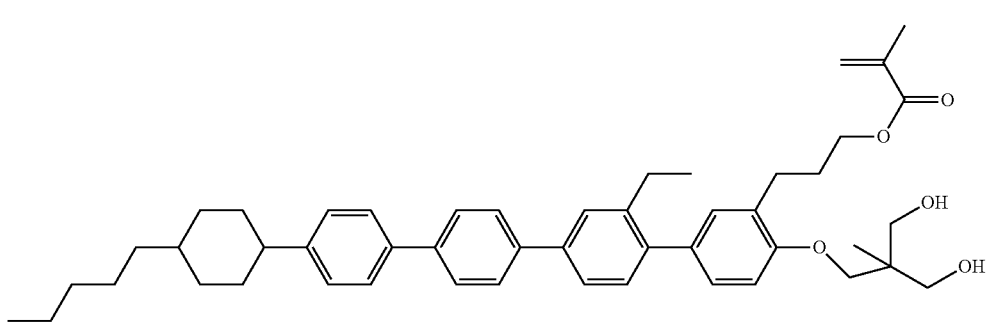
95

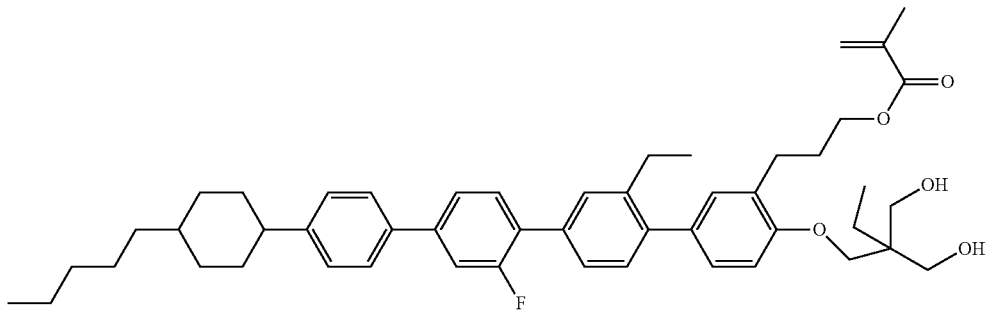
96
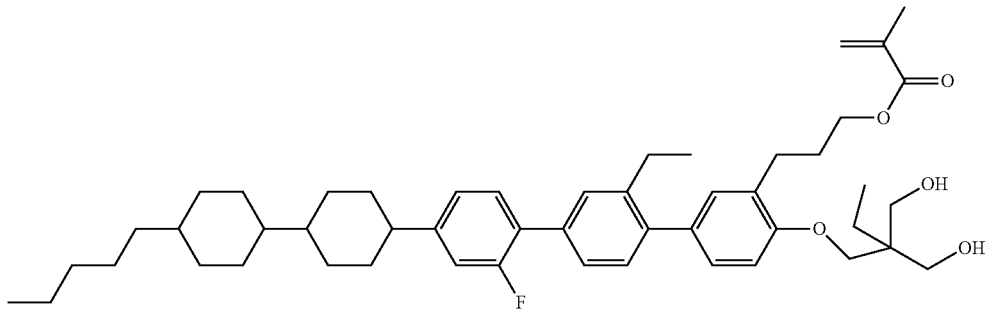
97
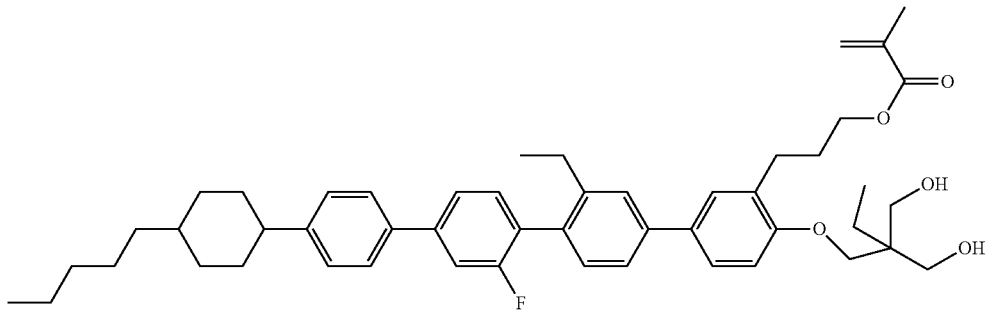
98
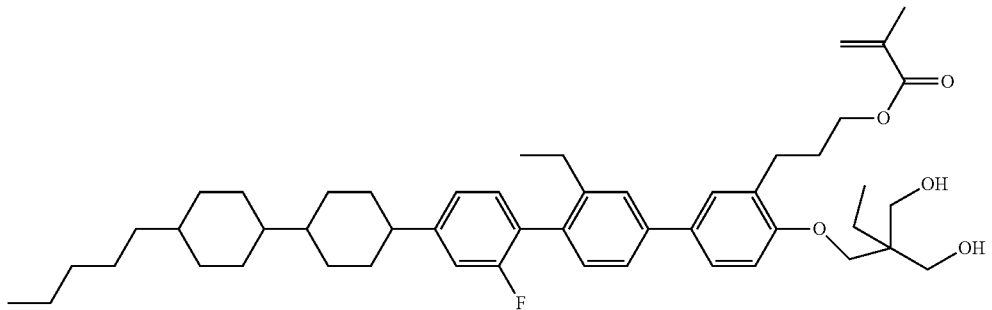
99
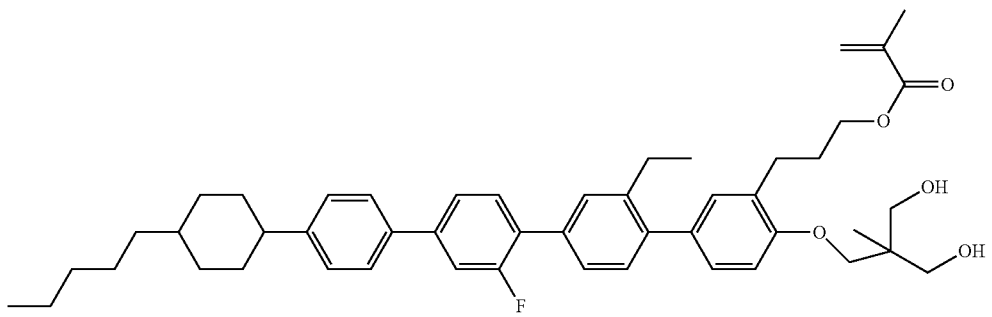
100

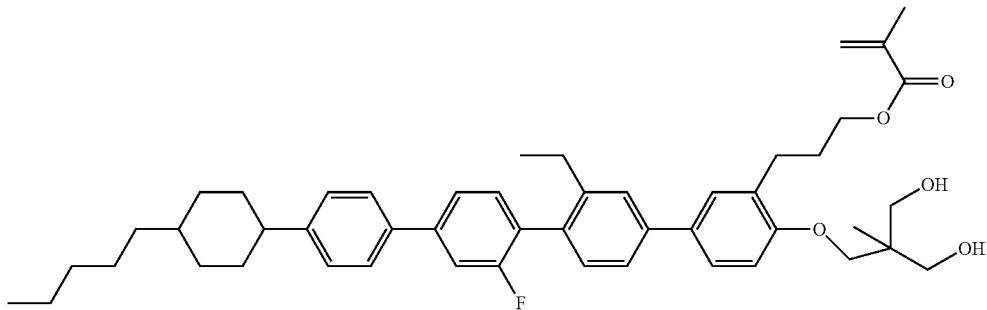

101

B) Mixture Examples

LC media according to the invention are prepared using the following liquid-crystalline mixtures consisting of low-molecular-weight components in the percentage proportions by weight indicated (acronyms cf. Tables A-D above).

H1: Nematic Host Mixture ($\Delta\varepsilon<0$)

| | | | |
|---|---|---|---|
| CY-3-O2 | 10.0% | Clearing point [° C.]: | 81 |
| CCY-3-O1 | 8.0% | $\Delta n$ (589 nm, 20° C.): | 0.103 |
| CCY-3-O2 | 11.0% | $\Delta\varepsilon$ (1 kHz, 20° C.): | −3.8 |
| CCY-4-O2 | 5.0% | $K_1$ (20° C.) [pN]: | 13.9 |
| CCY-5-O2 | 2.0% | $K_3$ (20° C.) [pN]: | 15.0 |
| CPY-2-O2 | 9.0% | $\gamma_1$ (20° C.) [mPa · s]: | 133 |
| CPY-3-O2 | 9.0% | $V_0$ (20° C.) [V]: | 2.10 |
| CCH-34 | 9.0% | | |
| CCH-23 | 17.5% | | |
| CP-3-O1 | 9.0% | | |
| PYP-2-3 | 2.5% | | |
| PY-3-O2 | 8.0% | | |

H2: Nematic Host Mixture ($\Delta\varepsilon<0$)

| | | | |
|---|---|---|---|
| B-2O-O5 | 4.00% | Clearing point [° C.]: | 74.2 |
| CPP-3-2 | 8.00% | $\Delta n$ (589 nm, 20° C.): | 0.109 |
| CC-3-V1 | 9.00% | $\Delta\varepsilon$ (1 kHz, 20° C.): | −3.1 |
| CC-3-O1 | 2.00% | $\varepsilon_{\parallel}$ (1 kHz, 20° C.): | 3.6 |
| CC-3-4 | 8.00% | $\varepsilon_{\perp}$ (1 kHz, 20° C.): | 6.7 |
| CC-3-5 | 7.00% | $K_1$ (20° C.) [pN]: | 14.5 |
| CCP-3-1 | 8.00% | $K_3$ (20° C.) [pN]: | 16.5 |
| CCP-V2-1 | 5.00% | $\gamma_1$ (20° C.) [mPa · s]: | 108 |
| CCY-3-O2 | 10.50% | $V_0$ (20° C.) [V]: | 2.41 |
| CLY-3-O2 | 1.00% | | |
| CPY-3-O2 | 2.50% | | |
| CY-3-O2 | 11.5% | | |
| CP-3-O1 | 5.50% | | |
| PY-3-O2 | 18.0% | | |

H3: Nematic Host Mixture ($\Delta\varepsilon<0$)

| | | | |
|---|---|---|---|
| CPP-3-2 | 6.0% | Clearing point [° C.]: | 74.8 |
| CC-3-V1 | 6.0% | $\Delta n$ (589 nm, 20° C.): | 0.107 |
| CC-3-4 | 9.0% | $\Delta\varepsilon$ (1 kHz, 20° C.): | −3.3 |
| CC-3-5 | 7.0% | $\varepsilon_{\parallel}$ (1 kHz, 20° C.): | 3.6 |
| CCP-3-1 | 8.0% | $\varepsilon_{\perp}$ (1 kHz, 20° C.): | 6.9 |
| CCP-3-3 | 3.0% | $K_1$ (20° C.) [pN]: | 14.2 |
| CCY-3-1 | 2.0% | $K_3$ (20° C.) [pN]: | 16.5 |
| CCY-3-O2 | 10.5% | $\gamma_1$ (20° C.) [mPa · s]: | 118 |
| CCY-4-O2 | 5.0% | $V_0$ (20° C.) [V]: | |
| CPY-3-O2 | 3.5% | | |
| CY-3-O2 | 14% | | |
| CP-3-O1 | 5.5% | | |
| PY-1-O4 | 6.5% | | |
| PY-3-O2 | 14% | | |

H4: Nematic Host Mixture ($\Delta\varepsilon<0$)

| | | | |
|---|---|---|---|
| CY-3-O2 | 15.5% | Clearing point [° C.]: | 75.1 |
| CCY-3-O3 | 8.00% | $\Delta n$ (589 nm, 20° C.): | 0.098 |
| CCY-4-O2 | 10.0% | $\Delta\varepsilon$ (1 kHz, 20° C.): | −3.0 |
| CPY-2-O2 | 5.50% | $\varepsilon_{\parallel}$ (1 kHz, 20° C.): | 3.4 |
| CPY-3-O2 | 11.5% | $\varepsilon_{\perp}$ (1 kHz, 20° C.): | 6.4 |
| CC-3-4 | 9.25% | $K_1$ (20° C.) [pN]: | 13.1 |
| CC-2-3 | 24.5% | $K_3$ (20° C.) [pN]: | 13.3 |
| PYP-2-3 | 8.75% | $\gamma_1$ (20° C.) [mPa · s]: | 113 |
| CP-3-O1 | 7.00% | $V_0$ (20° C.) [V]: | 2.22 |

H5: Nematic Host Mixture ($\Delta\varepsilon<0$)

| | | | |
|---|---|---|---|
| CY-3-O4 | 14.0% | Clearing point [° C.]: | 80.0 |
| CCY-3-O2 | 9.00% | $\Delta n$ (589 nm, 20° C.): | 0.090 |
| CCY-3-O3 | 9.00% | $\Delta\varepsilon$ (1 kHz, 20° C.): | −3.3 |
| CPY-2-O2 | 10.0% | $\varepsilon_{\parallel}$ (1 kHz, 20° C.): | 3.4 |
| CPY-3-O2 | 10.0% | $\varepsilon_{\perp}$ (1 kHz, 20° C.): | 6.7 |
| CCY-3-1 | 8.00% | $K_1$ (20° C.) [pN]: | 15.1 |
| CC-3-4 | 9.00% | $K_3$ (20° C.) [pN]: | 14.6 |
| CC-3-5 | 6.00% | $\gamma_1$ (20° C.) [mPa · s]: | 140 |
| CP-5-3 | 10.0% | $V_0$ (20° C.) [V]: | 2.23 |
| CC-3-O1 | 6.00% | | |
| CC-3-O3 | 9.00% | | |

H6: Nematic Host Mixture ($\Delta\varepsilon<0$)

| | | | |
|---|---|---|---|
| CC-3-V1 | 9.00% | Clearing point [° C.]: | 74.7 |
| CC-2-3 | 18.0% | $\Delta n$ (589 nm, 20° C.): | 0.098 |
| CC-3-4 | 3.00% | $\Delta\varepsilon$ (1 kHz, 20° C.): | −3.4 |
| CC-3-5 | 7.00% | $\varepsilon_{\parallel}$ (1 kHz, 20° C.): | 3.5 |
| CCP-3-1 | 5.50% | $\varepsilon_{\perp}$ (1 kHz, 20° C.): | 6.9 |
| CCY-3-O2 | 11.5% | $K_1$ (20° C.) [pN]: | 14.9 |
| CPY-2-O2 | 8.00% | $K_3$ (20° C.) [pN]: | 15.9 |
| CPY-3-O2 | 11.0% | $\gamma_1$ (20° C.) [mPa · s]: | 108 |
| CY-3-O2 | 15.5% | $V_0$ (20° C.) [V]: | 2.28 |
| PY-3-O2 | 11.5% | | |

H7: Nematic Host Mixture ($\Delta\varepsilon<0$)

| | | | |
|---|---|---|---|
| CC-3-V | 37.5% | Clearing point [° C.]: | 74.8 |
| CC-3-V1 | 2.00% | $\Delta n$ (589 nm, 20° C.): | 0.099 |
| CCY-4-O2 | 14.5% | $\Delta\varepsilon$ (1 kHz, 20° C.): | −2.9 |
| CPY-2-O2 | 10.5% | $\varepsilon_{\parallel}$ (1 kHz, 20° C.): | 3.7 |
| CPY-3-O2 | 9.50% | $\varepsilon_{\perp}$ (1 kHz, 20° C.): | 6.6 |
| CY-3-O2 | 15.0% | $K_1$ (20° C.) [pN]: | 12.2 |
| CY-3-O4 | 4.50% | $K_3$ (20° C.) [pN]: | 13.4 |
| PYP-2-4 | 5.50% | $\gamma_1$ (20° C.) [mPa · s]: | 92 |
| PPGU-3-F | 1.00% | $V_0$ (20° C.) [V]: | 2.28 |

H8: Nematic Host Mixture ($\Delta\varepsilon<0$)

| | | | |
|---|---|---|---|
| CC-2-3 | 20.0% | Clearing point [° C.]: | 74.8 |
| CC-3-O1 | 6.00% | $\Delta n$ (589 nm, 20° C.): | 0.105 |
| CC-3-4 | 6.00% | $\Delta\varepsilon$ (1 kHz, 20° C.): | -3.2 |
| CCP-3-1 | 3.00% | $\varepsilon_{\parallel}$ (1 kHz, 20° C.): | 3.5 |
| CCY-3-O2 | 11.0% | $\varepsilon_{\perp}$ (1 kHz, 20° C.): | 6.8 |
| CPY-2-O2 | 12.0% | $K_1$ (20° C.) [pN]: | 12.7 |
| CPY-3-O2 | 11.0% | $K_3$ (20° C.) [pN]: | 13.6 |
| CY-3-O2 | 14.0% | $\gamma_1$ (20° C.) [mPa·s]: | 120 |
| CY-3-O4 | 4.00% | $V_0$ (20° C.) [V]: | 2.16 |
| CP-3-O1 | 4.00% | | |
| PYP-2-3 | 9.00% | | |

H9: Nematic Host Mixture ($\Delta\varepsilon<0$)

| | | | |
|---|---|---|---|
| CC-4-V | 17.0% | Clearing point [° C.]: | 106.1 |
| CCP-V-1 | 15.0% | $\Delta n$ (589 nm, 20° C.): | 0.120 |
| CCEPC-3-3 | 2.50% | $\Delta\varepsilon$ (1 kHz, 20° C.): | -3.6 |
| CCY-3-O2 | 4.00% | $\varepsilon_{\parallel}$ (1 kHz, 20° C.): | 3.5 |
| CCY-3-O3 | 5.00% | $\varepsilon_{\perp}$ (1 kHz, 20° C.): | 7.0 |
| CCY-4-O2 | 5.00% | $K_1$ (20° C.) [pN]: | 16.8 |
| CLY-3-O2 | 3.50% | $K_3$ (20° C.) [pN]: | 17.3 |
| CLY-3-O3 | 2.00% | $\gamma_1$ (20° C.) [mPa·s]: | 207 |
| CPY-2-O2 | 8.00% | $V_0$ (20° C.) [V]: | 2.33 |
| CPY-3-O2 | 10.0% | | |
| CY-3-O4 | 17.0% | | |
| PYP-2-3 | 11.0% | | |

H10: Nematic Host Mixture ($\Delta\varepsilon<0$)

| | | | |
|---|---|---|---|
| CY-3-O2 | 15.0% | Clearing point [° C.]: | 75.5 |
| CCY-4-O2 | 9.50% | $\Delta n$ (589 nm, 20° C.): | 0.108 |
| CCY-5-O2 | 5.00% | $\Delta\varepsilon$ (1 kHz, 20° C.): | -3.0 |
| CPY-2-O2 | 9.00% | $\varepsilon_{\parallel}$ (1 kHz, 20° C.): | 3.5 |
| CPY-3-O2 | 9.00% | $\varepsilon_{\perp}$ (1 kHz, 20° C.): | 6.5 |
| CC-3-4 | 9.00% | $K_1$ (20° C.) [pN]: | 12.9 |
| CC-2-3 | 22.0% | $K_3$ (20° C.) [pN]: | 13.0 |
| PYP-2-3 | 7.00% | $\gamma_1$ (20° C.) [mPa·s]: | 115 |
| PYP-2-4 | 7.50% | $V_0$ (20° C.) [V]: | 2.20 |
| CP-3-O1 | 7.00% | | |

H11: Nematic Host Mixture ($\Delta\varepsilon<0$)

| | | | |
|---|---|---|---|
| CY-3-O2 | 15.0% | Clearing point [° C.]: | 74.7 |
| CY-5-O2 | 6.50% | $\Delta n$ (589 nm, 20° C.): | 0.108 |
| CCY-3-O2 | 11.0% | $\Delta\varepsilon$ (1 kHz, 20° C.): | -3.0 |
| CPY-2-O2 | 5.50% | $\varepsilon_{\parallel}$ (1 kHz, 20° C.): | 3.6 |
| CPY-3-O2 | 10.5% | $\varepsilon_{\perp}$ (1 kHz, 20° C.): | 6.6 |
| CC-3-V | 28.5% | $K_1$ (20° C.) [pN]: | 12.9 |
| CC-3-V1 | 10.0% | $K_3$ (20° C.) [pN]: | 15.7 |
| PYP-2-3 | 12.5% | $\gamma_1$ (20° C.) [mPa·s]: | 97 |
| PPGU-3-F | 0.50% | $V_0$ (20° C.) [V]: | 2.42 |

H12: Nematic Host Mixture ($\Delta\varepsilon<0$)

| | | | |
|---|---|---|---|
| CC-3-5 | 9.50% | Clearing point [° C.]: | 79.1 |
| CC-5-O1 | 5.00% | $\Delta n$ (589 nm, 20° C.): | 0.091 |
| CCY-2-1 | 9.50% | $\Delta\varepsilon$ (1 kHz, 20° C.): | -3.6 |
| CCY-3-1 | 10.5% | $\varepsilon_{\parallel}$ (1 kHz, 20° C.): | 3.5 |
| CCY-3-O2 | 10.5% | $\varepsilon_{\perp}$ (1 kHz, 20° C.): | 7.1 |
| CCY-5-O2 | 9.50% | $K_1$ (20° C.) [pN]: | 14.6 |
| CPY-2-O2 | 12.0% | $K_3$ (20° C.) [pN]: | 14.5 |
| CY-3-O4 | 9.00% | $\gamma_1$ (20° C.) [mPa·s]: | 178 |
| CY-5-O4 | 11.0% | $V_0$ (20° C.) [V]: | 2.12 |
| CP-5-3 | 13.5% | | |

H13: Nematic Host Mixture ($\Delta\varepsilon<0$)

| | | | |
|---|---|---|---|
| CPP-3-2 | 4.00% | Clearing point [° C.]: | 74.8 |
| CC-3-V1 | 8.00% | $\Delta n$ (589 nm, 20° C.): | 0.106 |
| CC-2-3 | 13.0% | $\Delta\varepsilon$ (1 kHz, 20° C.): | -3.5 |
| CC-3-4 | 7.00% | $\varepsilon_{\parallel}$ (1 kHz, 20° C.): | 3.6 |
| CC-3-5 | 7.00% | $\varepsilon_{\perp}$ (1 kHz, 20° C.): | 7.1 |
| CCY-3-O2 | 13.0% | $K_1$ (20° C.) [pN]: | 14.8 |
| CPY-2-O2 | 7.00% | $K_3$ (20° C.) [pN]: | 15.8 |
| CPY-3-O2 | 12.0% | $\gamma_1$ (20° C.) [mPa·s]: | 115 |
| CY-3-O2 | 12.0% | $V_0$ (20° C.) [V]: | 2.23 |
| CP-3-O1 | 2.00% | | |
| PY-3-O2 | 15.0% | | |

H14: Nematic Host Mixture ($\Delta\varepsilon<0$)

| | | | |
|---|---|---|---|
| CY-3-O4 | 22.0% | Clearing point [° C.]: | 86.9 |
| CY-5-O4 | 12.0% | $\Delta n$ (589 nm, 20° C.): | 0.111 |
| CCY-3-O2 | 6.00% | $\Delta\varepsilon$ (1 kHz, 20° C.): | -4.9 |
| CCY-3-O3 | 6.00% | $\varepsilon_{\parallel}$ (1 kHz, 20° C.): | 3.8 |
| CCY-4-O2 | 6.00% | $\varepsilon_{\perp}$ (1 kHz, 20° C.): | 8.7 |
| CPY-2-O2 | 10.0% | $K_1$ (20° C.) [pN]: | 14.9 |
| CPY-3-O2 | 10.0% | $K_3$ (20° C.) [pN]: | 15.9 |
| PYP-2-3 | 7.00% | $\gamma_1$ (20° C.) [mPa·s]: | 222 |
| CC-3-V1 | 7.00% | $V_0$ (20° C.) [V]: | 1.91 |
| CC-5-V | 10.0% | | |
| CCEPC-3-3 | 2.00% | | |
| CCEPC-3-5 | 2.00% | | |

H15: Nematic Host Mixture ($\Delta\varepsilon<0$)

| | | | |
|---|---|---|---|
| CY-3-O4 | 12.0% | Clearing point [° C.]: | 86.0 |
| CY-5-O2 | 10.0% | $\Delta n$ (589 nm, 20° C.): | 0.110 |
| CY-5-O4 | 8.00% | $\Delta\varepsilon$ (1 kHz, 20° C.): | -5.0 |
| CCY-3-O2 | 8.00% | $\varepsilon_{\parallel}$ (1 kHz, 20° C.): | 3.8 |
| CCY-4-O2 | 7.00% | $\varepsilon_{\perp}$ (1 kHz, 20° C.): | 8.8 |
| CCY-5-O2 | 6.00% | $K_1$ (20° C.) [pN]: | 14.7 |
| CCY-2-1 | 8.00% | $K_3$ (20° C.) [pN]: | 16.0 |
| CCY-3-1 | 7.00% | $\gamma_1$ (20° C.) [mPa·s]: | 250 |
| CPY-3-O2 | 9.00% | $V_0$ (20° C.) [V]: | 1.90 |
| CPY-3-O2 | 9.00% | | |
| CPP-3-2 | 6.00% | | |
| CP-5-3 | 10.0% | | |

H16: Nematic Host Mixture ($\Delta\varepsilon<0$)

| | | | |
|---|---|---|---|
| CC-3-V1 | 10.25% | Clearing point [° C.]: | 74.7 |
| CC-2-3 | 18.5% | $\Delta n$ (589 nm, 20° C.): | 0.103 |
| CC-3-5 | 6.75% | $\Delta\varepsilon$ (1 kHz, 20° C.): | -3.1 |
| CCP-3-1 | 6.00% | $\varepsilon_{\parallel}$ (1 kHz, 20° C.): | 3.4 |
| CCY-3-1 | 2.50% | $\varepsilon_{\perp}$ (1 kHz, 20° C.): | 6.4 |
| CCY-3-O2 | 12.0% | $K_1$ (20° C.) [pN]: | 15.4 |
| CPY-2-O2 | 6.00% | $K_3$ (20° C.) [pN]: | 16.8 |
| CPY-3-O2 | 9.75% | $\gamma_1$ (20° C.) [mPa·s]: | 104 |
| CY-3-O2 | 11.5% | $V_0$ (20° C.) [V]: | 2.46 |
| PP-1-2V1 | 3.75% | | |
| PY-3-O2 | 13.0% | | |

H17: Nematic Host Mixture ($\Delta\varepsilon<0$)

| | | | |
|---|---|---|---|
| CC-3-V | 27.5% | Clearing point [° C.]: | 74.7 |
| CC-3-V1 | 10.0% | $\Delta n$ (589 nm, 20° C.): | 0.104 |
| CC-3-5 | 8.00% | $\Delta\varepsilon$ (1 kHz, 20° C.): | -3.0 |
| CCY-3-O2 | 9.25% | $\varepsilon_{\parallel}$ (1 kHz, 20° C.): | 3.4 |
| CLY-3-O2 | 10.0% | $\varepsilon_{\perp}$ (1 kHz, 20° C.): | 6.4 |
| CPY-3-O2 | 11.75% | $K_1$ (20° C.) [pN]: | 15.3 |
| PY-3-O2 | 14.0% | $K_3$ (20° C.) [pN]: | 16.2 |
| PY-4-O2 | 9.00% | $\gamma_1$ (20° C.) [mPa·s]: | 88 |
| PYP-2-4 | 0.50% | $V_0$ (20° C.) [V]: | 2.44 |

H18: Nematic Host Mixture (Δε<0)

| Component | % | Property | Value |
|---|---|---|---|
| CPP-3-2 | 6.50% | Clearing point [° C.]: | 74.7 |
| CC-3-V1 | 8.00% | Δn (589 nm, 20° C.): | 0.104 |
| CC-2-3 | 17.0% | Δε (1 kHz, 20° C.): | −3.0 |
| CC-3-4 | 6.50% | $\varepsilon_\parallel$ (1 kHz, 20° C.): | 3.4 |
| CCY-3-O1 | 3.50% | $\varepsilon_\perp$ (1 kHz, 20° C.): | 6.3 |
| CCY-3-O2 | 12.5% | $K_1$ (20° C.) [pN]: | 14.8 |
| CPY-2-O2 | 5.50% | $K_3$ (20° C.) [pN]: | 15.8 |
| CPY-3-O2 | 10.0% | $\gamma_1$ (20° C.) [mPa·s]: | 106 |
| CY-3-O2 | 15.5% | | |
| CP-3-O1 | 4.50% | | |
| PP-1-2V1 | 5.00% | | |
| PY-3-O2 | 5.50% | | |

H19: Nematic Host Mixture (Δε<0)

| Component | % | Property | Value |
|---|---|---|---|
| CPP-3-2 | 10.5% | Clearing point [° C.]: | 74.5 |
| CC-3-4 | 9.0% | Δn (589 nm, 20° C.): | 0.104 |
| CC-3-5 | 9.0% | Δε (1 kHz, 20° C.): | −3.4 |
| CCP-3-1 | 8.0% | $\varepsilon_\parallel$ (1 kHz, 20° C.): | 3.7 |
| CCY-3-O2 | 9.5% | $\varepsilon_\perp$ (1 kHz, 20° C.): | 7 |
| CCY-4-O2 | 5.5% | $K_1$ (20° C.) [pN]: | 14 |
| CPY-3-O2 | 5.5% | $K_3$ (20° C.) [pN]: | 15.7 |
| CY-3-O2 | 15% | $\gamma_1$ (20° C.) [mPa·s]: | 128 |
| CY-5-O2 | 5.0% | | |
| CP-3-O1 | 7.0% | | |
| PY-3-O2 | 16% | | |

H20: Nematic Host Mixture (Δε>0)

| Component | % | Property | Value |
|---|---|---|---|
| CC-4-V | 10.0% | Clearing point [° C.]: | 77.0 |
| CC-5-V | 13.5% | Δn (589 nm, 20° C.): | 0.113 |
| PGU-3-F | 6.50% | Δε (1 kHz, 20° C.): | 19.2 |
| ACQU-2-F | 10.0% | $\varepsilon_\parallel$ (1 kHz, 20° C.): | 23.8 |
| ACQU-3-F | 12.0% | $\varepsilon_\perp$ (1 kHz, 20° C.): | 4.6 |
| PUQU-3-F | 11.0% | $K_1$ (20° C.) [pN]: | 11.5 |
| CCP-V-1 | 12.0% | $K_3$ (20° C.) [pN]: | 11.1 |
| APUQU-2-F | 6.00% | $\gamma_1$ (20° C.) [mPa·s]: | 122 |
| APUQU-3-F | 7.00% | $V_0$ (20° C.) [V]: | 0.81 |
| PGUQU-3-F | 8.00% | | |
| CPGU-3-OT | 4.00% | | |

H21: Nematic Host Mixture (Δε>0)

| Component | % | Property | Value |
|---|---|---|---|
| PGU-2-F | 3.50% | Clearing point [° C.]: | 77.0 |
| PGU-3-F | 7.00% | Δn (589 nm, 20° C.): | 0.105 |
| CC-3-V1 | 15.0% | Δε (1 kHz, 20° C.): | 7.2 |
| CC-4-V | 18.0% | $\varepsilon_\parallel$ (1 kHz, 20° C.): | 10.3 |
| CC-5-V | 20.0% | $\varepsilon_\perp$ (1 kHz, 20° C.): | 3.1 |
| CCP-V-1 | 6.00% | $K_1$ (20° C.) [pN]: | 15.3 |
| APUQU-3-F | 15.0% | $K_3$ (20° C.) [pN]: | 13.5 |
| PUQU-3-F | 5.50% | $\gamma_1$ (20° C.) [mPa·s]: | 63 |
| PGP-2-4 | 3.00% | $V_0$ (20° C.) [V]: | 1.53 |
| CPP-3-2 | 7.00% | | |

H22: Nematic Host Mixture (Δε>0)

| Component | % | Property | Value |
|---|---|---|---|
| APUQU-2-F | 6.00% | Clearing point [° C.]: | 74.0 |
| APUQU-3-F | 12.0% | Δn (589 nm, 20° C.): | 0.120 |
| PUQU-3-F | 18.0% | Δε (1 kHz, 20° C.): | 17.4 |
| CPGU-3-OT | 9.00% | $\varepsilon_\parallel$ (1 kHz, 20° C.): | 22.0 |
| CCGU-3-F | 3.00% | $\varepsilon_\perp$ (1 kHz, 20° C.): | 4.5 |
| CPU-3-F | 14.0% | $K_1$ (20° C.) [pN]: | 10.1 |
| CCQU-3-F | 10.0% | $K_3$ (20° C.) [pN]: | 10.8 |
| CC-3-V | 25.0% | $\gamma_1$ (20° C.) [mPa·s]: | 111 |
| PGP-2-2V | 3.00% | $V_0$ (20° C.) [V]: | 0.80 |

H23: Nematic Host Mixture (Δε>0)

| Component | % | Property | Value |
|---|---|---|---|
| PUQU-3-F | 15.0% | Clearing point [° C.]: | 74.3 |
| APUQU-2-F | 5.00% | Δn (589 nm, 20° C.): | 0.120 |
| APUQU-3-F | 12.0% | Δε (1 kHz, 20° C.): | 14.9 |
| CCQU-3-F | 11.0% | $\varepsilon_\parallel$ (1 kHz, 20° C.): | 19.1 |
| CCQU-5-F | 1.50% | $\varepsilon_\perp$ (1 kHz, 20° C.): | 4.3 |
| CPGU-3-OT | 5.00% | $K_1$ (20° C.) [pN]: | 11.2 |
| CPP-3-OT | 4.50% | $K_3$ (20° C.) [pN]: | 10.8 |
| CGU-3-F | 10.0% | $\gamma_1$ (20° C.) [mPa·s]: | 98 |
| PGP-2-3 | 1.50% | $V_0$ (20° C.) [V]: | 0.91 |
| PGP-2-2V | 8.00% | | |
| CC-3-V | 26.5% | | |

H24: Nematic Host Mixture (Δε>0)

| Component | % | Property | Value |
|---|---|---|---|
| CCQU-3-F | 9.00% | Clearing point [° C.]: | 94.5 |
| CCQU-5-F | 9.00% | Δn (589 nm, 20° C.): | 0.121 |
| PUQU-3-F | 16.0% | Δε (1 kHz, 20° C.): | 20.4 |
| APUQU-2-F | 8.00% | $\varepsilon_\parallel$ (1 kHz, 20° C.): | 24.7 |
| APUQU-3-F | 9.00% | $\varepsilon_\perp$ (1 kHz, 20° C.): | 4.3 |
| PGUQU-3-F | 8.00% | $K_1$ (20° C.) [pN]: | 12.1 |
| CPGU-3-OT | 7.00% | $K_3$ (20° C.) [pN]: | 13.9 |
| CC-4-V | 18.0% | $\gamma_1$ (20° C.) [mPa·s]: | 163 |
| CC-5-V | 5.00% | $V_0$ (20° C.) [V]: | 0.81 |
| CCP-V-1 | 6.00% | | |
| CCEPC-3-3 | 3.00% | | |
| PPGU-3-F | 2.00% | | |

H25: Nematic Host Mixture (Δε>0)

| Component | % | Property | Value |
|---|---|---|---|
| CC-3-V | 28.50% | Clearing point [° C.]: | 85.6 |
| CCP-V-1 | 3.00% | Δn (589 nm, 20° C.): | 0.121 |
| CCEPC-3-3 | 2.00% | Δε (1 kHz, 20° C.): | 19.5 |
| PGU-2-F | 4.00% | $\varepsilon_\parallel$ (1 kHz, 20° C.): | 23.8 |
| CCQU-3-F | 8.00% | $\varepsilon_\perp$ (1 kHz, 20° C.): | 4.3 |
| CCQU-5-F | 6.00% | $K_1$ (20° C.) [pN]: | 11.6 |
| CCGU-3-F | 3.00% | $K_3$ (20° C.) [pN]: | 12.7 |
| PUQU-2-F | 2.00% | $\gamma_1$ (20° C.) [mPa·s]: | 126 |
| PUQU-3-F | 10.0% | $V_0$ (20° C.) [V]: | 0.81 |
| APUQU-2-F | 6.00% | | |
| APUQU-3-F | 9.00% | | |
| PGUQU-3-F | 5.00% | | |
| PGUQU-4-F | 5.00% | | |
| PGUQU-5-F | 4.00% | | |
| CPGU-3-OT | 4.00% | | |
| PPGU-3-F | 0.50% | | |

H26: Nematic Host Mixture (Δε<0)

| Component | % | Property | Value |
|---|---|---|---|
| CC-3-V1 | 9.00% | Clearing point [° C.]: | 74.6 |
| CC-3-O1 | 3.50% | Δn (589 nm, 20° C.): | 0.0984 |
| CC-3-4 | 8.00% | Δε (1 kHz, 20° C.): | −3.6 |
| CC-3-5 | 8.00% | $\varepsilon_\parallel$ (1 kHz, 20° C.): | 3.6 |
| CCP-3-1 | 6.00% | $\varepsilon_\perp$ (1 kHz, 20° C.): | 7.1 |
| CCY-3-O1 | 6.50% | $K_1$ (20° C.) [pN]: | 14.1 |
| CCY-3-O2 | 12.5% | $K_3$ (20° C.) [pN]: | 17 |
| CPY-3-O2 | 10.0% | $\gamma_1$ (20° C.) [mPa·s]: | 119 |
| CY-3-O2 | 15.5% | $V_0$ (20° C.) [V]: | 2.31 |
| CP-3-O1 | 8.5% | | |
| PY-3-O2 | 12.5% | | |

H27: Nematic Host Mixture (Δε<0)

| Component | % | Property | Value |
|---|---|---|---|
| CC-3-5 | 9.50% | Clearing point [° C.]: | 79.1 |
| CC-5-O1 | 5.00% | Δn (589 nm, 20° C.): | 0.0911 |
| CCY-2-1 | 9.50% | Δε (1 kHz, 20° C.): | −3.6 |
| CCY-3-1 | 10.5% | $\varepsilon_\parallel$ (1 kHz, 20° C.): | 3.5 |
| CCY-3-O2 | 10.5% | $\varepsilon_\perp$ (1 kHz, 20° C.): | 7.1 |
| CCY-5-O2 | 9.50% | $K_1$ (20° C.) [pN]: | 14.6 |
| CPY-2-O2 | 12.0% | $K_3$ (20° C.) [pN]: | 14.5 |

-continued

| | | | |
|---|---|---|---|
| CY-3-O4 | 9.00% | γ₁ (20° C.) [mPa·s]: | 178 |
| CY-5-O4 | 11.0% | V₀ (20° C.) [V]: | 2.12 |
| CP-5-3 | 13.5% | | |

H28: Nematic Host Mixture (Δε<0)

| | | | |
|---|---|---|---|
| CC-3-V | 37.5% | Clearing point [° C.]: | 74.8 |
| CC-3-V1 | 2.00% | Δn (589 nm, 20° C.): | 0.0987 |
| CCY-4-O2 | 14.5% | Δε (1 kHz, 20° C.): | −2.9 |
| CPY-2-O2 | 10.5% | ε∥ (1 kHz, 20° C.): | 3.7 |
| CPY-3-O2 | 9.5% | ε⊥ (1 kHz, 20° C.): | 6.6 |
| CY-3-O2 | 15.0% | K₁ (20° C.) [pN]: | 12.2 |
| CY-3-O4 | 4.50% | K₃ (20° C.) [pN]: | 13.4 |
| PYP-2-4 | 5.50% | γ₁ (20° C.) [mPa·s]: | 92 |
| PPGU-3-F | 1.00% | V₀ (20° C.) [V]: | 2.28 |

H29: Nematic Host Mixture (Δε<0)

| | | | |
|---|---|---|---|
| CC-3-V | 37.5% | Clearing point [° C.]: | 75.4 |
| CC-5-O1 | 2.00% | Δn (589 nm, 20° C.): | 0.1034 |
| CCY-3-O2 | 12.0% | Δε (1 kHz, 20° C.): | −3.3 |
| CCY-3-O3 | 6.50% | ε∥ (1 kHz, 20° C.): | 3.6 |
| CPY-2-O2 | 12.0% | ε⊥ (1 kHz, 20° C.): | 6.9 |
| CPY-3-O2 | 10.0% | K₁ (20° C.) [pN]: | 13.4 |
| CY-3-O2 | 2.00% | K₃ (20° C.) [pN]: | 15 |
| PY-3-O2 | 16.0% | γ₁ (20° C.) [mPa·s]: | 95 |
| CP-3-O1 | 2.00% | V₀ (20° C.) [V]: | 2.24 |

H30: Nematic Host Mixture (Δε<0)

| | | | |
|---|---|---|---|
| CC-3-V | 22.5% | Clearing point [° C.]: | 74.8 |
| CC-3-V1 | 9.75% | Δn (589 nm, 20° C.): | 0.1027 |
| CC-1-3 | 0.75% | Δε (1 kHz, 20° C.): | −3.2 |
| CC-3-4 | 5.5% | ε∥ (1 kHz, 20° C.): | 3.5 |
| CC-3-5 | 4.00% | ε⊥ (1 kHz, 20° C.): | 6.8 |
| CCY-3-O1 | 10% | K₁ (20° C.) [pN]: | 14.4 |
| CCY-3-O2 | 12% | K₃ (20° C.) [pN]: | 15.2 |
| CPY-2-O2 | 10% | γ₁ (20° C.) [mPa·s]: | |
| CPY-3-O2 | 2.0% | V₀ (20° C.) [V]: | 2.29 |
| CY-3-O2 | 0.5% | | |
| PP-1-2V1 | 0.25% | | |
| PY-1-O4 | 4.25% | | |
| PY-3-O2 | 17% | | |
| PYP-2-3 | 1.5% | | |

H31: Nematic Host Mixture (Δε<0)

| | | | |
|---|---|---|---|
| CPP-3-2 | 4.0% | Clearing point [° C.]: | 74.6 |
| CC-3-V | 10% | Δn (589 nm, 20° C.): | 0.099 |
| CC-3-V1 | 8.5% | Δε (1 kHz, 20° C.): | −3.4 |
| CC-3-4 | 4.5% | ε∥ (1 kHz, 20° C.): | 3.6 |
| CC-3-5 | 8.0% | ε⊥ (1 kHz, 20° C.): | 7 |
| CCP-3-1 | 4.25% | K₁ (20° C.) [pN]: | 14.2 |
| CCY-3-O1 | 6.5% | K₃ (20° C.) [pN]: | 15.9 |
| CCY-3-O2 | 12.75% | γ₁ (20° C.) [mPa·s]: | 108 |
| CCY-4-O2 | 6.0% | V₀ (20° C.) [V]: | 2.28 |
| CY-3-O2 | 15.5% | | |
| CP-3-O1 | 2.0% | | |
| PY-3-O2 | 16% | | |
| PYP-2-3 | 2.0% | | |

H32: Nematic Host Mixture (Δε<0)

| | | | |
|---|---|---|---|
| CC-3-V | 15% | Clearing point [° C.]: | 74.4 |
| CC-3-V1 | 9.0% | Δn (589 nm, 20° C.): | 0.1086 |
| CC-2-3 | 8.0% | Δε (1 kHz, 20° C.): | −3.2 |
| CC-3-4 | 7.5% | ε∥ (1 kHz, 20° C.): | 3.5 |
| CCY-3-O2 | 10% | ε⊥ (1 kHz, 20° C.): | 6.7 |
| CCY-5-O2 | 8.0% | K₁ (20° C.) [pN]: | 14.3 |
| CPY-2-O2 | 3.0% | K₃ (20° C.) [pN]: | 15.7 |
| CPY-3-O2 | 8.5% | γ₁ (20° C.) [mPa·s]: | 102 |
| CY-3-O2 | 7.0% | V₀ (20° C.) [V]: | 2.33 |
| PY-3-O2 | 16% | | |
| PYP-2-3 | 8.0% | | |

H33: Nematic Host Mixture (Δε<0)

| | | | |
|---|---|---|---|
| CPP-3-2 | 6.0% | Clearing point [° C.]: | 75.2 |
| CC-3-O1 | 4.0% | Δn (589 nm, 20° C.): | 0.1095 |
| CC-3-4 | 9.0% | Δε (1 kHz, 20° C.): | −3.1 |
| CC-3-5 | 9.0% | ε∥ (1 kHz, 20° C.): | 3.6 |
| CCP-3-1 | 8.0% | ε⊥ (1 kHz, 20° C.): | 6.7 |
| CCP-3-3 | 1.0% | K₁ (20° C.) [pN]: | 13.8 |
| CCY-3-O2 | 12% | K₃ (20° C.) [pN]: | 16.5 |
| CLY-3-O2 | 1.0% | γ₁ (20° C.) [mPa·s]: | 119 |
| CPY-3-O2 | 11% | V₀ (20° C.) [V]: | 2.41 |
| CY-3-O2 | 9.5% | | |
| CP-3-O1 | 11.5% | | |
| PY-3-O2 | 18% | | |

H34: Nematic Host Mixture (Δε<0)

| | | | |
|---|---|---|---|
| CPP-3-2 | 3.0% | Clearing point [° C.]: | 75.2 |
| CC-3-V1 | 9.0% | Δn (589 nm, 20° C.): | 0.1098 |
| CC-3-O1 | 2.5% | Δε (1 kHz, 20° C.): | −3.1 |
| CC-3-4 | 9.0% | ε∥ (1 kHz, 20° C.): | 3.6 |
| CC-3-5 | 9.0% | ε⊥ (1 kHz, 20° C.): | 6.7 |
| CCP-3-1 | 7.5% | K₁ (20° C.) [pN]: | 14.6 |
| CCP-V2-1 | 5.0% | K₃ (20° C.) [pN]: | 16.6 |
| CCY-3-O2 | 4.0% | γ₁ (20° C.) [mPa·s]: | 114 |
| CPY-2-O2 | 5.5% | V₀ (20° C.) [V]: | 2.43 |
| CPY-3-O2 | 10.5% | | |
| CY-3-O2 | 15% | | |
| CP-3-O1 | 1.5% | | |
| PY-3-O2 | 18% | | |
| PPGU-3-F | 0.5% | | |

H35: Nematic Host Mixture (Δε<0)

| | | | |
|---|---|---|---|
| CPP-3-2 | 8.5% | Clearing point [° C.]: | 74.7 |
| CC-3-V1 | 9.0% | Δn (589 nm, 20° C.): | 0.1097 |
| CC-3-O1 | 2.0% | Δε (1 kHz, 20° C.): | −3.1 |
| CC-3-4 | 9.0% | ε∥ (1 kHz, 20° C.): | 3.5 |
| CC-3-5 | 9.0% | ε⊥ (1 kHz, 20° C.): | 6.6 |
| CCP-3-1 | 2.5% | K₁ (20° C.) [pN]: | 14.2 |
| CCP-V2-1 | 5.0% | K₃ (20° C.) [pN]: | 16.6 |
| CCY-3-O2 | 7.5% | γ₁ (20° C.) [mPa·s]: | 112 |
| CLY-3-O2 | 1.0% | V₀ (20° C.) [V]: | 2.44 |
| CPY-3-O2 | 10.5% | | |
| CY-3-O2 | 15% | | |
| CP-3-O1 | 3.0% | | |
| PY-3-O2 | 18% | | |

H36: Nematic Host Mixture (Δε<0)

| | | | |
|---|---|---|---|
| B-2O-O5 | 4.0% | Clearing point [° C.]: | 75 |
| CPP-3-2 | 2.0% | Δn (589 nm, 20° C.): | 0.1094 |
| CC-3-O1 | 5.0% | Δε (1 kHz, 20° C.): | −3.1 |
| CC-3-4 | 9.0% | ε∥ (1 kHz, 20° C.): | 3.6 |
| CC-3-5 | 9.0% | ε⊥ (1 kHz, 20° C.): | 6.7 |
| CCP-3-1 | 8.0% | K₁ (20° C.) [pN]: | 13.9 |
| CCP-3-3 | 5.0% | K₃ (20° C.) [pN]: | 16.4 |
| CCY-3-O2 | 11.5% | γ₁ (20° C.) [mPa·s]: | 117 |
| CLY-3-O2 | 1.0% | V₀ (20° C.) [V]: | 2.42 |
| CPY-3-O2 | 10.5% | | |
| CY-3-O2 | 2.0% | | |

-continued

| | |
|---|---|
| CP-3-O1 | 15% |
| PY-3-O2 | 18% |

H37: Nematic Host Mixture ($\Delta\varepsilon<0$)

| | | | |
|---|---|---|---|
| CPP-3-2 | 7.5% | Clearing point [° C.]: | 74.8 |
| CC-3-V1 | 9.0% | $\Delta n$ (589 nm, 20° C.): | 0.1098 |
| CC-3-O1 | 1.5% | $\Delta\varepsilon$ (1 kHz, 20° C.): | −3.1 |
| CC-3-4 | 9.0% | $\varepsilon_{\parallel}$ (1 kHz, 20° C.): | 3.5 |
| CC-3-5 | 9.0% | $\varepsilon_{\perp}$ (1 kHz, 20° C.): | 6.6 |
| CCP-3-1 | 4.0% | $K_1$ (20° C.) [pN]: | 14.4 |
| CCP-V2-1 | 5.0% | $K_3$ (20° C.) [pN]: | 16.6 |
| CCY-3-O2 | 7.0% | $\gamma_1$ (20° C.) [mPa·s]: | 112 |
| CPY-2-O2 | 2.0% | $V_0$ (20° C.) [V]: | 2.44 |
| CPY-3-O2 | 10% | | |
| CY-3-O2 | 15% | | |
| CP-3-O1 | 3.0% | | |
| PY-3-O2 | 18% | | |

H38: Nematic Host Mixture ($\Delta\varepsilon<0$)

| | | | |
|---|---|---|---|
| CY-3-O2 | 10% | Clearing point [° C.]: | 100 |
| CY-3-O4 | 20% | $\Delta n$ (589 nm, 20° C.): | 0.0865 |
| CY-5-O4 | 20% | $\Delta\varepsilon$ (1 kHz, 20° C.): | −5.4 |
| CCY-3-O2 | 6.0% | $\varepsilon_{\parallel}$ (1 kHz, 20° C.): | 3.9 |
| CCY-3-O3 | 6.0% | $\varepsilon_{\perp}$ (1 kHz, 20° C.): | 9.3 |
| CCY-4-O2 | 6.0% | $K_1$ (20° C.) [pN]: | 15.6 |
| CCY-5-O2 | 6.0% | $K_3$ (20° C.) [pN]: | 16.6 |
| CCZC-3-3 | 3.0% | $\gamma_1$ (20° C.) [mPa·s]: | 347 |
| CCZC-3-5 | 3.5% | $V_0$ (20° C.) [V]: | 1.84 |
| CCZC-4-3 | 3.5% | | |
| CCZC-4-5 | 3.5% | | |
| CCEPC-3-3 | 4.0% | | |
| CCEPC-3-4 | 4.5% | | |
| CCEPC-3-5 | 4.0% | | |

H39: Nematic Host Mixture ($\Delta\varepsilon<0$)

| | | | |
|---|---|---|---|
| Y-4O-O4 | 12.5% | Clearing point [° C.]: | 105 |
| CY-3-O4 | 5.0% | $\Delta n$ (589 nm, 20° C.): | 0.0868 |
| CY-5-O4 | 18% | $\Delta\varepsilon$ (1 kHz, 20° C.): | −5.4 |
| CCY-3-O1 | 4.0% | $\varepsilon_{\parallel}$ (1 kHz, 20° C.): | 4.2 |
| CCY-3-O2 | 6.0% | $\varepsilon_{\perp}$ (1 kHz, 20° C.): | 9.6 |
| CCY-3-O3 | 6.0% | $K_1$ (20° C.) [pN]: | 16.7 |
| CCY-4-O2 | 6.0% | $K_3$ (20° C.) [pN]: | 16.5 |
| CCY-5-O2 | 6.0% | $\gamma_1$ (20° C.) [mPa·s]: | |
| CPY-3-O2 | 4.5% | $V_0$ (20° C.) [V]: | 1.85 |
| CCZC-3-3 | 4.0% | | |
| CCZC-3-5 | 4.0% | | |
| CCZC-4-3 | 4.0% | | |
| CCZC-4-5 | 4.0% | | |
| CCOC-3-3 | 2.0% | | |
| CCOC-4-3 | 2.0% | | |
| CCEPC-3-3 | 4.0% | | |
| CCEPC-3-4 | 4.0% | | |
| CCEPC-3-5 | 4.0% | | |

H40: Nematic Host Mixture ($\Delta\varepsilon<0$)

| | | | |
|---|---|---|---|
| Y-4O-O4 | 3.0% | Clearing point [° C.]: | 108 |
| CY-3-O4 | 8.0% | $\Delta n$ (589 nm, 20° C.): | 0.1096 |
| CCY-3-O1 | 4.0% | $\Delta\varepsilon$ (1 kHz, 20° C.): | −2.4 |
| CCY-3-O2 | 6.0% | $\varepsilon_{\parallel}$ (1 kHz, 20° C.): | 3.2 |
| CCY-3-O3 | 6.0% | $\varepsilon_{\perp}$ (1 kHz, 20° C.): | 5.6 |
| CPY-2-O2 | 8.0% | $K_1$ (20° C.) [pN]: | 16.3 |
| CPY-3-O2 | 8.0% | $K_3$ (20° C.) [pN]: | 18.9 |
| CP-3-O1 | 5.5% | $\gamma_1$ (20° C.) [mPa·s]: | |
| CC-4-V | 15% | $V_0$ (20° C.) [V]: | 2.99 |
| CC-3-V1 | 5.5% | | |
| CCP-V-1 | 13% | | |

-continued

| | |
|---|---|
| CCP-V2-1 | 13% |
| CPTP-3-O1 | 5.0% |

H41: Nematic Host Mixture ($\Delta\varepsilon<0$)

| | | | |
|---|---|---|---|
| CY-3-O4 | 16% | Clearing point [° C.]: | 109 |
| CCY-3-O1 | 4.0% | $\Delta n$ (589 nm, 20° C.): | 0.0854 |
| CCY-3-O2 | 6.0% | $\Delta\varepsilon$ (1 kHz, 20° C.): | −2.3 |
| CCY-3-O3 | 6.0% | $\varepsilon_{\parallel}$ (1 kHz, 20° C.): | 3.1 |
| CCY-4-O2 | 6.0% | $\varepsilon_{\perp}$ (1 kHz, 20° C.): | 5.4 |
| CCY-5-O2 | 5.0% | $K_1$ (20° C.) [pN]: | 16.3 |
| CC-3-O1 | 6.0% | $K_3$ (20° C.) [pN]: | 19.4 |
| CC-4-V | 15% | $\gamma_1$ (20° C.) [mPa·s]: | |
| CC-3-V1 | 6.0% | $V_0$ (20° C.) [V]: | 3.08 |
| CCP-V-1 | 13% | | |
| CCP-V2-1 | 13% | | |
| CCEPC-3-3 | 4.0% | | |

H42: Nematic Host Mixture ($\Delta\varepsilon<0$)

| | | | |
|---|---|---|---|
| Y-4O-O4 | 10% | Clearing point [° C.]: | 107 |
| CY-3-O2 | 7.0% | $\Delta n$ (589 nm, 20° C.): | 0.1104 |
| CY-3-O4 | 15% | $\Delta\varepsilon$ (1 kHz, 20° C.): | −6 |
| CCY-3-O1 | 4.0% | $\varepsilon_{\parallel}$ (1 kHz, 20° C.): | 4.3 |
| CCY-3-O2 | 6.0% | $\varepsilon_{\perp}$ (1 kHz, 20° C.): | 10.3 |
| CCY-3-O3 | 6.0% | $K_1$ (20° C.) [pN]: | 15.7 |
| CCY-4-O2 | 6.0% | $K_3$ (20° C.) [pN]: | 19.1 |
| CCY-5-O2 | 6.0% | $\gamma_1$ (20° C.) [mPa·s]: | |
| CPY-2-O2 | 9.0% | $V_0$ (20° C.) [V]: | 1.88 |
| CPY-3-O2 | 9.0% | | |
| CCP-V-1 | 8.5% | | |
| CCEPC-3-3 | 4.0% | | |
| CCEPC-3-4 | 4.0% | | |
| CCEPC-3-5 | 3.5% | | |
| CGPC-3-3 | 2.0% | | |

H43: Nematic Host Mixture ($\Delta\varepsilon<0$)

| | | | |
|---|---|---|---|
| Y-4O-O4 | 10% | Clearing point [° C.]: | 108 |
| CY-3-O2 | 4.0% | $\Delta n$ (589 nm, 20° C.): | 0.1403 |
| CY-3-O4 | 15% | $\Delta\varepsilon$ (1 kHz, 20° C.): | −6.4 |
| CCY-3-O1 | 4.0% | $\varepsilon_{\parallel}$ (1 kHz, 20° C.): | 4.3 |
| CCY-3-O2 | 6.0% | $\varepsilon_{\perp}$ (1 kHz, 20° C.): | 10.7 |
| CCY-3-O3 | 6.0% | $K_1$ (20° C.) [pN]: | 16.8 |
| CCY-4-O2 | 6.0% | $K_3$ (20° C.) [pN]: | 20.5 |
| CLY-3-O2 | 5.0% | $\gamma_1$ (20° C.) [mPa·s]: | |
| CPY-2-O2 | 5.0% | $V_0$ (20° C.) [V]: | 1.89 |
| CPY-3-O2 | 5.0% | | |
| PTY-3-O2 | 10% | | |
| PTY-5-O2 | 10% | | |
| CCP-V-1 | 7.0% | | |
| CCP-V2-1 | 7.0% | | |

H44: Nematic Host Mixture ($\Delta\varepsilon<0$)

| | | | |
|---|---|---|---|
| Y-4O-O4 | 10% | Clearing point [° C.]: | 109 |
| CCY-3-O1 | 5.0% | $\Delta n$ (589 nm, 20° C.): | 0.1405 |
| PTY-3-O2 | 3.0% | $\Delta\varepsilon$ (1 kHz, 20° C.): | −2 |
| PTY-3-O2 | 10% | $\varepsilon_{\parallel}$ (1 kHz, 20° C.): | 3.4 |
| PTY-5-O2 | 10% | $\varepsilon_{\perp}$ (1 kHz, 20° C.): | 5.4 |
| CP-3-O1 | 4.0% | $K_1$ (20° C.) [pN]: | 16.5 |
| CC-4-V | 15% | $K_3$ (20° C.) [pN]: | 19.9 |
| CC-3-V1 | 8.0% | $\gamma_1$ (20° C.) [mPa·s]: | |
| CCP-V-1 | 13% | $V_0$ (20° C.) [V]: | 3.34 |
| CCP-V2-1 | 13% | | |
| CPTP-3-1 | 4.5% | | |
| CPTP-3-2 | 4.5% | | |

H45: Nematic Host Mixture (Δε<0)

| | | | |
|---|---|---|---|
| CY-3-O4 | 13% | Clearing point [° C.]: | 107 |
| CCY-3-O1 | 4.0% | Δn (589 nm, 20° C.): | 0.082 |
| CCY-3-O2 | 5.0% | Δε (1 kHz, 20° C.): | −2 |
| CCY-3-O3 | 5.0% | $\varepsilon_{\parallel}$ (1 kHz, 20° C.): | 3 |
| CCY-4-O2 | 5.0% | $\varepsilon_{\perp}$ (1 kHz, 20° C.): | 5 |
| CCY-5-O2 | 5.0% | $K_1$ (20° C.) [pN]: | 16.3 |
| CC-3-O1 | 13% | $K_3$ (20° C.) [pN]: | 19.2 |
| CC-4-V | 12% | $\gamma_1$ (20° C.) [mPa · s]: | |
| CC-3-V1 | 6.0% | $V_0$ (20° C.) [V]: | 3.29 |
| CCP-V-1 | 13% | | |
| CCP-V2-1 | 13% | | |
| CCZC-3-3 | 3.0% | | |
| CCEPC-3-3 | 3.0% | | |

H46: Nematic Host Mixture (Δε<0)

| | | | |
|---|---|---|---|
| Y-4O-O4 | 5.0% | Clearing point [° C.]: | 107 |
| CY-3-O4 | 15% | Δn (589 nm, 20° C.): | 0.0821 |
| CY-5-O4 | 14.5% | Δε (1 kHz, 20° C.): | −4.5 |
| CCY-3-O1 | 5.0% | $\varepsilon_{\parallel}$ (1 kHz, 20° C.): | 3.7 |
| CCY-3-O2 | 6.0% | $\varepsilon_{\perp}$ (1 kHz, 20° C.): | 8.2 |
| CCY-3-O3 | 6.0% | $K_1$ (20° C.) [pN]: | 16 |
| CCY-4-O2 | 6.0% | $K_3$ (20° C.) [pN]: | 17 |
| CCY-5-O2 | 6.0% | $\gamma_1$ (20° C.) [mPa · s]: | |
| CC-4-V | 8.5% | $V_0$ (20° C.) [V]: | 2.04 |
| CCZC-3-3 | 3.0% | | |
| CCZC-3-5 | 3.0% | | |
| CCZC-4-3 | 3.0% | | |
| CCZC-4-5 | 3.0% | | |
| CCOC-3-3 | 4.0% | | |
| CCEPC-3-3 | 4.0% | | |
| CCEPC-3-4 | 4.0% | | |
| CCEPC-3-5 | 4.0% | | |

H47: Nematic Host Mixture (Δε<0)

| | | | |
|---|---|---|---|
| B-2O-O5 | 4.0% | Clearing point [° C.]: | 75 |
| CPP-3-2 | 4.5% | Δn (589 nm, 20° C.): | 0.1095 |
| CC-3-V1 | 9.0% | Δε (1 kHz, 20° C.): | −3.1 |
| CC-3-O1 | 3.0% | $\varepsilon_{\parallel}$ (1 kHz, 20° C.): | 3.6 |
| CC-3-4 | 9.0% | $\varepsilon_{\perp}$ (1 kHz, 20° C.): | 6.7 |
| CC-3-5 | 9.0% | $K_1$ (20° C.) [pN]: | 14.5 |
| CCP-3-1 | 8.0% | $K_3$ (20° C.) [pN]: | 16.7 |
| CCP-V2-1 | 5.0% | $\gamma_1$ (20° C.) [mPa · s]: | 109 |
| CCY-3-O2 | 6.0% | $V_0$ (20° C.) [V]: | 2.43 |
| CPY-3-O2 | 10.5% | | |
| CY-3-O2 | 9.5% | | |
| CP-3-O1 | 4.5% | | |
| PY-3-O2 | 18% | | |

H48: Nematic Host Mixture (Δε<0)

| | | | |
|---|---|---|---|
| B-2O-O5 | 4.0% | Clearing point [° C.]: | 75.2 |
| CPP-3-2 | 12% | Δn (589 nm, 20° C.): | 0.1101 |
| CC-3-V1 | 9.0% | Δε (1 kHz, 20° C.): | −3.1 |
| CC-3-5 | 5.5% | $\varepsilon_{\parallel}$ (1 kHz, 20° C.): | 3.6 |
| CCP-3-1 | 5.5% | $\varepsilon_{\perp}$ (1 kHz, 20° C.): | 6.7 |
| CCP-V2-1 | 5.0% | $K_1$ (20° C.) [pN]: | 13 |
| CCY-3-O2 | 4.0% | $K_3$ (20° C.) [pN]: | 16.3 |
| CLY-3-O2 | 1.0% | $\gamma_1$ (20° C.) [mPa · s]: | 121 |
| CPY-3-O2 | 2.5% | $V_0$ (20° C.) [V]: | 2.39 |
| CPY-3-O2 | 10.5% | | |
| CY-3-O2 | 15% | | |
| CY-3-O4 | 11% | | |
| CP-3-O1 | 15% | | |

The following (polymerisable) self-alignment additives are used:

| No. | Structure of self-alignment additive |
|---|---|
| 1 | |
| 2 | |

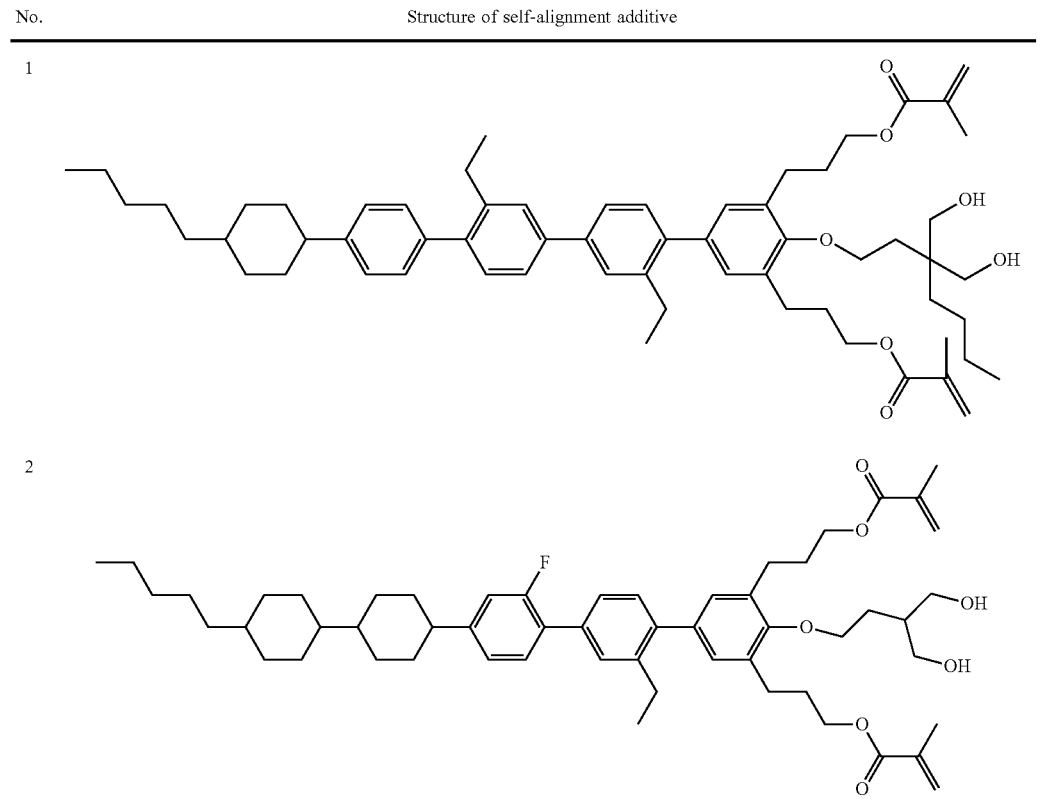

-continued

| No. | Structure of self-alignment additive |
|---|---|
| V1 | 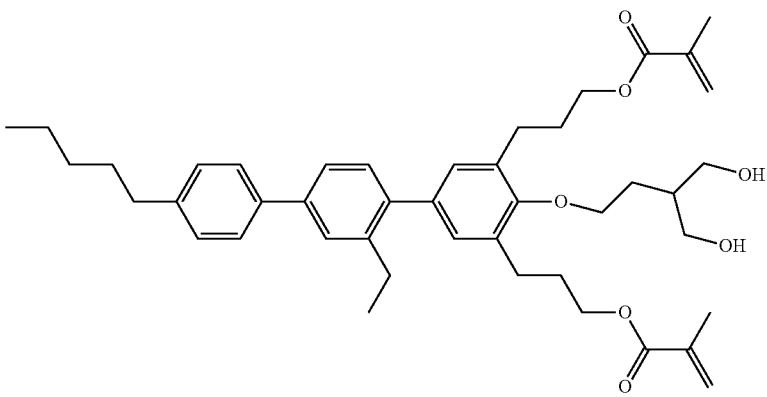 [SMILES: C=C(C)C(=O)OCCCc1cc(-c2ccc(-c3ccc(CCCCC)cc3)cc2CC)cc(CCCOC(=O)C(=C)C)c1OCCC(CO)CO] |

The following polymerisable compounds are used:

RM-1

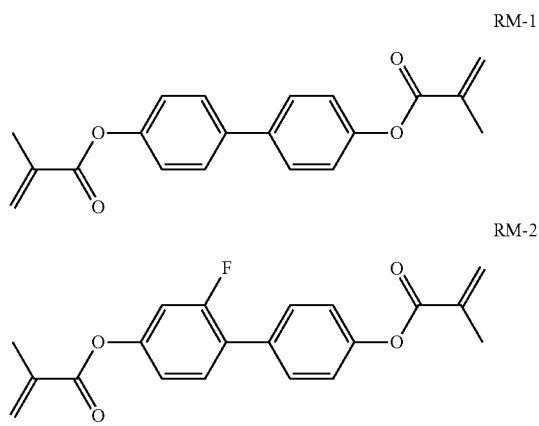

RM-2

Working Examples

Self-alignment additives Nos. 1 and 2 are generally dissolved in one of host mixtures H1 to H47 in an amount of 0.02-1.5% by weight.

General Procedure for Mixture Examples

Firstly 0.3% of the polymerisable compound RM-1 is added to the host mixture. The self-alignment additive according to the invention is subsequently added to this host mixture in the amount indicated (generally 0.02-2.5% by weight).

The mixture formed is introduced into a test cell (without polyimide alignment layer, layer thickness d≈4.0 μm, ITO coating on both sides for VHR measurements). The LC medium has spontaneous homeotropic (vertical) alignment with the substrate surfaces.

With application of a voltage greater than the optical threshold voltage (for example 14 Vpp), the VA cell is irradiated with UV light of intensity 100 mW/cm² at 20° C. or 40° C. with a 320 nm band-pass filter. This causes polymerisation of the polymerisable compounds. This generates a 'pre-tilt'.

Conditions for the UV process for pre-tilt setting: metal halide lamp (100 mW/cm³, 320 nm cut-off filter, irradiation for 60 minutes, adjustment of the sample temperature to 40° C., applied voltage: 20 V (200 Hz AC).

Pre-tilt measurements: the pre-tilt angles of the cells are measured directly after setting of the pre-tilt using an AXOSCAN (Axometrics, Inc., 103 Quality Circle, Suite 215 Huntsville, Ala. 35806 U.S.A.) at a wavelength of 578 nm.

Conditions for determination of the pre-tilt stability: the cells are subjected to 60 Vpp for 60 hours. The pre-tilt is measured before and after application of the voltage. A change in the pre-tilt after application of the voltage is a measure of the stability of the pre-tilt.

UV process for VHR measurements: metal halide lamp (100 mW/cm³, with a 320 nm cut-off filter for 60 minutes) at 40° C. with test cells coated with ITO over the entire surface.

VHR measurements are carried out using a Toyo VHR instrument: the VHR is measured one hour after processing of the test cells, with the following conditions: applied voltage: 1 V, frequency: 0.6 Hz, in bipolar mode at 60° C.

Backlight test: 7 days between two backlight modules with applied voltage (30 V(pp), 1 MHz, about 50° C.).

Measurements of "additive spreading" (distribution behaviour of the additive): test cells (8 cm×4 cm) are filled with the test mixture. The lower part (close to the fill opening) has good alignment; the upper part (opposite the fill opening) in some cases has poor alignment, which is characterised by higher transmission between crossed polarisers. The ratio of these two regions is a measure of the spreading properties of the additive.

Mixture Example V1 (For Comparison)

A polymerisable compound RM-1 (0.3% by weight) and the polymerisable self-alignment additive V1 based on a terphenyl structure (0.3% by weight) are added to a nematic LC medium H1 of the VA type (Δε<0) and homogenised.

Characterisation of the mixture, see Mixture Examples 1 and 2 below.

Mixture Example M1

Addition of 0.7% by weight of self-alignment additive No. 1 to a nematic LC medium H1 of the VA type (Δε<0), which additionally comprises 0.3% of RM-1. The resultant medium is polymerised as indicated using UV light under an applied voltage.

Alignment (optical assessment): very good vertical alignment. The cell without polyimide layer can be switched reversibly.

"Additive spreading": 95% of the area of the test cell show good VA alignment (comparison with V1: 95%)

VHR Measurement:

The VHR (voltage holding ratio) values of the test cells are measured before and after the polymerisation operation (PS stabilisation), which is initiated by UV irradiation (Table 1).

TABLE 1

Comparison of VHR values (100° C. 0.6 Hz) in test cells with host mixture H1 before and after exposure to backlight.

| VHR [%] | Mixture Example | |
| --- | --- | --- |
| | M1 | V1 |
| Before exposure | 90 | 84 |
| After exposure | 96 | 83 |

LTS (−20° C.)>1000 h (comparison with V1, 0.3% by weight: 144 h)

Tilt angle generation (20° C.): 11° (comparison with V1: 3°)

Pre-tilt stability (after irradiation for 60 min.): 0.4° change after stress (comparison with V1: 0.4°)

Compared with V1 (3% by weight of a self-alignment additive having a terphenyl structure), the low-temperature stability, VHR and tilt angle generation, in particular, are improved.

Mixture Example M2

Addition of 0.6% by weight of self-alignment additive No. 2 to a nematic LC medium H1 of the VA type (Δε<0) which additionally comprises 0.3% of RM-1. The resultant medium is polymerised as indicated using UV light under an applied voltage.

Alignment (optical assessment): very good vertical alignment. The cell without polyimide layer can be switched reversibly.

Additive spreading: 95% of the area of the test cell exhibit good VA alignment (comparison with V1: 95%)

LTS (−20° C.)>600 h (comparison with V1, 0.3%: 144 h)

Tilt angle generation (20° C.): 10.5° (comparison with V1: 3°)

Pre-tilt stability (after irradiation for 60 min.): 0.3° change after stress (comparison with V1: 0.4°)

VHR Measurement:

The VHR (voltage holding ratio) values of the test cells are measured before and after the polymerisation operation (PS stabilisation), which is initiated by UV irradiation (Table 2).

TABLE 2

Comparison of VHR values (100° C. 0.6 Hz) in test cells with host mixture H1 before and after exposure to backlight.

| VHR [%] | Mixture Example | |
| --- | --- | --- |
| | M2 | V1 |
| Before exposure | 92 | 84 |
| After exposure | 83 | 83 |

The invention claimed is:

1. A compound of the formula I-A

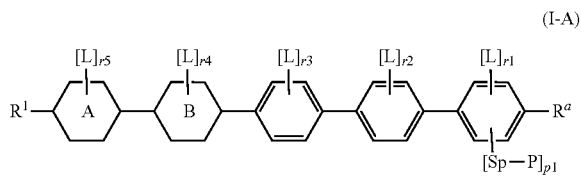

in which

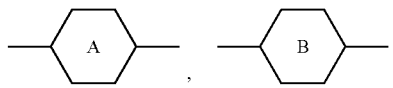

independently denote a ring of the formula

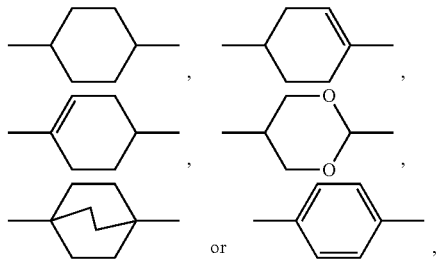

p1 denotes 2,
r1 denotes 0, 1 or 2,
r2 denotes 1,
r3 denotes 1,
r4 denotes 0 or 1, and
r5 denotes 0 or 1
L in each case, independently of one another, denotes unbranched alkyl, alkenyl, alkoxy, alkylcarbonyl, alkoxycarbonyl, alkylcarbonyloxy or alkoxycarbonyloxy having 1 to 25 C atoms, in which, in addition, one or more H atoms may be replaced by F or Cl, branched alkyl, alkenyl, alkoxy, alkylcarbonyl, alkoxycarbonyl, alkylcarbonyloxy or alkoxycarbonyloxy having 3 to 25 C atoms, in which, in addition, one or more H atoms may be replaced by F or Cl, or denotes F, Cl, Br, I, —CN, —NO$_2$, —NCO, —NCS, —OCN, —SCN, —C(=O)N(R$^0$R$^{00}$ or cycloalkyl having 3 to 6 C atoms,
P denotes a polymerisable methacrylate group,
Sp denotes a spacer group or a single bond,
R$^0$ in each case, independently of one another, denotes alkyl having 1 to 12 C atoms,
R$^{00}$ in each case, independently of one another, denotes H or alkyl having 1 to 12 C atoms,
R$^1$ denotes an alkyl radical having 1 to 25 C atoms, where, in addition, one or more CH$_2$ groups in this radical may each be replaced, independently of one another, by —CH=CH—, —C≡C—, —CF$_2$O—, —OCF$_2$—

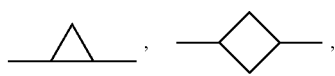

-continued

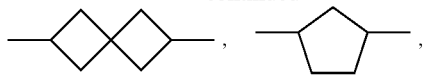

—O—, —S—, —CO—, —CO—O— or —O—CO— in such a way that O/S atoms are not linked directly to one another, and in which, in addition, one or more H atoms may be replaced by F or Cl, or denotes H, or a group -Sp-P, $R^a$ denotes an anchor group of the formula

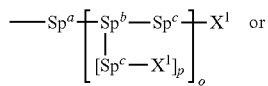

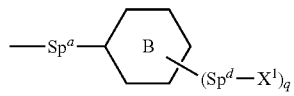

p denotes 1 or 2,
q denotes 2 or 3,
B denotes a substituted or unsubstituted ring system or condensed ring system,
denotes 1,
$X^1$, independently of one another, denotes OH, SH, $NH_2$, $NHR^{11}$, $NR^{11}{}_2$, C(O)OH or —CHO,
$R^{11}$ denotes alkyl having 1 to 12 C atoms, when linear or 3 to 12 C atoms when branched, and in which H may be substituted by fluorine or alkoxy having 1 to 8 C atoms,
$Sp^a$, $Sp^c$, $Sp^d$ in each case, independently of one another, denote a spacer group or a single bond, and
$Sp^b$ denotes a tri- or tetravalent group.

2. A compound according to claim 1, wherein

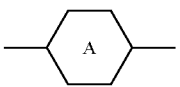

denotes a ring of the formula

 and 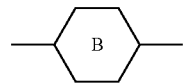

denotes a ring of the formula

 or .

3. A compound according to claim 1, wherein
$Sp^a$ denotes an unbranched alkylene chain having 1 to 8 C atoms or branched alkylene chain having 3 to 8 C atoms, in which, in each case, one or more $CH_2$ groups may be replaced by —O—, —NH—, —$NR^3$—, —S— or —(CO)—, so that O/S atoms are not linked directly to one another, and in which, in addition, one or more H atoms may be replaced by F, Cl or —OH, or a single bond.

4. A compound according to claim 1, wherein in the group $R^a$,
$Sp^b$ denotes —CH or —$CR^3$ (for p=1) or C (for p=2), in which $R^3$ is an unbranched alkyl radical having 1 to 10 C atoms or branched alkyl radical having 3 to 10 C atoms,
and
$Sp^c$ denotes an unbranched alkylene chain having 1 to 8 C atoms or branched alkylene chain having 3 to 8 C atoms, in which one or more $CH_2$ groups may be replaced by —O—, and in which, in addition, one or more H atoms may be replaced by F, Cl or —OH, or a single bond.

5. A compound selected from the following formulae:

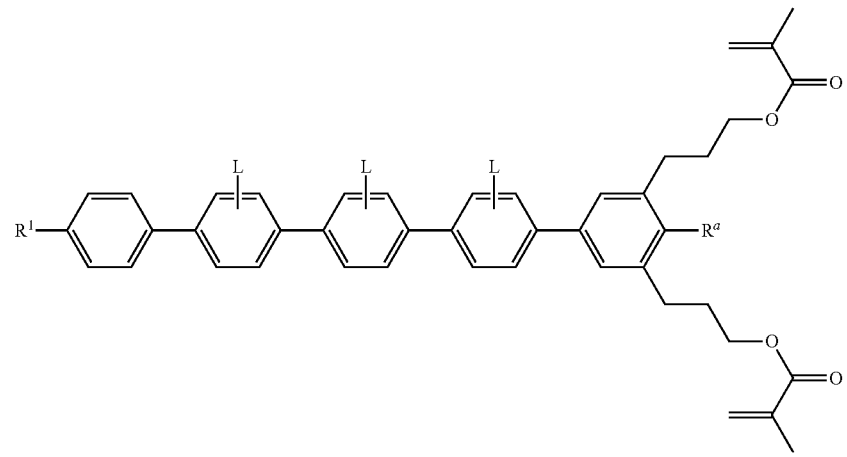

I1-1

-continued
I1-2
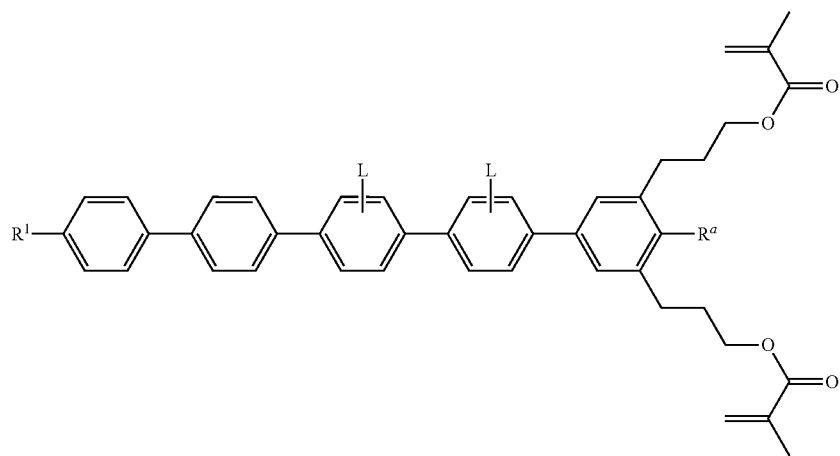
I1-3
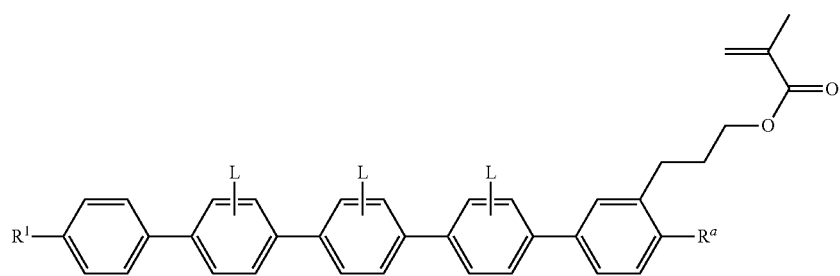
I1-4
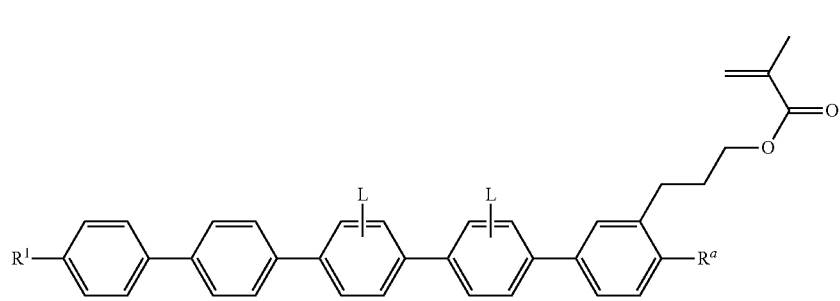
I1-5
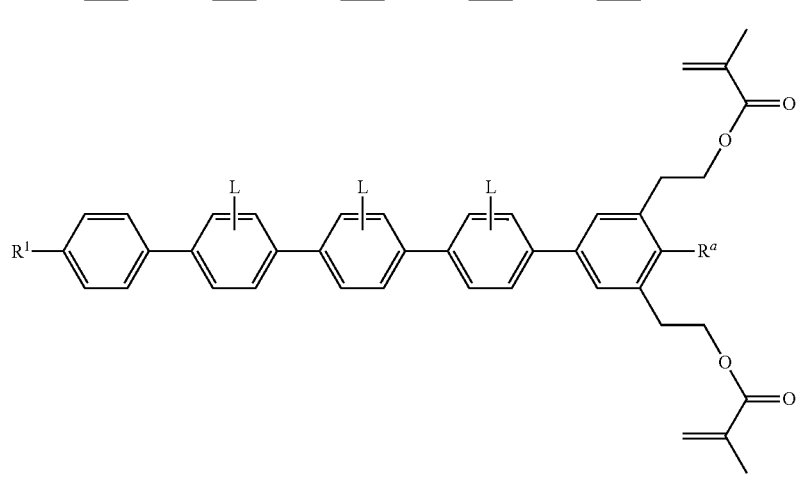

I1-6
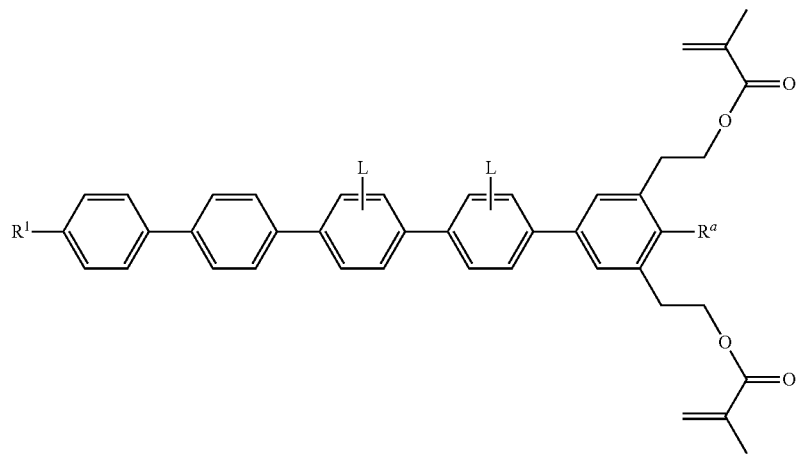
I1-7
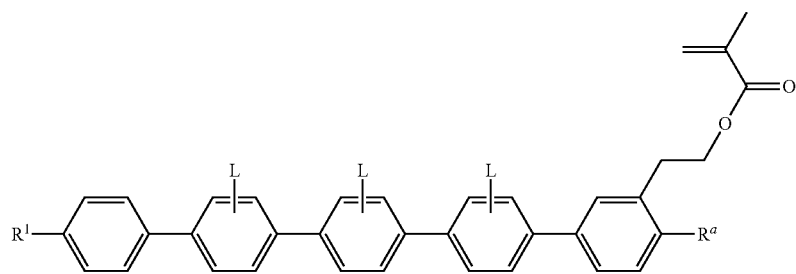
I1-8
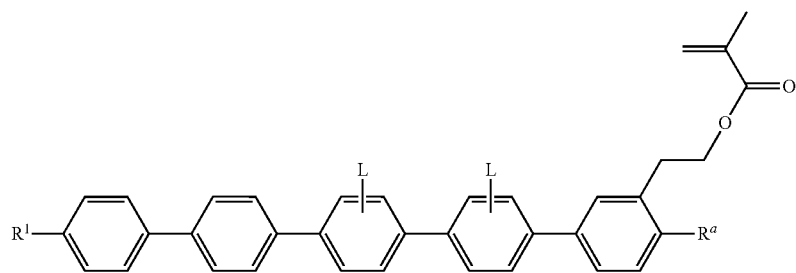
I2-1
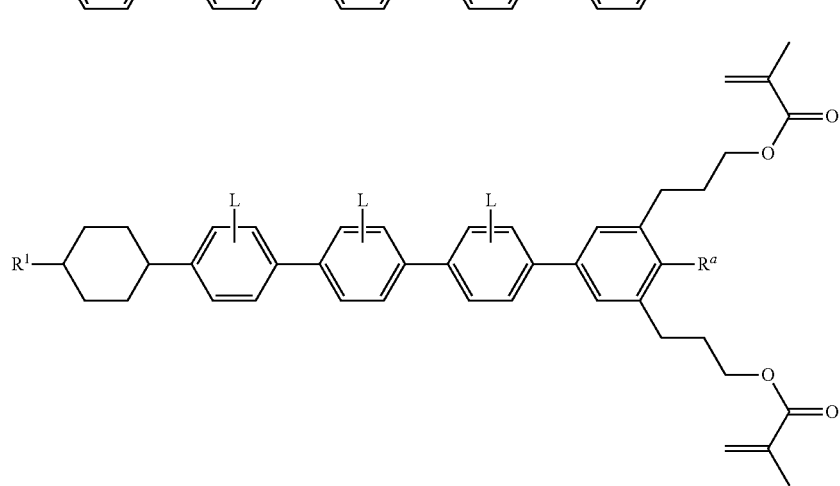

-continued
I2-2
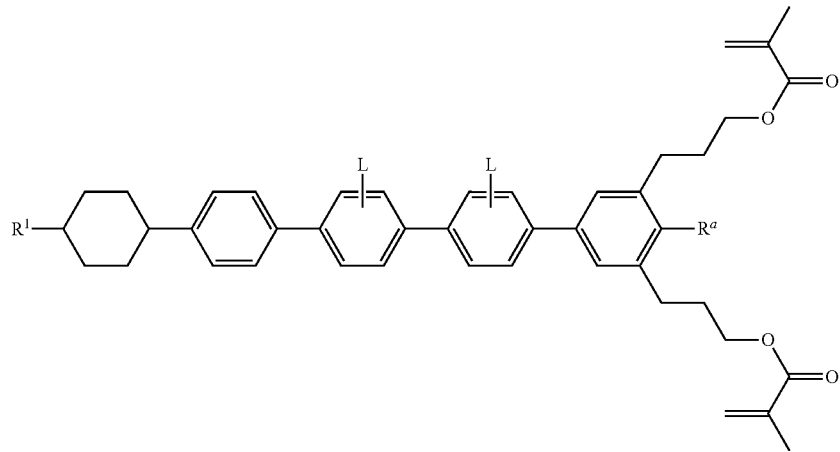
I2-3
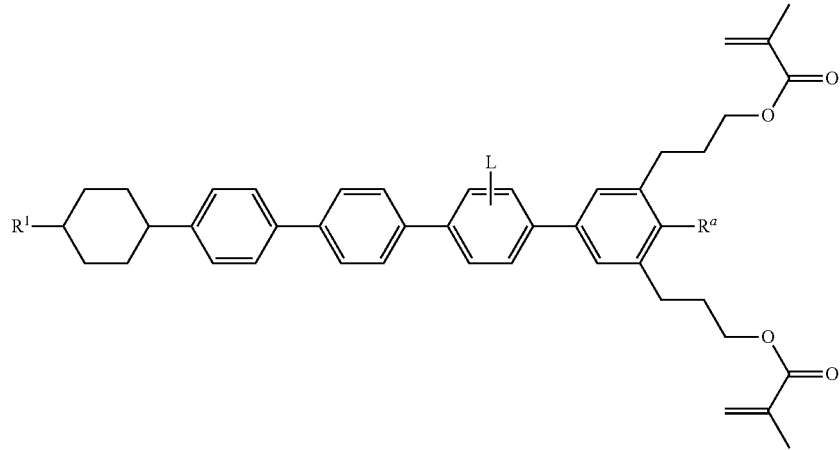
I2-4
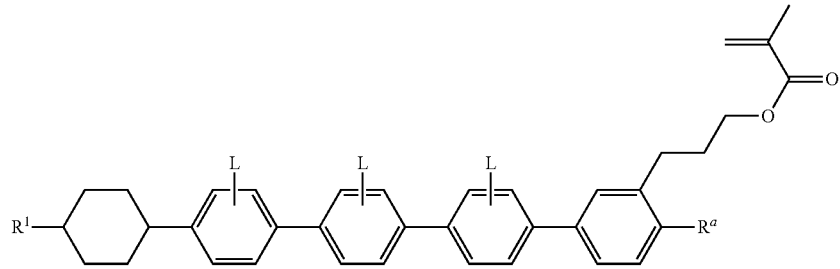
I2-5
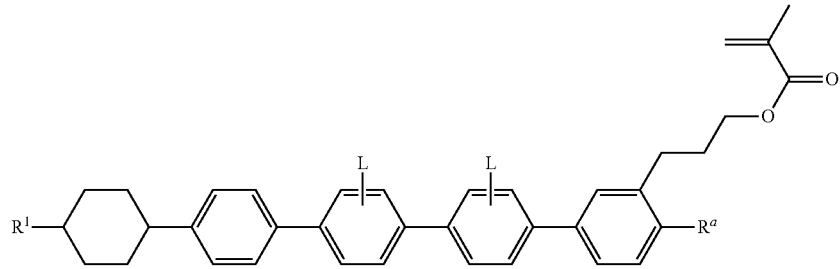

-continued
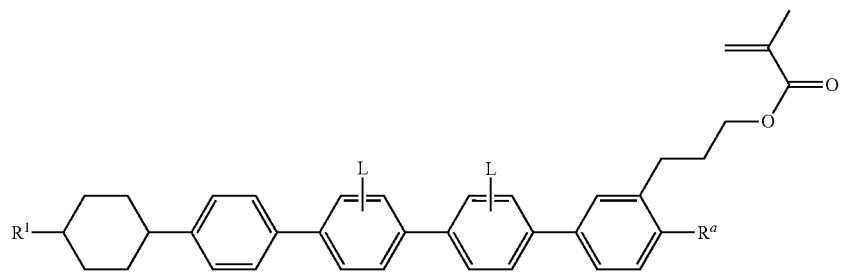
I2-6
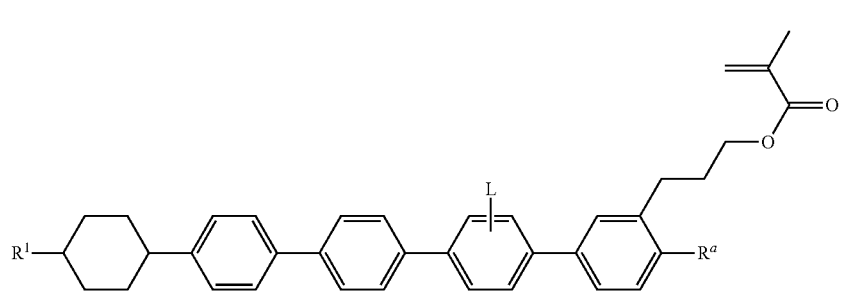
I2-7
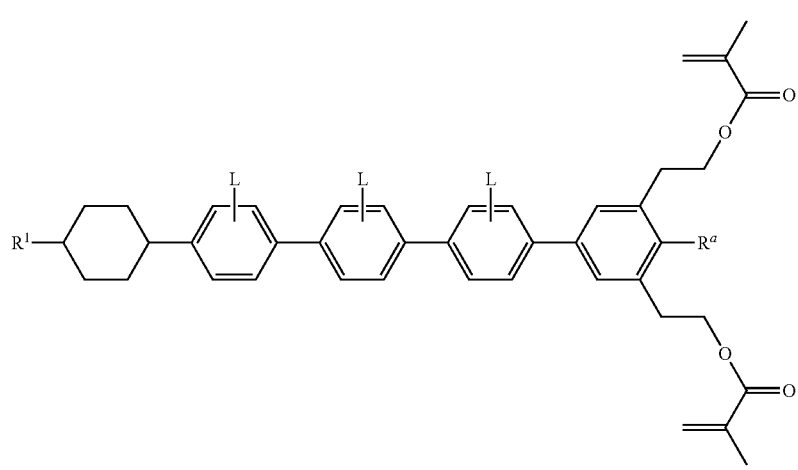
I2-8
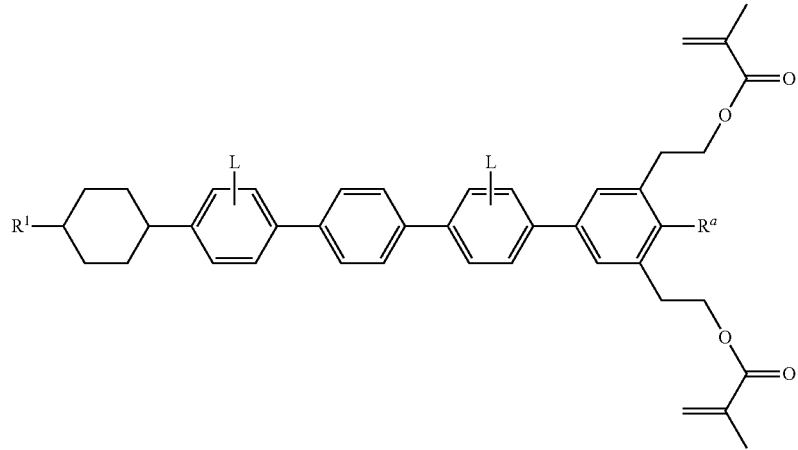
I2-9

I2-10
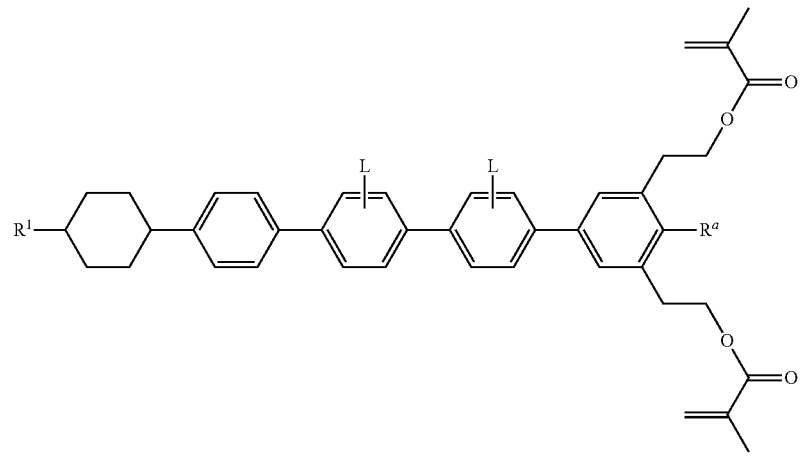
I2-11
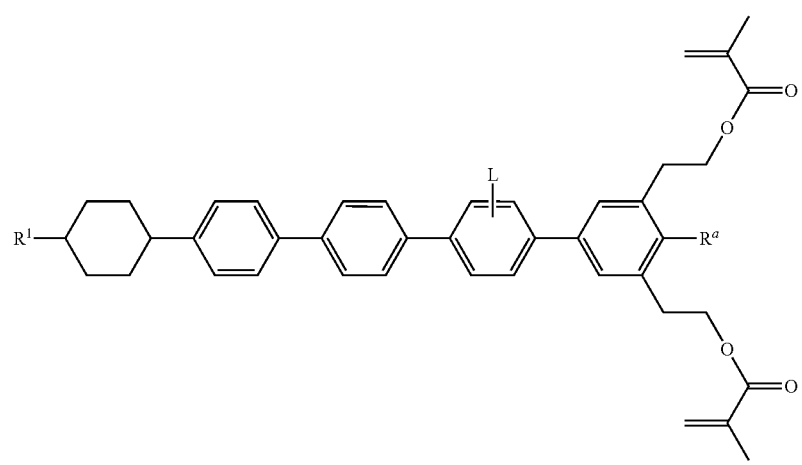
I2-12
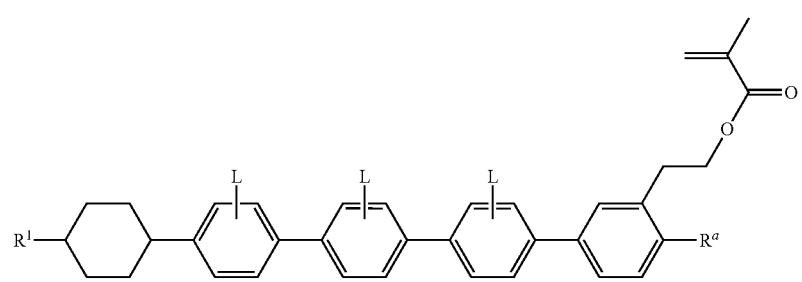
I2-13
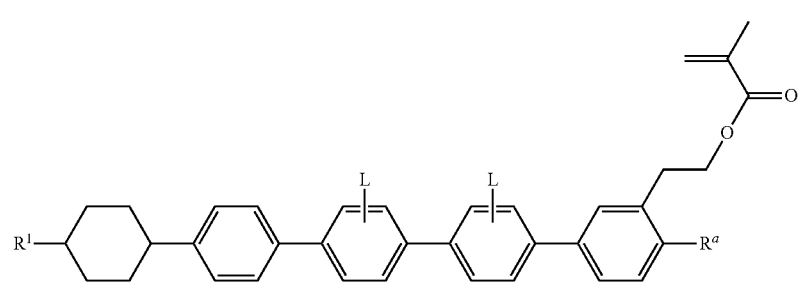

I2-14
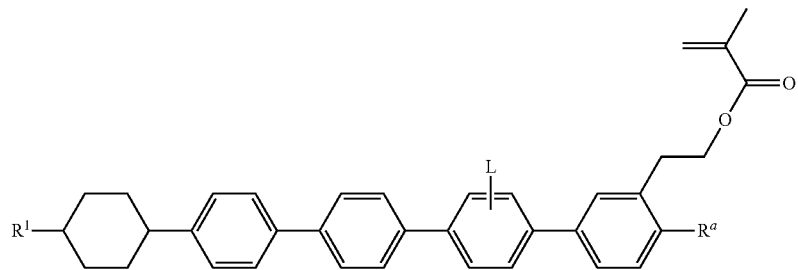
I3-1
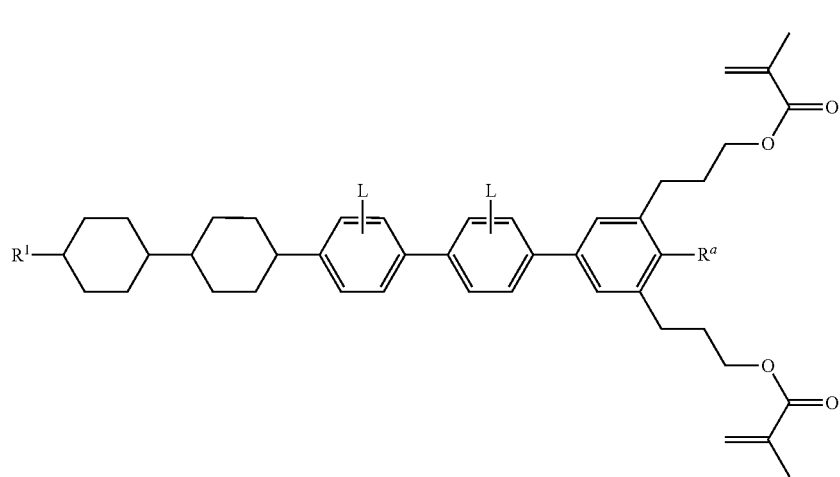
I3-2
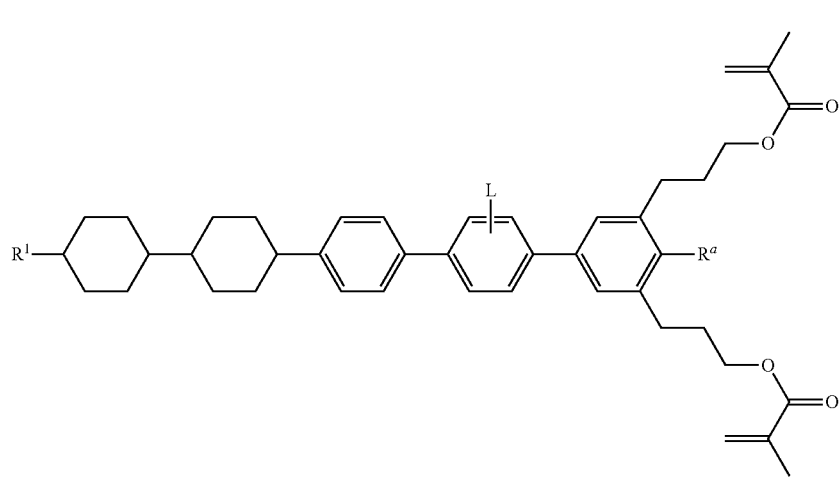
I3-3
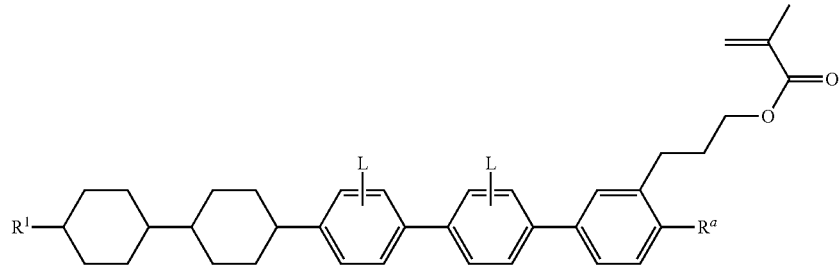

-continued
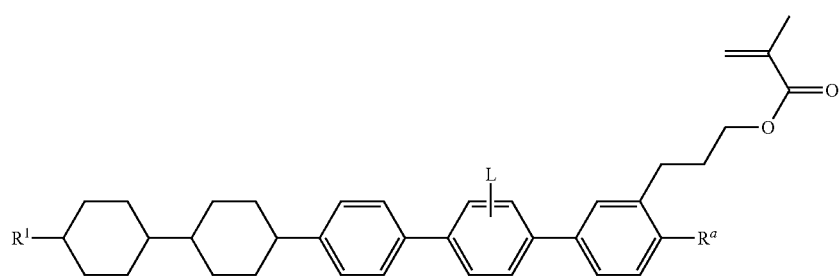
I3-4
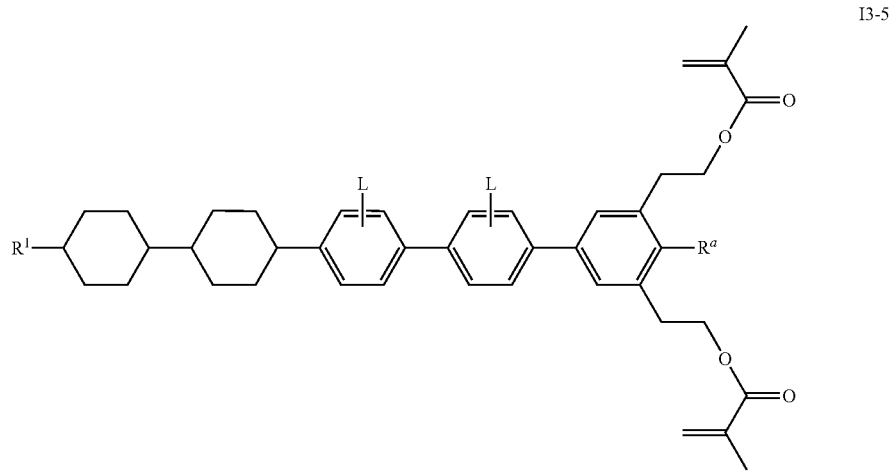
I3-5
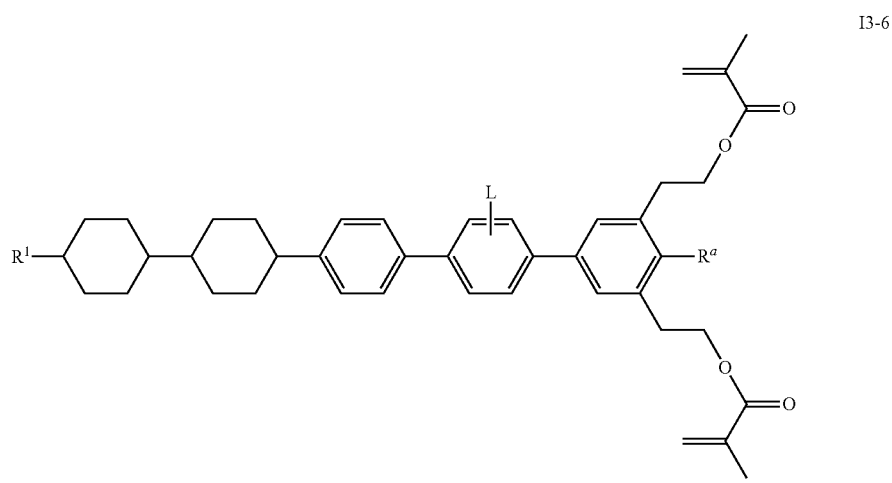
I3-6
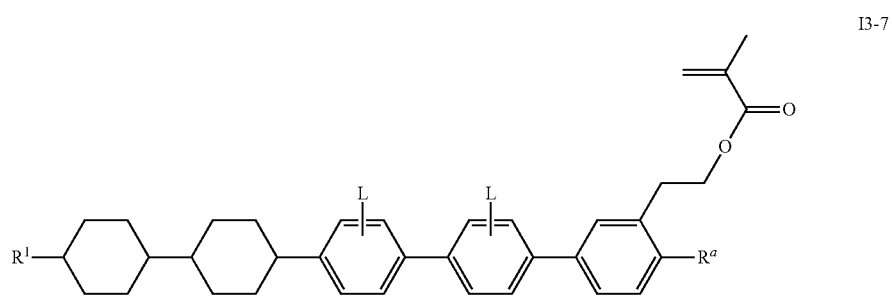
I3-7 in which

R[1] denotes an alkyl radical having 1 to 25 C atoms, where, in addition, one or more CH₂ groups in this radical may each be replaced, independently of one another, by —CH=CH—, —C≡C—, —CF₂O—, —OCF₂—,

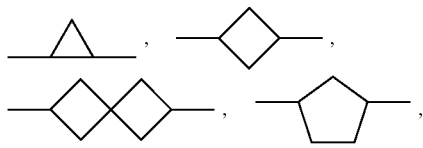

—O—, —S—, —CO—, —CO—O— or —O—CO— in such a way that O/S atoms are not linked directly to one another, and in which, in addition, one or more H atoms may be replaced by F or Cl, or denotes H, or a group -Sp-P, wherein P denotes a polymerisable group and Sp denotes a spacer group or a single bond, L denotes in each case, independently of one another, denotes unbranched alkyl, alkenyl, alkoxy, alkylcarbonyl, alkoxycarbonyl, alkylcarbonyloxy or alkoxycarbonyloxy having 1 to 25 C atoms, in which, in addition, one or more H atoms may be replaced by F or Cl, or branched alkyl, alkenyl, alkoxy, alkylcarbonyl, alkoxycarbonyl, alkylcarbonyloxy or alkoxycarbonyloxy having 3 to 25 C atoms, in which, in addition, one or more H atoms may be replaced by F or Cl, or denotes F, Cl, Br, I, —CN, —NO₂, —NCO, —NCS, —OCN, —SCN, —C(=O)N(R⁰R⁰⁰ or cycloalkyl having 3 to 6 C atoms, wherein R⁰ in each case, independently of one another, denotes alkyl having 1 to 12 C atoms, and R⁰⁰ in each case, independently of one another, denotes H or alkyl having 1 to 12 C atoms, and R$^a$ denotes an anchor group of the formula

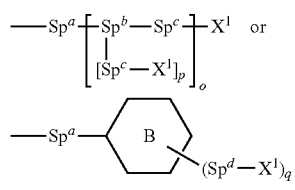

p denotes 1 or 2,
q denotes 2 or 3,
B denotes a substituted or unsubstituted ring system or condensed ring system,
denotes 0 or 1,
X[1], independently of one another, denotes OH, SH, NH₂, NHR[11], NR[11]₂, C(O)OH or —CHO,
R[11] denotes alkyl having 1 to 12 C atoms when linear or 3 to 12 C atoms when branched, and in which H may be substituted by fluorine or alkoxy having 1 to 8 C atoms,
Sp$^a$, Sp$^c$, Sp$^d$ in each case, independently of one another, denote a spacer group or a single bond, and
Sp$^b$ denotes a tri- or tetravalent group.

6. A compound according to claim 5, wherein
L denotes F, Cl, CH₃, ethyl, propyl, cyclopropyl or isopropyl.

7. A compound according to claim 5, wherein the group R$^a$ denotes a group selected from the sub-formulae

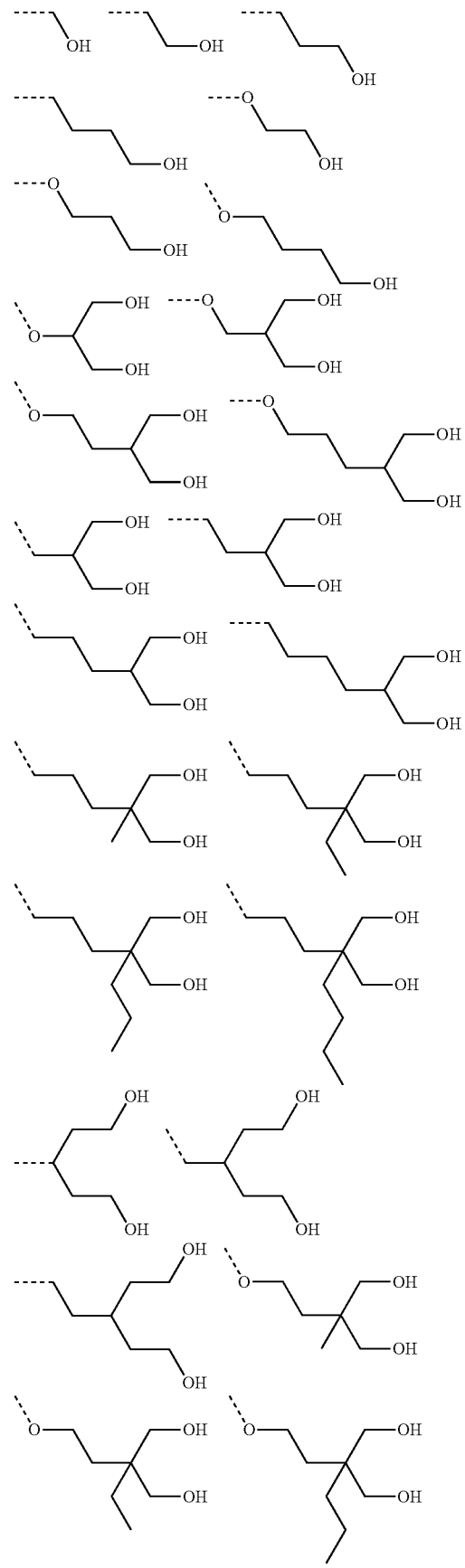

329
-continued

330
-continued

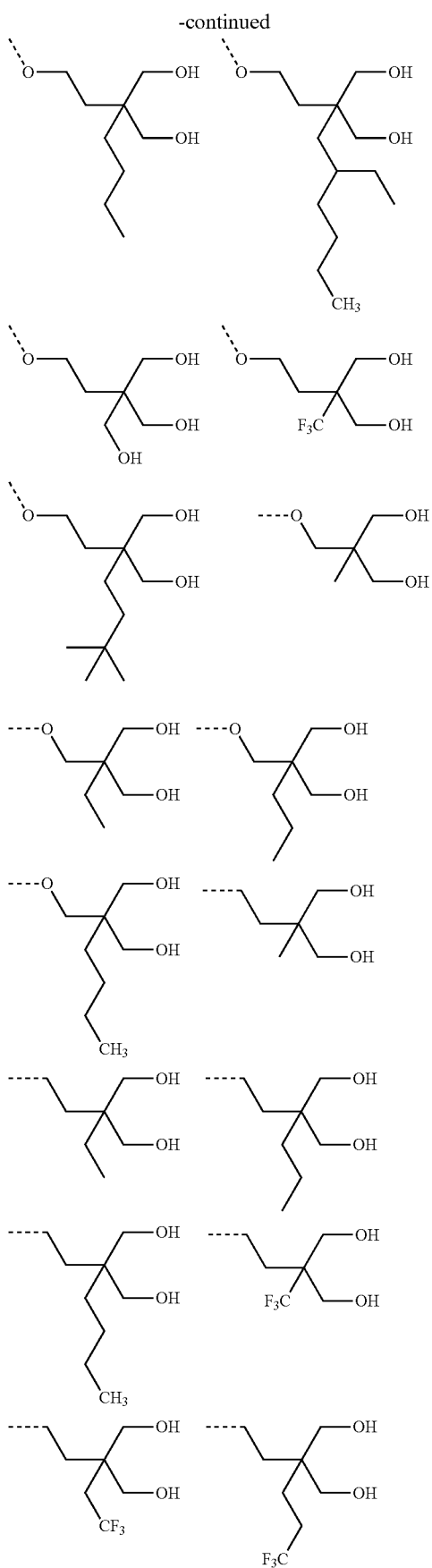

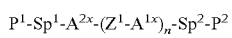

8. A method which comprises including a compound of claim 5 in a LC medium as an additive to effect a homeotropic alignment with respect to a surface delimiting the LC medium, where the compounds are optionally polymerised after effecting the homeotropic alignment.

9. A LC medium comprising a low-molecular-weight, unpolymerisable, liquid-crystalline component and one or more compounds according to claim 5 or a (co)polymer comprising one or more compounds of claim 5 in polymerised form.

10. A LC medium according to claim 9, which comprises a polymerisable or polymerised component, where the polymerisable or polymerised component encompasses a compound containing one, two or more polymerisable groups P, where the polymerised component is obtained by polymerisation of the polymerisable component.

11. A LC medium according to claim 9, which comprises one or more polymerisable compounds of the formula M or a (co)polymer comprising compounds of the formula M in polymerised form:

$$P^1\text{-}Sp^1\text{-}A^{2x}\text{-}(Z^1\text{-}A^{1x})_n\text{-}Sp^2\text{-}P^2 \qquad M$$

in which the individual radicals have the following meanings:
P$^1$, P2 each independently denote a polymerisable group,
sp$^1$, Sp$^2$ each independently denote a spacer group,
A$^{1x}$, A$^{2x}$ each, independently of one another, denote a radical selected from the following groups:
a) the group consisting of trans-1,4-cyclohexylene, 1,4-cyclohexenylene and 4,4'-bicyclohexylene, in which, in addition, one or more non-adjacent CH$_2$ groups may be replaced by —O— and/or —S— and in which, in addition, one or more H atoms may be replaced by a group L$^X$, or selected from

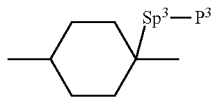

b) the group consisting of 1,4-phenylene and 1,3-phenylene, in which, in addition, one or two CH groups may be replaced by N and in which, in addition, one or more H atoms may be replaced by a group L$^X$ or -Sp$^3$-P,
c) the group consisting of tetrahydropyran-2,5-diyl, 1,3-dioxane-2,5-diyl, tetrahydrofuran-2,5-diyl, cyclobutane- 1,3-diyl, piperidine- 1,4-diyl, thiophene-2,5-diyl and selenophene-2,5-diyl, each of which may also be mono- or polysubstituted by a group L$^X$,
d) the group consisting of saturated, partially unsaturated or fully unsaturated, and optionally substituted, polycyclic radicals having 5 to 20 cyclic C atoms, one or more of which may, in addition, be replaced by heteroatoms, P$^3$ denotes a polymerisable group,
Sp$^3$ denotes a spacer group,
n denotes 0, 1, 2 or 3,
Z$^1$ in each case, independently of one another, denotes —CO—O—, —O—CO—, —CH$_2$O—, —OCH$_2$—, —CF$_2$O—, —OCF$_2$—, or —(CH$_2$)$_n$—, where n is 2, 3 or 4, —O—, —CO—, —C(R$^c$R$^d$)—, —CH$_2$CF$_2$—, —CF$_2$CF$_2$— or a single bond,
L$^X$ on each occurrence, identically or differently, denotes F, Cl, CN, SCN, SF$_5$ or unbranched, optionally fluorinated, alkyl, alkoxy, alkylcarbonyl, alkoxycarbonyl, alkylcarbonyloxy or alkoxycarbonyloxy having 1 to 12 C atoms, or branched, optionally fluorinated, alkyl, alkoxy, alkylcarbonyl, alkoxycarbonyl, alkylcarbonyloxy or alkoxycarbonyloxy having 3 to 12 C atoms,
R$^c$ and R$^d$ each, independently of one another, denote H or alkyl having 1 to 6 C atoms,
where one or more of the groups P$^1$-Sp$^1$, -Sp$^2$-P$^2$ and -Sp$^3$-P$^3$ may denote a radical R$^{aa}$, with the proviso that at least one of the groups P$^1$-Sp$^1$-, -Sp$^2$-P$^2$ and -Sp$^3$-P$^3$ present does not denote R$^{aa}$,
R$^{aa}$ denotes H, F, Cl, CN or unbranched alkyl having 1 to 25 C atoms, or branched alkyl having 3 to 25 C atoms, in which, in addition, one or more non-adjacent CH$_2$ groups may each be replaced, independently of one another, by C(R$^0$)=C(R$^{00}$)—, —C≡C—, —O—, —S—, —CO—, —CO—O—, —O—CO—, —O—CO—O— in such a way that O and/or S atoms are not linked directly to one another, and in which, in addition, one or more H atoms may be replaced by F, Cl, CN or P$^1$-Sp$^1$-, where the groups —OH, —NH$_2$, —SH, —NHR, —C(O)OH and —CHO are not present in R$^{aa}$.

12. A LC medium according to claim 9, which comprises 95% by weight or more of a low-molecular-weight, unpolymerisable, liquid-crystalline component, and
5% by weight or less of a polymerisable or polymerised component.

13. A LC medium according to claim 9, which comprises one or more compounds selected from the group of the compounds of the formulae A, B and C:

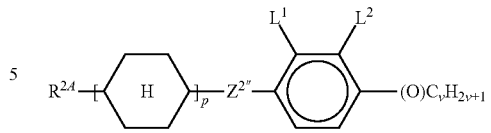

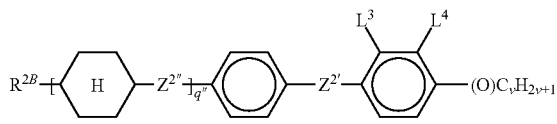

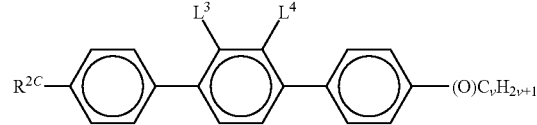

in which
R$^{2A}$, R$^{2B}$ and R$^{2C}$
each, independently of one another, denote H, an alkyl radical having 1 to 15 C atoms which is unsubstituted, monosubstituted by CN or CF$_3$ or at least monosubstituted by halogen, where, in addition, one or more CH$_2$ groups in these radicals may be replaced by —O—, —S—,

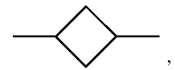

—C≡C—, —CH=CH—, —CF$_2$O—, —OCF$_2$—, —OC—O— or —O—CO— in such a way that O atoms are not linked directly to one another,
L$^{1-4}$ each, independently of one another, denote F, Cl, CF$_3$ or CHF$_2$,
Z$^{2"}$ and Z$^{2'}$ each, independently of one another, denote a single bond, —CH$_2$CH$_2$—, —CH=CH—, —CF$_2$O—, —OCF$_2$—, —CH$_2$O—, —OCH$_2$—, —COO—, —OCO—, —C$_2$F$_4$—, —CF=CF— or —CH=CHCH$_2$O—,
P denotes 1 or 2,
q" denotes 0 or 1,
(O) denotes —O— or a single bond, and
v denotes 1 to 6.

14. A LC display comprising an LC cell having two substrates and at least two electrodes, where at least one substrate is transparent to light and at least one substrate has one or two electrodes, and having a layer of a LC medium according to claim 9, located between the substrates.

15. A LC display according to claim 14, wherein one or both of the substrates have no alignment layers for homeotropic alignment of the LC medium.

16. A process for the preparation of an LC medium, wherein one or more compounds according to claim 5 are mixed with a low-molecular-weight liquid-crystalline component, and one or more further polymerisable compounds and/or any desired additives are optionally added.

17. A process for the production of an LC display comprising an LC cell having two substrates and at least two electrodes, where at least one substrate is transparent to light and at least one substrate has one or two electrodes, comprising the process steps of:

filling of the cell with an LC medium according to claim 9, where homeotropic alignment of the LC medium with respect to the substrate surfaces is established, and optionally polymerisation of the polymerisable component(s), optionally with application of a voltage to the cell or under the action of an electric field, in one or more process steps.

18. A compound according to claim 1 wherein r1 denotes 0.

* * * * *